US008802596B2

(12) United States Patent
Rogers et al.

(10) Patent No.: US 8,802,596 B2
(45) Date of Patent: Aug. 12, 2014

(54) MULTI-FUNCTIONAL IONIC LIQUID COMPOSITIONS FOR OVERCOMING POLYMORPHISM AND IMPARTING IMPROVED PROPERTIES FOR ACTIVE PHARMACEUTICAL, BIOLOGICAL, NUTRITIONAL, AND ENERGETIC INGREDIENTS

(75) Inventors: Robin D. Rogers, Tuscaloosa, AL (US); Daniel T. Daly, Tuscaloosa, AL (US); Richard P. Swatloski, Tuscaloosa, AL (US); Whitney L. Hough-Troutman, Tuscaloosa, AL (US); James Hilliard Davis, Jr., Mobile, AL (US); Marcin Smiglak, Tuscaloosa, AL (US); Juliusz Pernak, Pozan (PL); Scott K. Spear, Bankston, AL (US)

(73) Assignee: Board of Trustees of the University of Alabama, Tuscaloosa, AL (US)

( * ) Notice: Subject to any disclaimer, the term of this patent is extended or adjusted under 35 U.S.C. 154(b) by 0 days.

(21) Appl. No.: 13/491,053

(22) Filed: Jun. 7, 2012

(65) Prior Publication Data

US 2012/0264605 A1 Oct. 18, 2012

Related U.S. Application Data

(62) Division of application No. 11/545,938, filed on Oct. 10, 2006, now Pat. No. 8,232,265.

(60) Provisional application No. 60/764,850, filed on Feb. 2, 2006, provisional application No. 60/724,604, filed on Oct. 7, 2005, provisional application No. 60/724,605, filed on Oct. 7, 2005.

(51) Int. Cl.
| | |
|---|---|
| *A01N 57/18* | (2006.01) |
| *A01N 43/707* | (2006.01) |
| *A01N 43/66* | (2006.01) |
| *A01N 43/68* | (2006.01) |
| *A01N 43/58* | (2006.01) |
| *A01N 43/82* | (2006.01) |
| *A01N 43/78* | (2006.01) |
| *A01N 43/76* | (2006.01) |
| *A01N 43/80* | (2006.01) |
| *A01N 43/653* | (2006.01) |
| *A01N 43/10* | (2006.01) |
| *A01N 37/00* | (2006.01) |
| *A01N 37/18* | (2006.01) |
| *A01N 33/18* | (2006.01) |
| *A01N 43/90* | (2006.01) |
| *A01N 43/54* | (2006.01) |
| *A01N 43/40* | (2006.01) |
| *A01N 43/42* | (2006.01) |
| *A01N 43/48* | (2006.01) |

(52) U.S. Cl.
USPC ........ 504/206; 504/229; 504/231; 504/232; 504/236; 504/238; 504/262; 504/267; 504/270; 504/271; 504/272; 504/289; 504/307; 504/334; 504/347; 504/241; 504/243; 504/244; 504/247; 504/253; 504/255

(58) Field of Classification Search
None
See application file for complete search history.

(56) References Cited

U.S. PATENT DOCUMENTS

| | | | |
|---|---|---|---|
| 1,943,176 A | 1/1934 | Graenacher | |
| 3,223,704 A | 12/1965 | Shibe | |
| 3,344,018 A | 9/1967 | Shibe | |
| 3,414,569 A | 12/1968 | Wieden | |
| 3,471,423 A | 10/1969 | Elmer | |
| 4,097,666 A | 6/1978 | Johnson et al. | |
| 4,104,368 A | 8/1978 | Lala et al. | |
| 4,188,263 A | 2/1980 | Hulsmann et al. | |
| 4,224,319 A | 9/1980 | Marcadet | |
| 4,228,162 A | 10/1980 | Luzzi et al. | |
| 4,491,574 A | 1/1985 | Seifter et al. | |
| 4,520,105 A | 5/1985 | Sinner et al. | |
| 4,637,830 A | 1/1987 | Dyer et al. | |
| 4,761,164 A | 8/1988 | Pez et al. | |
| 4,973,456 A | 11/1990 | Quinn et al. | |
| 5,175,353 A | 12/1992 | Jones et al. | |
| 5,221,758 A | 6/1993 | Maynard | |
| 5,246,716 A | 9/1993 | Sedun et al. | |
| 5,275,820 A | 1/1994 | Chang | |
| 5,428,000 A | 6/1995 | Innami et al. | |
| 5,654,337 A | 8/1997 | Roentsch et al. | |
| 5,679,146 A | 10/1997 | Kalt et al. | |
| 5,683,832 A | 11/1997 | Bonhote et al. | |

(Continued)

FOREIGN PATENT DOCUMENTS

| | | |
|---|---|---|
| CA | 2619367 | 7/2009 |
| DE | 93-4308410 | 3/1993 |

(Continued)

OTHER PUBLICATIONS

Office Action for Application No. JP 2008-534766 dated Sep. 13, 2012.
Avent et al., Evidence for hydrogen bonding in solutions of 1-Ehtyl-3-imidazolium Halides, and its implications for ambient temperature Halogenoaluminate (III) ionic liquids, J. Chem. Soc. Dalton Trans., 3405-3413 (1994).
Bates et al., CO2 capture by a task-specific ionic liquid, J. Am. Chem Soc., 124(6):926-927 (2002).

(Continued)

*Primary Examiner* — Alton Pryor
(74) *Attorney, Agent, or Firm* — Meunier Carlin & Curfman, LLC

(57) ABSTRACT

Disclosed are ionic liquids and methods of preparing ionic liquid compositions of active pharmaceutical, biological, nutritional, and energetic ingredients. Also disclosed are methods of using the compositions described herein to overcome polymorphism, overcome solubility and delivery problems, to control release rates, add functionality, enhance efficacy (synergy), and improve ease of use and manufacture.

13 Claims, 6 Drawing Sheets

(56) References Cited

U.S. PATENT DOCUMENTS

| | | | |
|---|---|---|---|
| 5,731,101 A | 3/1998 | Sherif et al. | |
| 5,792,399 A | 8/1998 | Miester et al. | |
| 5,827,602 A | 10/1998 | Koch et al. | |
| 5,856,513 A | 1/1999 | Ue et al. | |
| 5,908,697 A | 6/1999 | Roux et al. | |
| 6,759,544 B2 | 7/2004 | Burgard | |
| 6,774,240 B2 | 8/2004 | Seddon et al. | |
| 6,808,557 B2 | 10/2004 | Holbrey et al. | |
| 6,824,599 B2 | 11/2004 | Swatloski et al. | |
| 6,846,926 B1 | 1/2005 | Koppes et al. | |
| 6,906,004 B2 | 6/2005 | Parrish et al. | |
| 6,939,882 B1 | 9/2005 | Cooke et al. | |
| 6,939,974 B2 | 9/2005 | Earle et al. | |
| 2002/0010291 A1 | 1/2002 | Murphy | |
| 2002/0019314 A1* | 2/2002 | Frisch et al. | 504/358 |
| 2002/0115569 A1 | 8/2002 | Schnabel et al. | |
| 2002/0161261 A1 | 10/2002 | Bahrmann et al. | |
| 2003/0073604 A1 | 4/2003 | McGolf et al. | |
| 2004/0007693 A1 | 1/2004 | Moulton | |
| 2004/0026666 A1 | 2/2004 | Chauvin et al. | |
| 2004/0146549 A1 | 7/2004 | Ben-Sesson et al. | |
| 2004/0234966 A1 | 11/2004 | Bryning et al. | |
| 2005/0058702 A1 | 3/2005 | Ben-Sasson et al. | |
| 2005/0136103 A1 | 6/2005 | Ben-Sasson et al. | |
| 2005/0194561 A1 | 9/2005 | Davis | |
| 2005/0232981 A1 | 10/2005 | Ben-Sasson | |
| 2006/0118755 A1 | 6/2006 | Fujioka et al. | |
| 2006/0159632 A1 | 7/2006 | Ishibashi et al. | |
| 2007/0053939 A1 | 3/2007 | Yokoyama et al. | |
| 2007/0054952 A1 | 3/2007 | Hamamoto et al. | |
| 2008/0190013 A1 | 8/2008 | Argyropoulos | |
| 2008/0207452 A1* | 8/2008 | Kramer et al. | 504/127 |
| 2009/0264664 A1 | 10/2009 | Endo et al. | |
| 2010/0004608 A1 | 1/2010 | Hamamoto et al. | |
| 2010/0029704 A1 | 2/2010 | Hanma et al. | |
| 2010/0280090 A1 | 11/2010 | Hamamoto et al. | |

FOREIGN PATENT DOCUMENTS

| | | |
|---|---|---|
| ES | 8406412 | 4/1983 |
| FR | 1404697 | 5/1965 |
| GB | 869149 | 5/1961 |
| GB | 1067094 | 5/1964 |
| GB | 1473603 | 5/1977 |
| JP | 61-236818 | 10/1986 |
| JP | 62-198609 | 9/1987 |
| JP | 63-056501 | 3/1988 |
| JP | 2001525820 | 3/2005 |
| JP | 2005082512 | 3/2005 |
| NL | 302478 | 10/1965 |
| WO | 91/13552 | 9/1991 |
| WO | 95/21806 | 8/1995 |
| WO | 95/21871 | 8/1995 |
| WO | 95/21872 | 8/1995 |
| WO | 96/06593 | 3/1996 |
| WO | 97/43012 | 11/1997 |
| WO | 98/51283 | 11/1998 |
| WO | 03/029329 | 4/2003 |
| WO | 2004/075877 | 9/2004 |
| WO | 2005/028446 | 3/2005 |
| WO | 2005/097731 | 10/2005 |
| WO | 2007/005470 | 1/2007 |
| WO | 2007/044693 | 4/2007 |
| WO | 2009/060629 | 5/2009 |
| WO | 2009/066457 | 5/2009 |
| WO | 2009/075094 | 6/2009 |
| WO | 2009/119836 | 10/2009 |

OTHER PUBLICATIONS

Bernstein, Polymorphism of high energy materials, Polymorphism in Molecular Crystals, 275-296 (2002).
Bernstein, Introduction and historical background, Polymorphism in Molecular Crystals, 1-28 (2002).
Bernstein, Crystal structure prediction and polymorphism, ACA Transactions, 39:14-23 (2004).
Black et al., Increased chemical purity using a hydrage, Crystal Growth & Design, 4(3):539-544 (2004).
Bônhote et al., Hydrophobic, highly conductive ambient-temperature molten salts, Inorg. Chem., 35:1168-1178 (1996).
Bowlas et al., Liquid crystalline ionic liquids, Chem. Comm., 1625-1626 (1996).
Browning et al., Relationships between antiseptic action and chemical constitution with special reference to compounds of the pyridine, quinoline, acridine and phenazine seriers, Proc. Royal Soc. London, 93(653):329-366 (1922).
Browning et al., The antiseptic properties of the amino derivatives of styryl and anil quinoline, Proc. Royal Soc. London, 100(703):293-325 (1926).
Butcher et al., Initial Screening trials of some quaternary ammonium compounds and amine salts as wood preservatives, For. Prod. J., 27:19-22 (1977).
Butcher et al., Efficacy of acidic and alkaline solutions of alkylammonium compounds as wood preservatives, J. Forestry Sci.., 8:403-409 (1978).
Campanella et al., Benzylpenicillin PVC membrane electrode for the determination of antibiotics in formulations, J. Pharm. Biomed. Analysis, 6(3):299-305 (1988).
Campanella et al., Polymeric membrane electrodes for drug analysis, J. Pharm Biomed. Analysis, 6:717-723 (1988).
Carmichael, A solution in sight, Chem. Britia, 36 (2000).
Carter et al., Sweet success: Ionic liquids derived from non-nutritive sweeteners, Chem. Comm., 630-631 (2004).
Chawala et al., Challenges in polymorphism of pharmaceuticals, CRISPS, 5(1):9-12 (2004).
Cole et al., Novel Bronstead acidic ionic liquids and their use as dual solvent catalysts, J. Am. Chem. Soc., 124:5962-5963 (2002).
Cuppen et al., Crystal structure and growth behavior of aspartame form I-A, Crystal Growth & Design, 5(3):917-923 (2005).
Davis et al., Thiazolium-ion based organic ionic liquids (OILs). Novel OILs which promote the benzoinc condensation, Tetrahedron Lett., 40:1621-1622 (1999).
Davis et al., From curiosities to commodities: Ionic liquids begin the transformation, Chem. Comm. 1209-1212 (2003).
Domagk, A new class of disinfectants, Deut. Med. Wochenschr., 61:829-832 (1935).
Dupont et al., Room temperature molten salts: Neuteric "Green" solvents for chemical reactions and processes, Braz. Chem. Soc. 11(4):337-344 (2000).
Elaiwi et al., Hydrogen bonding in Imidazolium salts and its implications for ambient-temperature Halogenoaluminate (III) ionic liquids, J. Chem. Soc. Dalton Trans., 3467-3472 (1995).
Extended European Search Report for Application No. 06774039.9 dated Jul. 8, 2011.
Fannin et a., Properties of 1,3-Dialkylimidazolium chloride-aluminum chloride ionic liquids. 2. Phase transitions, densities, electrical conductivities, and viscosities, J. Phys. Chem., 88:2614-2621 (1984).
Fraga-Dubreuil et al., Grafted ionic liquid-phase-supported synthesis of small organic molecules, Tetrahedron Lett., 42:6097-6100 (2001).
Freemantle, Ionic liquids show promise for clean separation technology, Chem. Eng. New, 76(34):12 (1998).
Freemantle, Eyes on ionic liquids, Chem. Eng. News, 78(2):37-50 (2000).
Fukumoto et al., Room temperature ionic liquids from 20 natural amino acids, J. Am. Chem. Soc., 127(8):2398-2399 (2005).
Geppi et al., Molecular properties of ibuprofen and its solid idpersions with eudragit RL 100 studied by solid-state nuclear magnetic resonance, Pharm. Res., 22(9):1544-1555 (2005).
Gordon et al., Fused organic salts. 8. Properties of molten straight-chain isomers of tetra-N-Pentylammonium salts, J. Amer. Chem. Soc., 100(24):7445-7454 (1978).
Hamaguchi et al., Structure of ionic liquids and ionic compounds: Are ionic liquids genuine liquids in the convention sense, Advances in Chem. Physics, 131:85-104 (2005).
Hartman et al., Acid soaps, J. Applied Chem., 41:137 (1928).

(56) References Cited

OTHER PUBLICATIONS

Hayes et al., Occurrence of pharmaceutically acceptable anions and cations in the Cambridge structural database, J. Pharm. Sci., 94(10):2111-2120 (2005).
Holbrey et al., The Phase Behaviour of 1-Alkyl-3-Methlimidazolium Tetrafluoroborates; Ionic Liquids and Ionic Liquid Crystals, J. Chem. Soc. Dalton Trans., 2133-2139 (1999).
Huddleston et al., Characterization and Comparison of Hydrophilic and Hydrophobic Room Temperature Ionic Liquids Incorporating the Imidazolium Cation, Green Chem., 3:156-164 (2001).
International Preliminary Report on Patentability and Written Opinion for PCT/US2009/069652 dated Jul. 7, 2011.
International Search Report and Written Opinion of the International Searching Authority for PCT/US06/39454, 2010.
Jacobs et al., On a New Group of Bactericidal Substances Obtained from Hexamethylenetetramine, Proc. Nat. Acad. Sci. USA, 1:226-228 (1915).
Jacobs et al., The Quaternary Salts of Hexamethylenetetramine. I. Substituted Benzyl Halides and the Hexamethylenetetraminium Salts Derived Therefrom, J. Biol. Chem., 20:659-683 (1915).
Jacobs et al., The bactericidal properties of the quaternary salts of hexamethylenetetramine, J. Exptl. Med., 23:569-576 (1916).
Katritzky et al., 1-Butyl-3-methylimidazolium 3,5-dinitro-1,2,4-triazolate: a novel ionic liquid containing a rigid planar energetic anion, Chem. Comm. 868-870 (2005).
Katritzky et al., ILs Based on Energetic Imidazolium Cations: Nitro- and Nitrile-substituted N,N' Dialkylimidazolium Salts, New J. Chem., 30:349-358 (2006).
Katritzky et al., ILs Based on Energetic Azolate Anions, Chem. Eur. J., 12:4630-4641 (2006).
Klinguer et al., Lipophilic quaternary ammonium salt acts as muscosal adjuvant when co-administered by the nasal route with vaccine antigens, Vaccine, 19:4236-4244 (2001).
Lee et al., Ionic liquid-mediated selective extraction of lighin from wood leading to enhanced enzymatic cellulose hydrolsis, Biotechnology and Bioengineering. Published online Oct. 24, 2008, in Wiley InterScience (www.wileyinterscience.com). DOI 10.1002/bit.22179. p. 1372, Table 2.
Liu et al., Development of non-viral vectors for systemic gene delivery, J. Contr. Rel., 78:259-266 (2002).
MacFarlane et al., Pyrrolidinium imides: A new family of molten salts and conductive plastic crystal phases, J. Phys. Chem., 103:4164-4170 (1999).
Martion et al., Influence of crystal habit on the compression and densification mechanism of ibuprofen, J. Crystal Growth, 243:345-355 (2002).
Matsumoto et al., Room temperature ionic liquids based on small aliphalic ammonium cations and asymmetric amide anions, Chem. Comm. 1726-1727 (2002).
Meguro et al., Crystal structure of the low-humidity form of aspartame sweetener, J. Peptide Re., 56:97-104 (2000).
Merrigan et al., New fluorous ionic liquids function as surfactants in conventional room-termperature ionic liquids, Chem. Comm., 2051-2052 (2000).
Morrison et al., Base-promoted reactions in ionic liquid solvents. The Knoevenagel and Robinson annulations reactions, Tetrahedron Lett., 42:6053-6057 (2001).
Ngo et al., Thermal Properties of Imidazolium Ionic Liquids, Thermochimica Acta, 357-358:97-102 (2000).
Oertel, Novel hard to wash-out water soluble wood protecting agents and their application, Holztechnologie, 6:243 (1965).
Office Action for AU Patent Application No. 2006302237 dated Aug. 23, 2011.
Ohno et al., A new type of polymer gel electrolyte: Zwitterionic liquid/polar polymer mixture, Electrochimica Acta, 48:2079-2083 (2003).
Okamato et al., Synthesis, spectra, and reactions of N-triphenylmethylpyridinium salts. Reactions of Triphenylmethyl chlordie with pyridine under high pressure, J. Org. Chem., 35(11):3752-3756 (1970).
Okutucu et al., Covalent Attachment of Oligonucleotides to Cellulose Acetate Membranes, Artificial Cells, Blood Substitutes, and Biotechnology, 32(4):599-608 (2004).
Oldham et al., Unusual solvent system shows potential to revoluntionize separation and purification technologies, The Actinide Research Quarterly, 1st Quarter, 50-53 (2004).
Pernak et al., Phosphonium acesulfamate based ionic liquids, Eur. J. Org. Chem., 650-652 (2005).
Picquet et al., Ionic liquids: media for better molecular catalysis, Topics in Catalysis, 29(3-4):139-143 (2004).
Quinn et al., Salt hydrates: New reversible absorbents for carbon dioxide, J. Am. Chem. Soc., 117:329-335 (1995).
Rasenack et al., Properties of ibuprofen crystallized under various conditions: A comparative study, Drug Dev. Industrial Pharm., 28(9):1077-1089 (2002).
Remenar et al., Salt selection and simultaneous polymorphism assessment via high-throughput crystallization: The case of sertraline, Org. Proc. Res. & Dev., 7(6):990-996 (2003).
Reutzel-Edens et al., Anhydrates and hydrates of olanzapine: Crystallization solid-state characterization, and structural relationships, Crystal Growth & Design, 3(6):897-907 (2003).
Rogers et al., Ionic Liquids—Solvents of the Future? Science, 302:792-793 (2003).
Seddon et al., Ionic liquids for clean technology, J. Chem. Tech. Biotechnol., 68:351-356 (1997).
Stöllner et al., Activation of Cellulose Membranes with 1,1'-Carbonyldiimidazole or 1-Cyano-4-dimethylaminopyridinium tetrafluoroborate as a Basis for the Development of Immunosensors, Analytical Biochemistry, 304:157-165 (2002).
Swatloski et al., Ionic liquids are not always green: Hydroanalysis of 1-butyl-e-methylimidazoliums hexafluorophosphate, Green Chem., 5:361-363 (2003).
Trask et al., Screening for crystalline salts via mechanochemistry, Chem. Comm., 51-53 (2006).
Visser et al., Task Specific Ionic Liquids for the Extraction of Metal Ions from Aqueous Solutions, Chem. Commun., 135-136 (2001).
Visser et al., Hydrophobic ionic liquids incorporating N-alkylisoquinolinium cations and their utilization in liquid separation, Chem. Comm. 2484-2485 (2001).
Wasserscheid et al., Ionic liquids-new "solutions" for transition metal catalysis, Angew Chem. Int. Ed. Engl., 39:3772-3789 (2000).
Welton, Room temperature ionic liquids, solvents for synthesis and catalysis, Chem. Rev. 99:2071-2083 (1999).
Wilkes et al., Air and water stable 1-ethyl-3-methylimidazolium based ionic liquids, J. Chem. Soc., 965-967 (1992).
Office Action for U.S. Appl. No. 13/808,790 dated Jan. 22, 2014.
BAF Corporation Safety Data Sheet for 2-(2-Aminoethoxy)ethanol, Version 1.0 (obtained online with printed date: Oct. 21, 2011), 8 pages.
Office Action for Application No. JP 2012-186605 dated Nov. 15, 2013.

* cited by examiner

Hex Sulfacetamide and DDA Sulfacetamide Dissolution

1mM-MPE

100mM-MPE

MULTI-FUNCTIONAL IONIC LIQUID COMPOSITIONS FOR OVERCOMING POLYMORPHISM AND IMPARTING IMPROVED PROPERTIES FOR ACTIVE PHARMACEUTICAL, BIOLOGICAL, NUTRITIONAL, AND ENERGETIC INGREDIENTS

CROSS-REFERENCE TO RELATED APPLICATIONS

This patent application is a divisional of U.S. application Ser. No. 11/545,938 filed Oct. 10, 2006, whose status is allowed, and which claims the benefit of priority to U.S. Provisional Application No. 60/764,850, filed Feb. 2, 2006, U.S. Provisional Application No. 60/724,604, filed Oct. 7, 2005, and U.S. Provisional Application No. 60/724,605, filed Oct. 7, 2005, which are each incorporated by reference herein in their entireties

FIELD

The subject matter disclosed herein generally relates to ionic liquids and to methods of preparing ionic liquid compositions of active pharmaceutical, biological, nutritional, and energetic ingredients. Also the subject matter disclosed herein generally relates to methods of using the compositions described herein to overcome polymorphism, overcome solubility and delivery problems, to control release rates, add functionality, enhance efficacy (synergy), and improve ease of use and manufacture.

BACKGROUND

Polymorphism is the ability of a substance to exist in two or more crystalline forms that have a different arrangement and/or conformation of molecules in a crystalline lattice (see e.g., Chawla and Bansal, *CRIPS* 2004, 5(1):9-12; Bernstein, "Polymorphism in Molecular Crystals," *IUCR Monographs on Crystallography* 14, Oxford Science Publications, 2002, pp. 1-28, 240-256). It has been estimated that a large number of pharmaceuticals exhibit polymorphism. For example, 70% of barbiturates, 60% of sulfonamides, and 23% of steroids are believed to exist in different polymorphic forms or "polymorphs" (Haleblian et al., *J Pharm Sci* 1975, 64:1269-1288).

In some cases, when crystals of a compound are forming (e.g., crystallizing from a solution), solvent molecules may become entrapped or bound within the crystal lattice. The presence of the entrapped solvent molecules may affect the three-dimensional crystal lattice that eventually crystallizes. The occurrence of a compound (target molecule) crystallizing in different three-dimensional lattices based upon the presence of solvent molecules has been termed "pseudo-polymorphism." Akin to polymorphs, such "pseudo-polymorphs," also known as "solvates" (or "hydrates" when the solvent is water), are crystalline solids containing either stoichiometric (i.e., whole number ratios of target molecules to solvent molecules) or non-stoichiometric (i.e., non-whole number ratios of target molecules to solvent molecules) amounts of a solvent incorporated within the crystal structure. In general, different crystalline forms of molecules (e.g., pharmaceutical compounds) can exist in the same or different hydrated or solvated states.

The Cambridge Structural Database (Allen, "The Cambridge Structural Database: a quarter of a million crystal structures and rising," *Acta Crystallographica*, 2002, B58, 380-388) is a database of over 300,000 organic crystal structures and is a widely used reference source in crystallography. One survey of the Cambridge Structural Database shows that pharmaceutical compounds have been reported to exist as hemi-hydrates (0.5 water molecules) through decahydrates (10 water molecules). (Morris, "Structural Aspect of Hydrates and Solvates," Ch. 4 in *Polymorphism in Pharmaceutical Solids*, in Brittain, H. G., Ed., Vol. 95 of *Drugs and the Pharmaceutical Sciences*, Marcel Dekker, Inc., New York, N.Y., 1999, 125-181.)

The possibility of polymorphism or pseudo-polymorphism may exist for any particular compound, but the conditions required to prepare as yet unknown polymorphs or pseudo-polymorphs are not easily determined (see e.g., Bernstein, "Crystal Structure Prediction and Polymorphism," *Am Crystallographic Assoc Trans*, 2004, 39:14-23). The knowledge that one type of polymorph or pseudo-polymorph of a crystalline form of a compound exists, or that a given set of crystallization conditions leads to the production of one type of polymorph or pseudo-polymorph, does not typically allow researchers to predict what other types of polymorph or pseudo-polymorph might exist, or what type of polymorph or pseudo-polymorph would be produced by other crystallization conditions (Guillory, "Generation of Polymorphs, Hydrates, Solvates, and Amorphous Solids," Ch. 5 in *Polymorphism in Pharmaceutical Solids*, Brittain, H. G., Ed., Vol. 95 of *Drugs and the Pharmaceutical Sciences*, Marcel Dekker, Inc., New York, N.Y., 1999, pp. 183-226).

The existence of various polymorphs or pseudo-polymorphs can greatly affect a pharmaceutical's performance since each form can have different physical and chemical properties. For example, one particular polymorph pseudo-polymorph may be more bioavailable, more stable (e.g., longer shelf life), or more easily formulated or tableted than another polymorph. Similarly, one polymorph pseudo-polymorph may be more active or less toxic than another. Some specific examples of the dramatic difference that can exist between various pharmaceutical polymorphs are described in, e.g., Brittain et al., *J Pharm Sci* 2002, 91:1573-1580 and Morissette et al., *Proc Natl Acad Sci USA* 2003, 100:2180-2184.

The effects of polymorphism and pseudo-polymorphism on quality and performance of a drug is widely recognized. The exact solid state polymorph (or pseudo-polymorph) of a compound determines its physical properties such as dissolution rate, solubility, bioavailability, crystal habit, mechanical strength, etc. (Datta et al., *Nature Reviews—Drug Discovery*, 2004, 3:42-57). The delivery of an exact dosage in manufacture and the manufacturing process itself often depend on which of several possible polymorphs or pseudo-polymorphs are present.

The variation in properties among different polymorphs (or pseudo-polymorphs) usually means that one crystalline form is desired or preferred over other forms. Obtaining a particular form can be difficult, however. Typically, researchers have to experiment with a multitude of variables in crystallization conditions, such as aqueous solvent mixtures, amount of water, amount of target compound, relative humidity, temperature of incubation, incubation time, etc., in a process characterized by trial and error. Further, the search for salts of crystalline forms (usually sought after to control dissolution rate and solubility) can require extensive experimentation. Each salt of a drug or each different solvent used to crystallize the drug or a salt of the drug may lead to polymorphs or pseudo-polymorphs that have to be fully investigated and that have different properties (see e.g., Reutzel-Edens et al., "Anhydrates and hydrates of olanzapine: Crystallization, solid-state characterization, and structural relationships," *Crystal Growth & Design*, 2003, 3:897-907).

Moreover, the inadvertent production of an undesired polymorph (or pseudo-polymorph), or the spontaneous transformation from the desired crystalline form to an undesired form, can result in crystalline forms of a drug that are less effective or even toxic. Thus, the existence and control of polymorphism and pseudo-polymorphism can be the biggest challenge to obtaining a drug product of constant quality.

Another important issue regarding polymorphism and pseudo-polymorphism is that there can be considerable regulatory hurdles for a drug that exists in various crystalline forms. The FDA's regulatory guidelines emphasize control of crystal form and the use of appropriate techniques to detect and characterize different forms of a drug (see Guidance for Industry ANDAs: Pharmaceutical Solid Polymorphism Chemistry, Manufacturing, and Controls Information, U.S. Department of Health and Human Services, FDA, 2004). Thus, an applicant seeking FDA approval of a drug must demonstrate the ability to maintain a constant crystalline form throughout the life of the product. Such an endeavor is costly and can be extremely difficult or even impossible.

Similar challenges can exist when one seeks approval of a generic product by filing an Abbreviated New Drug Application (ANDA), in which case the applicant must show equivalence between the generic drug and an approved drug. Such a showing can be complicated when various polymorphic and/or pseudo-polymorphic forms exist for the drug.

Amorphous forms of drugs are now being studied because they are higher energy forms that have higher dissolution rates and solubilities since there is no lattice structure to overcome or to inhibit solvation (Bernstein, "Polymorphism in Molecular Crystals," *IUCR Monographs on Crystallography* 14, Oxford Science Publications, 2002, pp. 240-256). This increasing attention to amorphous forms has also shown, however, that the amorphous forms have a tendency to crystallize spontaneously to a lower energy crystalline form, usually at inopportune times.

The phenomenon of polymorphism and pseudo-polymorphism is not limited to pharmaceuticals as many other (if not all) organic and inorganic compounds can crystallize into different forms. Thus, the existence of various forms of a given compound (e.g., a pesticide, herbicide, nutraceutical, cosmetic, food additive, explosive, etc.) can result in the same synthetic, analytical, regulatory, and commercial difficulties that plague the pharmaceutical industry because of polymorphic and pseudo-polymorphic drugs. In each of these industries, it is not currently possible to simply alter the chemical nature of the active compound in order to tune the chemical (e.g., rate of dissolution and solubility) or physical (crystal habit, mechanical strength) properties. Rather, it is often the strategy to search for polymorphs or pseudo-polymorphs that have the most desirable "obtainable" properties.

Another common problem that exists with many pharmaceuticals is low solubility. Low solubility can make formulating a particular compound difficult, and generally low solubility translates into low bioavailability. Much research is conducted on finding ways to improve a compound's solubility and availability. Typically methods include complex delivery devices and chemical modifications of the drug.

Given that polymorphism and pseudo-polymorphism cannot be predicted; that the exact crystalline state affects chemical properties (e.g., dissolution rate, solubility), biological properties (e.g., bioavailability, pharmacokinetics), mechanical and physical properties, and manufacturing processes, and that polymorphs and pseudo-polymorphs can inconveniently interconvert, what are needed are compositions that are at least effective for their intended purpose, but can also have controlled and tunable chemical, biological, and physical properties, are in a form that is not subject to polymorphism, and for which controlled, tunable dissolution and solubility are possible. Methods of preparing and using such compositions are also needed. Further methods of converting a compound that is difficult to solubilize into a more soluble form are also desired. The compositions and methods disclosed herein meet these and other needs including the introduction of enhanced or new functionality.

SUMMARY

In accordance with the purposes of the disclosed materials, compounds, compositions, devices, and methods, as embodied and broadly described herein, the disclosed subject matter, in one aspect, relates to compounds and compositions and methods for preparing and using such compounds and compositions. In a further aspect, the disclosed subject matter relates to ionic liquid compositions that can be used for or in biological, pharmaceutical, nutritional, cosmetic, industrial, and commercial compositions. Methods for making the disclosed ionic liquid compositions are also disclosed. Also disclosed are methods of preparing ionic liquid compositions of active pharmaceutical, biological, nutritional, and energetic ingredients. Also the disclosed are methods of using the compositions described herein to overcome polymorphism, overcome solubility and delivery problems, to control release rates, add functionality, enhance efficacy (synergy), and improve ease of use and manufacture.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying Figures, which are incorporated in and constitute a part of this specification, illustrate several aspects described below.

DETAILED DESCRIPTION

Figure 1:
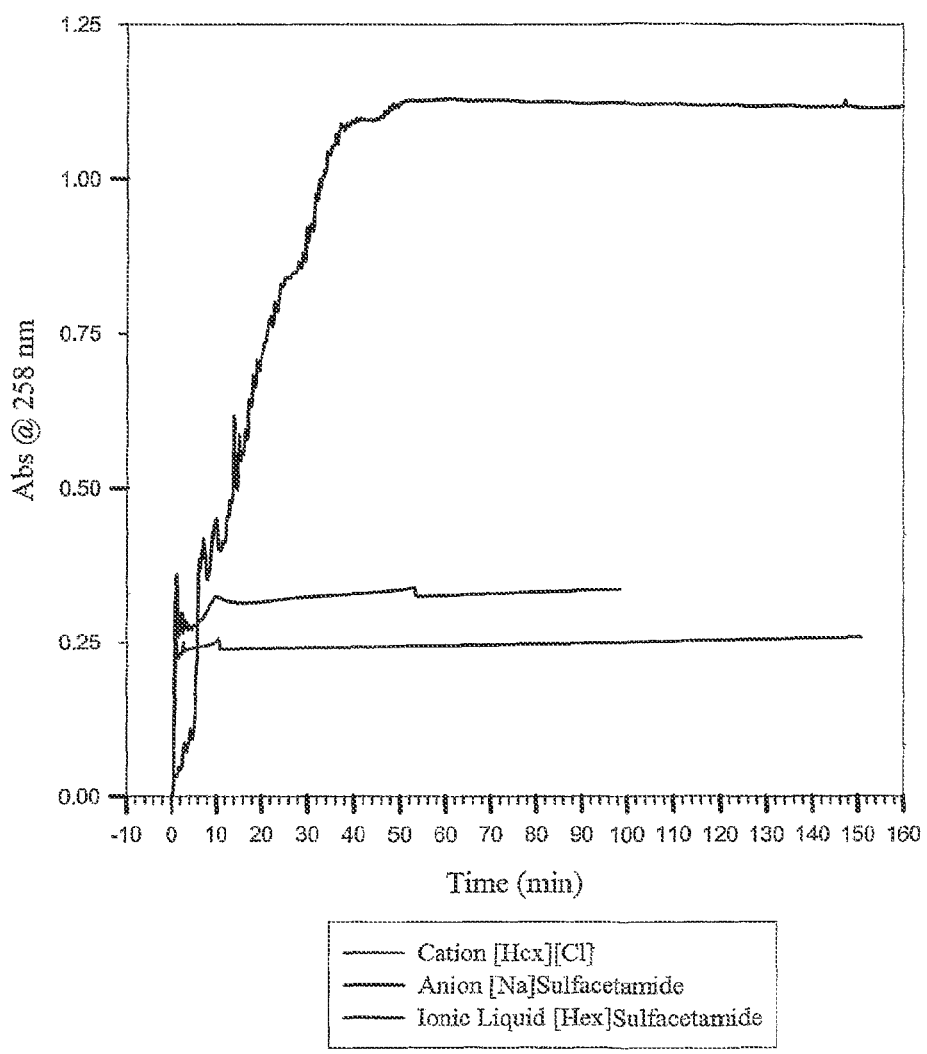
FIG. 1 is a graph of absorbance at 258 nanometers (nm) over time (minutes) for hexadecylpyridinium sulfacetamide ([Hex]sulfacetamide), hexadecylpyridinium chloride ([Hex][Cl]), and sodium sulfacetamide dissolution.
Figure 2:
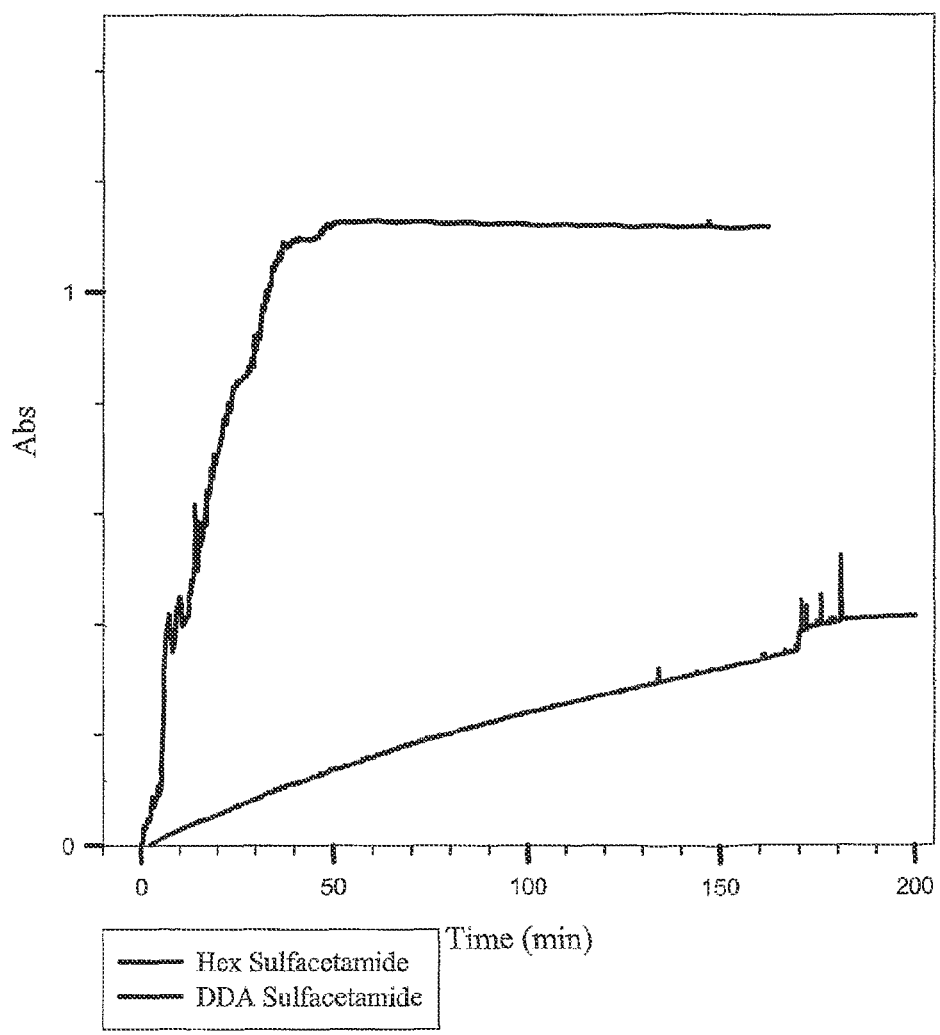
FIG. 2 is a graph of absorbance at 258 nm over time for hexadecylpyridinium sulfacetamide and didecyldimethylammonium (DDA) sulfacetamide dissolution.

The materials, compounds, compositions, articles, and methods described herein may be understood more readily by reference to the following detailed description of specific aspects of the disclosed subject matter and the Examples included therein.

Before the present materials, compounds, compositions, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

GENERAL DEFINITIONS

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an ionic liquid" includes mixtures of two or more such ionic liquids, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., microorganism growth or survival). It is understood that this is typically in relation to some standard or expected value, in other words it is relative, but that it is not always necessary for the standard or relative value to be referred to. For example, "reduces bacteria growth" means lowering the amount of bacteria relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, break-down, or eliminate a particular characteristic or event (e.g., microorganism growth or survival). The term "control" is used synonymously with the term "treat."

By "antimicrobial" is meant the ability to treat or control (e.g., reduce, prevent, inhibit, break-down, or eliminate) microorganism growth or survival at any concentration. Similarly, the terms "antibacterial," "antiviral," and "antifungal" respectively mean the ability to treat or control (e.g., reduce, prevent, inhibit, break-down, or eliminate) bacterial, viral, and fungal growth or survival at any concentration.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

CHEMICAL DEFINITIONS

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

The term "ion," as used herein, refers to any molecule, portion of a molecule, cluster of molecules, molecular complex, moiety, or atom that contains a charge (positive, negative, or both (e.g., zwitterions)) or that can be made to contain a charge. Methods for producing a charge in a molecule, portion of a molecule, cluster of molecules, molecular complex, moiety, or atom are disclosed herein and can be accomplished by methods known in the art, e.g., protonation, deprotonation, oxidation, reduction, alkylation, etc.

The term "anion" is a type of ion and is included within the meaning of the term "ion." An "anion" is any molecule, portion of a molecule (e.g., Zwitterion), cluster of molecules, molecular complex, moiety, or atom that contains a net negative charge or that can be made to contain a net negative charge. The term "anion precursor" is used herein to specifically refer to a molecule that can be converted to an anion via a chemical reaction (e.g., deprotonation).

The term "cation" is a type of ion and is included within the meaning of the term "ion." A "cation" is any molecule, portion of a molecule (e.g., Zwitterion), cluster of molecules, molecular complex, moiety, or atom, that contains a net positive charge or that can be made to contain a net positive charge. The term "cation precursor" is used herein to specifically refer to a molecule that can be converted to a cation via a chemical reaction (e.g., protonation or alkylation).

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C═O.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula —C(O)O⁻.

The term "ester" as used herein is represented by the formula —OC(O)$A^1$ or —C(O)O$A^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —$NO_2$.

The term "silyl" as used herein is represented by the formula —Si$A^1A^2A^3$, where $A^1$, $A^2$, and $A^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfo-oxo" as used herein is represented by the formulas —S(O)$A^1$, —S(O)$_2A^1$, —OS(O)$_2A^1$, or —OS(O)$_2$O$A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above. Throughout this specification "S(O)" is a short hand notation for S═O.

The term "sulfonyl" is used herein to refer to the sulfo-oxo group represented by the formula —S(O)$_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "sulfone" as used herein is represented by the formula $A^1$S(O)$_2A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "sulfoxide" as used herein is represented by the formula $A^1$S(O)$A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "thiol" as used herein is represented by the formula —SH.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

The term "bioactive property" is any local or systemic biological, physiological, or therapeutic effect in a biological system. For example, the bioactive property can be the control of infection or inflammation, enhancement or suppression of growth, action as an analgesic, anti-viral, pesticidal, herbicidal, or nutrientional action, etc. Many examples of bioactive properties are disclosed herein.

The term "energetic" is used to described a compound having a heat of combustion of greater than about 500 kcal/mol (e.g., about 750, 1000, 1500 kcal/mol or more).

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples.

Materials and Compositions

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), Sigma (St. Louis, Mo.), Pfizer (New York, N.Y.), GlaxoSmithKline (Raleigh, N.C.), Merck (Whitehouse Station, N.J.), Johnson & Johnson (New Brunswick, N.J.), Aventis (Bridgewater, N.J.), AstraZeneca (Wilmington, Del.), Novartis (Basel, Switzerland), Wyeth (Madison, N.J.), Bristol-Myers-Squibb (New York, N.Y.), Roche (Basel, Switzerland), Lilly (Indianapolis, Ind.), Abbott (Abbott Park, Ill.), Schering Plough (Kenilworth, N.J.), or Boehringer Ingelheim (Ingelheim, Germany), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the active pharmaceutical ingredients, pesticides, herbicides, and other biological agents disclosed herein can be obtained from commercial sources.

In one aspect, disclosed herein are ionic liquid compositions. The term "ionic liquid" has many definitions in the art, but is used herein to refer to salts (i.e., compositions comprising cations and anions) that are liquid at a temperature of at or below about 150° C. That is, at one or more temperature ranges or points at or below about 150° C. the disclosed ionic liquid compositions are liquid; although, it is understood that they can be solids at other temperature ranges or points. Since the disclosed ionic liquid compositions are liquid, and thus not crystalline solids, at a given temperature, the disclosed compositions do not suffer from the problems of polymorphism associated with crystalline solids.

The use of the term "liquid" to describe the disclosed ionic liquid compositions is meant to describe a generally amorphous, non-crystalline, or semi-crystalline state. For example, while some structured association and packing of cations and anions can occur at the atomic level, the disclosed ionic liquid compositions have minor amounts of such ordered structures and are therefore not crystalline solids. The compositions disclosed herein can be fluid and free-flowing liquids or amorphous solids such as glasses or waxes at a temperature at or below about 150° C. In particular examples disclosed herein, the disclosed ionic liquid compositions are liquid at the body temperature of a subject.

Further, the disclosed ionic liquid compositions are materials composed of at least two different ions; each of which can independently and simultaneously introduce a specific characteristic to the composition not easily obtainable with traditional dissolution and formulation techniques. Thus, by providing different ions and ion combinations, one can change the characteristics or properties of the disclosed ionic liquid compositions in a way not seen by simply preparing various crystalline salt forms. Examples of characteristics that can be controlled in the disclosed compositions include, but are not limited to, melting, solubility control, and rate of dissolution. It is this multi-nature/functionality of the disclosed ionic liquid compositions which allows one to fine-tune or design in very specific desired material properties.

It is further understood that the disclosed ionic liquid compositions can include solvent molecules (e.g., water); however, these solvent molecules should not be present in excess in the sense that the disclosed ionic liquid compositions are dissolved in the solvent, forming a solution. That is, the disclosed ionic liquid compositions contain no or minimal amounts of solvent molecules that are free and not bound or associated with the ions present in the ionic liquid composition. Thus, the disclosed ionic liquid compositions can be liquid hydrates or solvates, but not solutions.

Ionic liquids have been of general interest because they are environmentally-friendly alternatives to organic solvents for various chemical processes, e.g., liquid/liquid extractions, catalysis, separations, and electrochemistry. Ionic liquids have also become popular alternative media for chemical synthesis because of their low volatility and low toxicity. See e.g., Wasserscheid and Keim, *Angew Chem Int Ed Engl*, 2000, 39:3772; and Wasserscheid, "Ionic Liquids in Synthesis," 1$^{st}$ Ed., Wiley-VCH, 2002. Further, ionic liquids can reduce costs, disposal requirements, and hazards associated with volatile organic compounds. Other exemplary properties of ionic liquids are high ionic conductivity, non-volatility, non-flammability, high thermal stability, wide temperature for liquid phase, highly solvability, and non-coordinating. For a review of ionic liquids see, for example, Welton, *Chem. Rev.* 1999, 99:2071-2083; and Carlin et al., Advances in Nonaqueous Chemistry, Mamantov et al. Eds., VCH Publishing, New York, 1994.

The specific physical properties (e.g., melting point, viscosity, density, water solubility, etc.) of ionic liquids are determined by the choice of cation and anion, as is disclosed more fully herein. As an example, the melting point for an ionic liquid can be changed by making structural modifications to the ions or by combining different ions. Similarly, the particular chemical properties (e.g., bioactivity, toxicity, pharmacokinetics, etc.), can be selected by changing the constituent ions of the ionic liquid.

The ionic liquid compositions disclosed herein are comprised of at least one kind of anion and at least one kind of cation. The at least one kind of cation, the at least one kind of anion, or both can be a pharmaceutical active, a pesticidal active, a herbicidal active, a food additive, a nutraceutical, or the like, including any combination thereof, as is disclosed herein. It is contemplated that the disclosed ionic liquid compositions can comprise one kind of cation with more than one kind of anion (e.g., 2, 3, 4, 5, 6, 7, 8, 9, 10, or more different kinds of anions). Likewise, it is contemplated that the disclosed ionic liquid compositions can comprise one kind of anion with more than one kind of cation (e.g., 2, 3, 4, 5, 6, 7, 8, 9, 10, or more different kinds of cations). Further, the disclosed ionic liquids can comprise more than one kind of anion (e.g., 2, 3, 4, 5, 6, 7, 8, 9, 10, or more different kinds of anions) with more than one kind of cation (e.g., 2, 3, 4, 5, 6, 7, 8, 9, 10 or more different kinds of cations). Specific examples include, but are not limited to, one kind of cation with 1, 2, 3, 4, 5, 6, 7, 8, 9, 10, or more kinds of anions, 2 kinds of cations with 1, 2, 3, 4, 5, 6, 7, 8, 9, 10, or more kinds of anions, 3 kinds of cations with 1, 2, 3, 4, 5, 6, 7, 8, 9, 10, or more kinds of anions, 4 kinds of cations with 1, 2, 3, 4, 5, 6, 7, 8, 9, 10, or more kinds of anions, 5 kinds of cations with 1, 2, 3, 4, 5, 6, 7, 8, 9, 10, or more kinds of anions, 6 kinds of cations with 1, 2, 3, 4, 5, 6, 7, 8, 9, 10, or more kinds of anions, 7 kinds of cations with 1, 2, 3, 4, 5, 6, 7, 8, 9, 10, or more kinds of anions, 8 kinds of cations with 1, 2, 3, 4, 5, 6, 7, 8, 9, 10, or more kinds of anions, 9 kinds of cations with 1, 2, 3, 4, 5, 6, 7, 8, 9, 10, or more kinds of anions, 10 kinds of cations with 1, 2, 3, 4, 5, 6, 7, 8, 9, 10, or more kinds of anions, or more than 10 kinds of cations with 1, 2, 3, 4, 5, 6, 7, 8, 9, 10, or more kinds of anions.

Other specific examples include, but are not limited to, one kind of anion with 1, 2, 3, 4, 5, 6, 7, 8, 9, 10, or more kinds of cations, 2 kinds of anions with 1, 2, 3, 4, 5, 6, 7, 8, 9, 10, or more kinds of cations, 3 kinds of anions with 1, 2, 3, 4, 5, 6, 7, 8, 9, 10, or more kinds of cations, 4 kinds of anions with 1, 2, 3, 4, 5, 6, 7, 8, 9, 10, or more kinds of cations, 5 kinds of anions with 1, 2, 3, 4, 5, 6, 7, 8, 9, 10, or more kinds of cations, 6 kinds of anions with 1, 2, 3, 4, 5, 6, 7, 8, 9, 10, or more kinds of cations, 7 kinds of anions with 1, 2, 3, 4, 5, 6, 7, 8, 9, 10, or more kinds of cations, 8 kinds of anions with 1, 2, 3, 4, 5, 6, 7, 8, 9, 10, or more kinds of cations, 9 kinds of anions with 1, 2, 3, 4, 5, 6, 7, 8, 9, 10, or more kinds of cations, 10 kinds of anions with 1, 2, 3, 4, 5, 6, 7, 8, 9, 10, or more kinds of cations, or more than 10 kinds of anions with 1, 2, 3, 4, 5, 6, 7, 8, 9, 10, or more kinds of cations.

In addition to the cations and anions, the ionic liquid compositions disclosed herein can also contain nonionic species, such as solvents, preservatives, dyes, colorants, thickeners, surfactants, viscosity modifiers, mixtures and combinations thereof and the like. However, the amount of such nonionic species is typically low (e.g., less than about 10, 9, 8, 7, 6, 5, 4, 3, 2, or 1 wt. % based on the total weight of the composition). In some examples described herein, the disclosed ionic liquid compositions are neat; that is, the only materials present in the disclosed ionic liquids are the cations and anions that make up the ionic liquid compositions. It is understood, however, that with neat compositions, some additional materials or impurities can sometimes be present, albeit at low to trace amounts (e.g., less than about 10, 9, 8, 7, 6, 5, 4, 3, 2, or 1 wt. % based on the total weight of the composition).

The disclosed ionic liquid compositions are liquid at some temperature range or point at or below about 150° C. For example, the disclosed ionic liquids can be a liquid at or below about 150, 149, 148, 147, 146, 145, 144, 143, 142, 141, 140, 139, 138, 137, 136, 135, 134, 133, 132, 131, 130, 129, 128, 127, 126, 125, 124, 123, 122, 121, 120, 119, 118, 117, 116, 115, 114, 113, 112, 111, 110, 109, 108, 107, 106, 105, 104, 103, 102, 101, 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, 0, −1, −2, −3, −4, −5, −6, −7, −8, −9, −10, −11, −12, −13, −14, −15, −16, −17, −18, −19, −20, −21, −22, −23, −24, −25, −26, −27, −28, −29, or −30° C., where any of the stated values can form an upper or lower endpoint when appropriate. In further examples, the disclosed ionic liquids can be liquid at any point from about −30° C. to about 150° C., from about −20° C. to about 140° C., −10° C. to about 130° C., from about 0° C. to about 120° C., from about 10° C. to about 110° C., from about 20° C. to about 100° C., from about 30° C. to about 90° C., from about 40° C. to about 80° C., from about 50° C. to about 70° C., from about −30° C. to about 50° C., from about −30° C. to about 90° C., from about −30° C. to about 110° C., from about −30° C. to about 130° C., from about −30° C. to about 150° C., from about 30° C. to about 90° C., from about 30° C. to about 110° C., from about 30° C. to about 130° C., from about 30° C. to about 150° C., from about 0° C. to about 100° C., from about 0° C. to about 70° C., from about 0° to about 50° C., and the like.

Further, in some examples the disclosed ionic liquid compositions can be liquid over a wide range of temperatures, not just a narrow range of, say, 1-2 degrees. For example, the disclosed ionic liquid compositions can be liquids over a range of at least about 4, 5, 6, 7, 8, 9, 10, or more degrees. In other example, the disclosed ionic liquid compositions can be liquid over at least about a 11, 12, 13, 14, 15, 16, 17, 18, 19, 20, or more degree temperature range. Such temperature ranges can begin and/or end at any of the temperature points disclosed in the preceding paragraph.

In many examples disclosed herein the disclosed ionic liquid compositions are liquid at the temperature at which they will be used or processed. For example, many of the disclosed ionic liquid compositions can be used for therapeutic or nutritional purposes in a subject. In this case, the disclosed ionic liquid compositions can be liquid at the subject's body temperature (e.g., about 37° C. for a human). Other examples include compositions that can be used as herbicides or pesticides, which are liquid at the temperature of their use (e.g., ambient temperature). In still other examples, the disclosed compositions can be liquid at the temperature at which they are formulated or processed.

It is understood, however, that the disclosed ionic liquid compositions can, though need not, be solubilized, and solutions of the disclosed ionic liquids are contemplated herein. Further, the disclosed ionic liquid compositions can be formulated in an extended or controlled release vehicle, for example, by encapsulating the ionic liquids in microspheres or microcapsules using methods known in the art. Still further, the disclosed ionic liquid compositions can themselves be solvents for other solutes. For example, the disclosed ionic liquids can be used to dissolve a particular nonionic or ionic pharmaceutical active. These and other formulations of the disclosed ionic liquids are disclosed elsewhere herein.

In some examples, the disclosed ionic liquids are not solutions where ions are dissolved in a solute. In other examples, the disclosed ionic liquid compositions do not contain ionic exchange resins. In still other examples, the disclosed ionic liquids are substantially free of water. By substantially free is meant that water is present at less than about 10, 9, 8, 7, 6, 5, 4, 3, 2, 1, 0.5, 0.25, or 0.1 wt. %, based on the total weight of the composition.

The disclosed ionic liquid compositions can be prepared by methods described herein. Generally, the particular cation(s) and anion(s) used to prepare the disclosed ionic liquids are selected as described herein. Then, with the particular cation(s) and anion(s) in hand, they can be combined, resulting in ionic liquid compositions as disclosed herein. Additionally, the method for the preparation of the disclosed ionic liquid compositions can include the reaction in which two neutral species: an anion precursor (e.g., in the form of an inorganic acid, carboxylic organic acid, non-carboxylic acid, or Zwitterion species) and a cation precursor (e.g., inorganic base, organic base, Zwitterion species) are combined resulting in ionic liquid compositions as disclosed herein.

Providing ions used to prepare the disclosed ionic liquids depends, in one aspect, on the desired properties of the resulting ionic liquid composition. As described herein, the disclosed ionic liquid compositions can have multiple desired properties, which, at least in part, come from the properties of the cation(s) and/or anion(s) used to prepare the ionic liquid. Thus, to prepare the disclosed ionic liquids, one or more kinds of cations with a desired property(ies) are provided. One or more kinds of anions with a desired property(ies) that is similar or different to that of the cation(s) can likewise be provided. Of course, providing a desired anion(s) and cation(s) can be done in any order, depending on the preference and aims of the practitioner. For example, a particular cation(s) can be provided and then a particular anion(s) can be provided. Alternatively, a particular anion(s) can be provided and then a particular cation(s) can be provided. Further, the cation(s) and anion(s) can be provided simultaneously.

As noted, providing a suitable ion can be based on selecting an ion that possesses a property that is desired (e.g., the ion has a property that is desired to be possessed by the resulting ionic liquid). Examples of properties that could be desired in a suitable cation and/or anion (and thus the ionic liquid made therefrom) include, but are not limited to, biological, therapeutic, prophylactic, nutritional, pesticidal, and/or herbicidal activity. Inertness, taste, viscosity modulation, solubility modulation, stability, and toxicity are other properties of a given ion that could be desired and considered. While more specific properties are disclosed elsewhere herein, the disclosed methods and compositions are not limited to any particular combination of properties, as such will depend on the preferences and goals of the practitioner.

Typically, the desired properties of the cation(s) and anion(s) will be different or complimentary to one another. In this way, the resulting ionic liquid can possess multiple desired properties: those properties imparted by the cation(s) and those imparted by the anion(s). In other words, some or all of the ions present in the disclosed ionic liquids can independently and simultaneously introduce a specific functionality or property to the disclosed ionic liquid compositions. It is this multiple functionality characteristic that can allow one to fine-tune or design very specific physical, chemical, and bioactive properties in the disclosed ionic liquid compositions. Additional functionality can be obtained by using the disclosed ionic liquid compositions as solvents to dissolve a solute(s) with another desired property, thus resulting in a solution where the ions of the ionic liquid as well as the solute contribute desired properties to the composition. General and specific examples of various combinations of ions and their associated properties are disclosed herein.

In some particular examples, one or more ions in the disclosed ionic liquid composition (e.g., the anions, cations, or both) can be a pharmaceutical active, e.g., an existing drug that is ionic or that can be made ionic. Many drugs exist naturally or at physiological conditions as an ion, or they can be converted to ions via simple chemical transformations (e.g., alkylation, protonation, deprotonation, etc.). As such, these drugs can be used to prepare an ionic liquid composition as disclosed herein. Such drugs can possess any therapeutic or prophylactic activity, many of which are described herein. Combining such drugs with other ions to prepare an ionic liquid, as is disclosed herein, can result in the modification and/or enhancement of the drug's properties. For example, a first drug ion with a given property can be combined with an oppositely charged second ion with another property to effect the controlled release, controlled delivery, biological impact, taste, physical properties (stability, solubility, toxicity, melting point, etc.), or to overcome polymorphism in the first drug ion. In this way, new drug compositions can be created by forming ionic liquids with functionality crafted into the combination of the ions, as disclosed herein.

As another example, the first drug ion may be combined with a second drug ion that has properties complimentary to the first. Examples of this can include, but are not limited to, an ion having anesthetic properties being combined with an ion having antibacterial properties, an ion having anesthetic properties being combined with an ion having coagulation properties, or an ion having coagulation properties being combined with an ion having antibacterial properties. Ionic liquids resulting from such combinations could find uses in wound repair, for example. Still other examples of desirable combination include ions having therapeutic or prophylactic efficacy being combined with ions having taste enhancement properties (i.e., taste modifiers). Ionic liquids resulting from this combination can be useful in enhancing the taste and palatability of medicines. Still further examples can include two differently charged ions each with similar uses but with different mechanisms of action. Specific examples of such combinations can include, but are not limited to, combinations of ions with antineoplastic properties or antiviral properties. Ionic liquids prepared from such ion combinations can be useful as drug "cocktails," where two or more bioactive agents are present in a single ionic liquid combination.

According to the methods and compositions disclosed herein, ion identification and combination, as disclosed herein, can involve any ion, not just ionic drugs, as long as the combination results in an ionic liquid. For example, ions that have pesticidal properties can be combined with oppositely charged ions having pesticidal, herbicidal, antimicrobial properties, and the like. In other examples, ions with antibacterial properties can be combined with oppositely charges ions that have preservative properties, taste modifiers, etc. In still other examples, an ion with one therapeutic or prophylactic property can be combined with another therapeutic or prophylactic ion. As should be appreciated, the various combinations of ions according to the disclosed methods are numerous, and depend only on the desired combination of properties and whether the resulting ion combination is an ionic liquid as defined herein.

Specific examples of properties that can be exhibited by the disclosed compositions include antibacterial, FDA approved dyes, anti-acne, antibiotic, UV blocker, wetting agents, preservative, emollient, anti-inflammatory, and vitamin.

Ions

The disclosed ionic liquids contain at least one kind of cation and at least one kind of anion. Examples of suitable cations and anions are disclosed herein. It should be understood that when a particular compound is disclosed as being a cation, for example, it can also, in other circumstances, be an anion and vice versa. Many compounds are known to exist as cations in some environments and anions in other environments. Further, many compounds are known to be convertible to cations and anions through various chemical transformations. Examples of such compounds are disclosed herein.

The materials, compounds, compositions, and components that can be used for, can be used in conjunction with, can be used in preparation for, or are products of the disclosed methods and compositions are disclosed herein. It is understood that when combinations, subsets, interactions, groups, etc. of these materials are disclosed that while specific reference of each various individual and collective combinations and permutation of these compounds may not be explicitly disclosed, each is specifically contemplated and described herein. For example, if an ionic liquid composition is disclosed and a number of modifications that can be made to a number of components of the ionic liquid composition are discussed, each and every combination and permutation that are possible are specifically contemplated unless specifically indicated to the contrary. Thus, if a class of cations A, B, and C are disclosed as well as a class of anions D, E, and F and an example of a ionic liquid A-D is disclosed, then even if each is not individually recited, each is individually and collectively contemplated. Thus, in this example, each of the ionic liquids A-E, A-F, B-D, B-E, B-F, C-D, C-E, and C-F are specifically contemplated and should be considered disclosed from disclosure of A, B, and C; D, E, and F; and the example ionic liquid A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, and that each such combination is specifically contemplated and should be considered disclosed.

Cations

Particular examples of cationic compounds that can be present in the disclosed ionic liquid compositions are compounds that contain nitrogen atoms. Nitrogen atoms can exist or can be converted to positively-charged quaternary ammonium species, for example, through alkylation or protonation of the nitrogen atom. Thus compounds that possess a quaternary nitrogen atom (known as quaternary ammonium compounds (QACs)) are typically cations. According to the methods and compositions disclosed herein, any compound that contains a quaternary nitrogen atom or a nitrogen atom that can be converted into a quaternary nitrogen atom can be a suitable cation for the disclosed ionic liquid compositions.

QACs can have numerous biological properties that one may desire to be present in the disclosed ionic liquid compositions. For example, many QACs are known to have antibacterial properties. The antibacterial properties of QACs were first observed toward the end of the 19$^{th}$ century among the carbonium dyestuffs, such as auramin, methyl violet, and malachite green. These types of compounds are effective chiefly against the Gram-positive organisms. Jacobs and Heidelberger first discovered QACs antibacterial effect in 1915 studying the antibacterial activity of substituted hexamethylene-tetrammonium salts (Jacobs and Heidelberger, *Proc Nat Acad Sci USA*, 1915, 1:226; Jacobs and Heidelberger, *J Biol Chem*, 1915, 20:659; Jacobs and Heidelberger, *J Exptl Med*, 1916, 23:569).

Browning et al. found great and somewhat less selective bactericidal powers among quaternary derivatives of pyridine, quinoline, and phenazine (Browning et al., *Proc Roy Soc London*, 1922, 93B:329; Browning et al., *Proc Roy Soc London*, 1926, 100B:293). Hartman and Kagi observed antibacterial activity in QACs of acylated alkylene diamines (Hartman and Kagi, *Z Angew Chem*, 1928, 4:127).

In 1935, Domagk synthesized long-chain QACs, including benzalkonium chloride, and characterized their antibacterial activities (Domagk, *Deut Med Wochenschr*, 1935, 61:829). He showed that these salts are effective against a wide variety of bacterial strains. This study of the use of QACs as germicides was greatly stimulated.

Many scientists have focused their attention on water soluble QACs because they exhibit a range of properties: they are surfactants, they destroy bacteria and fungi, they serve as a catalyst in phase-transfer catalysis, and they show anti-electrostatic and anticorrosive properties. They exert antibacterial action against both Gram-positive and Gram-negative bacterial as well as against some pathogen species of fungi and protozoa. These multifunctional salts have also been used in wood preservation, their application promoted in the papers of Oertel and Butcher et al. (Oertel, *Holztechnologie*, 1965, 6:243; Butcher et al., *For Prod J*, 1977, 27:19; Butcher et al., *J For Sci*, 1978, 8:403).

QACs are also widely used as skin antiseptics, disinfectants, fabric softeners, antistatic agents, cleaning agents, and preservatives. Detergent properties and antimicrobial activities of QACs have made them useful for general environmental sanitations, for examples, in hospitals and food production facilities. In pharmacological preparations they are used such as mouth rinses, lozenges, sprays and gels.

In humans and animals QACs have been considered too toxic for systematic applications, but are accepted to be safe for topical applications. Furthermore, QACs have recently been used as penetration enhancers for transnasal and transbuccal drug delivery, as well as in nasal vaccination (Klinguer et al., *Vaccine*, 2001, 19:4236). This ability to penetrate and open cell membrane has been widely used in drug delivery via liposomes (mainly QACs with two long alkyl chains) and non-viral gene delivery (Liu and Huang, *J Contr Rel*, 2002, 78:259). Many examples of compounds having nitrogen atoms, which exist as quaternary ammonium species or can be converted into quaternary ammonium species, are disclosed herein.

In some examples, when the cation is a quaternary ammonium compound, the anion is not an inorganic anion, examples of which are disclosed herein. In other examples, where the cation is a quaternary ammonium compound, the anion is not a halide.

Aliphatic Heteroaryls

Some specific QACs suitable for use herein are aliphatic heteroaryls. An aliphatic heteroaryl cation is a compound that comprises an aliphatic moiety bonded to a heteroaryl moiety. In the aliphatic heteroaryl cation, the aliphatic moiety can be any alkyl, alkenyl, alkynyl, cycloalkyl, or cycloalkenyl group, as described herein. Generally, the aliphatic moiety can comprise at least 10, at least 12, at least 14, at least 16, at least 18, or at least 20 carbon atoms. In other examples, the aliphatic moiety can comprise a mixture of aliphatic groups having a range of carbon atoms. For example, the aliphatic moiety can comprise from 10 to 40, from 12 to 38, from 14 to 36, from 16 to 34, from 18 to 32, from 14 to 18, or from 20 to 30 carbon atoms. In some specific examples, the aliphatic moiety can contain 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 carbon atoms, where any of the stated values can form an upper or lower endpoint when appropriate. Examples of specific aliphatic moieties that can be used include, but are not limited to, decyl, dodecyl (lauryl), tetradecyl (myristyl), hexadecyl (palmityl or cetyl), octadecyl (stearyl), eicosyl (arachidyl), and linolenyl groups, including branched derivatives thereof and any mixtures thereof. In the aliphatic heteroaryl cations, the aliphatic moiety is bonded to a heteroatom in the heteroaryl moiety.

In the aliphatic heteroaryl cation, the heteroaryl moiety can be any heteroaryl moiety as described herein. For example, the heteroaryl moiety can be an aryl group having one or more heteroatoms (e.g., nitrogen, oxygen, sulfur, phosphorous, or halonium). Examples of specific heteroaryl moieties that can be used in the aliphatic heteroaryl cations include, but are not limited to, pyrazole, pyridine, pyrazine, pyrimidine, pryidazine, indolizine, isoindole, indole, indazole, imidazole, oxazole, triazole, thiazole, purine, isoquinoline, quinoline, phthalazine, quinooxaline, phenazine, and the like, including substituted derivatives and mixtures thereof. In the aliphatic heteroaryl cations, a heteroatom in the heteroaryl moiety is bonded to the aliphatic moiety. When the heteroatom of the heteroaryl is nitrogen, this forms a quaternary ammonium cation, as described herein.

Further examples of aliphatic heteroaryl cations are those having the following structures:

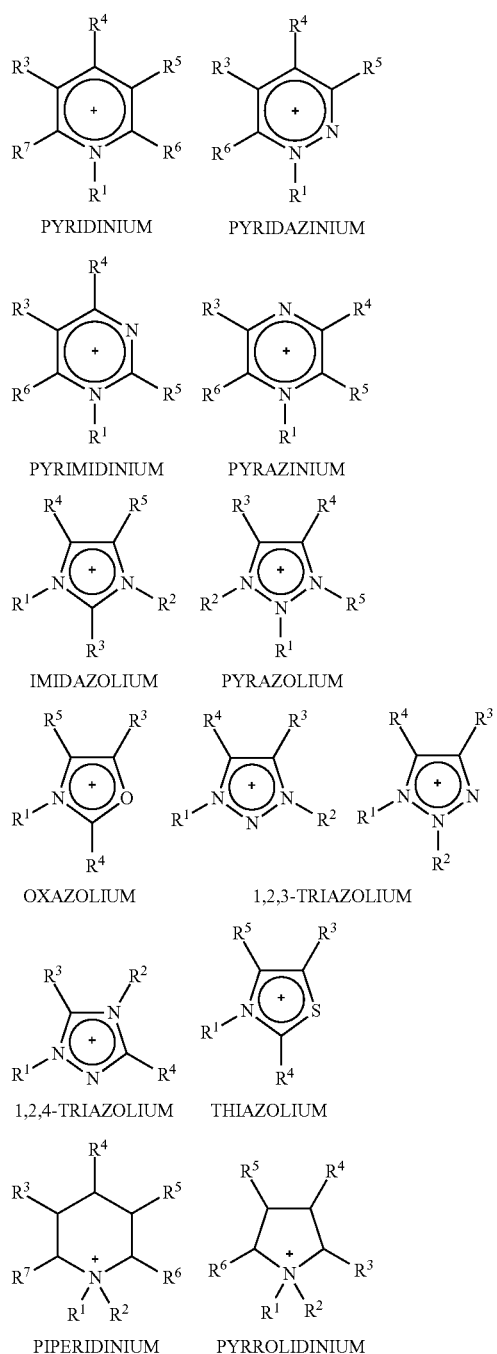

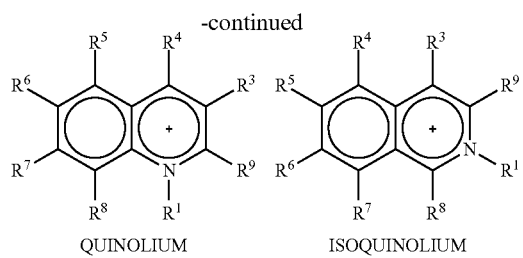

wherein $R^1$ and $R^2$ are, independently, a $C_1$-$C_6$ alkyl group or a $C_1$-$C_6$ alkoxyalkyl group, and $R^3$, $R^4$, $R^5$, $R^6$, $R^7$, $R^8$, and $R^9$ ($R^3$-$R^9$), when present, are independently H, a $C_1$-$C_6$ alkyl, a $C_1$-$C_6$ alkoxyalkyl group, a $C_1$-$C_6$ alkoxy group, or an energetic substituents such as nitro, amino, cyano, azido, alkyl nitro, alkyl amino, alkyl cyano, alkyl azido, alkoxy nitro, alkoxy amino, alkoxy cyano, and alkoxy azido. In other examples, both $R^1$ and $R^2$ groups are $C_1$-$C_4$ alkyl, with one being methyl, and $R^3$-$R^9$, when present, are H. Exemplary $C_1$-$C_6$ alkyl groups and $C_1$-$C_4$ alkyl groups include methyl, ethyl, propyl, iso-propyl, butyl, sec-butyl, iso-butyl, pentyl, iso-pentyl, hexyl, 2-ethylbutyl, 2-methylpentyl, and the like. Corresponding $C_1$-$C_6$ alkoxy groups contain the above $C_1$-$C_6$ alkyl group bonded to an oxygen atom that is also bonded to the cation ring. An alkoxyalkyl group contains an ether group bonded to an alkyl group, and here contains a total of up to six carbon atoms. It is to be noted that there are two isomeric 1,2,3-triazoles. In some examples, all R groups not required for cation formation can be H.

The phrase "when present" is often used herein in regard to substituent R group because not all cations have all of the numbered R groups. All of the contemplated cations contain at least four R groups, which can be H, although $R^2$ need not be present in all cations.

In one example, all R groups that are not required for cation formation; i.e., those other than $R^1$ and $R^2$ for compounds other than the imidazolium, pyrazolium, and triazolium cations shown above, are H.

A cation that contains a single five-membered ring that is free of fusion to other ring structures is suitable for use herein. Exemplary cations are illustrated below wherein $R^1$, $R^2$, and $R^3$-$R^5$, when present, are as defined before.

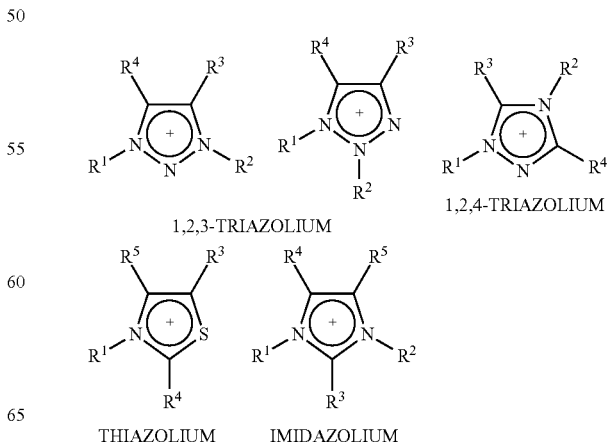

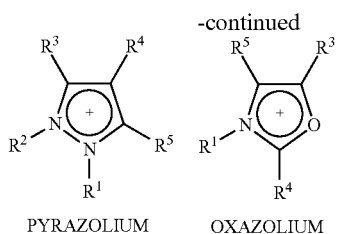

PYRAZOLIUM          OXAZOLIUM

Of the cations that contain a single five-membered ring free of fusion to other ring structures, an imidazolium cation that corresponds in structure to Formula A is also suitable, wherein $R^1$, $R^2$, and $R^3$-$R^5$, are as defined before.

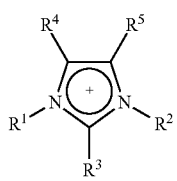

(A)

In a further example, an N,N-1,3-di-($C_1$-$C_6$ alkyl)-substituted-imidazolium ion can be used; i.e., an imidazolium cation wherein $R^3$-$R^5$ of Formula A are each H, and $R^1$ and $R^2$ are independently each a $C_1$-$C_6$ alkyl group or a $C_1$-$C_6$ alkoxyalkyl group. In yet another example, the cation illustrated by a compound that corresponds in structure to Formula B, below, wherein $R^3$-$R^5$ of Formula A are each hydrogen and $R^1$ is a $C_1$-$C_6$-alkyl group or a $C_1$-$C_6$ alkoxyalkyl group.

(B)

Aliphatic Benzylalkyl Ammonium

The disclosed ionic liquid compositions can also comprise an aliphatic benzylalkyl ammonium cation. An aliphatic benzylalkyl ammonium cation is a cation that comprises an aliphatic moiety bonded to the nitrogen atom of a benzylalkyl amine moiety. The aliphatic moiety can be as described herein. The benzylalkyl amine moiety can be a benzyl amine where the amine is bonded to an alkyl or cyclic alkyl group, as described herein. One or more types of aliphatic benzylalkyl ammonium cation can be used in the ionic liquid compositions disclosed herein. The aliphatic benzylalkyl ammonium cation suitable for use herein can be prepared by methods known in the art or can be obtained from commercial sources.

In one aspect, the aliphatic benzylalkyl ammonium cation can be represented by the following formula:

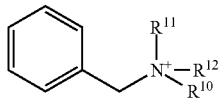

wherein $R^{10}$ is an aliphatic group, as described above, $R^{11}$ and $R^{12}$ are, independent of one another, alkyl groups or cyclic alkyl groups as described herein. In some examples, one or more of the "R" substituents can be a long chain alkyl group (e.g., the number of carbon atoms is 10 or greater). In other examples, one or more of the "R" substituents can be a short chain alkyl group (e.g., the number of carbon atoms is less than 10). In still other examples, one of the "R" substituents is a long chain alkyl group and the other two "R" substituents are short chain alkyl groups.

In one aspect, the aliphatic benzylalkyl ammonium cation can have any of the aliphatic moieties disclosed herein bonded to any benzylalkyl amine moieties disclosed herein. In some specific examples, $R^{10}$ in the formula of aliphatic benzylalkyl ammonium cation can be an aliphatic group of from 10 to 40 carbon atoms, e.g., a decyl, dodecyl (lauryl), tetradecyl (myristyl), hexadecyl (palmityl or cetyl), octadecyl (stearyl), or eicosyl (arachidyl) group, and $R^{11}$ and $R^{12}$ can each be, independent of one another, a methyl, ethyl, propyl, butyl, pentyl, or hexyl group.

In another aspect, the aliphatic benzylalkyl ammonium cation can include, but are not limited to, alkyl dimethyl benzyl ammonium cations. Specific examples of alkyl dimethyl benzyl ammonium cations include, but are not limited to, cetyl dimethyl benzyl ammonium, lauryl dimethyl benzyl ammonium, myristyl dimethyl benzyl ammonium, stearyl dimethyl benzyl ammonium, and arachidyl dimethyl benzyl ammonium.

In yet another aspect, the aliphatic benzylalkyl ammonium cation can include, but are not limited to, alkyl methylethyl benzyl ammonium cations. Specific examples of alkyl methylethyl benzyl ammonium cations include, but are not limited to, cetyl methylethyl benzyl ammonium, lauryl methylethyl benzyl ammonium, myristyl methylethyl benzyl ammonium, stearyl methylethyl benzyl ammonium, and arachidyl methylethyl benzyl ammonium.

Dialiphatic Dialkyl Ammonium

Still further examples of QACs that can be used in the disclosed ionic liquid compositions are dialiphatic dialkyl ammonium cations. A dialiphatic dialkyl ammonium cation is a compound that comprises two aliphatic moieties and two alkyl moieties bonded to a nitrogen atom. The aliphatic moieties can be the same or different and can be any aliphatic group as described above. The alkyl moieties can be the same or different can be any alkyl group as described above. In the disclosed dialiphatic dialkyl ammoniums cations, the two aliphatic moieties can have 10 or more carbon atoms and the two alkyl moieties can have less than 10 carbon atoms. In another alternative, the two aliphatic moieties can have less than 10 carbon atoms and the two alkyl moieties can have 10 or more carbon atoms. One or more types of dialiphatic dialkyl ammonium cations can be used in the ionic liquid compositions disclosed herein.

In some particular examples, the dialiphatic dialkyl ammonium cation can be di-dodecyl dimethyl ammonium, di-tetradecyl dimethyl ammonium, dihexadecyl dimethyl ammonium, and the like, including combinations thereof.

Tetraalkyl Ammonium

The disclosed ionic liquid compositions can also comprise a tetraalkyl ammonium cation. Suitable tetraalkyl ammonium cations comprise four alkyl moieties, as disclosed herein. In one example, a tetraalkyl ammonium cation can comprise one long chain alkyl moiety (e.g., 10 or more carbon atoms in length) and three short chain alkyl moieties (e.g., less than 10 carbon atoms in length).

Some specific examples of tetraalkyl ammonium cations that can be included in the disclosed ionic liquid compositions include, but are not limited to, cetyl trimethyl ammonium, lauryl trimethyl ammonium, myristyl trimethyl ammonium, stearyl trimethyl ammonium, arachidyl trimethyl ammonium, or mixtures thereof. Other examples include, but are not limited to, cetyl dimethylethyl ammonium, lauryl dimethylethyl ammonium, myristyl dimethylethyl ammonium, stearyl dimethylethyl ammonium, arachidyl dimethylethyl ammonium, or mixtures thereof.

Other Cations

Other cations that are suitable for use in the disclosed methods and compositions are compounds that contain metals. According to the methods and compositions disclosed herein, any compound that contains a metal atom can be a suitable cation. Organometallic compounds or metal complexes commonly have one or more metal atom in a positive oxidation state. Examples of metals that can be present in a suitable cation include, but are not limited to, lithium, sodium, potassium beryllium, magnesium, calcium, strontium, chromium, manganese, iron, cobalt, nickel, copper, and zinc. Silver nanoparticles can also be used. Examples of suitable organometallic cations include, but are not limited to, metallocenium, alkylgermanyl, alkyltin, or alkylsilyl (e.g., trimethylsilylium, triethylsilylium, tris(trimethylsilyl)silylium, tribenzylsilylium, triphenylsilylium, tricyclohexylsilylium, and dimethyloctadecylsilylium).

Another suitable group of quaternary ammonium cations are those that have been prepared by esterifying a compound containing a carboxylic acid moiety or transesterifying a compound with an ester moiety with a choline moiety. Such choline esters can be biofriendly, permanent ions that are amenable to being added to various compounds while still being easily cleavable under physiological conditions. The choline esters can be used to increase the solubility and bioavailability of many neutral compounds.

Further examples of cations include (2-hydroxyethyl)-dimethylundecyloxymethylammonium, (2-acetoxyethyl)-heptyloxymethyldimethylammonium, and (2-acetoxyethyl)-dodecyloxymethyldimethylammonium, mepenzolate, sulfathiazole, thimerosal, and valproic acid.

In other examples, the cation can be an energetic cation as disclosed in Katritzky et al., "ILs Based on Energetic Imidazolium Cations: Nitro- and Nitrile-substituted N,N' Dialkylimidazolium Salts" *New J Chem* 30:349, 2006, which is incorporated by reference herein at least for its teachings of energetic ions.

Anions

Particular examples of anionic compounds that can be present in the disclosed ionic liquids are compounds that contain oxygen atoms. Oxygen atoms can exist or can be converted to negatively charged, anionic species, for example, through deprotonation of alcohols or acids, through saponification of esters, or through alkylation of ketones. Likewise, compounds that contain sulfur atoms can also exist or be converted to anionic species through similar reactions. Still further, compounds that contain nitrogen atoms, especially nitrogen atoms adjacent to electron withdrawing groups or resonance stabilizing structures, can be converted to anions through deprotonation. According to the methods and compositions disclosed herein, any compound that contains an oxygen, sulfur, or nitrogen atom can be a suitable anion for the disclosed ionic liquid compositions.

Other suitable anions include, but are not limited to, halides (e.g., fluoride, chloride, bromide, and iodide), sulfates ($SO_4^-$), carbonates, bicarbonates, phosphates, phosphates, nitrates ($NO_3^-$), nitrites ($NO_2^-$), acetates ($CH_3CO_2^-$), and the like. Other examples of anions include, but are not limited to $PF_6^-$ that is immiscible in water and $BF_4^-$ that is miscible in water depending on the ratio of ionic liquid to water, system temperature, and alkyl chain length of cation. Other anions include triflate (TfO; $CF_3SO_2^-$), nonaflate (NfO; $CF_3(CF_2)_3 SO_2^-$), bis(triflyl)amide ($Tf_2N$; $(CF_3SO_2)_2N^-$), trifluoroacetate (TA; $CF_3CO_2^-$), and heptafluororobutanoate (HB; $CF_3(CF_2)_3SO_2^-$). Other types of ionic liquids include haloaluminates, such as chloroaluminate.

Other suitable anions contemplated herein are saccharin and acesulfame. Saccharin, as an alkali metal salt, and acesulfame (6-methyl-3,4-dihydro-1,2,3-oxathiazin-4-one 2,2-dioxide), which has previously only been offered as potassium salt, are in widespread use in foodstuffs as non-nutritive sweeteners. Such anions can be used when one desires to prepare an ionic liquid composition that has sweetness as one of its desired properties. For example, saccharin and acesulfame can be combined with pharmaceutically active cations to prepare sweet tasting ionic liquids that have pharmaceutical activity.

Specific examples of other anions include piperacillin, folic acid, ibuprofen, fast green FCF, docusate, acesulfamate, penicillin G, Colawet MA-80, salicylic acid, saccharinate, sulfacetamide, naproxen, benzoate, diclofenac, and trans-cinnamic acid.

Other suitable anions include, but are not limited to, substituted and un-substituted imidazolates, 1,2,3-triazolates, and 1,2,4-triazolates, benzimidazolates, benz-1,2,3-triazolates, as shown bellow:

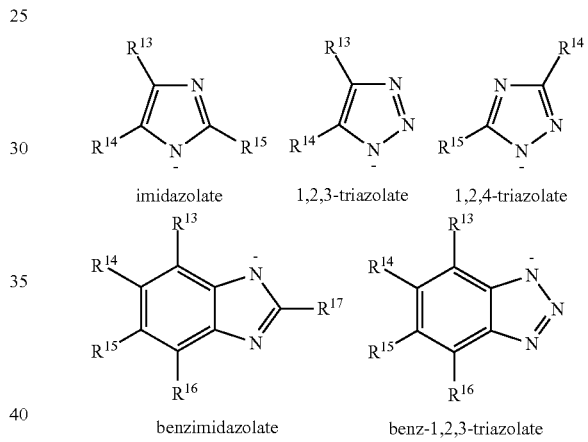

wherein $R^{13}$, $R^{14}$, $R^{15}$, $R^{16}$, $R^{17}$, ($R^{13-17}$), when present, are independently H, a $C_1$-$C_6$ alkyl, a $C_1$-$C_6$ alkoxyalkyl group, a $C_1$-$C_6$ alkoxy group, or energetic substituents like nitro, amino, cyano, azido, alkyl nitro, alkyl amino, alkyl cyano, alkyl azido, alkoxy nitro, alkoxy amino, alkoxy cyano, and alkoxy azido. Exemplary $C_1$-$C_6$ alkyl groups and $C_1$-$C_4$ alkyl groups include methyl, ethyl, propyl, iso-propyl, butyl, sec-butyl, iso-butyl, pentyl, iso-pentyl, hexyl, 2-ethylbutyl, 2-methylpentyl, and the like. Corresponding $C_1$-$C_6$ alkoxy groups contain the above $C_1$-$C_6$ alkyl group bonded to an oxygen atom that is also bonded to the cation ring. An alkoxyalkyl group contains an ether 10 group bonded to an alkyl group, and here contains a total of up to six carbon atoms. It is to be noted that there are two isomeric 1,2,3-triazoles. In some examples, all R groups not required for anion formation can be H.

Further examples of suitable energetic anions are disclosed in Katritzky et al., "ILs Based on Energetic Azolate Anions," *Chem Eur J* 12:4630, 2006, which is incorporated by reference herein at least for its teachings of energetic anions.

Compound that Exist that as Both: Anion or Cation

Examples of compounds that exist as cations in some environments and anions in other environments include, but are not limited to, 1,3-dimethylimidazolium, 1-butyl-3-methylimidazolium, 1,2,3-triazolium, tetrazolium, 1,2,4-triazolium, 1,3-dimethyl-1,2,3-triazolium, and 1,3-dimethyl-4-nitroimidazolium, which exist as a cations, and 4-nitroimidazolate, 4,5-dinitroimidazolate, 3,5-dinitro-1,2,4-triazolate, tetrazolate, 5-aminotetrazolate, 2-nitroimidazolate, which exist as an anion. Those separate ions can still form single product ionic liquids.

Examples of compounds that can change from an anion in one environment to a cation in another environment due to chemical modifications are the sulfur ylides through the reaction of a sulfide with methyliodide to form the sulfonium ion.

Specific Examples of Pharmaceutical Actives

When pharmaceutical activity is a desired property of the disclosed ionic liquids, one or more of the ions in the disclosed ionic liquid compositions can be a pharmaceutical active. Pharmaceutical actives that exist as ions or can be converted to ions, and which are suitable for use in preparing the disclosed ionic liquid compositions, include the following categories and specific examples. It is not intended that the category be limited by the specific examples. Those of ordinary skill in the art will be able to readily identify those pharmaceutical actives that can be used in the disclosed methods and compositions. For example, one can identify a compound with a given property or activity by consulting various sources, such as the Merck Index (13$^{th}$ Edition, Wiley, 2001), The United States Pharmacopeia-National Formulary (USP-NF), and the FDA's Orange book, which are each incorporated by reference herein at least for their teachings of pharmaceutical actives. Once a compound with a desired property is identified, the skilled artisan can determine whether the compound is ionic or can be made ionic. Such determinations can be performed based on the compound's structure, which can readily be determined by consulting the sources mentioned herein or experimentally. Knowing a compound's structure can readily reveal if the compound is ionic. In fact, many pharmaceutical actives exist as salts and are thus suitable for use in preparing the disclosed ionic liquid compositions. Further, if a compound is not ionic, but contains an ion forming moiety (e.g., nitrogen, oxygen, sulfur, or metal atoms, as described herein), the compound can be converted to an ion and then combined with a suitable counterion to prepare the disclosed ionic liquid compositions. Those of ordinary skill in the art will recognize numerous other compounds that fall within the categories and that are useful according to the disclosed compositions and methods.

Some specific examples of pharmaceutical actives that can be used in the disclosed ionic liquids include, but are not limited to, aspirin, LIBRIUM™, isoniazid, penicillin, PRONTOSIL™, cisplatin, 6-mercaptopurine, RITUXAN™, TAXOL™, phenobarbital, PROZAC™, ALLEGRA™, VIOXX™, quinine, ivermectin, L-dopa, THORAZINE™, salvarsan, TAGAMET™, AZT, crixivan, salbutamol, digoxin, fluride, LOVASTATIN™, erythropoietin, hydrocortisone, insulin, oral contraceptives, oxytocin, PREMARIN™, RU-486, thyroxine, thalidomide, cyclosporine, fentanyl, methadone, morphine, botox, vitamins, FOSAMAX™, RITALIN™, and VIAGRA™, including ionic derivatives thereof.

Other examples of pharmaceutical active ions or pharmaceutical actives that can be made ionic include, but are not limited to, pantoprazole, sold under the trade names PROTONIX™ and PANTOZOL™, and rabeprazole, sold under the trade names ACIPHEX™ and PARIET™, which are used to treat gastrointestinal disorders. Risedronate, sold under the trade name ACTONEL™, and alendronate, sold under the trade name FOSAMAX™, are used to treat osteoporosis and are further examples of suitable compounds that can be used to prepare the disclosed ionic liquid compositions. Further examples include losartan, sold under the trade names NU-LOTAN™, COZAAR™, and HYZAAR™, and fosinopril, sold under the trade name MONOPRIL™, which are used to treat hypertension and are other examples of suitable compounds that can be used to prepare the disclosed ionic liquid compositions. Atorvastatin, sold under the trade name LIPITOR™, and pravastatin, sold under the trade name PRAVACHOL™, are used to treat cholesterol and are further examples of suitable compounds that can be used to prepare the disclosed ionic liquid compositions. A further example is montelukast, which is used to treat asthma and is sold under the trade name SINGULAIR™.

The following table illustrates further examples of pharmaceutical actives that are ionic or can be made ionic and combined with other ions to form the disclosed ionic liquid compositions.

TABLE 1

| Name | Compound | MP | Pat. No. | Other Names |
|---|---|---|---|---|
| Function: Abortifacient/Interceptive | | | | |
| Prostaglandin E$_2$ | [structure] | 66-68° | U.S. Pat. No. 3,598,858 | PGE2, U-12062, Cerviprost, Minprostin E2, Prepidil, Propess, Prostarmon-E, Prostin E2 |
| Prostaglandin F2$_A$ | [structure] | 25-35° | U.S. Pat. No. 3,657,327 | PGF2A, U-14583 Enzaprost F, Glandin, Prostarmon F |

TABLE 1-continued

| Name | Compound | MP | Pat. No. | Other Names |
|---|---|---|---|---|
| Sulprostone | | | U.S. Pat. No. 4,024,179 | Nalador |
| Function: ACE- Inhibitor (Antihypertensive) | | | | |
| Cetapril | | 155-156° | U.S. Pat. No. 4,248,883 | Alacepril |
| Benzaepril | | 148-149° | U.S. Pat. No. 4,410,520 | |
| Captopril | | 103-104° | U.S. Pat. Nos. 4,046,889 4,105,776 | Acediur, Acepril, Alopresin, Acepress, Capoten, Captolane, Captoril, Cesplon, Dilabar, Garranil, Hipertil, Lopirin, Lopril, Tensobon, Tensoprel |
| Function: A-Adrenergic Agonist | | | | |
| Methyl hexaneamine | | | U.S. Pat. Nos. 2,350,318 2,386,273 | Forthane |
| Synephrine | | 184-185° | DE 566578 | Analeptin, Ethaphene, Oxedrine, Parasympatol, Simpalon, Synephrin, Synthenale |
| Function: B-Adrenergic Agonist | | | | |
| Isoetharine | | 212-213° | DE 638650 | Win -3046, Dilabron, Neoisuprel |
| Methoxyphenamine | | 97-99° | JP 612921 | |

TABLE 1-continued

| Name | Compound | MP | Pat. No. | Other Names |
|------|----------|----|----|-------------|

Function: A-Adrenergic Blocker

| Tamsulosin | 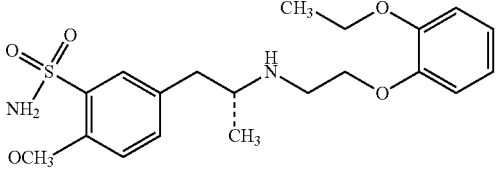 [SMILES: CCOc1ccccc1OCCN[C@H](C)Cc1ccc(OC)c(S(N)(=O)=O)c1] | 228–230° | U.S. Pat. No. 4,703,063 | Flomaz, Harnali, Omnic, Pradif |
| Tolazoline | 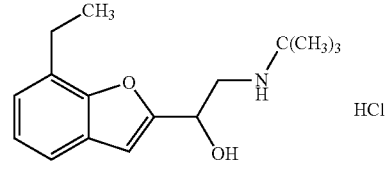 [SMILES: CCc1cccc2cc(C(O)CNC(C)(C)C)oc12 ; Cl] | 174° | U.S. Pat. No. 2,161,938 | Lambral, Priscol, Priscoline, Vaso-Dilatan |

Function: B-Adrenergic Blocker

| Bufuralol | 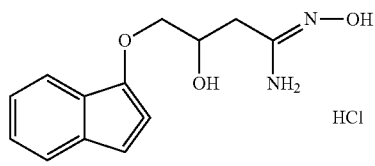 [SMILES: N/C(CC(O)COC1=C=Cc2ccccc21)=N\O ; Cl] | 146° | U.S. Pat. No. 3,929,836 | Angium |
| Nadoxolol | 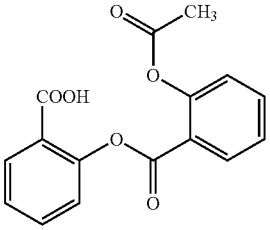 [SMILES: CC(=O)Oc1ccccc1C(=O)Oc1ccccc1C(=O)O] | 188° | U.S. Pat. No. 3,819,702 | Bradyl |

Function: Analgesic (non-narcotic)

| Acetylsalicyl salicylic acid | 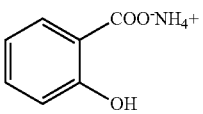 | 154° | | |
| Ammonium Salicylate | 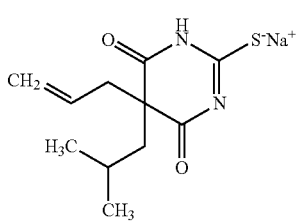 | | | |

Function: Anesthetic (Intravenous)

| Buthalital Sodium | | | | Baytinal, Buthaliton Sodium, Thialisobumalnatrium, Transithal, Ulbreval |

TABLE 1-continued

| Name | Compound | MP | Pat. No. | Other Names |
|---|---|---|---|---|
| Thiopental Sodium | | | U.S. Pat. Nos. 2,153,729 2,876,225 3,109,001 | |
| *Function: Anesthetic (Local)* | | | | |
| Isobutyl p-Aminobenzoate | | 65° | | Cycloform, Isobutyl Kelofom, Isocaine |
| Phenol | | | | |
| *Function: Anorexic* | | | | |
| Clortermine | | 116-118° | U.S. Pat. No. 3,415,937 | |
| Fenproporex | | 126-127° | U.S. Pat. No. 3,485,924 | |
| *Function: Antacid* | | | | |
| Dermatol | | | | |
| *Function: Anthelmintic (Cesodes)* | | | | |
| Niclosamide | | 225-230° | U.S. Pat. No. 3,079,297 3,113,067 | |
| Pelletierine | | | | Punicine |
| *Function: Anthelimintic (Nematodes)* | | | | |
| Dithiazanine Iodide | | | U.S. Pat. No. 2,412,815 | Anelmid, Anguifugan, Delvex, Dejo, Deselmine, Dilombrin, Dizan, Nectocyd, Partel, Telmicid, Telmid |

TABLE 1-continued

| Name | Compound | MP | Pat. No. | Other Names |
|---|---|---|---|---|
| Thiabendazole | 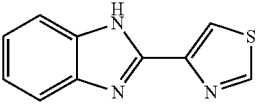 [SMILES: c1ccc2[nH]c(-c3cscn3)nc2c1] | 304-305° | U.S. Pat. No. 3,017,415 | Thibenzole, Equizole, Mertect, Storite, TBZ, Tecto |

Function: Anthelmintic (Schistosoma)

| | | | | |
|---|---|---|---|---|
| Antimony Sodium Thioglycolate | 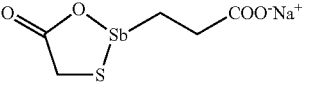 | | | |
| Niridazole | 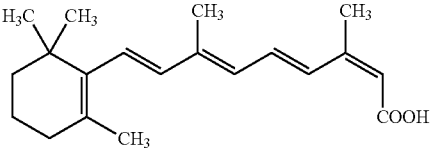 [SMILES: CC1=C(/C=C/C(C)=C/C=C/C(C)=C\C(=O)O)C(C)(C)CCC1] | 260-262° | BE 632989 | Ba-32644, Ciba 32644-Ba, Ambilnar |

Function: Antiacne

| | | | | |
|---|---|---|---|---|
| Isotretinoin | 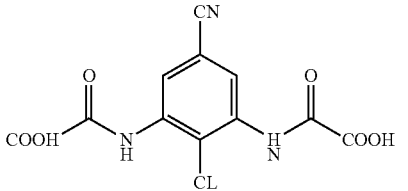 | 174-175° | U.S. Pat. No. 4,556,518 | Accitame, Isotrex, Oratane, Roaccutane |

Function: Antiallergic

| | | | | |
|---|---|---|---|---|
| Lodoxamide | 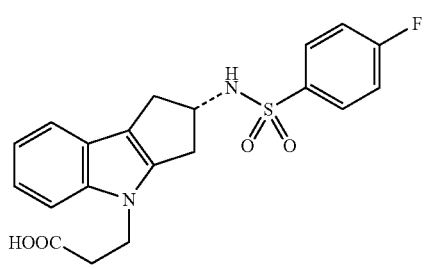 [SMILES: O=C(O)CCn1c2c(c3ccccc31)C[C@H](NS(=O)(=O)c1ccc(F)cc1)C2] | 212° | U.S. Pat. No. 3,993,679 | |
| Ramatroban | 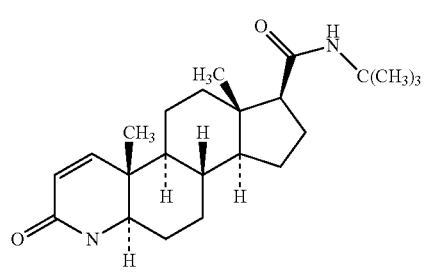 | 134-135° | U.S. Pat. No. 4,965,258 | |

Function: Antialopecia Agent

| | | | | |
|---|---|---|---|---|
| Finasteride | | ~257° | U.S. Pat. No. 4,760,071 | Chibro-Proscar, Finasid, Propecia, Proscar, Prostide |

TABLE 1-continued

| Name | Compound | MP | Pat. No. | Other Names |
|---|---|---|---|---|
| Minoxidil | | 248° | U.S. Pat. Nos. 3,382,247 3,644,364 | Alopexil, Alostil, Loniten, Lonolox, Minoximen, Normoxidil, Prexidil, Regaine, Rogaine, Tricoxidil |

Function: Antiamebic

| Carbarsone | | 174° | JP 584418 | Amabevan, Ameban, Amibiarson, Arsambide, Carb-O-Selo, Histocarb, Fenarsone, Leucarsone, Aminarsone, Amebarsone |
|---|---|---|---|---|
| Diphetarsone | | | | Amebarsin, Bemarsal, Rodameb |

Function: Antiandrogen

| Flutamide | | 111.5-112.5° | U.S. Pat. No. 3,847,988 | Drogenil, Eulexin, Euflex, Flucinom, Flutamin, Fugerel |
|---|---|---|---|---|
| Nilutamide | | 149° | U.S. Pat. No. 4,097,578 | RU-23908, Anandron, Nilandron |

Function: Antianginal

| Nicorandil | | 92-93° | U.S. Pat. No. 4,200,640 | Adancor, Ikorel, Perisalol, Sigmart |
|---|---|---|---|---|
| Ozagrel | | 223-224° | | |

TABLE 1-continued

| Name | Compound | MP | Pat. No. | Other Names |
| --- | --- | --- | --- | --- |
| Function: Antiarrhythmic | | | | |
| Bunitrolol | | 163-165° | U.S. Pat. No. 3,541,130 | |
| Ipratropium Bromide | | 230-232° | U.S. Pat. No. 3,505,337 | Atem, Atrovent, Bitrop, Itrop, Narilet, Inatec |
| Function: Anti-arteriosclerotic | | | | |
| Pyridinol Carbamate | | 136-137° | | Anginin, Angioxione, Aterosan, Atover, Cicloven, Colesterinex, Duvaline, Morecil, Prodectin, Ravenil, Sospitan, Vasagin, Vasapril, Vasocil, Vasoverin |
| Function: Antiarthritic/Antirheumatic | | | | |
| Bucillamine | | 139-140° | U.S. Pat. No. 4,305,958 | Rimatil |
| Diacerein | | 217-218° | U.S. Pat. No. 4,244,968 | Artrodar, Fisiodar |

TABLE 1-continued

| Name | Compound | MP | Pat. No. | Other Names |
|------|----------|-----|----------|-------------|
| Function: Antiasthmatic (Non-bronchodilator) ||||||
| Amlexanox | 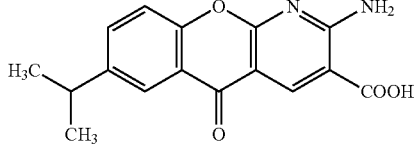 [SMILES: CC(C)c1ccc2oc3nc(N)c(C(=O)O)cc3c(=O)c2c1] | >300° | U.S. Pat. No. 4,143,042 | Aphthasol, Elics, Solfa |
| Cromolyn | 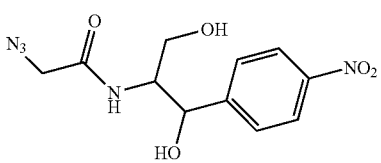 [SMILES: [N-]=[N+]=NCC(=O)NC(CO)C(O)c1ccc([N+](=O)[O-])cc1] | | | Aarane, Alercrom, Alerion, Allegocrom, Colimune, Cromoret, Firent, Gastro frenal, Inostral, Intal, Introl, Irtan Lomudal, Lomupren, Lomusol, Lomuspray, Nalcrom, Nalcron, Nasalcrom, Nasmil, Opticrom, Opticron, Rynacrom, Sofro, Vicrom, Vividrin |
| Function: Antibacterial (Antibiotics) ||||||
| Azidamfenicol | 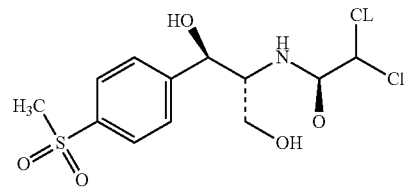 | 107° | U.S. Pat. No. 2,882,275 | Berlicetin, Leukomycin-N, Posifenicol, Thilocanfol |
| Thiamphenicol | 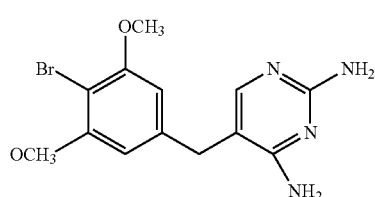 | 164.3-166.3° | U.S. Pat. Nos. 2,759,927 2,759,970 2,759,971 2,759,972 2,759,976 | Hyrazin, Igralin, Neomyson, Rigelon, Thiamcol, Thionicol, Thiophenicol, Urfamycine, Urophenil |
| Function: Antibacterial (Synthetic) ||||||
| Brodimoprim | 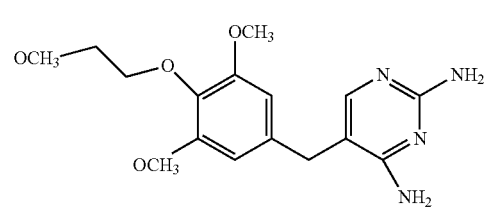 [SMILES: COCCOc1c(OC)cc(Cc2cnc(N)nc2N)cc1OC] | 225-228° | U.S. Pat. No. 4,024,145 | Hyprim, Unitrim |
| Tetroxoprim |  | 153-156° | U.S. Pat. No. 3,992,379 | |

TABLE 1-continued

| Name | Compound | MP | Pat. No. | Other Names |
|---|---|---|---|---|
| Function: Antibacterial (Leprostatic) | | | | |
| Acetosulfone Sodium | 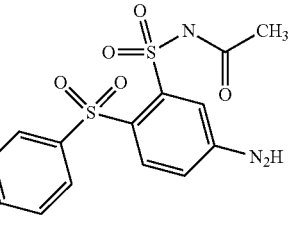 | ~285° | U.S. Pat. No. 2,358,365 | |
| Dapsone | 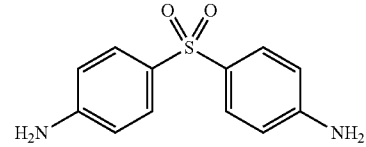 [SMILES: Nc1ccc(S(=O)(=O)c2ccc(N)cc2)cc1] | 175-176° | FR 829926 | Avlosulfon, Croysulfone, Diphenasone, Disulone, Dumitone, Eporal, Novophone, Sulfona-Mae, Sulphadione, Udolac |
| Function: Antibacterial (Tuberculostatic) | | | | |
| Benzoylpas | 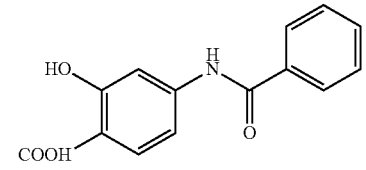 [SMILES: O=C(Nc1ccc(C(=O)O)c(O)c1)c1ccccc1] | 260-261° | GB 676363 | |
| Cyamelide | 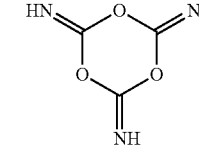 | | | |
| Function: Anticoagulant | | | | |
| Picotamide | 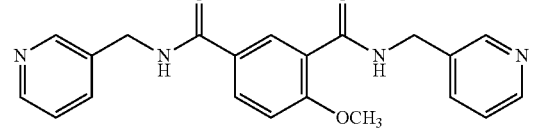 | 124° | U.S. Pat. No. 3,973,026 | |
| Function: Anticonvulsant | | | | |
| Acetylpheneturide | 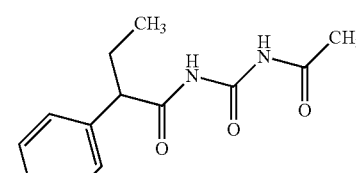 | 100-101° | U.S. Pat. No. 3,110,728 | Crampol |
| Albutoin | 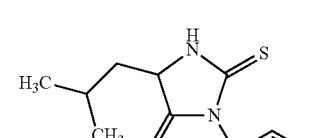 | 210-211° | | Euprax |

TABLE 1-continued

| Name | Compound | MP | Pat. No. | Other Names |
|---|---|---|---|---|
| Function: Antidepressant | | | | |
| Caroxazone | 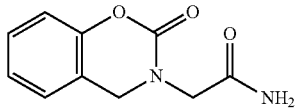 | 203-205° | U.S. Pat. No. 3,427,313 | Timostenil |
| Indalpine | 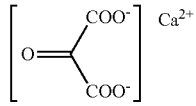 | | U.S. Pat. No. 4,064,255 | Upstene |
| Function: Antidiabetic | | | | |
| Calcium Mesoxalate | 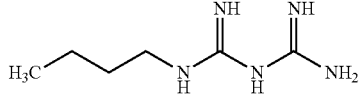 | Dec. 210-220° C. | JP 524157 JP 607463 | Mesoxan |
| Buformin | 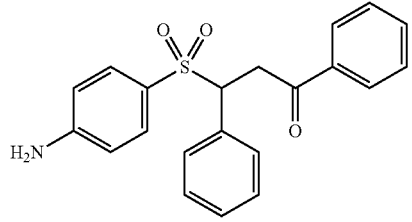 [SMILES: Nc1ccc(S(=O)(=O)C(CC(=O)c2ccccc2)c2ccccc2)cc1] | | U.S. Pat. No. 2,961,377 | |
| Function: Antidiarrheal | | | | |
| Alkofanone | 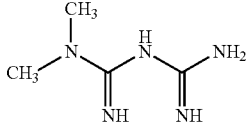 | Dec. 221-223° | U.S. Pat. No. 2,421,836 | Alfone |
| Metformin | 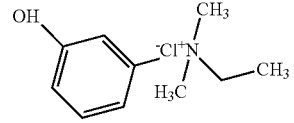 | | U.S. Pat. No. 3,174,901 | DMG5, LA-6023 |
| Function: Antidote (Curare) | | | | |
| Edrphomium Chloride | 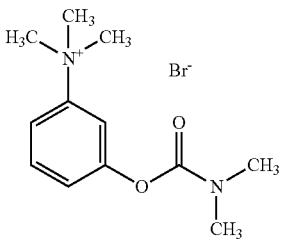 | Dec. 162-163° | U.S. Pat. No. 2,647,924 | Antirex, Enlon, Reversol, Tensiolon |
| Neostigmine |  | Dec. ~167° | U.S. Pat. No. 1,905,990 | |

TABLE 1-continued

| Name | Compound | MP | Pat. No. | Other Names |
|---|---|---|---|---|
| Function: Antidote (Cyanide) | | | | |
| p-Aminopropiophenon | | 140° | | DMSO |
| Methylene Blue | · 3H₂O | | | |
| Function: Antidote (Folic Acid Antagonists) | | | | |
| Folinic Acid | | Dec. 240-250° | U.S. Pat. No. 2,741,608 | |
| Function: Antidote (Heavy Metal Poisoning) | | | | |
| Tiopronin | | 95-97° | | Acadione, Capen, Epatiol, Mucolysin, Thiola, Thiosol |
| Function: Antidote (Methanol and Ethylene Glycol Poisoning) | | | | |
| Fomepizole | | 15.5-18.5° | | |
| Function: Antidote (Organophophate poisoning) | | | | |
| Asoxime Chloride | | 145-147° | U.S. Pat. No. 3,773,775 | |
| Obidoxime Chloride | | Syn: 235-236° Anti: 218-220° | U.S. Pat. No. 3,137,702 | Toksobidin, Toxogonin |
| Function: Antidyskinetic | | | | |
| Chloride | | 130° | U.S. Pat. No. 3,202,660 | |

TABLE 1-continued

| Name | Compound | MP | Pat. No. | Other Names |
|---|---|---|---|---|
| Tiapride | | 123-125° C. | GB 1394563 | |
| | Function: Antiemetic | | | |
| Alizapride | | 139° | U.S. Pat. No. 4,093,672 | |
| Bromopride | | | U.S. Pat. No. 3,177,252 | Emepride, Emoril, Viadil |
| | Function: Antifibrotic | | | |
| Potassium p-Aminobenzoate | | | | Potaba |
| | Function: (synthetic) | | | |
| Chlordantoin | | | | |
| Bromo-salicylchloranilide | | 238-243° | U.S. Pat. No. 2,802,029 | Multifungin |
| | Function: Antiglaucoma | | | |
| Acetazolamide | | 258-259° | U.S. Pat. No. 2,554,816 | Acetamox, Atenezol, Defiltran, Diamox, Didoc, Diuriwas, Donmox, Edemox, Fonurit, Glaupax |

TABLE 1-continued

| Name | Compound | MP | Pat. No. | Other Names |
|---|---|---|---|---|
| Benfunolol | (structure: 1-benzyl-1H-indazol-3-yloxy acetic acid) | 160° | U.S. Pat. No. 3,470,194 | Versus, Zildasac |

Function: Antigout

| Name | Compound | MP | Pat. No. | Other Names |
|---|---|---|---|---|
| Allopurinol | (structure: pyrazolo[3,4-d]pyrimidin-4-ol) | above 360° | U.S. Pat. No. 3,474,098 | |
| Carprofen | (structure: 6-chloro-α-methyl-9H-carbazole-2-acetic acid) | 197-198° | U.S. Pat. No. 3,896,145 | Imadyl, Rimadyl |

Function: Antihistaminic

| Name | Compound | MP | Pat. No. | Other Names |
|---|---|---|---|---|
| Acrivastine | (structure) | Dec. 222° | U.S. Pat. No. 4,501,893 | Semprex |
| Metron S | (structure) | 84-85° | | |

Function: Anti-hyperlipoproteninemic

| Name | Compound | MP | Pat. No. | Other Names |
|---|---|---|---|---|
| Acifran | (structure) | 176° | U.S. Pat. No. 4,244,958 | Reductol |
| Benfluorex | (structure) | | U.S. Pat. No. 3,607,909 | |

TABLE 1-continued

| Name | Compound | MP | Pat. No. | Other Names |
|---|---|---|---|---|
| Function: Anti-hypertensive | | | | |
| Chlorisonclamine Chloride | | 258-265° | U.S. Pat. No. 3,025,294 | Ecolid, Ecolid Chloride |
| Pentamethonium Bromide | $(H_3C)_3 \;^-Br^+N{-}{-}{-}{-}{-}N^+Br^-\; (CH_3)_3$ | | | Penthonium, Lytensium |
| Function: Anti-hyperthyroid | | | | |
| 2-Aminothiazole | | 93° | U.S. Pat. No. 2,242,237 | |
| Methylthio-uracil | | Dec. 326-331° | | Alkiron, Antibason, Basecil, Basethyrin, Methiacil, Methicil, Methiocil, Muracil, Prostrumyl, Strumacil, Thimecil, Thyreostat I |
| Function: Anti-hypotensive | | | | |
| Amexinium Methyl Sulfate | | 176° | U.S. Pat. No. 3,631,038 | Regulton, Risumic, Supratonin |
| Dopamine Hydrochloride | | Dec. 241° | | Cardiosteril, Dopastat, Dynatra, Inovan, Inotropin |
| Function: Anti-Inflammatory (Gastrointestinal) | | | | |
| Balsalazide | | >350° | U.S. Pat. No. 4,412,992 | |
| Mesalamine | | dec. 280° | GB 751386 | Asacol, Ascolitin, Claversal, Lixacol, Mesasal, Pentasa, Rowasa, Salofalk |

TABLE 1-continued

| Name | Compound | MP | Pat. No. | Other Names |
|---|---|---|---|---|
| Function: Anti-Inflammatory (Nonsteroidal) | | | | |
| Enfenamic Acid | | 116-117° | IN 103066 IN 114805 | Tromaril |
| Menfenamic Acid | | | | |
| Flufenamic Acid Aluminum Salt | | | | Alfenamin, Opyrin |
| Function: Antimalarial | | | | |
| Berberine | | 145° | | |
| Chloguanide | | 129° | FR 1001548 | |
| Function: Antimanic | | | | |
| Valproic Acid | | liquid | | Convulex, Depakene, Mylproin |
| Function: Antimigraine | | | | |
| Lisuride | | 186° | | |

TABLE 1-continued

| Name | Compound | MP | Pat. No. | Other Names |
|---|---|---|---|---|
| Naratriptan | | 170-171° | U.S. Pat. No. 4,997,841 | |

Function: Antimuscarinic

| Name | Compound | MP | Pat. No. | Other Names |
|---|---|---|---|---|
| Ambutonium Bromide | | 228-229° | | |
| Benzilonium Bromide | | 203-204° | GP 821436 | Minelsin, Minelcin, Portyn, Ulcoban |

Function: Antineoplastic

| Name | Compound | MP | Pat. No. | Other Names |
|---|---|---|---|---|
| 9-Amino-camptothecin | | 300° | JP KoKai 59 51289 (to Yakult Honsha) | |
| Tenuazonic Acid | | | | |

Function: Antiobsessional

| Name | Compound | MP | Pat. No. | Other Names |
|---|---|---|---|---|
| Clometocillin | | | U.S. Pat. No. 3,007,920 | Rixapen |

TABLE 1-continued

| Name | Compound | MP | Pat. No. | Other Names |
|---|---|---|---|---|
| Fluoxetine Hydrochloride | (structure) | 157-158° | U.S. Pat. No. 4,314,081 | Adofen, Fluctin, Fluoxeren, Fontex, Foxetin, Lovan, Prozac, Reneuron, Sarafem |

Function: Antiosteoporotic

| Name | Compound | MP | Pat. No. | Other Names |
|---|---|---|---|---|
| Pamidronic Acid | (structure) | | U.S. Pat. No. 4,327,039 | |
| Risedronate Sodium | (structure) | | U.S. Pat. No. 5,583,122 | Acetonel, Optinate |

Function: Antiparkinsonian

| Name | Compound | MP | Pat. No. | Other Names |
|---|---|---|---|---|
| Benserazide Hydrochloride | (structure) | 146-148° | U.S. Pat. No. 3,178,476 | |
| Carbidopa | (structure) | 203-205° | U.S. Pat. No. 3,462,536 | Lodosyn |

Function: Antipheochromoc-ytoma

| Name | Compound | MP | Pat. No. | Other Names |
|---|---|---|---|---|
| Metyrosine | (structure) | 310-315° | U.S. Pat. No. 2,868,818 | Demser |
| Phentolamine | (structure) | 174-175° | U.S. Pat. No. 2,503,059 | |

Function: Anti-pneumocystic

| Name | Compound | MP | Pat. No. | Other Names |
|---|---|---|---|---|
| Elfornithine Hydrochloride monohydrate | 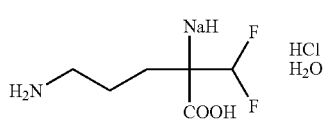 | 183° | | |

TABLE 1-continued

| Name | Compound | MP | Pat. No. | Other Names |
|---|---|---|---|---|
| Sulfamethoxazole | (structure) | 167° | U.S. Pat. No. 2,888,455 | Gantanol, Sinomin |

Function: Antiprostatic Hypertrophy

| Name | Compound | MP | Pat. No. | Other Names |
|---|---|---|---|---|
| Tamsulosin Hydrochloride | (structure) | 228-230° | U.S. Pat. No. 4,703,063 | Flomax, Harnal, Omnic, Pradif |
| Terazosin | (structure) | 272-274° | U.S. Pat. No. 4,026,894 U.S. Pat. No. 4,251,532 | |

Function: Antiprotozoal Cryptosporidium

| Name | Compound | MP | Pat. No. | Other Names |
|---|---|---|---|---|
| Nitazoxanide | (structure) | 202° | U.S. Pat. No. 3,950,351 | Cryptaz |

Function: Antiprotozoal (Giardia)

| Name | Compound | MP | Pat. No. | Other Names |
|---|---|---|---|---|
| Acranil" | (structure) | 237-238° | U.S. Pat. No. 2,113,357 | |

TABLE 1-continued

| Name | Compound | MP | Pat. No. | Other Names |
|---|---|---|---|---|
| Function: Antiprotozoal (Leishmania) | | | | |
| Hydroxystilbamidine | | 235° | U.S. Pat. No. 2,510,047 | |
| Pentamidine | | dec. 186° | U.S. Pat. No. 2,394,003 | |
| Function: Antiprotozoal (Toxoplasma) | | | | |
| Pyrimethamine | | 233-234° | U.S. Pat. No. 2,680,740 | Chloridin, Daraprim, Malcoide, Tindurin |
| Function: Antiprotozoal (Trichomonas) | | | | |
| Acetarsone | | 240-250° | | Gynoplix, Orarsan, Spirocid, Stovarsol |
| Aminitrozole | | 264-265° | U.S. Pat. No. 2,531,756 | Tritheon, Trichorad, Enheptin-A |

| Name | Compound | MP | Pat. No. | Other Names |
|---|---|---|---|---|
| Function: Antiprotozoal (Trypanosoma) | | | | |
| Benznidazole | | 188-190° | GB 1138529 | Radanil |
| Eflornithine Hydrochloride | | 183° | | Ornidyl |
| Function: Antipsoriatic | | | | |
| Acitretin | | 228-230° | U.S. Pat. No. 4,105,681 | Neotigason, Soriatane |
| 6-Azauridine | | 160-161° | | |
| Function: Antipsychotic | | | | |
| Amisulpride | | 126-127° | U.S. Pat. No. 4,401,822 | Deniban, Socian, Solian, Sulamid |
| Remoxipride Hydrochloride Monohydrate | | 173° | U.S. Pat. No. 4,232,037 | Roxiam |

TABLE 1-continued

| Name | Compound | MP | Pat. No. | Other Names |
|---|---|---|---|---|
| Function: Antipyretic | | | | |
| Bufexamac | | 153-155° | U.S. Pat. No. 3,479,396 | Droxaryl, Feximac, Malipuran, Mofenar, Norfemae, Parfenac, Parfenal |
| Bumadizon | | 116-117° | U.S. Pat. No. 3,455,999 | |
| Function: Antirickettsial | | | | |
| Chloramphenicol | | 150-151° | U.S. Pat. No. 2,839,577 | |
| Function: Antiseptic/Disinfectant | | | | |
| Benzoxonium Chloride | n = 10 | 107-109° | CH 306648 | Absonal, Bactofen, Bialcol |
| Cetalkonium Chloride | n = 14 | 59° | U.S. Pat. No. 2,075,958 | Banicol, Acetoquate CDAC, Ammonyx G, Zettyn, Ammonyx T, Cetol |
| Function: Antispasmodic | | | | |
| Alibendol | | 95° | U.S. Pat. No. 3,668,238 | Cebera |
| Ambutonium Bromide | | 228-229° | | |

TABLE 1-continued

| Name | Compound | MP | Pat. No. | Other Names |
|------|----------|----|----|----|
| Function: Antisyphilitic | | | | |
| Arshpenamine | 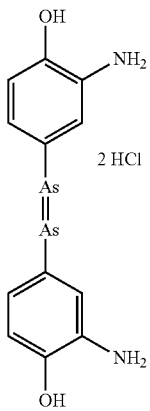 | | U.S. Pat. No. 986,148 | Ehrlich 606, Salvarsan |
| Sodium Arsanilate | 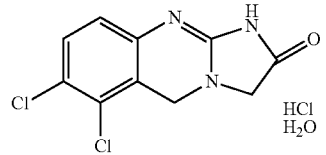 | | | Arsamin, Atoxyl, Nuarsol, Protoxyl, Soamin, Sonate, Piglet Pro-Gen V, Trypoxyl |
| Function: Antithrom-boxythemic | | | | |
| Anagrelide | 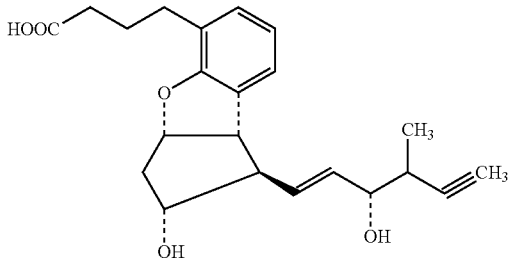 | >280° | U.S. Pat. No. 4,146,718 | Agrylin |
| Function: Antihrombotic | | | | |
| Beraprost | 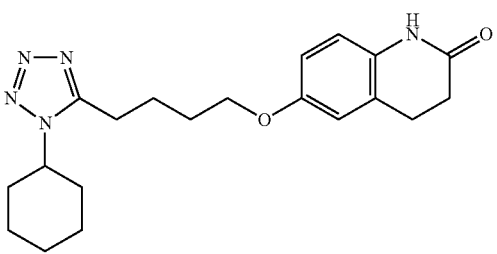 [SMILES: O=C1CCc2cc(OCCCCc3nnnn3C3CCCCC3)ccc2N1] | | U.S. Pat. No. 4,474,802 | Dorner, Procylin |
| Cilostazol | 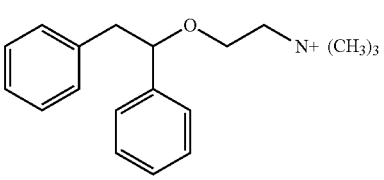 | 159-160° | BE 878548 | Pletal |
| Function: Antitussive | | | | |
| Bibenzonium Bromide |  | 144-147° | U.S. Pat. No. 2,913,459 | Sedobex, Lysobex, Lysibex, Thoragol, Lysbex, Medipectol |

TABLE 1-continued

| Name | Compound | MP | Pat. No. | Other Names |
|---|---|---|---|---|
| Sodium Dibunate | | dec. >300° | | Labaz, Becantal, Becantex, Dibunafon, Keuten, Linctussal |

Function: Antiulcerative

| Name | Compound | MP | Pat. No. | Other Names |
|---|---|---|---|---|
| Aldioxa | | 230° | U.S. Pat. No. 2,761,867 | Alanetorin, Alusa, Arlanto, Ascomp, Chlokale, Isalon, Nische, Peptilate |
| Cimetidine | | 141-143° | U.S. Pat. No. 3,950,333 | Acibilin, Acinil, Cimal, Cimetag, Cimetum Edalene, Dyspamet, Eureceptor, Gastromet, Peptol |

Function: Antiurolithic

| Name | Compound | MP | Pat. No. | Other Names |
|---|---|---|---|---|
| Allopurinol | | >350° | U.S. Pat. No. 3,474,098 | |
| Succinimide | | 125-127° | | Orotric |

Function: Antiviral

| Name | Compound | MP | Pat. No. | Other Names |
|---|---|---|---|---|
| Foscarnet Sodium | | >250° | U.S. Pat. No. 4,215,113 | Foscavir |
| Efavirenz | | 139-141° | U.S. Pat. No. 5,519,021 | |

Function: Anxiolytic

| Name | Compound | MP | Pat. No. | Other Names |
|---|---|---|---|---|
| Etifoxine | | 90-92° | U.S. Pat. No. 3,725,404 | |

TABLE 1-continued

| Name | Compound | MP | Pat. No. | Other Names |
|---|---|---|---|---|
| Valnoctamide | | 113-114° | | Axiquel, Nirvanil |
| | Function: Atriopeptidase Inhibitor | | | |
| Cannabinol | | 76-77° | | |
| | Function: Bronchodilator | | | |
| Oxitropium Bromide | | 203-204° | U.S. Pat. No. 3,472,861 | Oxivent, Tersigat, Ventilat |
| Tiotropium Bromide | | 218-220° | EP 418716 | |
| | Function: Calcium Channel Blocker | | | |
| Fendiline Hydrochloride | | 204-205° | U.S. Pat. No. 3,262,977 | Cordan, Fendilar, Sensit |
| Prenylamine | | 36-37° | U.S. Pat. No. 3,152,173 | Elecor |

TABLE 1-continued

| Name | Compound | MP | Pat. No. | Other Names |
|---|---|---|---|---|
| Function: Carbonic Anhydrase Inhibitor | | | | |
| Acetazolamide | | 258-259° | U.S. Pat. No. 2,554,816 | Acetamox, Atenezol, Diamox, Didoc, Diuriwas, Donmox, Edemox, Fonurit, Glaupax |
| Flumethiazide | | 305-307° | U.S. Pat. No. 3,040,042 | Ademol, Fludemil |
| Function: Cardioprotective | | | | |
| Acadesine | | 213-214° | | Arasine, Protara |
| Cariporide | | 90-94° | U.S. Pat. No. 5,591,754 | |
| Function: Cardotonic | | | | |
| Levosimendan | | 210-214° | U.S. Pat. No. 5,569,657 | Simdax |
| Pimobendan Hydrochloride | | 311° | U.S. Pat. No. 4,361,563 | |

TABLE 1-continued

| Name | Compound | MP | Pat. No. | Other Names |
|---|---|---|---|---|
| | Function: Cholelitholytic Agent | | | |
| Ursodiol | | 203° | | Actigall, Arsacol, Cholit-Ursan, Delursan, Desol, Destolit, Deursil, Litursol, Lyeton, Peptarom, Solutrat, Urdes, Ursacol, Urso, Ursochol, Ursofalk, Ursolvan. |
| Chenodiol | | 119° | | Chendol, Chenix, Chenocedon, Chenocol, Chenodex, Chenofaulk, Chenossil, Chenosaure, Cholanorm, Fluibil, Hekbilin, Ulmenide |
| | Function: Choleretic | | | |
| Cholic Acid Monohydrate | | 198° | | Colalin |
| Clanobutin | | 115-116° | U.S. Pat. No. 3,780,095 | Bykahepar |
| | Function: Cholinergic | | | |
| Echothiophate Iodide | | 138° | U.S. Pat. No. 2,911,430 | |
| Edrophonium Chloride | | 162-163° | U.S. Pat. No. 2,647,924 | Antirex, Enlon, Eversol, Tensilon |

TABLE 1-continued

| Name | Compound | MP | Pat. No. | Other Names |
|---|---|---|---|---|
| | Function: Cholinesterase Inhibitor | | | |
| Ambenonium Chloride | 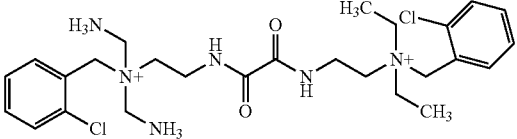 [SMILES: CC[N+](CC)(CCNC(=O)C(=O)NCC[N+](CN)(CN)Cc1ccccc1Cl)Cc1ccccc1Cl] | 196-199° | DE 1024517 | Mytelase |
| Distigmine Bromide | 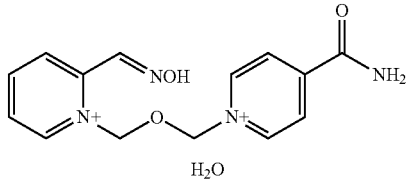<br>n = 6 | dec 143° | U.S. Pat. No. 2,789,981 | Ubretide |
| | Function: Cholinesterase Reactivator | | | |
| Asoxime Chloride | 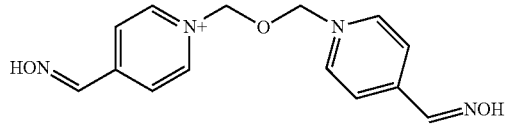<br>H₂O | 145-147° | U.S. Pat. No. 3,773,775 | |
| Obidoxime Chloride | 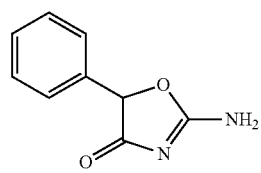 [SMILES: NC1=NC(=O)C(c2ccccc2)O1] | dec 225° | U.S. Pat. No. 3,137,702 | Toksobidin, Toxogonin |
| | Function: CNS Stimulant | | | |
| Pemoline | 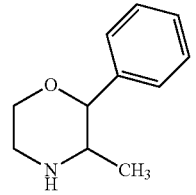 | 256-257° | U.S. Pat. No. 2,892,753 | Azoksodon, Cylert, Deltamine, Hyton Asa, Kethamed, Nitan, Pioxol, Pondex, Senior, Sigmadyn, Stimul, Tradon, Volital |
| Phenmetrazine |  | liquid | U.S. Pat. No. 2,835,669 | |

TABLE 1-continued

| Name | Compound | MP | Pat. No. | Other Names |
|---|---|---|---|---|
| Function: Cyclooxygenase-2 Inhibitor ||||| 
| Celecoxib | 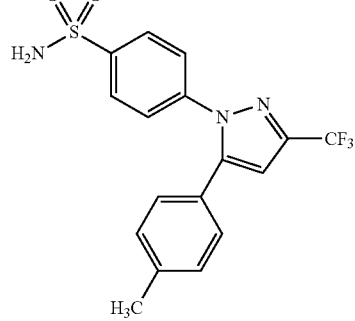 | 157-159° | WO 95 15316 | Celebrex |
| Function: Cytoprotectant (Gastric) |||||
| Cetraxate | 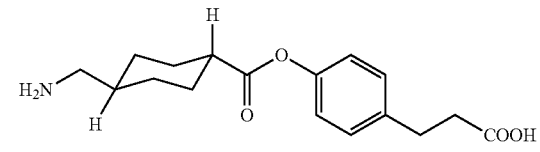 [SMILES: NCC1CCC(C(=O)Oc2ccc(CCC(=O)O)cc2)CC1] | 200-280° | U.S. Pat. No. 3,699,149 | |
| Irsogladine | 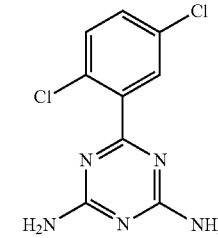 | 268-269° | U.S. Pat. No. 3,966,728 | |
| Function: Decongestant |||||
| Naphazoline Hydrochloride | 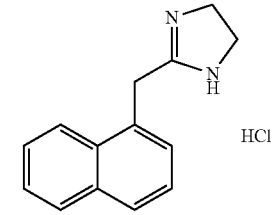 [SMILES: c1ccc2c(CC3=NCCN3)cccc2c1 ; Cl] | 255-260° | U.S. Pat. No. 2,161,938 | Ak-con, Albalon, Clera, Coldan, Iridina, Naphcon, Niazol, OpconRhinantin, Phinoperd, Sanorin, Sanorin-Spofa, Strictylon |
| Nordefrin Hydrochloride | 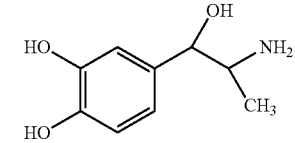 | 178-179° | U.S. Pat. No. 1,948,162 | Corbasil, Cobefrin |
| Function: Dermatitis Herpetiformis Suppressant |||||
| Dapsone | 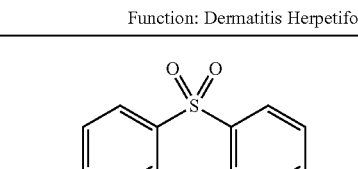 | 175-176° | | Avlosulfon, Croysulfone, Diphenasone, Disulone, Dumitone, Eporal, Novophone, Sulfona-Mae, Sulphadine, Udolac |

TABLE 1-continued

| Name | Compound | MP | Pat. No. | Other Names |
|---|---|---|---|---|
| Sulfapyridine Sodium Salt |  | 190-191° | U.S. Pat. No. 2,275,354 | Izopiridina, Soludagenan |

Function: Diuretic

| Name | Compound | MP | Pat. No. | Other Names |
|---|---|---|---|---|
| Mercaptomerin Sodium | 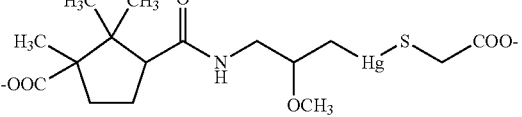 | 150-155° | U.S. Pat. No. 2,576,349 | |
| Mercumatilin Sodium | 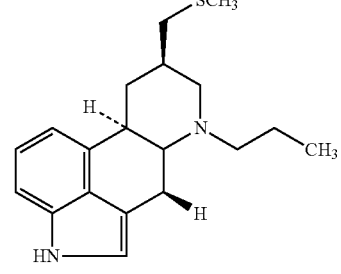 | 155-160° | U.S. Pat. No. 2,667,442 | |

Function: Dopamine Receptor Agonist

| Name | Compound | MP | Pat. No. | Other Names |
|---|---|---|---|---|
| Pergolid | 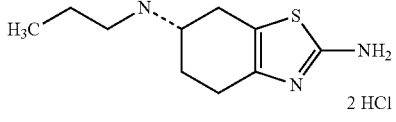 | 206-209° | U.S. Pat. No. 4,166,182 | |
| Pramipexole Dihydrochloride | 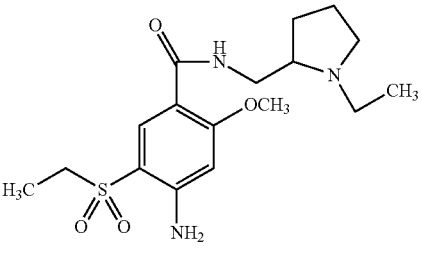 [SMILES: CCN1CCCC1CNC(=O)c1cc(S(=O)(=O)CC)c(N)cc1OC] | 296-298° | U.S. Pat. No. 4,886,812 | Mirapex, Mirapexin, Sifrol |

Function: Dopamine Receptor Antagonist

| Name | Compound | MP | Pat. No. | Other Names |
|---|---|---|---|---|
| Amisulpride | 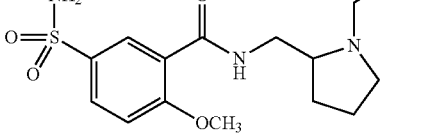 | 126-127° | U.S. Pat. No. 4,401,822 | |
| Sulpiride | | 178-180° | U.S. Pat. No. 3,342,826 | Alilit, Aiglonyl, Coolspan, Dobren, Dogmatil, Dogmatyl, Dolmatil, Guastil, Meresa, Miradol, Mierbanil, Misulvan, Neogama, Omperan, Pyrikappl, Sernevin, Splotin, Sulpitil, Sursumid, Trilan |

TABLE 1-continued

| Name | Compound | MP | Pat. No. | Other Names |
|---|---|---|---|---|
| | Function: Emetic | | | |
| Cephaeline | (structure) | 115-116° | | |
| | Function: Expectorant | | | |
| Bromhexine | (structure) | 237-238° | BE 625022 | |
| Ambroxol Hydrochloride | (structure) | 233-234° | U.S. Pat. No. 3,536,713 | Abramen, Ambril, Bronchopront, Duramucal, Fluibron, Fluixol, Frenopect, Lindoxyl, Motosol, Mucofar, Muscolvan, Mucoclear, Mucovent, Pect, Solvolan, Stas-Hustenloser, Surbronc, Surfactal |
| | Function: Gastric & Pancreatic Secretion Stimulant | | | |
| Carnitine | (structure) | | U.S. Pat. Nos. 4,255,449 4,315,944 | |
| | Function: Gastroprokinetic | | | |
| Cinitapride | (structure) | | U.S. Pat. No. 5,026,858 | Tartate, Cidine |
| Cisapride | (structure) | 109.8° | U.S. Pat. No. 4,962,115 | Acenalin, Alimix, Cipril, Prepulsick, Propulside, Risamol |

TABLE 1-continued

| Name | Compound | MP | Pat. No. | Other Names |
|---|---|---|---|---|
| Function: Glucocorticoid | | | | |
| Cortivazol | 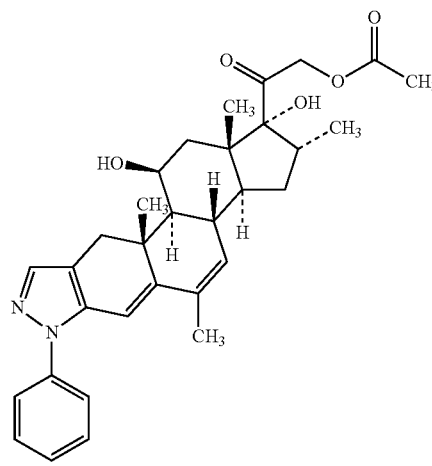 | 160-165° | U.S. Pat. No. 3,067,194/ U.S. Pat. No. 3,300,483 | |
| Enoxolone | 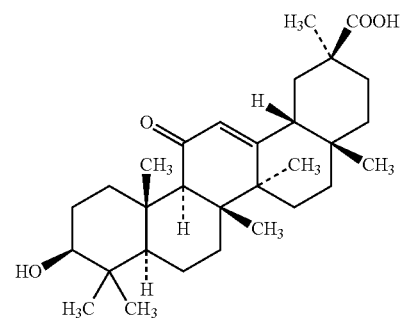 | 296° | GB 833184 | |
| Function: Gonad-Stimulating Principle | | | | |
| Clomiphene | | 116-118° | U.S. Pat. No. 2,914,563 | Citrate, Clomid, Clomphid, Clomricl, Clostilbeggt, Dyneric, Ikaclomine, Pergotime, Serophene |
| Function: Hemorheologic Agent | | | | |
| Pentoxifylline | 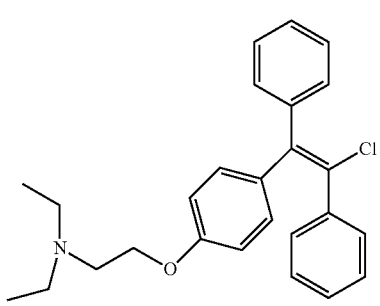 [SMILES: CCN(CC)CCOc1ccc(/C(=C(/Cl)c2ccccc2)c2ccccc2)cc1] | 105° | U.S. Pat. No. 3,422,107 | Oxpentifylline, Vasofirin, Azopentat, Dorapental, Rentglin, Torental, Trental |

TABLE 1-continued

| Name | Compound | MP | Pat. No. | Other Names |
|---|---|---|---|---|
| Function: Hemostatic | | | | |
| Adrenalone | 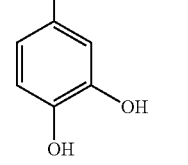 | 235° | DE 152814<br>DE 277540 | Adrenone, Stryphon |
| Carbazo-<br>chrome<br>Sodium<br>Sulfonate | 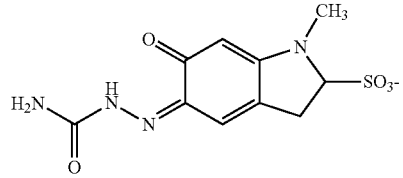 | 227-228° | GB 795184 | AC17, Adenaron,<br>Adona, Carbazon,<br>Donaseren, Emex,<br>Odanon, Tazin |
| Function: Hepatoprotectant | | | | |
| Thioctic Acid | 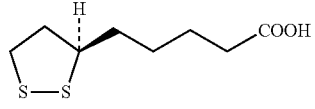 [SMILES: O=C(O)CCCC[C@@H]1CCSS1] | | U.S. Pat. Nos.<br>2,980,716<br>3,049,549<br>3,223,712 | Biletan, Thioctacid,<br>Thioctan, Tioctan |
| Timonacid | 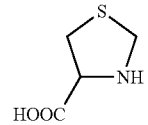 | | FR 173184 | Norgemen,<br>Thioproline, Detokepa,<br>Hepalidine,<br>Heparegen,<br>Thiazolidin |
| Function: Immono modulator | | | | |
| Pidotimod | 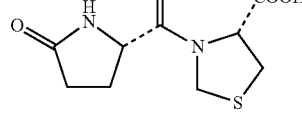 | 194-198° | U.S. Pat. No.<br>4,839,387 | |
| Bucillamine | | 139-140° | U.S. Pat. No.<br>4,305,958 | Rimatil |
| Function: Immono suppressant | | | | |
| 6-Mercapto-<br>purine | 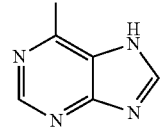 | 313-314° | U.S. Pat. Nos.<br>2,697,709<br>2,721,866 | Leuberin, Mercaleubin |
| Brequinar | 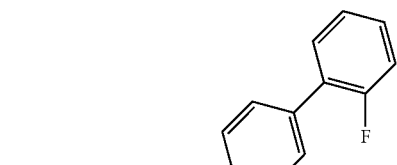 | 315-317° | U.S. Pat. No.<br>4,680,299 | |

TABLE 1-continued

| Name | Compound | MP | Pat. No. | Other Names |
|---|---|---|---|---|
| Function: Keratolytic ||||| 
| Retinoic Acid | 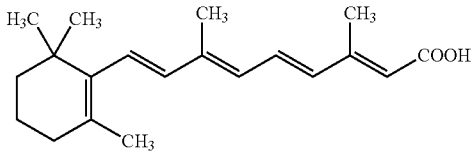 [SMILES: CC1=C(/C=C/C(C)=C/C=C/C(C)=C/C(=O)O)C(C)(C)CCC1] | 180-181° | U.S. Pat. No. 3,746,730 | Aberd, Airol, Arite, Eudgna, Kerlocal, Renova |
| Salicylic Acid | 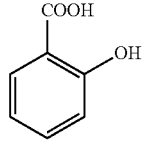 | 159° | | Acnisal, Duofilm, Duoplant, Keralyt, Occlusal, Verrugon |
| Function: Lexative/Cathartic |||||
| Docusate Calcium (Sodium) | 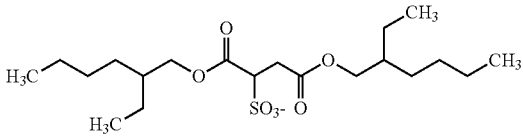 | | U.S. Pat. Nos. 3,035,973 2,028,091 | Sofale |
| Picosolfate Sodium | 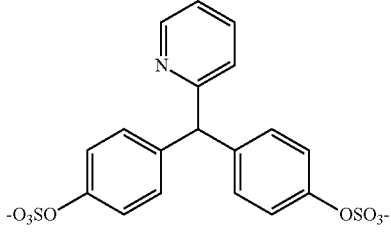 | 272-275° | U.S. Pat. Nos. 3,528,986 3,558,643 | Guttalax-Fher, Laxoberal, Laxoberon, Neopax, Pico-Salax |
| Function: Leukotriene Antagonist |||||
| Ibudilast | 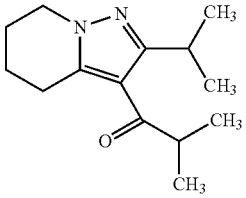 [SMILES: CC(C)C(=O)c1c(C(C)C)nn2c1CCCC2] | 53-54° | U.S. Pat. No. 3,850,941 | Ketas |
| Zafirlukast | 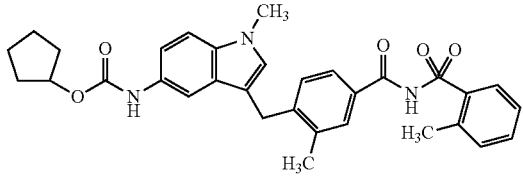 | 138-140° | U.S. Pat. No. 4,859,692 | Accolate |
| Function: Lipotropic |||||
| Choline Chloride | 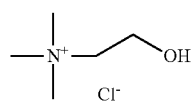 | | U.S. Pat. No. 2,623,901 | Biocolina, Hepacholine, Lipotril |
| Methionine | 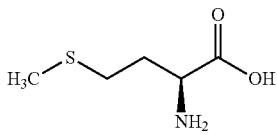 | 280-282° | | Acimethin |

TABLE 1-continued

| Name | Compound | MP | Pat. No. | Other Names |
|---|---|---|---|---|
| Function: Lupos Erythematosos Suppressant | | | | |
| Bismuth Sodium Triglycollamate | 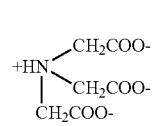 | | U.S. Pat. No. 2,348,984 | Bistrimate |
| Chloroquine | 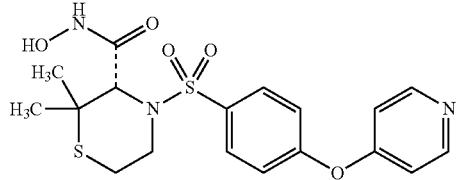 [SMILES: CC1(C)SCCN(S(=O)(=O)c2ccc(Oc3ccncc3)cc2)[C@H]1C(=O)NO] | 193-195° | U.S. Pat. No. 2,233,970 | Aralen, Artriclin, Bemaphate, Capquin, Nivaquine B, Reamachlor, Sanoquin |
| Function: Matrix Metallo-proteinase Inhibitor | | | | |
| Prinomastat | 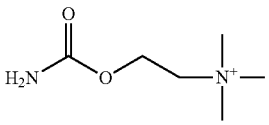 | 149.8° | WO 97 20824 | |
| Function: Miotic | | | | |
| Carbachol | 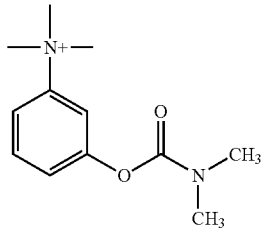 | 207° | U.S. Pat. No. 1,894,162 | Doryl, Isopto Carbachol, Zestryl, Miostat |
| Neostigmine | 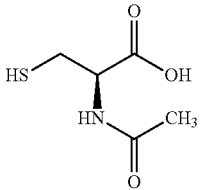 | 167° | U.S. Pat. No. 1,905,990 | |
| Function: Mucolytic | | | | |
| Acetylcysteine | 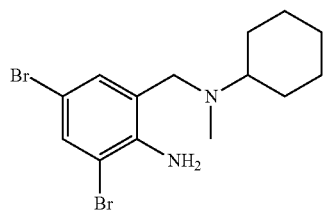 [SMILES: CN(Cc1cc(Br)cc(Br)c1N)C1CCCCC1] | 109-110° | U.S. Pat. No. 3,184,505 | Bronac, Fabrol, Fluimueil, Mocosil, Moeret |
| Bromhexine |  | 237.5° | BE 625022 | |

TABLE 1-continued

| Name | Compound | MP | Pat. No. | Other Names |
|---|---|---|---|---|
| *Function: Muscle Relaxant (Skeletal)* | | | | |
| Tetrazepam | | 144° | U.S. Pat. No. 3,426,014 | Muscaril, Muokelat, Myolastan |
| Tizanidine | | 221-223° | U.S. Pat. No. 3,843,668 | |
| *Function: Mydriatic* | | | | |
| Tropicamide | | 96-97° | U.S. Pat. No. 2,726,245 | Mydriacyl, Mydriaticum |
| Phenylephrine Hydrochloride | | 140-145° | U.S. Pat. No. 1,932,347/ U.S. Pat. No. 1,954,389 | Adrianol, Ak-Dilate, Alc-Nefrin, Isophirin, m-Sympatol, Neophryn |
| *Function: Naroctic Antagonist* | | | | |
| Cyclazocine | | 201-204° | BE 611000 | |
| Amiphenazole | | 163-164° | | Dizol, Daptazole, Daptazile, Fenamizol |

TABLE 1-continued

| Name | Compound | MP | Pat. No. | Other Names |
|---|---|---|---|---|
| | Function: Neuraminidase Inhibitor | | | |
| Zanamivir | 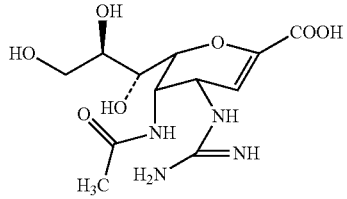 [SMILES: CC(=O)NC1C(NC(=N)N)C=C(C(=O)O)OC1[C@H](O)[C@H](O)CO] | 256° | WO 91 16320 | |
| | Function: Neuromuscular Blocking Agent | | | |
| Succinyl-choline Bromide/ Chloride/ Iodide | 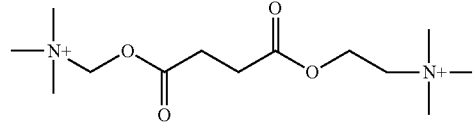 | 156-163° | | |
| Fazadinium Bromide | 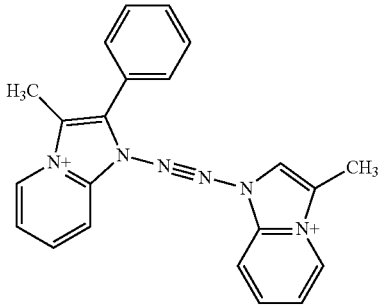 | 215° | U.S. Pat. No. 3,773,746 | Fazadon |
| | Function: Neutral Endopetidase Inhibitor | | | |
| Omapatrilat | 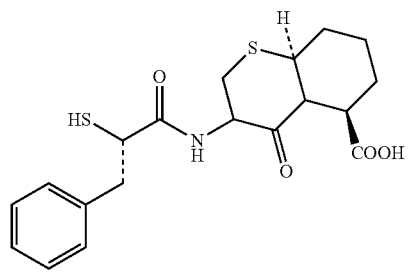 | 218-220° | U.S. Pat. No. 5,508,272 | Vauler |
| | Function: Neuroprotective | | | |
| Riluzole | 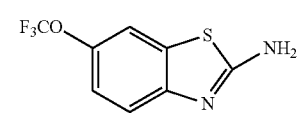 [SMILES: Nc1nc2ccc(OC(F)(F)F)cc2s1] | 119° | U.S. Pat. No. 4,370,338 | Rilutek |
| Repinotan | 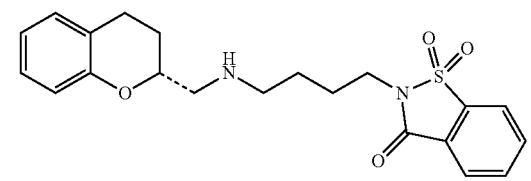 [SMILES: O=C1c2ccccc2S(=O)(=O)N1CCCCNC[C@H]1CCc2ccccc2O1] | 192-194° | U.S. Pat. No. 5,137,901 | |

TABLE 1-continued

| Name | Compound | MP | Pat. No. | Other Names |
|---|---|---|---|---|
| Function: Nootropic | | | | |
| Indeloxazine Hydrochloride | 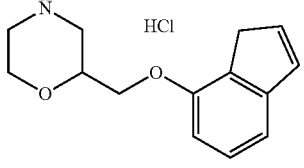 | | U.S. Pat. No. 4,109,088 | Elen, Noin |
| Donepezil | 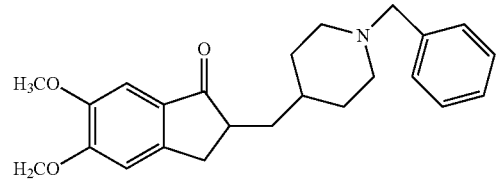 | 211-212° | U.S. Pat. No. 4,895,841 | Aricept |
| Function: Oxytocic | | | | |
| Carboprost | 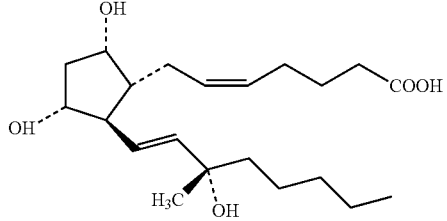 [SMILES: CCCCC[C@](C)(O)/C=C/[C@@H]1[C@@H](C/C=C\CCCC(=O)O)[C@@H](O)C[C@H]1O] | 55-56° | U.S. Pat. No. 3,728,382 | |
| Function: Potassium Channel Activator/Opener | | | | |
| Pinacidil | 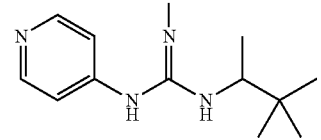 | 164-165° | U.S. Pat. No. 4,057,636 | Pindac |
| Nicorandil | 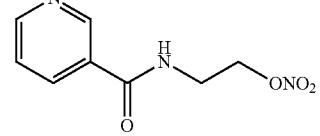 | 92-93° | U.S. Pat. No. 4,200,640 | Adancor, Ikorel, Perisalol, Sigmart |
| Function: Potassium Channel Blocker | | | | |
| Fampridine | 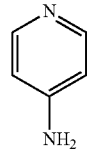 | 158-159° | | |
| Tedisamil | 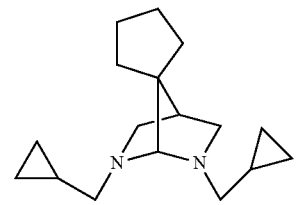 [SMILES: C1CCC2(C1)C1CN(CC3CC3)C2N(CC2CC2)C1] | 195-197° | U.S. Pat. No. 4,550,112 | |

TABLE 1-continued
| Name | Compound | MP | Pat. No. | Other Names |
|---|---|---|---|---|
| Function: Prolactin Inhibitor ||||||
| Cabergoline | 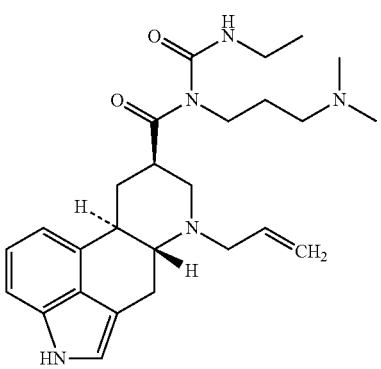 [SMILES: C=CCN1C[C@H](C(=O)N(CCCN(C)C)C(=O)NCC)C[C@@H]2c3cccc4[nH]cc(c34)C[C@H]21] | 102° | U.S. Pat. No. 4,526,892 | Cabaser, Dostinex |
| Function: Prostaglandin ||||||
| Beraprost | 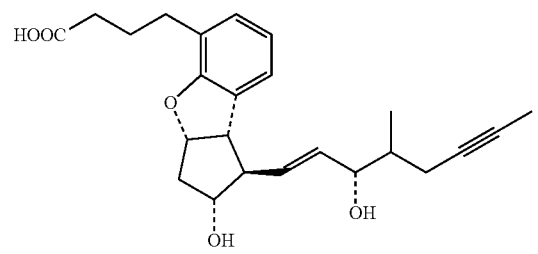 | | U.S. Pat. No. 4,479,802 | |
| Function: Respiratory Stimulant ||||||
| Dimefline | 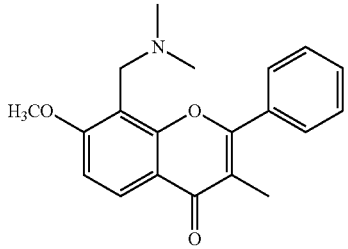 [SMILES: COc1ccc2c(=O)c(C)c(-c3ccccc3)oc2c1CN(C)C] | 213-214° | U.S. Pat. No. 3,147,258 | |
| Fominoben | 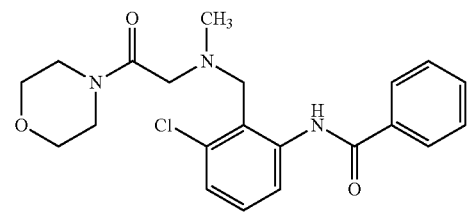 [SMILES: CN(CC(=O)N1CCOCC1)Cc1c(Cl)cccc1NC(=O)c1ccccc1] | 122-123° | U.S. Pat. No. 3,661,903 | |
| Function: Sclerosing Agent ||||||
| 2-Hexyl-decanoic Acid | 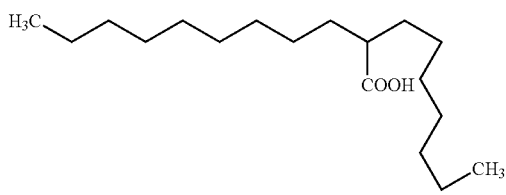 [SMILES: CCCCCCCCCC(CCCCCCC)C(=O)O] | 140-150° | | |

TABLE 1-continued

| Name | Compound | MP | Pat. No. | Other Names |
|---|---|---|---|---|
| Sodium Tetradecyl Sulfate | (structure) | | | Sotradecol, Tergitol |

Function: Sedative/Hypnotic

| Name | Compound | MP | Pat. No. | Other Names |
|---|---|---|---|---|
| Flurazepam | (structure) | 77-82° | U.S. Pat. Nos. 3,299,053 3,567,710 | Felmeme, Noctosom, Stacuroderm |
| Etodroxizine | (structure) | liquid | GB 8172321 | |

Function: Succinylcholine Synergist

| Name | Compound | MP | Pat. No. | Other Names |
|---|---|---|---|---|
| Hexafluorenium Bromide | (structure) | 188-189° | U.S. Pat. No. 2,783,237 | Mylexen |

Function: Tocolytic

| Name | Compound | MP | Pat. No. | Other Names |
|---|---|---|---|---|
| Ritodrine | (structure) | 88-90° | U.S. Pat. No. 3,410,944 | |
| Terbutaline | (structure) | 119-122° | U.S. Pat. No. 3,937,838 | |

TABLE 1-continued
| Name | Compound | MP | Pat. No. | Other Names |
|---|---|---|---|---|
| Function: Ultraviolet Screen | | | | |
| p-Amino-benzoic Acid | 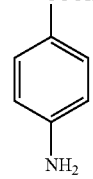 | 187-187-5° | U.S. Pat. Nos. 2,878,282 2,947,781 2,735,865 | Pabanol |
| Solisobenzone | 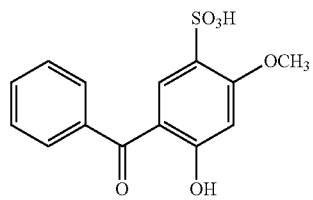 [SMILES: COc1cc(O)c(C(=O)c2ccccc2)cc1S(=O)(=O)O] | 145° | GB 1136525 | Songard, Uvinol |
| Function: Uricosuric | | | | |
| Ticrynafen | 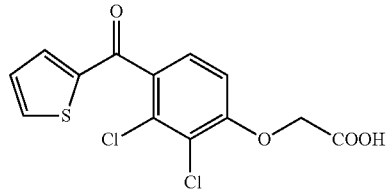 [SMILES: O=C(O)COc1ccc(C(=O)c2cccs2)c(Cl)c1Cl] | 148° | U.S. Pat. No. 3,758,506 | |
| Orotic Acid | 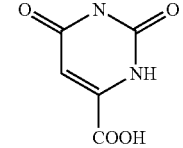 [SMILES: O=C(O)c1cc(=O)[nH]c(=O)[nH]1] | 345° | U.S. Pat. Nos. 2,937,175 3,086,917 | Oropor, Orotyl |
| Function: Vasodilator (Cerebral) | | | | |
| Nafronyl | 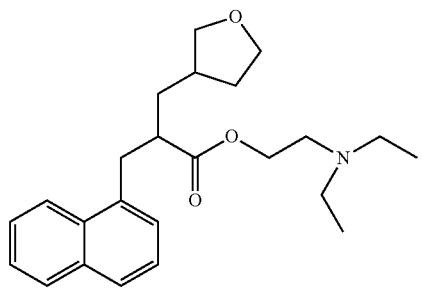 [SMILES: CCN(CC)CCOC(=O)C(Cc1cccc2ccccc12)CC1CCOC1] | 190° | U.S. Pat. No. 3,334,096 | Dubimax, Gevatran |
| Nicametate | 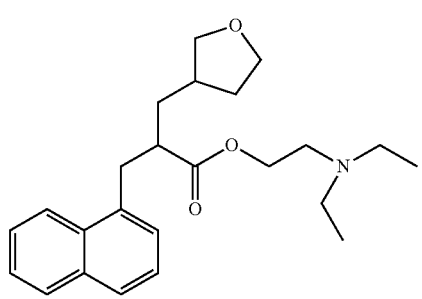 [SMILES: CCN(CC)CCOC(=O)C(Cc1cccc2ccccc12)CC1CCOC1] | 155-157° | | Eucast |

TABLE 1-continued
| Name | Compound | MP | Pat. No. | Other Names |
|---|---|---|---|---|
| Function: Vasodilator (Coronary) | | | | |
| Perhexiline | 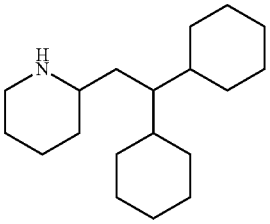 [SMILES: C1CCC(C(CC2CCCCN2)C2CCCCC2)CC1] | 243-245.5° | GB 1025578 | |
| Cloricromen | 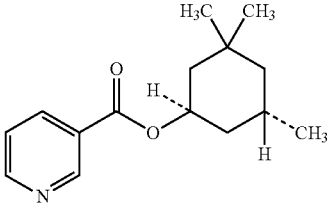 [SMILES: C[C@@H]1C[C@@H](OC(=O)c2cccnc2)CC(C)(C)C1] | 147-148° | U.S. Pat. No. 4,452,811 | |
| Function: Vasodilator (Peripheral) | | | | |
| Ciclonicate | 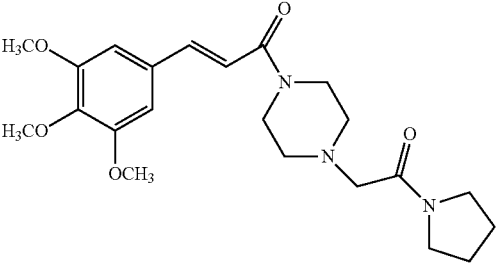 [SMILES: COc1cc(/C=C/C(=O)N2CCN(CC(=O)N3CCCC3)CC2)cc(OC)c1OC] | 127-128° | DE 1910481 2406849 | |
| Cinepazide | 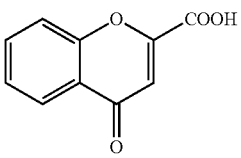 [SMILES: O=C(O)c1cc(=O)c2ccccc2o1] | 135° | U.S. Pat. No. 3,634,411 | |
| Function: Vasprotectant | | | | |
| Chromocarb | 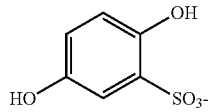 | 250-251° | U.S. Pat. No. 3,816,470 | |
| Dobesilate Calcium | 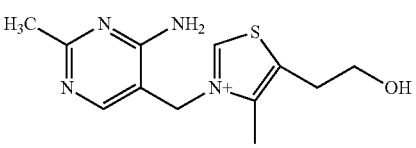 [SMILES: Cc1ncc(C[n+]2csc(CCO)c2C)c(N)n1] | >300° | U.S. Pat. No. 3,509,207 | |
| Function: Vitamin/Vitamin Source | | | | |
| Thiamine (Vit. B) | | dec 248° | | |

TABLE 1-continued

| Name | Compound | MP | Pat. No. | Other Names |
|---|---|---|---|---|
| Pyridoxine Hydrochloride (Vit. B$_5$) | [structure] | 205-212° | U.S. Pat. Nos. 2,680,743 2,734,063 2,904,551 3,024,244 | |

Function: Vulnerary

| Name | Compound | MP | Pat. No. | Other Names |
|---|---|---|---|---|
| Oxaceprol | [structure] | 133-134° | U.S. Pat. Nos. 3,860,607 3,891,765 3,932,638 | |
| Acetylcysteine | [structure] | 109-110° | U.S. Pat. No. 3,184,505 | Brunac, Fabrol, Fluimucil, Fluprowit, Mucomgst, Mocosil, Tixair |

Function: Wilson's Disease Treatment

| Name | Compound | MP | Pat. No. | Other Names |
|---|---|---|---|---|
| Penicillamine | [structure] | 202-206° | | Depen, Distamine, Mercaptyl, Sofortan, Trolovol |

Function: Xanthine Oxidase Inhibitor

| Name | Compound | MP | Pat. No. | Other Names |
|---|---|---|---|---|
| Allopurinol | [structure] | >350° | U.S. Pat. Nos. 2,868,803 3,474,098 | Adenoal, Aloral, Cosonic, Remid, Riball |

Further examples of pharmaceutical actives that are ionic or can be made ionic and combined with other ions to form the disclosed ionic liquid compositions are detailed below, along with their typically pharmaceutical use.

Adrenergic: adrenalone, amidephrine mesylate, apraclonidine hydrochloride, brimonidine tartrate, dapiprazole hydrochloride, deterenol hydrochloride, dipivefrin, dopamine hydrochloride, ephedrine sulfate, epinephrine, epinephrine bitartrate, epinephryl borate, esproquin hydrochloride, etafedrine hydrochloride, hydroxyamphetamine hydrobromide, levonordefrin, mephentermine sulfate, metaraminol bitartrate, metizoline hydrochloride, naphazoline hydrochloride, norepinephrine bitartrate, oxidopamine, oxymetazoline hydrochloride, phenylephrine hydrochloride, phenylpropanolamine hydrochloride, phenylpropanolamine polistirex, prenalterol hydrochloride, propylhexedrine, pseudoephedrine hydrochloride, tetrahydrozoline hydrochloride, tramazoline hydrochloride, xylometazoline hydrochloride.

Adrenocortical steroid: ciprocinonide, desoxycorticosterone acetate, desoxycorticosterone pivalate, dexamethasone acetate, fludrocortisone acetate, flumoxonide, hydrocortisone hemisuccinate, methylprednisolone hemisuccinate, naflocort, procinonide, timobesone acetate, tipredane.

Adrenocortical suppressant: aminoglutethimide, trilostane.

Alcohol deterrent: disulfuram.

Aldosterone antagonist: canrenoate potassium, canrenone, dicirenone, mexrenoate potassium, prorenoate potassium, spironolactone.

Amino acid: alanine, aspartic acid, cysteine hydrochloride, cystine, histidine, isoleucine, leucine, lysine, lysine acetate, lysine hydrochloride, methionine, phenylalanine, proline, serine, threonine, tryptophan, tyrosine, valine.

Ammonia detoxicant: arginine: arginine glutamate, arginine hydrochloride.

Anabolic: bolandiol dipropionate, bolasterone, boldenone undecylenate, bolenol, bolnantalate, ethylestrenol, methenolone acetate, methenolone enanthate, mibolerone, nandrolone cyclotate, norbolethone, pizotyline, quinbolone, stenbolone acetate, tibolone, zeranol.

Analeptic: modafinil.

Analgesic: acetaminophen, alfentanil hydrochloride, aminobenzoate potassium, aminobenzoate sodium, anidoxime, anileridine, anileridine hydrochloride, anilopam hydrochloride, anirolac, antipyrine, aspirin, benoxaprofen, benzydamine hydrochloride, bicifadine hydrochloride, brifentanil hydrochloride, bromadoline maleate, bromfenac sodium, buprenorphine hydrochloride, butacetin, butixirate, butorphanol, butorphanol tartrate, carbamazepine, carbaspirin calcium, carbiphene hydrochloride, carfentanil citrate, ciprefadol succinate, ciramadol, ciramadol hydrochloride, clonixeril, clonixin, codeine, codeine phosphate, codeine sulfate, conorphone hydrochloride, cyclazocine, dexoxadrol hydrochloride, dexpemedolac, dezocine, diflunisal, dihydrocodeine bitartrate, dimefadane, dipyrone, doxpicomine hydrochloride, drinidene, enadoline hydrochloride, epirizole, ergotamine tartrate, ethoxazene hydrochloride, etofenamate, eugenol, fenoprofen, fenoprofen calcium, fentanyl citrate, floctafenine, flufenisal, flunixin, flunixin meglumine, flupirtine maleate, fluproquazone, fluradoline hydrochloride, flurbiprofen, hydromorphone hydrochloride, ibufenac, indoprofen, ketazocine, ketorfanol, ketorolac tromethamine, letimide hydrochloride, levomethadyl acetate, levomethadyl acetate hydrochloride, levonantradol hydrochloride, levorphanol tartrate, lofemizole hydrochloride, lofentanil oxalate, lorcinadol, lomoxicam, magnesium salicylate, mefenamic acid, menabitan hydrochloride, meperidine hydrochloride, meptazinol hydrochloride, methadone hydrochloride, methadyl acetate, methopholine, methotrimeprazine, metkephamid acetate, mimbane hydrochloride, mirfentanil hydrochloride, molinazone, morphine sulfate, moxazocine, nabitan hydrochloride, nalbuphine hydrochloride, nalmexone hydrochloride, namoxyrate, nantradol hydrochloride, naproxen, naproxen sodium, naproxol, nefopam hydrochloride, nexeridine hydrochloride, noracymethadol hydrochloride, ocfentanil hydrochloride, octazamide, olvanil, oxetorone fumarate, oxycodone, oxycodone hydrochloride, oxycodone terephthalate, oxymorphone hydrochloride, pemedolac, pentamorphone, pentazocine, pentazocine hydrochloride, pentazocine lactate, phenazopyridine hydrochloride, phenyramidol hydrochloride, picenadol hydrochloride, pinadoline, pirfenidone, piroxicam olamine, pravadoline maleate, prodilidine hydrochloride, profadol hydrochloride, propiram fumarate, propoxyphene hydrochloride, propoxyphene napsylate, proxazole, proxazole citrate, proxorphan tartrate, pyrroliphene hydrochloride, remifentanil hydrochloride, salcolex, salethamide maleate, salicylamide, salicylate meglumine, salsalate, sodium salicylate, spiradoline mesylate, sufentanil, sufentanil citrate, talmetacin, talniflumate, talosalate, tazadolene succinate, tebufelone, tetrydamine, tifurac sodium, tilidine hydrochloride, tiopinac, tonazocine mesylate, tramadol hydrochloride, trefentanil hydrochloride, trolamine, veradoline hydrochloride, verilopam hydrochloride, volazocine, xorphanol mesylate, xylazine hydrochloride, zenazocine mesylate, zomepirac sodium, zucapsaicin.

Androgen: fluoxymesterone, mesterolone, methyltestosterone, nandrolone decanoate, nandrolone phenpropionate, nisterime acetate, oxandrolone, oxymetholone, silandrone, stanozolol, testosterone, testosterone cypionate, testosterone enanthate, testosterone ketolaurate, testosterone phenylacetate, testosterone propionate, trestolone acetate.

Anesthesia, adjunct to: sodium oxybate.

Anesthetic: aliflurane, benoxinate hydrochloride, benzocaine, biphenamine hydrochloride, bupivacaine hydrochloride, butamben, butamben picrate, chloroprocaine hydrochloride, cocaine, cocaine hydrochloride, cyclopropane, desflurane, dexivacaine, diamocainc cyclamate, dibucaine, dibucaine hydrochloride, dyclonine hydrochloride, enflurane, ether, ethyl chloride, etidocaine, etoxadrol hydrochloride, euprocin hydrochloride, fluoroxene, halothane, isobutamben, isoflurane, ketamine hydrochloride, levoxadrol hydrochloride, lidocaine, lidocaine hydrochloride, mepivacaine hydrochloride, methohexital sodium, methoxyflurane, midazolam hydrochloride, midazolam maleate, minaxolone, nitrous oxide, norflurane, octodrine, oxethazaine, phencyclidine hydrochloride, pramoxine hydrochloride, prilocalne hydrochloride, procaine hydrochloride, propanidid, proparacaine hydrochloride, propofol, propoxycaine hydrochloride, pyrrocaine, risocaine, rodocaine, roflurane, salicyl alcohol, sevoflurane, teflurane, tetracaine, tetracaine hydrochloride, thiamylal, thiamylal sodium, thiopental sodium, tiletamine hydrochloride, zolamine hydrochloride.

Anorectic compounds including dexfenfluramine.

Anorexic: a minorex, amphecloral, chlorphentermine hydrochloride, clominorex, clortermine hydrochloride, diethylpropion hydrochloride, fenfluramine hydrochloride, fenisorex, fludorex, fluminorex, levamfetamine succinate, mazindol, mefenorex hydrochloride, phenmetrazine hydrochloride, phentermine, sibutramine hydrochloride.

Antagonist: atipamezole, atosiban, bosentan, cimetidine, cimetidine hydrochloride, clentiazem maleate, detirelix acetate, devazepide, donetidine, etintidine hydrochloride, famotidine, fenmetozole hydrochloride, flumazenil, icatibant acetate, icotidine, isradipine, metiamide, nadide, nalmefene, nalmexone hydrochloride, naloxone hydrochloride, naltrexone, nilvadipine, oxilorphan, oxmetidine hydrochloride, oxmetidine mesylate, quadazocine mesylate, ranitidine, ranitidine bismuth citrate, ranitidine hydrochloride, sufotidinei, teludipine hydrochloride, tiapamil hydrochloride, tiotidine, vapiprost hydrochloride, zaltidine hydrochloride.

Anterior pituitary activator: epimestrol.

Anterior pituitary suppressant: danazol.

Anthelmintic: albendazole, anthelmycin, bromoxanide, bunamidine hydrochloride, butonate, cambendazole, carbantel lauryl sulfate, clioxanide, closantel, cyclobendazole, dichlorvos, diethylcarbamazine citrate, dribendazole, dymanthine hydrochloride, etibendazole, fenbendazole, furodazole, hexylresorcinol, mebendazole, morantel tartrate, niclosamide, nitramisole hydrochloride, nitrodan, oxantel pamoate, oxfendazole, oxibendazole, parbendazole, piperamide maleate, piperazine, piperazine citrate, piperazine edetate calcium, proclonol, pyrantel pamoate, pyrantel tartrate, pyrvinium pamoate, rafoxanide, stilbazium iodide, tetramisole hydrochloride, thiabendazole, ticarbodine, tioxidazole, triclofenol piperazine, vincofos, zilantel.

Anti-acne: adapalene, erythromycin salnacedin, inocoterone acetate, accutane.

Anti-adrenergic: acebutolol, alprenolol hydrochloride, atenolol, bretylium tosylate, bunolol hydrochloride, carteolol hydrochloride, celiprolol hydrochloride, cetamolol hydrochloride, ciclprolol hydrochloride, dexpropranolol hydrochloride, diacetolol hydrochloride, dihydroergotamine mesylate, dilevalol hydrochloride, esmolol hydrochloride, exaprolol hydrochloride, fenspiride hydrochloride, flestolol sulfate, labetalol hydrochloride, levobetaxolol hydrochloride, levobunolol hydrochloride, metalol hydrochloride, metoprolol, metoprolol tartrate, nadolol, pamatolol sulfate, penbutolol sulfate, phentolamine mesylate, practolol, propranolol hydrochloride, proroxan hydrochloride, solypertine tartrate, sotalol hydrochloride, timolol, timolol maleate, tiprenolol hydrochloride, tolamolol, zolertine hydrochloride.

Anti-allergic: amlexanox, astemizole, azelastine hydrochloride, eclazolast, minocromil, nedocromil, nedocromil calcium, nedocromil sodium, nivimedone sodium, pemirolast potassium, pentigetide, pirquinozol, poisonoak extract, probicromil calcium, proxicromil, repirinast, tetrazolast meglumine, thiazinamium chloride, tiacrilast, tiacrilast sodium, tiprinast meglumine, tixanox.

Anti-amebic: berythromycin, bialamicol hydrochloride, chloroquine, chloroquine hydrochloride, chloroquine phosphate, clamoxyquin hydrochloride, clioquinol, emetine hydrochloride, iodoquinol, paromomycin sulfate, quinfamide, symetine hydrochloride, teclozan, tetracycline, tetracycline hydrochloride.

anti-androgen: benorterone, cioteronel, cyproterone acetate, delmadinone acetate, oxendolone, topterone, zanoterone.

Anti-anemic: epoetin alfa, epoetin beta, ferrous sulfate, dried, leucovorin calcium.

Anti-anginal: amlodipine besylate, amlodipine maleate, betaxolol hydrochloride, bevantolol hydrochloride, butoprozine hydrochloride, carvedilol, cinepazet maleate, metoprolol succinate, molsidomine, monatepil maleate, primidolol, ranolazine hydrochloride, tosifen, verapamil hydrochloride.

Anti-anxiety agent: adatanserin hydrochloride, alpidem, binospirone mesylate, bretazenil, glemanserin, ipsapirone hydrochloride, mirisetron maleate, ocinaplon, ondansetron hydrochloride, panadiplon, pancopride, pazinaclone, serazapine hydrochloride, tandospirone citrate, zalospirone hydrochloride.

Anti-arthritic: lodelaben.

Anti-asthmatic: ablukast, ablukast sodium, azelastine hydrochloride, bunaprolast, cinalukast, crornitrile sodium, cromolyn sodium, enofelast, isamoxole, ketotifen fumarate, levcromakalim, lodoxamide ethyl, lodoxamide tromethamine, montelukast sodium, ontazolast, oxarbazole, oxatomide, piriprost, piriprost potassium, pirolate, pobilukast edamine, quazolast, repirinast, ritolukast, sulukast, tetrazolast meglumine, tiaramide hydrochloride, tibenelast sodium, tomelukast, tranilast, verlukast, verofylline, zarirlukast.

Anti-atherosclerotic: mifobate, timefuronc.

Anticholelithic: monoctanoin.

Anticholelithogenic: chenodiol, ursodiol.

Anticholinergic: alverinc citrate, anisotropine methylbromide, atropine, atropine oxide hydrochloride, atropine sulfate, belladonna, benapryzine hydrochloride, benzetimide hydrochloride, benzilonium bromide, biperiden, biperiden hydrochloride, biperiden lactate, clidinium bromide, cyclopentolate hydrochloride, dexetimide, dicyclomine hydrochloride, dihexyverine hydrochloride, domazoline fumarate, elantrine, elucaine, ethybenztropine, eucatropine hydrochloride, glycopyrrolate, heteronium bromide, homatropine hydrobromide, homatropine methylbromide, hyoscyamine, hyoscyamine hydrobromide, hyoscyamine sulfate, isopropamide iodide, mepenzolate bromide, methylatropine nitrate, metoquizine, oxybutynin chloride, parapenzolate bromide, pentapiperium methylsulfate, phencarbamide, poldine methylsulfate, proglumide, propantheline bromide, propenzolate hydrochloride, scopolamine hydrobromide, tematropium methylsulfate, tiquinamide hydrochloride, tofenacin hydrochloride, toquizine, triampyzine sulfate, trihexyphenidyl hydrochloride, tropicamide.

Anticoagulant: ancrod, anticoagulant citrate dextrose solution, anticoagulant citrate phosphate dextrose adenine solution, anticoagulant citrate phosphate dextrose solution, anticoagulant heparin solution, anticoagulant sodium citrate solution, ardeparin sodium, bivalirudin, bromindione, dalteparin sodium, desirudin, dicumnarol, heparin calcium, heparin sodium, lyapolate sodium, nafamostat mesylate, phenprocoumon, tinzaparin sodium, warfarin sodium.

Anticoccidal: maduramicin.

Anticonvulsant: albutoin, ameltolide, atolide, buramate, carbamazepine, cinromide, citenamide, clonazepam, cyheptamide, dezinamide, dimethadione, divalproex sodium, eterobarb, ethosuximide, ethotoin, flurazepam hydrochloride, fluzinamide, fosphenyloin sodium, gabapentin, ilepcimide, lamotrigine, magnesium sulfate, mephenyloin, mephobarbital, methetoin, methsuximide, milacemide hydrochloride, nabazenil, nafimidone hydrochloride, nitrazepam, phenacemide, phenobarbital, phenobarbital sodium, phensuximide, phenyloin, phenyloin sodium, primidone, progabide, ralitoline, remacemide hydrochloride, ropizine, sabeluzole, stiripentol, sulthiame, thiopental sodium, tiletamine hydrochloride, topiramate, trimethadione, valproate sodium, valproic acid, vigabatrin, zoniclezole hydrochloride, zonisamide.

Antidepressant: adatanserin hydrochloride, adinazolam, adinazolam mesylate, alaproclate, aletamine hydrochloride, amedalin hydrochloride, amitriptyline hydrochloride, amoxapine, aptazapine maleate, azaloxan fumarate, azepindole, azipramine hydrochloride, bipenamol hydrochloride, bupropion hydrochloride, butacetin, butriptyline hydrochloride, caroxazone, cartazolate, ciclazindol, cidoxepin hydrochloride, cilobamine mesylate, clodazon hydrochloride, clomipramine hydrochloride, cotinine fumarate, cyclindole, cypenamine hydrochloride, cyprolidol hydrochloride, cyproximide, daledalin tosylate, dapoxetine hydrochloride, dazadrol maleate, dazepinil hydrochloride, desipramine hydrochloride, dexamisole, deximafen, dibenzepin hydrochloride, dioxadrol hydrochloride, dothiepin hydrochloride, doxepin hydrochloride, duloxetine hydrochloride, eclanamine maleate, encyprate, etoperidone hydrochloride, fantridone hydrochloride, fehmetozole hydrochloride, fenmetramide, fezolamine fumarate, fluotracen hydrochloride, fluoxetine, fluoxetine hydrochloride, fluparoxan hydrochloride, gamfexine, guanoxyfen sulfate, imafen hydrochloride, imiloxan hydrochloride, imipramine hydrochloride, indeloxazine hydrochloride, intriptyline hydrochloride, iprindole, isocarboxazid, ketipramine fumarate, lofepramine hydrochloride, lortalamine, maprotiline, maprotiline hydrochloride, melitracen hydrochloride, milacemide hydrochloride, minaprine hydrochloride, mirtazapine, moclobemide, modaline sulfate, napactadine hydrochloride, napamezole hydrochloride, nefazodone hydrochloride, nisoxetine, nitrafudam hydrochloride, nomifensine maleate, nortriptyline hydrochloride, octriptyline phosphate, opipramol hydrochloride, oxaprotiline hydrochloride, oxypertine, paroxetine, phenelzine sulfate, pirandamine hydrochloride, pizotyline, pridefine hydrochloride, prolintane hydrochloride, protriptyline hydrochloride, quipazine maleate, rolicyprine, seproxetine hydrochloride, sertraline hydrochloride, sibutramine hydrochloride, sulpiride, suritozole, tametraline hydrochloride, tampramine fumarate, tandamine hydrochloride, thiazesim hydrochloride, thozalinone, tomoxetine hydrochloride, trazodone hydrochloride, trebenzomine hydrochloride, trimipramine, trimipramine maleate, venlafaxine hydrochloride, viloxazine hydrochloride, zimeldine hydrochloride, zometapine.

Antidiabetic: acetohexamide, buformin, butoxamine hydrochloride, camiglibose, chlorpropamide, ciglitazone, englitazone sodium, etoformin hydrochloride, gliamilide, glibornuride, glicetanile sodium, gliflumide, glipizide, glucagon, glyburide, glyhexamide, glymidine sodium, glyoctamide, glyparamide, insulin, insulin, dalanated, insulin human, insulin human, isophane, insulin human zinc, insulin human zinc, extended, insulin, isophane, insulin lispro, insulin, neutral, insulin zinc, insulin zinc, extended, insulin zinc, prompt, linogliride, linogliride fumarate, metformin, methyl palmoxirate, palmoxirate sodium, pioglitazone hydrochloride, pirogliride tartrate, proinsulin human, seglitide acetate, tolazamide, tolbutamide, tolpyrramide, troglitazone, zopolrestat, and sitagliptin.

Antidiarrheal: rolgamidine, diphenoxylate hydrochloride (lomotil), metronidazole (flagyl), methylprednisolone (medrol), sulfasalazine (azulfidine).

Antidiuretic: argipressin tannate, desmopressin acetate, lypressin.

Antidote: dimercaprol, edrophonium chloride, fomepizole, leucovorin calcium, levoleucovorin calcium, methylene blue, protamine sulfate.

Antidyskinetic: selegiline hydrochloride.

Anti-emetic: alosetron hydrochloride, batanopride hydrochloride, bemesetron, benzquinamide, chlorpromazine, chlorpromazine hydrochloride, clebopride, cyclizine hydrochloride, dimenhydrinate, diphenidol, diphenidol hydrochloride, diphenidol pamoate, dolasetron mesylate, domperidone, dronabinol, fludorex, flumeridone, galdansetron hydrochloride, granisetron, granisetron hydrochloride, lurosetron mesylate, meclizine hydrochloride, metoclopramide hydrochloride, metopimazine, ondansetron hydrochloride, pancopride, prochlorperazine, prochlorperazine edisylate, prochlorperazine maleate, promethazine hydrochloride, thiethylperazine, thiethylperazine malate, thiethylperazine maleate, trimethobenzamide hydrochloride, zacopride hydrochloride.

Anti-epileptic: felbamate, loreclezole, tolgabide.

Anti-estrogen: clometherone, delmadinone acetate, nafoxidine hydrochloride, nitromifene citrate, raloxifene hydrochloride, tamoxifen citrate, toremifene citrate, trioxifene mesylate.

Antifibrinolytic: nafamostat mesylate.

Antifungal: acrisorcin, ambruticin, amphotericin b, azaconazole, azaserine, basifungin, bifonazole, biphenamine hydrochloride, bispyrithione magsulfex, butoconazole nitrate, calcium undecylenate, candicidin, carbol-fuchsin, chlordantoin, ciclopirox, ciclopirox olamine, cilofungin, cisconazole, clotrimazole, cuprimyxin, denofungin, dipyrithione, doconazole, econazole, econazole nitrate, enilconazole, ethonam nitrate, fenticonazole nitrate, filipin, fluconazole, flucytosine, fungimycin, griseofulvin, hamycin, isoconazole, itraconazole, kalafungin, ketoconazole, lomofimgin, lydimycin, mepartricin, miconazole, miconazole nitrate, monensin, monensin sodium, naftifine hydrochloride, neomycin undecylenate, nifuratel, nifurmerone, nitralamine hydrochloride, nystatin, octanoic acid, orconazole nitrate, oxiconazole nitrate, oxifungin hydrochloride, parconazole hydrochloride, partricin, potassium iodide, proclonol, pyrithione zinc, pyrrolnitrin, rutamycin, sanguinarium chloride, saperconazole, scopafungin, selenium sulfide, sinefungin, sulconazole nitrate, terbinafine, terconazole, thiram, ticlatone, tioconazole, tolciclate, tolindate, tolnaftate, triacetin, triafungin, undecylenic acid, viridofulvin, zinc undecylenate, zinoconazole hydrochloride. One specific antifungal that is suitable is itraconazole.

Antiglaucoma agent: alprenoxime hydrochloride, colforsin, dapiprazole hydrochloride, dipivefrin hydrochloride, naboctate hydrochloride, pilocarpine, pimabine.

Antihemophilic: antihemophilic factor.

Antihemorrhagic: poliglusam.

Antihistaminic: acrivastine, antazoline phosphate, astemizole, azatadine maleate, barmastine, bromodiphenhydramine hydrochloride, brompheniramine maleate, carbinoxamine maleate, cetirizine hydrochloride, chlorpheniramine maleate, chlorpheniramine polistirex, cinnarizine, clemastine, clemastine fumarate, closiramine aceturate, cycliramine maleate, cyclizine, cyproheptadine hydrochloride, dexbrompheniramine maleate, dexchlorpheniramine maleate, dimethindene maleate, diphenhydramine citrate, diphenhydramine hydrochloride, dorastine hydrochloride, doxylamine succinate, ebastine, levocabastine hydrochloride, loratadine, mianserin hydrochloride, noberastine, orphenadrine citrate, pyrabrom, pyrilamine maleate, pyroxamine maleate, rocastine hydrochloride, rotoxamine, tazifylline hydrochloride, temelastine, terfenadine, tripelennamine citrate, tripelennamine hydrochloride, triprolidine hydrochloride, zolamine hydrochloride.

Antihyperlipidemic: cholestyramine resin, clofibrate, colestipol hydrochloride, crilvastatin, dalvastatin, dextrothyroxine sodium, fluvastatin sodium, gemfibrozil, lecimibide, lovastatin, niacin, pravastatin sodium, probucol, simvastatin, tiqueside, xenbucin.

Antihyperlipoproteinemic: acifran, beloxamide, bezafibrate, boxidine, butoxamine hydrochloride, cetaben sodium, ciprofibrate, gemcadiol, halofenate, lifibrate, meglutol, nafenopin, pimetine hydrochloride, theofibrate, tibric acid, treloxinate.

Antihypertensive: alfuzosin hydrochloride, alipamide, althiazide, amiquinsin hydrochloride, amlodipine besylate, amlodipine maleate, anaritide acetate, atiprosin maleate, belfosdil, bemitradine, bendacalol mesylate, bendroflumethiazide, benzthiazide, betaxolol hydrochloride, bethanidine sulfate, bevantolol hydrochloride, biclodil hydrochloride, bisoprolol, bisoprolol fumarate, bucindolol hydrochloride, bupicomide, buthiazide: candoxatril, candoxatrilat, captopril, carvedilol, ceronapril, chlorothiazide sodium, cicletanine, cilazapril, clonidine, clonidine hydrochloride, clopamide, cyclopenthiazide, cyclothiazide, darodipine, debrisoquin sulfate, delapril hydrochloride, diapamide, diazoxide, dilevalol hydrochloride, diltiazem malate, ditekiren, doxazosin mesylate, ecadotril, enalapril maleate, enalaprilat, enalkiren, endralazine mesylate, epithiazide, eprosartan, eprosartan mesylate, fenoldopam mesylate, flavodilol maleate, flordipine, flosequinan, fosinopril sodium, fosinoprilat, guanabenz, guanabenz acetate, guanacline sulfate, guanadrel sulfate, guancydine, guanethidine monosulfate, guanethidine sulfate, guanfacine hydrochloride, guanisoquin sulfate, guanoclor sulfate, guanoctine hydrochloride, guanoxabenz, guanoxan sulfate, guanoxyfen sulfate, hydralazine hydrochloride, hydralazine polistirex, hydroflumethiazide, indacrinone, indapamide, indolaprif hydrochloride, indoramin, indoramin hydrochloride, indorenate hydrochloride, lacidipine, leniquinsin, levcromakalim, lisinopril, lofexidine hydrochloride, losartan potassium, losulazine hydrochloride, mebutamate, mecamylamine hydrochloride, medroxalol, medroxalol hydrochloride, methalthiazide, methyclothiazide, methyldopa, methyldopate hydrochloride, metipranolol, metolazone, metoprolol fumarate, metoprolol succinate, metyrosine, minoxidil, monatepil maleate, muzolimine, nebivolol, nitrendipine, oformine, pargyline hydrochloride, pazoxide, pelanserin hydrochloride, perindopril erbumine, phenoxybenzamine hydrochloride, pinacidil, pivopril, polythiazide, prazosin hydrochloride, primidolot, prizidilol hydrochloride, quinapril hydrochloride, quinaprilat, quinazosin hydrochloride, quinelorane hydrochloride, quinpirole hydrochloride, quinuclium bromide, ramipril, rauwolfia serpentina, reserpine, saprisartan potassium, saralasin acetate, sodium nitroprusside, sulfinalol hydrochloride, tasosartan, teludipine hydrochloride, temocapril hydrochloride, terazosin hydrochloride, terlakiren, tiamenidine, tiamenidine hydrochloride, ticrynafen, tinabinol, tiodazosin, tipentosin hydrochloride, trichlormethiazide, trimazosin hydrochloride, trimethaphan camsylate, trimoxamine hydrochloride, tripamide, xipamide, zankiren hydrochloride, zofenoprilat arginine.

Antihypotensive: ciclafrine hydrochloride, midodrine hydrochloride.

Anti-infective: difloxacin hydrochloride, lauryl isoquinolinium bromide, moxalactam disodium, ornidazole, pentisomicin, sarafloxacin hydrochloride, protease inhibitors of hiv and other retroviruses, integrase inhibitors of hiv and other retroviruses, cefaclor (CECLOR™), acyclovir (ZOVIRAX™), norfloxacin (NOROXIN™), cefoxitin (MEFOXIN™), cefuroxime axetil (CEFTIN™), ciprofloxacin (CIPRO™).

Anti-infective, topical: alcohol, aminacrine hydrochloride, benzethonium chloride: bithionolate sodium, bromchlorenone, carbamide peroxide, cetalkonium chloride, cetylpyridinium chloride: chlorhexidine hydrochloride, clioquinol, domiphen bromide, fenticlor, fludazonium chloride, fuchsin, basic, furazolidone, gentian violet, halquinols, hexachlorophene: hydrogen peroxide, ichthammol, imidecyl iodine, iodine, isopropyl alcohol, mafenide acetate, meralein sodium, mercufenol chloride, mercury, ammoniated, methylbenzethonium chloride, nitrofurazone, nitromersol, octenidine hydrochloride, oxychlorosene, oxychlorosene sodium, parachlorophenol, camphorated, potassium permanganate, povidone-iodine, sepazonium chloride, silver nitrate, sulfadiazine, silver, symclosene, thimerfonate sodium, thimerosal: troclosene potassium.

Anti-inflammatory: acetominophen, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysonc, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lornoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium.

Antikeratinizing agent: doretinel, linarotene, pelretin.

Antimalarial: acedapsone, amodiaquine hydrochloride, amquinate, arteflene, chloroquine, chloroquine hydrochloride, chloroquine phosphate, cycloguanil pamoate, enpiroline phosphate, halofantrine hydrochloride, hydroxychloroquine sulfate, mefloquine hydrochloride, menoctone, mirincamycin hydrochloride, primaquine phosphate, pyrimethamine, quinine sulfate, tebuquine.

Antimicrobial: aztreonam, chlorhexidine gluconate, imidurea, lycetamine, nibroxane, pirazmonam sodium, propionic acid, pyrithione sodium, sanguinarium chloride, tigemonam dicholine.

Antimigraine: dolasetron mesylate, naratriptan hydrochloride, sergolexole maleate, sumatriptan succinate, zatosetron maleate.

Antimitotic: podofilox.

Antimycotic: amorolfine.

Antinauseant: buclizine hydrochloride, cyclizine lactate, naboctate hydrochloride.

Antineoplastic: acivicin, aclarubicin, acodazole hydrochloride, acrqnine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, dacarbazine, dactinomycin, daunorubicin hydrochloride, decitabine, dexormaplatin, dezaguanine, dezaguanine mesylate, diaziquone, docetaxel, doxorubicin, doxorubicin hydrochloride, droloxifene, droloxifene citrate, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, estramustine phosphate sodium, etanidazole, ethiodized oil I 131, etoposide, etoposide phosphate, etoprine, fadrozole hydrochloride, fazarabine, fenretinide, floxuridine, fludarabine phosphate, fluorouracil, fluorocitabine, fosquidone, fostriecin sodium, gemcitabine, gemcitabine hydrochloride, gold au 198, hydroxyurea, idarubicin hydrochloride, ifosfamide, ilmofosine, interferon alfa-2a, interferon alfa-2b, interferon alfa-N1, interferon alfa-N3, interferon beta-Ia, interferon gamma-Ib, iproplatin, irinotecan hydrochloride, lanreotide acetate, letrozole, leuprolide acetate, liarozole hydrochloride, lometrexol sodium, lomustine, losoxantrone hydrochloride, masoprocol, maytansine, mechlorethamine hydrochloride, megestrol acetate, melengestrol acetate, melphalan, menogaril, mercaptopurine, methotrexate, methotrexate sodium, metoprine, meturedepa, mitindomide, mitocarcin, mitocromin, mitogillin, mitomalcin, mitomycin, mitosper, mitotane, mitoxantrone hydrochloride, mycophenolic acid, nocodazole, nogalamycin, ormaplatin, oxisuran, paclitaxel, pegaspargase, peliomycin, pentamustine, peplomycin sulfate, perfosfamide, pipobroman, piposulfan, piroxantrone hydrochloride, plicamycin, plomestane, porfimer sodium, porfiromycin, prednimustine, procarbazine hydrochloride, puromycin, puromycin hydrochloride, pyrazofurin, riboprine, rogletimide, safmgol, safingol hydrochloride, semustine, simtrazene, sparfosate sodium, sparsomycin, spirogermanium hydrochloride, spiromustine, spiroplatin, streptonigrin, streptozocin, strontium chloride sr 89, sulofenur, talisomycin, taxane, taxoid, tecogalan sodium, tegafur, teloxantrone hydrochloride, temoporfin, teniposide, teroxirone, testolactone, thiamiprine, thioguanine, thiotepa, tiazofurin, tirapazamine, topotecan hydrochloride, toremifene citrate, trestolone acetate, triciribine phosphate, trimetrexate, trimetrexate glucuronate, triptorelin, tubulozole hydrochloride, uracil mustard, uredepa, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, zinostatin, zorubicin hydrochloride.

Other anti-neoplastic compounds include: 20-epi-1,25 dihydroxyvitamin D3, 5-ethynyluracil, abiraterone, aclarubicin, acylfulvene, adecypenol, adozelesin, aldesleukin, ALL-TK antagonists, altretamine, ambamustine, amidox, amifostine, aminolevulinic acid, amrubicin, atrsacrine, anagrelide, anastrozole, andrographolide, angiogenesis inhibitors, antagonist D, antagonist G, antarelix, anti-dorsalizing morphogenetic protein-1, antiandrogen, prostatic carcinoma, antiestrogen, antineoplaston, antisense oligonucleotides, aphidicolin glycinate, apoptosis gene modulators, apoptosis regulators, apurinic acid, ara-CDP-DL-PTBA, arginine deaminase, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitor, bicalutamide, bisantrene, bisaziridinylspermine, bisnafide, bistratene A, bizelesin, breflate, bropirimine, budotitane, buthionine sulfoximine, calcipotriol, calphostin C, camptothecin derivatives, canarypox IL-2, capecitabine, carboxamide-amino-triazole, carboxyamidotriazole, CaRest M3, CARN 700, cartilage derived inhibitor, carzelesin, casein kinase inhibitors (ICOS), castanospermine, cecropin B, cetrorelix, chlorins, chloroquinoxaline sulfonamide, cicaprost, cis-porphyrin, cladribine, clomifene analogues, clotrimazole, collismycin A, collismycin B, combretastatin A4, combretastatin analogue, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, deslorelin, dexifosfamide, dexrazoxane, dexverapamil, diaziquone, didemnin B, didox, diethylnorspermine, dihydro-5-azacytidine, dihydrotaxol, 9-dioxamycin, diphenyl spiromustine, docosanol, dolasetron, doxifluridine, droloxifene, dronabinol, duocannycin SA, ebselen, ecomustine, edelfosine, edrecolomab, eflornithine, elemene, emitefur, epirubicin, epristeride, estramustine analogue, estrogen agonists, estrogen antagonists, etanidazole, etoposide phosphate, exemestane, fadrozole, fazarabine, fenretinide, filgrastim, fmasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, heregulin, hexamethylene bisacetamide, hypericin, ibandronic acid, idarubicin, idoxifene, idramantone, ilmofosine, ilomastat, imidazoacridones, imiquimod, immunostimulant peptides, insulin-like growth factor-1 receptor inhibitor, interferon agonists, interferons, interleukins, iobenguane, iododoxorubicin, ipomeanol, 4-irinotecan, iroplact, irsogladine, isobengazole, isohomohalicondrin B, itasetron, jasplakinolide, kahalalide F, lamellarin-N triacetate, lanreotide, leinamycin, lenograstim, lentinan sulfate, leptolstatin, letrozole, leukemia inhibiting factor, leukocyte alpha interferon, leuprolide+estrogen+progesterone, leuprorelin, levamisole, liarozole, linear polyamine analogue, lipophilic disaccharide peptide, lipophilic platinum compounds, lissoclinamide 7, lobaplatin, lombricine, lometrexol, lonidamine, losoxantrone, lovastatin, loxoribine, lurtotecan, lutetium texaphyrin, lysofylline, lytic peptides, maitansine, mannostatin A, marimastat, masoprocol, maspin, matrilysin inhibitors, matrix metalloproteinase inhibitors, menogaril, merbarone, meterelin, methioninase, metoclopramide, MIF inhibitor, mifepristone, miltefosine, mirimostim, mismatched double stranded RNA, mitoguazone, mitolactol, mitomycin analogues, mitonafide, mitotoxin fibroblast growth factor-saporin, mitoxantrone, mofarotene, molgramostim, monoclonal antibody, human chorionic gonadotrophin, monophosphoryl lipid A+myobacterium cell wall sk, mopidamol, multiple drug resistance genie inhibitor, multiple tumor suppressor 1-based therapy, mustard anticancer agent, mycaperoxide B, mycobacterial cell wall extract, myriaporone, N-acetyldinalinc, N-substituted benzamides, nafarelin, nagrestip, naloxone+pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, O6-benzylguanine, octreotide, okicenone, oligonucleotides, onapristone, ondansetron, ondansetron, oracin, oral cytokine inducer, ormaplatin, osaterone, oxaliplatin, oxaunomycin, paclitaxel analogues, paclitaxel derivatives, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, perillyl alcohol, phenazinomycin, phenylacetate, phosphatase inhibitors, picibanil, pilocarpine hydrochloride, pirarubicin, piritrexim, placetin A, placetin B, plasminogen activator inhibitor, platinum complex, platinum compounds, platinum-triamine complex, porfimer sodium, porfiromycin, propyl bis-acridone, prostaglandin J2, proteasome inhibitors, protein A-based immune modulator, protein kinase C inhibitor, protein kinase C inhibitors, microalgal, protein tyrosine phosphatase inhibitors, purine nucleoside phosphorylase inhibitors, purpurins, pyrazoloacridine, pyridoxylated hemoglobin polyoxyethylene conjugate, raf antagonists, raltitrexed, ramosetron, ras farnesyl protein transferase inhibitors, ras inhibitors, ras-GAP inhibitor, retelliptine demethylated, rhenium Re 186 etidronate, rhizoxin, ribozymes, RII retinamide, rogletimide, rohitukine, romurtide, roquinimex, rubiginone B1, ruboxyl, safingol, saintopin, SarCNU, sarcophytol A, sargramostim, Sdi 1 mimetics, semustine, senescence derived inhibitor 1, sense oligonucleotides, signal transduction inhibitors, signal transduction modulators, single chain antigen binding protein, sizofuran, sobuzoxane, sodium borocaptate, sodium phenylacetate, solverol, somatomedin binding protein, sonermin, sparfosic acid, spicamycin D, spiromustine, splenopentin, spongistatin 1, squalamine, stem cell inhibitor, stem-cell division inhibitors, stipiamide, stromelysin inhibitors, sulfmosine, superactive vasoactive intestinal peptide antagonist, suradista, suramin, swainsonine, synthetic glycosaminoglycans, tallimustine, tamoxifen methiodide, tauromustine, tazarotene, tecogalan sodium, tegafur, tellurapyrylium, telomerase inhibitors, temoporfin, temozolomide, teniposide, tetrachlorodecaoxide, tetrazomine, thaliblastine, thalidomide, thiocoraline, thrombopoietin, thrombopoietin mimetic, thymalfasin, thymopoietin receptor agonist, thymotrinan, thyroid stimulating hormone, tin ethyl etiopurprin, tirapazamine, titanocene dichloride, topotecan, topsentin, toremifene, totipotent stem cell factor, translation inhibitors, tretinoin, triacetyluridine, triciribine, trimetrexate, triptorelin, tropisetron, turosteride, tyrosine kinase inhibitors, tyrphostins, UBC inhibitors, ubenimex, urogenital sinus-derived growth inhibitory factor, urokinase receptor antagonists, vapreotide, variolin B, vector system, erythrocyte gene therapy, velaresol, veramine, verdins, verteporfin, vinorelbine, vinxaltine, vitaxin, vorozole, zanoterone, zeniplatin, zilascorb, zinostatin stimalamer.

Anti-cancer supplementary potentiating agents: tricyclic anti-depressant drugs (e.g., imipramine, desipramine, amitryptyline, clomiprainine, trimipramine, doxepin, nortriptyline, protriptyline, amoxapine and maprotiline), non-tricyclic anti-depressant drugs (e.g., sertraline, trazodone and citalopram), $Ca^{++}$ antagonists (e.g., verapamil, nifedipine, nitrendipine and caroverine), calmodulin inhibitors (e.g., prenylamine, trifluoroperazine and clomipramine), amphotericin B, triparanol analogues (e.g., tamoxifen), antiarrhythmic drugs (e.g., quinidine), antihypertensive drugs (e.g., reserpine), thiol depleters (e.g., buthionine and sulfoximine) and Multiple Drug Resistance reducing agents such as Cremaphor EL.

Antineutropenic: filgrastim, lenograstim, molgramostim, regramostim, sargramostim.

Antiobsessional agent: fluvoxamine maleate.

Antiparasitic: abamectin, clorsulon, ivermectin.

Antiparkinsonian: benztropine mesylate, biperiden, biperiden hydrochloride, biperiden lactate, carmantadine, ciladopa hydrochloride, dopamantine, ethopropazine hydrochloride, lazabemide, levodopa, lometraline hydrochloride, mofegiline hydrochloride, naxagolide hydrochloride, pareptide sulfate, procyclidine hydrochloride, quinetorane hydrochloride, ropinirole hydrochloride, selegiline hydrochloride, tolcapone, trihexyphenidyl hydrochloride. antiperistaltic: difenoximide hydrochloride, difenoxin, diphenoxylate hydrochloride, fluperamide, lidamidine hydrochloride, loperamide hydrochloride, malethamer, nufenoxole, paregoric.

Antipneumocystic: atovaquone.

Antiproliferative agent: piritrexim isethionate.

Antiprostatic hypertrophy: sitogluside.

Antiprotozoal: amodiaquine, azanidazole, bamidazole, carnidazole, chlortetracycline bisulfate, chlortetracycline hydrochloride, flubendazole, flunidazole, halofuginone hydrobromide, imidocarb hydrochloride, ipronidazole, metronidazole, misonidazole, moxnidazole, nitarsone, partricin, puromycin, puromycin hydrochloride, ronidazole, sulnidazole, tinidazole.

Antipruritic: cyproheptadine hydrochloride, methdilazine, methdilazine hydrochloride, trimeprazine tartrate.

Antipsoriatic: acitretin, anthralin, azaribine, calcipotriene, cycloheximide, enazadrem phosphate, etretinate, liarozole fumarate, lonapalene, tepoxalin.

Antipsychotic: acetophenazine maleate, alentemol hydrobromide, alpertine, azaperone, batelapine maleate, benperidol, benzindopyrine hydrochloride, brofbxine, bromperidol, bromperidol decanoate, butaclamol hydrochloride, butaperazine, butaperazine maleate, carphenazine maleate, carvotroline hydrochloride, chlorpromazine, chlorpromazine hydrochloride, chlorprothixene, cinperene, cintriamide, clomacran phosphate, clopenthixol, clopimozide, clopipazan mesylate, cloroperone hydrochloride, clothiapine, clothixamide maleate, clozapine, cyclophenazine hydrochloride, droperidol, etazolate hydrochloride, fenimide, flucindole, flumezapine, fluphenazine decanoate, fluphenazine enanthate, fluphenazine hydrochloride, fluspiperone, fluspirilene, flutroline, gevotroline hydrochloride, halopemide, haloperidol, haloperidol decanoate, iloperidone, imidoline hydrochloride, lenperone, mazapertine succinate, mesoridazine, mesoridazine besylate, metiapine, milenperone, milipertine, molindone hydrochloride, naranol hydrochloride, neflumozide hydrochloride, ocaperidone, olanzapine, oxiperomide, penfluridol, pentiapine maleate, perphenazine, pimozide, pinoxepin hydrochloride, pipamperone, piperacetazine, pipotiazine palniitate, piquindone hydrochloride, prochlorperazine edisylate, prochlorperazine maleate, promazine hydrochloride, remoxipride, remoxipride hydrochloride, rimcazole hydrochloride, seperidol hydrochloride, sertindole, setoperone, spiperone, thioridazine, thioridazine hydrochloride, thiothixene, thiothixene hydrochloride, tioperidone hydrochloride, tiospirone hydrochloride, trifluoperazine hydrochloride, trifluperidol, triflupromazine, triflupromazine hydrochloride, ziprasidone hydrochloride.

Antirheumatic: auranofin, aurothioglucose, bindarit, lobenzarit sodium, phenylbutazone, pirazolac, prinomide tromethamine, seprilose.

Antischistosomal: becanthone hydrochloride, hycanthone, lucanthone hydrochloride, niridazole, oxamniquine, pararosaniline pamoate, teroxalene hydrochloride.

Antiseborrheic: chloroxine, piroctone, piroctone olamine, resorcinol monoacetate. antisecretory: arbaprostil, deprostil, fenoctimine sulfate, octreotide, octreotide acetate, omeprazole sodium, rioprostil, trimoprostil.

Antispasmodic: stilonium iodide, tizanidine hydrochloride.

Antithrombotic: anagrelide hydrochloride, bivalirudin, dalteparin sodium, danaparoid sodium, dazoxiben hydrochloride, efegatran sulfate, enoxaparin sodium, ifetroban, ifetroban sodium, tinzaparin sodium, trifenagrel.

Antitussive: benzonatate, butamirate citrate, chlophedianol hydrochloride, codeine polistirex, codoxime, dextromethorphan, dextromethorphan hydrobromide, dextromethorphan polistirex, ethyl dibunate, guaiapate, hydrocodone bitartrate, hydrocodone polistirex, levopropoxyphene napsylate, noscapine, pemerid nitrate, pipazethate, suxemerid sulfate.

Anti-ulcerative: aceglutamide aluminum, cadexomer iodine, cetraxate hydrochloride, enisoprost, isotiquimide, lansoprazole, lavoltidine succinate, misoprostol, nizatidine, nolinium bromide, pantoprazole, pifamine, pirenzepine hydrochloride, rabeprazole sodium, remiprostol, roxatidine acetate hydrochloride, sucralfate, sucrosofate potassium, tolimidone.

Anti-urolithic: cysteamine, cysteamine hydrochloride, tricitrates.

Appetite suppressant: dexfenfluramine hydrochloride, phendimetrazine tartrate, phentermine hydrochloride.

Benign prostatic hyperplasia therapy agent: tamsulosin hydrochloride.

Blood glucose regulators: human insulin, glucagon, tolazamide, tolbutamide, chloropropamide, acetohexamide and glipizide.

Bone resorption inhibitor: alendronate sodium, etidronate disodium, pamidronate disodium.

Bronchodilator: albuterol, albuterol sulfate, azanator maleate, bamifylline hydrochloride, bitolterol mesyl ate, butaprost, carbuterol hydrochloride, clorprenaline hydrochloride, colterol mesylate, doxaprost, doxofylline, dyphylline, enprofylline, ephedrine, ephedrine hydrochloride, fenoterol, fenprinast hydrochloride, guaithylline, hexoprenaline sulfate, hoquizil hydrochloride, ipratropium bromide, isoetharine, isoetharine hydrochloride, isoetharine mesylate, isoproterenol hydrochloride, isoproterenol sulfate, metaproterenol polistirex, metaproterenol sulfate, nisbuterol mesylate, oxtriphylline, picumeterol fumarate, piquizil hydrochloride, pirbuterol acetate, pirbuterol hydrochloride, procaterol hydrochloride, pseudoephedrine sulfate, quazodine, quinterenol sulfate, racepinephrine, racepinephrine hydrochloride, reproterol hydrochloride, rimiterol hydrobromide, salmeterol, salmeterol xinafoate, soterenol hydrochloride, sulfonterol hydrochloride, suloxifen oxalate, terbutaline sulfate, theophylline, xanoxate sodium, zindotrine, zinterol hydrochloride.

Carbonic anhydrase inhibitor: acetazolamide, acetazolamide sodium, dichlorphenamide, dorzolamide hydrochloride, methazolamide, sezolamide hydrochloride.

Cardiac depressant: acecamide hydrochloride, acetylcholine chloride, actisomide, adenosine, amiodarone, aprindine, aprindine hydrochloride, artilide fumarate, azimilide Dihydrochloride, bidisomide, bucamide maleate, bucromarone, butoprozine hydrochloride, capobenate sodium, capobenic acid, cifenline, cifenline succinate, clofilium phosphate, disobutamide, disopyramide, disopyramide phosphate, dofetilide, drobuline, edifolone acetate, emilium tosylate, encamide hydrochloride, flecamide acetate, ibutilide fumarate, indecamide hydrochloride, ipazilide fumarate, lorajmine hydrochloride, lorcamide hydrochloride, meobentine sulfate, mexiletine hydrochloride, modecamide, moricizine, oxiramide, pirmenol hydrochloride, pirolazamide, pranolium chloride, procainamide hydrochloride, propafenone hydrochloride, pyrinoline, quindonium bromide, quinidine gluconate, quinidine sulfate, recainam hydrochloride, recainam tosylate, risotilide hydrochloride, ropitoin hydrochloride, sematilide hydrochloride, suricamide maleate, tocamide, tocamide hydrochloride, transcamide.

Cardioprotectant: dexrazoxane, draflazine.

Cardiotonic: actodigin, aminone, bemoradan, butopamine, carbazeran, carsatrin succinate, deslanoside, digitalis, digitoxin, digoxin, dobutamine, dobutamine hydrochloride, dobutamine lactobionate, dobutamine tartrate, enoximone, imazodan hydrochloride, indolidan, isomazole hydrochloride, levdobutamine lactobionate, lixazinone sulfate, medorinone, milrinone, pelrinone hydrochloride, pimobendan, piroximone, prinoxodan, proscillaridin, quazinone, tazolol hydrochloride, vesnarinone.

Cardiovascular agent: dopexamine, dopexamine hydrochloride.

Choleretic: dehydrocholic acid, fencibutirol, hymecromone, piprozolin, sincalide, tocamphyl.

Cholinergic: aceclidine, bethanechol chloride, carbachol, demecarium bromide, dexpanthenol, echothiophate iodide, isoflurophate, methacholine chloride, neostigmine bromide, neostigmine methylsulfate, physostigmine, physostigmine salicylate, physostigmine sulfate, pilocarpine, pilocarpine hydrochloride, pilocarpine nitrate, pyridostigmine bromide.

Cholinergic agonist: xanomeline, xanomeline tartrate.

Cholinesterase deactivator: obidoxime chloride, pralidoxime chloride, pralidoxime iodide, pralidoxime mesylate.

Coccidiostat: arprinocid, narasin, semduramicin, semduramicin sodium.

Dognition adjuvant: ergoloid mesylates, piracetam, pramiracetam hydrochloride, pramiracetam sulfate, tacrine hydrochloride.

Cognition enhancer: besipirdine hydrochloride, linopirdine, sibopirdine.

Depressant: omeprazole.

Diagnostic aid: aminohippurate sodium, anazolene sodium, arclofenin, arginine, bentiromide, benzylpenicilloyl polylysine, butedronate tetrasodium, butilfenin, coccidioidin, corticorelin ovine triflutate, corticotropin, repository, corticotropin zinc hydroxide, diatrizoate meglumine, diatrizoate sodium, diatrizoic acid, diphtheria toxin for schick test, disofenin, edrophonium chloride, ethiodized oil, etifenin, exametazime, ferristenc, ferumoxides, ferumoxsil, fluorescein, fluorescein sodium, gadobenate dimeglumine, gadoteridol, gadodiamide, gadopentetate dimegiumine, gadoversetamide, histoplasmin, impromidine hydrochloride, indigotindisulfonate sodium, indocyanine green, lobenguane sulfate $I^{123}$, iobenzamic acid, iocarmate meglumine, locarmic acid, iocetamic acid, iodamide, lodamide megiumine, iodipamide meglumine, iodixanol, iodoxamate meglumine, iodoxamic acid, ioglicic acid, ioglucol, ioglucomide, ioglycamic acid, iogulamide, lohexyl, iomeprol, iopamidol, iopanoic acid, iopentol, iophendylate, iprofenin, iopronic acid, ioprocemic acid, iopydol, iopydone, iosefamic acid, ioseric acid, iosulamide meglumine, iosumetic acid, iotasul, iotetric acid, iothalamate meglumine, iothalamate sodium, iothalamic acid, iotrolan, iotroxic acid, ioversol, ioxaglate meglumine, ioxagiate sodium, ioxaglic acid, ioxilan, ioxotrizoic acid, ipodate calcium, ipodate sodium, isosulfan blue, leukocyte typing serum, lidofenin, mebrofenin, meglumine, metrizamide, metrizoate sodium, metyrapone, metyrapone tartrate, mumps skin test antigen, pentetic acid, propyliodone, quinaldine blue, sermorelin acetate, sodium iodide $I^{123}$, sprodiamide, stannous pyrophosphate, stannous sulfur colloid, succimer, teriparatide acetate, tetrofosmin, tolbutamide sodium, tuberculin, tyropanoate sodium, xylose.

Diuretic: ambuphylline, ambuside, amiloride hydrochloride, azolimine, azosemide, brocrinat, bumetanide, chlorothiazide, chlorthalidone, clazolimine, clorexolone, ethacrynate sodium, ethacrynic acid, etozolin, fenquizone, furosemide, hydrochlorothiazide, isosorbide, mannitol, mefruside, ozolinone, piretanide, spiroxasone, torsemide, triamterene, triflocin, urea.

Dopaminergic agent: ibopamine.

Ectoparasiticide: nifluridide, permethrin.

Emetic: apomorphine hydrochloride.

Enzyme inhibitor: acetohydroxamic acid, alrestatin sodium, aprotinin, benazepril hydrochloride, benazeprilat, benurestat, bromocriptine, bromocriptine mesylate, cilastatin sodium, fluorofamide, lergotrile, lergotrile mesylate, levcycloserine, libenzapril, pentopril, pepstatin, perindopril, polignate sodium, sodium amylosulfate, sorbinil, spirapril hydrochloride, spiraprilat, taleranol, teprotide, tolfamide, zofenopril calcium.

Estrogen: chlorotrianisene, dienestrol, diethylstilbestrol, diethylstilbestrol diphosphate, equilin, estradiol, estradiol cypionate, estradiol enanthate, estradiol undecylate, estradiol valerate, estrazinol hydrobromide, estriol, estrofurate, estrogens, conjugated, estrogens, esterified, estrone, estropipate, ethinyl estradiol, fenestrel, mestranol, nylestriol, quinestrol.

Fibrinolytic: anistreplase, bisobrin lactate, brinolase.

Free oxygen radical scavenger: pegorgotein.

Gastrointestinal motility agents: cisapride (PROPULSID™), metoclopramide (REGLAN™), hyoscyamine (LEVSIN™)

Glucocorticoid: amcinonide, beclomethasone dipropionate, betamethasone, betamethasone acetate, betamethasone benzoate, betamethasone dipropionate, betamethasone sodium phosphate, betamethasone valerate, carbenoxolone sodium, clocortolone acetate, clocortolone pivalate, coprednol, corticotropin, corticotropin, repository, corticotropin zinc hydroxide, cortisone acetate, cortivazol, descinolone acetonide, dexamethasone, dexamethasone sodium phosphate, diflucortolone, diflucortolone pivalate, flucloronide, flumethasone, flumethasone pivalate, flunisolide, fluocinolone acetonide, fluocinonide, fluocortolone, fluocortolone caproate, fluorometholone, fluperolone acetate, fluprednisolone, fluprednisolone valerate, flurandrenolide, formocortal, hydrocortisone, hydrocortisone acetate, hydrocortisone buteprate, hydrocortisone butyrate, hydrocortisone sodium phosphate, hydrocortisone sodium succinate, hydrocortisone valerate, medrysone, methylprednisolone, methylprednisolone acetate, methylprednisoloime sodium phosphate, methylprednisolone sodium succinate, nivazol, paramethasone acetate, prednicarbate, prednisolone, prednisolone acetate, prednisolone hemisuccinate, prednisolone sodium phosphate, prednisolone sodium succinate, prednisolone tebutate, prednisone, prednival, ticabesone propionate, tralonide, triamcinolone, triamcinolone acetonide, triamcinolone acetonide sodium, triamcinolone diacetate, triamcinolone hexacetonide.

Gonad-stimulating principle: buserelin acetate, clomiphene citrate, ganirelix acetate, gonadorelin acetate, gonadorelin hydrochloride, gonadotropin, chorionic, menotropins.

Hair growth stimulant: minoxidil.

Hemostatic: aminocaproic acid, oxamarin hydrochloride, sulmarin, thrombin, tranexarnic acid.

Histamine H2 receptor antagonists: ranitidine (ZANTAC™), famotidine (PEPCID™), cimetidine (TAGAMET™), nizatidine (AXID™)

Hormone: diethylstilbestrol, progesterone, 17 hydroxy progesterone, medroxyprogesterone, norgestrel, norethynodrel, estradiol, megestrol (megace), norethindrone, levonorgestrel, ethyndiol, ethinyl estradiol, mestranol, estrone, equilin, 17 alpha dihydroequilin, equilenin, 17 alpha dihydroequilenin, 17 alpha estradiol, 17 beta estradiol, leuprolide (LUPRON™), glucagon, testolactone, clomiphene, human menopausal gonadotropins, human chorionic gonadotropin, urofollitropin, bromocriptine, gonadorelin, luteinizing hormone releasing hormone and analogs, gonadotropins, danazol, testosterone, dehydroepiandrosterone, androstenedione, dihydroestosterone, relaxin, oxytocin, vasopressin, folliculostatin, follicle regulatory protein, gonadoctrinins, oocyte maturation inhibitor, insulin growth factor, follicle stimulating hormone, luteinizing hormone, tamoxifen., corticorelin ovine triftutate, cosyntropin, metogest, pituitary, posterior, seractide acetate, somalapor, somatrem, somatropin, somenopor, somidobove.

Hypocholesterolemic: lifibrol.

Hypoglycemic: darglitazone sodium: glimepiride.

Hypolipidemic: azalanstat dihydrochloride, colestolone, surfomer, xenalipin.

Hypotensive: viprostol.

Hmgcoa reductase inhibitors: lovastatin (MEVACOR™), simvastatin (ZOCOR™), pravastatin (PRAVACHOL™), fluvasatin (LESCOL™).

Immunizing agent: antirabies serum, antivenin (*latrodectus mactans*), antivenin (*micrurus fulvius*), antivenin (*crotalidae*) polyvalent, BCG vaccine, botulism antitoxin, cholera vaccine, diphtheria antitoxin, diphtheria toxoid, diphtheria toxoid adsorbed, globulin, immune, hepatitis b immune globulin, hepatitis B virus vaccine inactivated, influenza virus vaccine, measles virus vaccine live, meningococcal polysaccharide vaccine group A, meningococcal polysaccharide vaccine group C, mumps virus vaccine live, pertussis immune globulin, pertussis vaccine, pertussis vaccine adsorbed, plague vaccine, poliovirus vaccine inactivated, poliovirus vaccine live oral, rabies immune globulin, rabies vaccine, $Rh_o$ (D) immune globulin, rubella virus vaccine live, smallpox vaccine, tetanus antitoxin, tetanus immune globulin, tetanus toxoid, tetanus toxoid adsorbed, typhoid vaccine, yellow fever vaccine, vaccinia immune globulin, varicella-zoster immune globulin.

Immunomodulator: dimepranol acedoben, imiquimod, interferon beta-Ib, lisofylline, mycophenolate mofetil, prezatide copper acetate.

Immunoregulator: azarole, fanetizole mesylate, frentizole, oxamisole hydrochloride, ristianol phosphate, thymopentin, tilomisole.

Immunostimulant: loxoribine, teceleukin.

Immunosuppressant: azathioprine, azathioprine sodium, cyclosporine, daltroban, gusperimus trihydrochloride, sirolimus, tacrolimus.

Impotence therapy adjunct: delequamine hydrochloride.

Inhibitor: acarbose, atorvastatin calcium, benserazide, brocresine, carbidopa, clavulanate potassium, dazmegrel, docebenone, epoprostenol, epoprostenol sodium, episteride, finasteride, flurbiprofen sodium, furegrelate sodium, lufironil, miglitol, orlistat, pimagedine hydrochloride, pirmagrel, ponalrestat, ridogrel, sulbactam benzathine, sulbactampivoxil, sulbactam sodium, suronacrine maleate, tazobactam, tazobactam sodium, ticlopidine hydrochloride, tirilazad mesylate, tolrestat, velnacrine maleate, zifrosilone, zileuton.

Keratolytic: alcloxa, aldioxa, benzoyl peroxide, dibenzothiophene, etarotene, isotretinoin, motretinide, picotrin diolamine, resorcinol, resorcinol monoacetate, salicylic acid, sumarotene, tazarotene, tetroquinone, tretinoin.

LHRL agonist: deslorelin, goserelin, histrelin, lutrelin acetate, nafarelin acetate.

Liver disorder treatment: malotilate.

Luteolysin: fenprostalene.

Memory adjuvant: dimoxamine hydrochloride, ribaminol.

Mental performance enhancer: aniracetam.

Mood regulator: fengabine.

Mucolytic: acetylcysteine, carbocysteine, domiodol.

Mucosal protective agents: misoprostol (CYTOTEC™).

Mydriatic: berefrine.

Nasal decongestant: nemazoline hydrochloride, pseudoephedrine polistirex.

Neuroleptic: duoperone fumarate, risperidone.

Neuromuscular blocking agent: atracurium besylate, cisatracurium besylate, doxacurium chloride, gallamine triethiodide, metocurine iodide, mivacurium chloride, pancuronium bromide, pipecuronium bromide, rocuronium bromide, succinylcholine chloride, tubocurarine chloride, vecuronium bromide.

Neuroprotective: dizocilpine maleate.

NMDA antagonist: selfotel.

Non-hormonal sterol derivative: pregnenolone succinate.

Oxytocic: carboprost, carboprost methyl, carboprost tromethamine, dinoprost, dinoprost tromethamine, dinoprostone, ergonovine maleate, meteneprost, methylergonovine maleate, oxytocin, sparteine sulfate.

Plasminogen activator: alteplase, urokinase.

Platelet activating factor antagonist: lexipafant.

Platelet aggregation inhibitor: acadesine, beraprost, beraprost sodium, ciprostene calcium, itazigrel, lifarizine, oxagrelate.

Post-stroke and post-head trauma treatment: citicoline sodium.

Potentiator: pentostatin, talopram hydrochloride.

Progestin: algestone acetophenide, amadinone acetate, anagestone acetate, chlormadinone acetate, cingestol, clogestone acetate, clomegestone acetate, desogestrel, dimethisterone, dydrogesterone, ethynerone, ethynodiol diacetate, etonogestrel, fluorogestone acetate, gestaclone, gestodene, gestonorone caproate, gestrinone, haloprogesterone, hydroxyprogesterone caproate, levonorgestrel, lynestrenol, medrogestone, medroxyprogesterone acetate, methynodiol diacetate, norethindrone, norethindrone acetate, norethynodrel, norgestimate, norgestomet, norgestrel, oxogestone phenpropionate, progesterone, quingestanol acetate, quingestrone, tigestol.

Prostaglandin: cloprostenol sodium, fluprostenol sodium, gemeprost, prostalene, sulprostone.

Prostate growth inhibitor: pentomone.

Prothyrotropin: protirelin.

Psychotropic: minaprine.

Pulmonary surface: beractant, colfosceril palmitate.

Radioactive agent: fibrinogen $I^{125}$, fludeoxyglucose $F^{18}$, fluorodopa $F^{18}$, insulin $I^{125}$, insulin $I^{131}$, iobenguane $I^{123}$, iodipamide sodium $I^{131}$, iodoantipyrine $I^{131}$, iodocholesterol $I^{131}$, iodohippurate sodium $I^{123}$, iodohippurate sodium $I^{125}$, iodohippurate sodium $I^{131}$, iodopyracet $I^{125}$, iodopyracet $I^{131}$, iofetamine hydrochloride $I^{123}$, iomethin $I^{125}$, iomethin $I^{131}$, iothalamate sodium $I^{125}$, iothalamate sodium $I^{131}$, iotyrosine $I^{131}$, liothyronine $I^{125}$, liothyronine $I^{131}$, merisoprol acetate $Hg^{197}$, merisoprol acetate $Hg^{203}$, merisoprol $Hg^{197}$, selenomethionine $Se^{75}$, technetium $Tc^{99m}$ antimony trisulfide colloid, technetium $Tc^{99m}$ bicisate, technetium $Tc^{99m}$ disofenin, technetium $Tc^{99m}$ etidronate, technetium $Tc^{99m}$ exametazime, technetium $Tc^{99m}$ furifosmin, technetium $Tc^{99m}$ gluceptate, technetium $Tc^{99m}$ lidofenin, technetium $Tc^{99m}$ mebrofenin, technetium $Tc^{99m}$ medronate, technetium $Tc^{99m}$ medronate disodium, technetium $Tc^{99m}$ mertiatide, technetium $Tc^{99m}$ oxidronate, technetium $Tc^{99m}$ pentetate, technetium $Tc^{99m}$ pentetate calcium trisodium, technetium $Tc^{99m}$ sestamibi, technetium $Tc^{99m}$ siboroxime, technetium $Tc^{99m}$ succimer, technetium $Tc^{99m}$ sulfur colloid, technetium $Tc^{99m}$ teboroxime, technetium $Tc^{99m}$ tetrofosmin, technetium $Tc^{99m}$ tiatide, thyroxine $I^{125}$, thyroxine $I^{131}$, tolpovidone $I^{131}$, triolein $I^{125}$, triolein $I^{131}$.

Regulator: calcifediol, calcitonin, calcitriol, clodronic acid, dihydrotachysterol, etidronic acid, oxidronic acid, piridronate sodium, risedronate sodium, secalciferol.

Relaxant: adiphenine hydrochloride, alcuronium chloride, aminophylline, azumolene sodium, baclofen, benzoctamine hydrochloride, carisoprodol, chlorphenesin carbamate, chlorzoxazone, cinflumide, cinnamedrine, clodanolene, cyclobenzaprine hydrochloride, dantrolene, dantrolene sodium, fenalamide, fenyripol hydrochloride, fetoxylate hydrochloride, flavoxate hydrochloride, fletazepam, flumetramide, -flurazepam hydrochloride, hexafluorenium bromide, isomylamine hydrochloride, lorbamate, mebeverine hydrochloride, mesuprine hydrochloride, metaxalone, methocarbamol, methixene hydrochloride, nafomine malate, nelezaprine maleate, papaverine hydrochloride, pipoxolan.

Hydrochloride, quinctolate, ritodrine, ritodrine hydrochloride, rolodine, theophylline sodium glycinate, thiphenamil hydrochloride, xilobam.

Repartitioning agent: cimaterol.

Scabicide: amitraz, crotamiton.

Sclerosing agent: ethanolamine oleate, morrhuate sodium, tribenoside.

Sedative: propiomazine.

Sedative-hypnotic: allobarbital, alonimid, alprazolam, amobarbital sodium, bentazepam, brotizolam, butabarbital, butabarbital sodium, butalbital, capuride, carbocloral, chloral betaine, chloral hydrate, chlordiazepoxide hydrochloride, cloperidone hydrochloride, clorethate, cyprazepam, dexclamol hydrochloride, diazepam, dichloralphenazone, estazolam, ethchlorvynol, etomidate, fenobam, flunitrazepam, fosazepam, glutethimide, halazepam, lormetazepam, mecloqualone, meprobamate, methaqualone, midaflur, paraldehyde, pentobarbital, pentobarbital sodium, perlapine, prazepam, quazepam, reclazepam, roletamide, secobarbital, secobarbital sodium, suproclone, thalidomide, tracazolate, trepipam maleate, triazolam, tricetamide, triclofos sodium, trimetozine, uldazepam, zaleplon, zolazepam hydrochloride, zolpidem tartrate.

Selective adenosine a1 antagonist: apaxifylline.

Serotonin antagonist: altanserin tartrate, amesergide, ketanserin, ritanserin.

Serotonin inhibitor: cinanserin hydrochloride, fenclonine, fonazine mesylate, xylamidine tosylate.

Serotonin receptor antagonist: tropanserin hydrochloride.

Steroid: dexamethasone aceflrate, mometasone furoate.

Stimulant: amfonelic acid, amphetamine sulfate, ampyzine sulfate, arbutamine hydrochloride, azabon, caffeine, ceruletide, ceruletide diethylamine, cisapride, dazopride fumarate, dextroamphetamine, dextroamphetamine sulfate, difluanine hydrochloride, dimefline hydrochloride, doxapram hydrochloride, etryptamine acetate, ethamivan, fenethylline hydrochloride, flubanilate hydrochloride, fluorothyl, histamine phosphate, indriline hydrochloride, mefexamide, methamphetamine hydrochloride, methylphenidate hydrochloride, pemoline, pyrovalerone hydrochloride, xamoterol, xamoterol fumarate.

Suppressant: amfhutizole, coxchicine, tazofelone.

Symptomatic multiple sclerosis: fampridine.

Synergist: proadifen hydrochloride.

Thyroid hormone: levothyroxine sodium, liothyronine sodium, liotrix.

Thyroid inhibitor: methimazole, propylthiouracil.

Thyromimetic: thyromedan hydrochloride.

Tranquilizer: bromazepam, buspirone hydrochloride, chlordiazepoxide, clazolam, clobazam, clorazepate dipotassium, clorazepate monopotassium, demoxepam, dexmedetomidine, enciprazine hydrochloride, gepirone hydrochloride, hydroxyphenamate, hydroxyzine Hydrochloride, hydroxyzine pamoate, ketazolam, lorazepam, lorzafone, loxapine, loxapine succinate, medazepam hydrochloride, nabilone, nisobamate, oxazepam, pentabamate, pirenperone, ripazepam, rolipram, sulazepam, taciamine hydrochloride, temazepam, triflubazam, tybamate, valnoctamide.

Amyotrophic lateral sclerosis agents: riluzole.

Cerebral ischemia agents: dextrorphan hydrochloride.

Paget's disease agents: tiludronate disodium.

Unstable angina agents: tirofiban hydrochloride.

Uricosuric: benzbromarone, irtemazole, probenecid, sulfinpyrazone.

Vasoconstrictor: angiotensin amide, felypressin, methysergide, methysergide maleate.

Vasodilator: alprostadil, azaclorzine hydrochloride, bamethan sulfate, bepridil hydrochloride, buterizine, cetiedil citrate, chromonar hydrochloride, clonitrate, diltiazem hydrochloride, dipyridamole, droprenilamine, erythrityl tetranitrate, felodipine, flunarizine hydrochloride, fostedil, hexobendine, inositol niacinate, iproxamine hydrochloride, isosorbide dinitrate, isosorbide mononitrate, isoxsuprine hydrochloride, lidoflazine, mefenidil, mefenidil fumarate, mibefradil dihydrochloride, mioflazine hydrochloride, mixidine, nafronyl oxalate, nicardipine hydrochloride, nicergoline, nicorandil, nicotinyl alcohol, nifedipine, nimodipine, nisoldipine, oxfenicine, oxprenolol hydrochloride, pentaerythritol tetranitrate, pentoxifylline, pentrinitrol, perhexyline maleate, pindolol, pirsidomine, prenylamine, propatyl nitrate, suloctidil, terodiline hydrochloride, tipropidil hydrochloride, tolazoline hydrochloride, xanthinol niacinate.

Vulnerary: allantoin.

Wound healing agent: ersofermin.

Xanthine oxidase inhibitor: allopurinol, oxypurinol.

Other pharmaceutical agents include: 1-decpyrrolidinone, 1-dodecpyrrolidinone, 16α-fluoroestradiol, 16-epiestriol, 16α-gitoxin, 17α estradiol, 17β estradiol, 1alpha-hydroxyvitamin D2,2'-nor-cGMP, 20-epi-1,25 dihydroxyvitamin D3,22-oxacalcitriol, 2CVV, 3-isobutyl GABA, 6-FUDCA, 7-methoxytacrine, abamectin, abanoquil, abecarnil, abiraterone, acadesine, acamprosate, acarbose, aceclofenac, acemannan, acetomepregenol, acetyl-L-carnitine, acetylcysteine, N-acetylmethadol, acifran, acipimox, acitemate, acitretin, aclarubicin, aclatonium, napadisilate, aconiazide, acrivastinet, adafenoxate, adapalene, adatanserin, adecypenol, adefovir dipivoxil, adelmidrol, ademetionine, adinazolam, adiposin, adozelesin, adrafinil, alacepril, aladapcin, alaptide, albendazole, albolabrin, aldecalmycin, aldesleukin, alendronic acid, alentemol, alfacalcidol, alfuizosin, alglucerase, alinastine, alosetron, alpha idosone, alprostadil, altretamine, altromycin B, ambamustine, amelometasone, amesergide, amezinium metilsulfate, amfebutamone, amidox, amifloxacin, amifostine, amiodarone, amisulpride, amlexanox, amlodipine, amlodipine, ampiroxicam, aminone, amrubicin, amsacrine, amylin, amythiamicin, anagrelide, anakinra, ananain, anaritide, anastrozole, andrographolide, anordrin, apadoline, apafant, apaxifylline, aphidicolin glycinate, apraclonidine, aprosulate sodium, aptiganel, apurinic acid, aranidipine, arbekacin, arbidol, arbutamine, ardeparin sodium, arecatannin B1, argatroban, aripiprazol, arotinolol, asimadoline, aspalatone, asperfuran, aspoxicillin, astemizole, asulacrine, atamestanie, atenolol, S-atevirdine, atosiban, atovaquone, atpenin B, atrimustine, atrinositol, aureobasidin A, azadirachtine, azasetron, azatyrosine, azelaic acid, azelastine, azelnidipine, azimilide, azithromycin, azosemide, aztreonam, baccatin III, bacoside A, bacoside B, bactobolamine, balazipone, balhimycin, balofloxacin, balsalazide, bambuterol, baohuoside 1, bamidipine, basifungin, batebulast, batimastat, beauvericin, becaplermin, becliconazole, befloxatone, belfosdil, bellenamine, benflumetol, benidipine, benzisoxazole, benzochlorins, benzoidazoxan, benzoylstaurosporine, benztropine, bepridil, beractant, beraprost, berlafenone, bertosamil, besipirdine, beta-alethine, betaclamycin B, betamipron, betaxolol, betulinic acid, bevantolol, bicalutamide, bifemelane, birnakalim, bimithil, binospirone, bioxalomycin alpha2, biriperone, bis-benzimidazole A, bis-benzimidazole B, bisantrene, bisaramil, bisaziridinylspermine, bisnafide, bisoprolol, bistramide D, bistramide K, bistratene A, boldine, bopindolol, brefeldin, breflate, brimonidinc, bromfenac, bromperidol, bropirimine, bucindolol, budesonide, budipine, budotitane, bunaprolast, bunazosin, butenafine, buthionine sulfoximine, butixocort propionate, cadexomer iodine, calanolide A, calcipotriol, calphostin C, camonagrel, candesartan, candesartan cilexetil, candoxatril, candoxatrilat, capecitabine, capromab, capsaicin, captopril, carbazomycin C, carbetocin, carbovir, carboxamide-amino-triazole, carboxyamidotriazole, carboxymethylated β-1,3-glucan, carperitide, carteolol, carumonam, carvedilol, carvotroline, carzelesin, castanospermine, cebaracetam, cecropin B, cefcapene pivoxil, cefdaloxime pentexil tosilate, cefdinir, cefditoren pivoxil, cefepime, cefetamet, cefetamet pivoxil, cefixime, cefluprenam, cefmnetazole, cefmninox, cefodizime, cefoselis, cefotetan, cefotiam, cefotiam hexetil, cefozopran, cefpimizole, cefpiramide, cefpirome, cefpodoxime proxetil, cefprozil, cefsulodin, cefteram, ceftibuten, cefriaxone, cefuroxime axetil, celastrol, celikalim, celiprolol, cepacidine A, cericlamine, cerivastatin, ceronapril, certoparin sodium, cetiedil, cetirizine, chloroorienticin A, chloroorienticin B, chloroquinoxaline sulfonamide, cibenzoline, cicaprost, ciclesonide, cicletanine, cicloprolol, cidofovir, cilansetron, cilazapril, cilnidipine, cilobradine, cilostazol, cimetropium bromide, cinitapride, cinolazepam, cioteronel, ciprofibrate, ciprofloxacin, ciprostene, cis-porphyrin, cisapride, cisatracurium besilate, cistinexine, citalopram, citicoline, citreamicin alpha, cladribine, clarithromycin, clausenamide, cleboprdc, clinafloxacin, clobazam, clobetasone butyrate, clodronic acid, clomethiazole, clopidogrel, clotrimazole, colestimide, colfosceril palmitate, collismycin A, collismycin B, combretastatin A4, complestatin, conagenin, contignasterol, contortrostatin, cosalane, costatolide, cotinine, coumermycin A1, cucumariosid, curacin A, curdlan sulfate, curiosin, cyclazosin, cyclic HPMPC, cyclobenzaprine, cyclobut A, cyclobut G, cyclocapron, cycloplatam, cyclosin, cyclothialidine, cyclothiazomycin, cypemycin, cyproterone, cytarabine ocfosfate, cytochalasin B, dacliximab, dactimicin, daidzein, daidzin, dalfopristin, dalteparin sodium, danaparoid, daphnodorin A, dapiprazole, dapitant, darifenacin, darlucin A, darsidomine, ddUTP, decitabine, deferiprone, deflazacort, dehydrodidemnin B, dehydroepiandrosterone, delapril, delequamine, delfaprazine, delmopinol, delphinidin, deoxypyridinoline, deprodone, depsidomycin, deramciclane, dermatan sulfate, desflurane, desirudin, deslorelin, desmopressin, desogestrel, desoxoarniodarone, detajmium bitartrate, dexifosfamide, dexketoprofen, dexloxiglumide, dexmedetomidine, dexpemedolac, dexrazoxane, dexsotalol, dextrin 2-sulphate, dexverapamil, dezinamide, dezocine, diaziquone, diclofenac digolil, diclofenac potassium, dicranin, didemnin B, didox, dienogest, diethylhomospermine, diethylnorspermine, dihydrexidine, dihydro-5-azacytidine, dimethyl prostaglandin A 1, dimethylhomospermine, dimiracetam, dioxamycin, diphencyprone, diphenyl spiromustine, diprafenone, dipropylnorspermine, dirithromycin, discodermolide, disulfuram, ditekiren, docarpamine, docosanol, 1-dofetilide, dolasetron, domitroban, dopexamine, dorzolamide, dosmalfate, dotarizine, doxacurium chloride, doxazosin, doxifluridine, doxofylline, draculin, draflazine, droloxifene, dronabinol, drosperidone, drotaverine acephyllinate, droxicam, ebiratide, ebrotidine, ebselen, ecabapide, ecabet, ecadotril, ecdisteron, echicetin, echistatin, ecomustine, ecteinascidin 722, ecteinascidin 729, ecteinascidin 743, edaravone, edelfosine, edobacomab, edrecolomab, efegatran, eflornithine, efonidipine, eguelen, elcatonin, eletriptan, elgodipine, eliprodil, eltenac, emakalim, emedastine, emiglitate, emitefur, emoctakin, enadoline hydrochloride, enalapril, enazadrem, englitazone, enlimomab, enoxacin, enoxaparin sodium, enoximone, entacapone, enterostatin, epoprostenol, epoxymexrenone, epristeride, eprosartan, eptastigmine, erdosteine, ersentilide, ersofermin, erytlritol, esuprone, etanidazole, etanterol, ethacizin, ethinylestradiol, etizolam, etodolac, etoposide phosphate, etrabamine, everninomicin, examorelin, exemestane, fadrozole, faeriefungin, famciclovir, fampridine, fantofarone, faropenem, fasidotril, fasudil, fazarabine, fedotozine, felbamate, fenofibrate, fenoldopam, fenretinide, fenspiride, fenticonazole, fepradinol, ferpifosate sodium, ferristene, ferrixan, ferumoxsil, fexofenadine, flavopiridol, flecamide, flerobuterol, fleroxacin, flesinoxan, flezelastine, flobufen, flomoxef, florfenicol, florifenine, flosatidil, fluasterone, fluconazole, fludarabine, flumazenil, flumecinol, flumequine, flunarizine, fluocalcitriol, fluorodaunorunicin hydrochloride, fluoxetine, R-fluoxetine, S-fluparoxan, flupirtine, flurbiprofen axetil, flurithromycin, fluticasone propionate, flutrimazole, fluvastatin, fluvoxamine, forasartan, forfenimex, formestane, formoterol, formoterol, R,R-fosfomycin, trometamol, fosinopril, fosphenyloin, fostriecin, fotemustine, gabapentin, gadobenic acid, gadobutrol, gadodiamide, gadodiamide-EOB-DTPA, gadolinium texaphyrin, gadoteric acid, gadoteridol, gadoversetamide, galantamine, galdansetron, gallopamil, galocitabine, gamolenic acid, ganirelix, gepirone, gestrinone, girisopam, glaspimod, glaucocalyxin A, glutapyrone, glycopine, glycopril, granisetron, grepafloxacin, halichondrin B, halofantrine, halomon, halopredone, hatomamicin, hatomarubigin A, hatomarubigin B, hatomarubigin C, hatomarubigin D, ibogaine, ibopamine, ibudilast, illimaquinone, ilmofosine, ilomastat, iloperidone, iloprost, imidapril, imidazenil, indinavir, indolidan, indometacin farnesil, indometacin, tropine ester, indoramin, inocoterone, inogatran, inolimomab, interferon alfa, interferon alfa-2a, interferon alfa-2B, interferon alfa-N1, interferon alfa-N3, interferon β, interferon β-1 A1, interferon β-1B, interferon gamma-1A, interferon gamma-1B, interferon omega, interferon, consensus, interleukin-1, interleukin-1 alpha, interleukin-1 β, interleukin-10, interleukin-11, interleukin-12, interleukin-12, interleukin-15, interleukin-2, interleukin-3, interleukin-4, interleukin-5, interleukin-7, interleukin-8, iobenguane, iobitridol, iodoamiloride, iododoxorubicin, iofratol, iomeprol, iopentol, iopromide, iopyrol, iotriside, ioversol, ioxilan, ipazilide, IpdR, ipenoxazone, ipidacrine, ipomeanol, 4-ipriflavone, ipsapirone, irbesartan, irinotecan, irloxacin, irsogladine, irtemazole, isalsteine, isbogrel, isepamicin, isobengazole, isofloxythepin, isohomohalicondrin B, isopropyl unoprostone, isradipine, itameline, itasetron, itopride, itraconazole, ketoprofen, R-ketoprofen, S-ketorolac, lacidipine, lactitol, lactivicin, laennec, lafutidine, lamelrarin-N triacetate, lamifiban, lamivudine, lamotrigine, lanoconazole, lanperisone, lanreotide, lansoprazole, latanoprost, lateritin, laurocapram, lazabemide, lemefloxacin, lemildipine, leminoprazole, lenercept, lenograstim, lentinan sulfate, leptin, leptolstatin, lercanidipine, lerisetron, lesopitron, letrazuril, letrozole, leucomyzin, leuprorelin, levcromakalim, levetiracetam, levobetaxolol, levobunolol, levobupivacaine, levocabastine, levocamitine, levodropropizine, levofloxacin, levomoprolol, levonorgestrel, levormeloxifene, levosimendan, levosulpiride, linotroban, linsidomine, lintitript, lintopride, liothyronine sodium, lirexapride, lisinopril, lobaplatin, lobucavir, lodoxamide, lombricine, lomefloxacin, lomerizine, lometrexol, lonazolac, lonidamine, loracarbef, loratadine, lorglumide, lornoxicam, losartan, losigamone, losoxantrone, loteprednol, loviride, loxoribine, lubeluzole, lurtotecan, luteinizing hormone, lutetium, luzindole, lydicamycin, lysofylline, lysostaphin, magainin 2 amide, magnolol, mallotochromene, mallotojaponin, malotilate, mangafodipir, manidipine, maniwamycin A, mannostatin A, manumycin E, manumycin F, mapinastine, marimastat, masoprocol, maspin, massetolide, meterelin, methoxatone, methylhistamine, R-alpha, methylinosine monophosphate, methylprednisolone aceponate, methylprednisolone suleptanate, metipamide, metoclopramide, metoprolol, S-metrifonate, mibefradil, michellarnine B, microcolin A, midodrine, mifepristone, miglitol, milacemide, milameline, mildronate, milnacipran, milrinone, miltefosine, minaprine, miokamycin, mipragoside, mirfentanil, mirimostim, mirtazapine, misoprostol, mitoguazone, mitolactol, mitonafide, mitoxantrone, mivacurium chloride, mivazerol, mixanpril, mizolastine, mizoribine, moclobemide, modafinil, moexipril, mofarotene, mofezolac, molgramostim, mometasone, montirelin, mopidamol, moracizine, mosapramine, mosapride, motilide, moxiraprine, moxonidine, nadifloxacin, nadroparin calcium, nafadotride, nafamostat, nafarelin, naftopidil, naglivan, nagrestip, nalmefene, naphterpin, napsagatran, naratriptan, nartograstim, nasaruplase, nateplase, niperotidine, niravoline, nisamycin, nisin, nisoldipine, nitazoxanide, nitecapone, nitrendipine, nitrendipine, S-nitrofurantoin monohydrate, nitrullyn, nizatidine, ofloxacin, okicenone, olanzapine, olopatadine, olprinone, olsalazine, omeprazole, onapristone, ondansetron, ondansetron, R-ontazolast, oracin, otenzepad, oxaliplatin, oxamisole, oxandrolone, oxaprozin, oxaunomycin, oxcarbazepine, oxiconazole, oxiracetam, oxodipine, ozagrel, palauamine, palinavir, palmitoylrhizoxin, pamaqueside, pamicogrel, pamidronic acid, panamesine, panaxytriol, panipenem, panipenum, pannorin, panomifene, pantethine, pantoprazole, parabactin, pamaparin sodium, paroxetine, parthenolide, pazelliptine, pazufloxacin, pefloxacin, pegaspargase, peldesine, pemedolac, pemirolast, penciclovir, pentafuside, pentamidine, pentamorphone, pentigetide, pentosan, pentostatin, pentrozole, perflubron, perfosfamide, pergolide, perindoprilat, perospirone, phenaridine, phenazinomycin, phenserine, phensuccinal, phentolamine mesilate, phenylacetate, phenylalanyl ketoconazole, picenadol, picibanil, picroliv, picumeterol, pidotimod, pilocarpine hydrochloride, pilsicamide, pimagedine, pimilprost, pimobendan, pinacidil, pinocebrin, pioglitazone, pipecuronium bromide, pirarubicin, piretanide, pirfenidone, piritrexim, pirlindole, pirmagrel, pirmenol, pirodavir, pirodomast, piroxicam cinnamate, propagermanium, propentofylline, propionylcamitine, L-propiram, propiram+paracetamol, propiverine, propyl bis-acridone, prostaglandin J2, prostratin, protegrin, protosufloxacin, prulifloxacin, pyrazoloacridine, quazepam, quetiapine, quiflapon, quinagolide, quinapril, quinfamide, quinupristin, raloxifene, raltitrexed, ramatroban, ramipril, ramosetron, ranelic acid, ranitidine bismuth citrate, ranolazine, recainam, regavirumab, relaxin, repirinast, resinferatoxin, reticulon, reviparin sodium, revizinone, ricasetron, ridogrel, rifabutin, rifapentine, rifaximin, rilopirox, riluzole, rimantadine, rimexolone, rimoprogin, riodipine, ripisartan, risedronic acid, rispenzepine, risperidone, ritanserin, ritipenem, ritipenem acoxil, ritolukast, ritonavir, rizatriptan benzoate, rohitukine, rokitamycin, ropinirole, ropivacaine, roquinimex, roxatidine, roxindole, roxithromycin, rubiginone B1, ruboxyl, rufloxacin, rupatidine, ruzadolane, safingol, safironil, saintopin, salbutamol, R-salmeterol, salmeterol, R-sainacedin, sameridine, sampatrilat, sanfetrinem, saprisartan, sapropterin, saquinavir, sarcophytol A sargramostim, sarpogrelate, saruplase, saterinone, satigrel, satumomab pendetide, selegiline, selenium thiosemicarbazone, sematilide, semduramicin, semotiadil, semustine, sermorelin, sertaconazole, sertindole, sertraline, setiptiline, sevirumab, sevoflurane, sezolamide, silipide, silteplase, simendan, simvastatin, sinitrodil, sinnabidol, sipatrigine, sirolimus, sizofuran, somatomedin B, somatomedin C, somatrem, somatropin, sonermin, stalol, staurosporine, stavudine, stepronin, stipiamide, stiripentol, stobadine, succibun, sucralfate, sulfasalazine, sulfmosine, sulfoxamine, sulopenem, sultamicillin, sultopride, sulukast, sumatriptan, symakalim, tandospirone, tapgen, taprostene, tasosartan, tazanolast, tazarotene, teicoplanin, telenzepine, tellurapyrylium, telmesteine, telmisartan, temocapril, temoporfin, temozolomide, tenidap, teniposide, tenosal, tenoxicam, tepirindole, tepoxalin, terazosin, terbinafine, terfenadine, terflavoxate, terguride, terlakiren, terlipressin, terodiline, tertatolol, testosterone buciclate, tetrachlorodecaoxide, tetrazomine, thaliblastine, thalidomide, thiocoraline, thiofedrine, thiomarinol, thioperamide, thyroid stimulating hormone, tiagabine, tianeptine, tiapafant, tibolone, ticlopidine, tienoxolol, tilisolol, tilnoprofen arbamel, tiludronic acid, tinzaparin sodium, tiotropium bromide, tipredane, tiqueside, tirandalydigin, tirapazamine, tirilazad, tirofiban, tiropramide, topsentin, torasemide, toremifene, tosufloxacin, trafermin, trandolapril, traxanox, tretinoin, tretinoin tocoferil, triacetyluridine, tricaprilin, trichohyalin, trichosanthin, alpha, triciribine, trientine, triflavin, trimegestone, triptorelin, troglitazone, trombodipine, tropisetron, trospectomycin, trovafloxacin, trovirdine, tucaresol, tulobuterol, tylogenin, urapidil, uridine triphosphate, valaciclovir, valproate magnesium, valproate semisodium, valsartan, vamicamide, vanadeine, vaninolol, vapreotide, variolin B, velaresol, venlafaxine, veramine, verapamil, S-verdins, veroxan, verteporfin, vesnarinone, vexibinol, vigabatrin, vinbumine citrate, vinbumine resinate, vinconate, vinorelbine, vinpocetine, vinpocetine citrate, vintoperol, vinxaltine, voriconazole, vorozole, voxergolide, xemilofiban, ximoprofen, yangambin, zabicipril, zacopride, zacopride, R-zafirlukast, zalcitabine, zaleplon, zalospirone, zaltoprofen, zanamivir, zankiren, zanoterone, zatebradine, zatosetron, zenarestat, zeniplatin, zifrosilone, zilascorb, zileuton, zinostatin stimalamer, ziprasidone, zoledronic acid, zolmitriptan, zolpidem, zonisamide, zopiclone, zopiclone, S-zopolrestat, zotepine.

Specific Examples of Antibacterials

When antibacterial activity is a desired property of the disclosed ionic liquids, one or more of the ions in the disclosed ionic liquids can be an antibacterial. That is the one or more kinds of cations, one or more kinds of anions, or both cations and anions can be an antibacterial. Many of suitable antibacterial have already been disclosed herein (e.g., many QACs have antibacterial properties). Further examples of suitable antibacterial agents include, but are not limited to, acedapsone, acetosulfone sodium, alamecin, alexidine, amdinocillin, amdinocillin pivoxil, amicycline, amifloxacin, amifloxacin mesylate, amikacin, amikacin sulfate, aminosalicylic acid, aminosalicylate sodium, amoxicillin, amphomycin, ampicillin, ampicillin sodium, apalcillin sodium, apramycin, aspartocin, astromicin sulfate, avilamycin, avoparcin, azithromycin, azlocillin, azlocillin sodium, bacampicillin hydrochloride, bacitracin, bacitracin methylene disalicylate, bacitracin zinc, bambermycins, benzoylpas calcium, berythromycin, betamicin sulfate, biapenem, biniramycin, biphenamine hydrochloride, bispyrithione magsulfex, butikacin, butirosin sulfate, capreomycin sulfate, carbadox, carbenicillin disodium, carbenicillin indanyl sodium, carbenicillin phenyl sodium, carbenicillin potassium, carumonam sodium, cefaclor, cefadroxil, cefamandole, cefamandole nafate, cefamandole sodium, cefaparole, cefatrizine, cefazaflur sodium, cefazolin, cefazolin sodium, cefbuperazone, cefdinir, cefepime, cefepime hydrochloride, cefetecol, cefixime, cefmenoxime hydrochloride, cefmetazole, cefmetazole sodium, cefonicid monosodium, cefonicid sodium, cefoperazone sodium, ceforanide, cefotaxime sodium, cefotetan, cefotetan disodium, cefotiam hydrochloride, cefoxitin, cefoxitin sodium, cefpimizole, cefpimizole sodium, cefpiramide, cefpiramide sodium, cefpirome sulfate, cefpodoxime proxetil, cefprozil, cefroxadine, cefsulodin sodium, ceftazidime, ceftibuten, ceftizoxime sodium, ceftriaxone sodium, cefuroxime, cefuroxime axetil, cefuroxime pivoxetil, cefuroxime sodium, cephacetrile sodium, cephalexin, cephalexin hydrochloride, cephaloglycin, cephaloridine, cephalothin sodium, cephapirin sodium, cephradine, cetocycline hydrochloride, cetophenicol, chloramphenicol, chloramphenicol palmitate, chloramphenicol pantothenate complex, chloramphenicol sodium succinate, chlorhexidine phosphanilate, chloroxylenol, chlortetracycline bisulfate, chlortetracycline hydrochloride, cinoxacin, ciprofloxacin, ciprofloxacin hydrochloride, cirolemycin, clarithromycin, clinafloxacin hydrochloride, clindamycin, clindamycin hydrochloride, clindamycin palmitate hydrochloride, clindamycin phosphate, clofazimine, cloxacillin benzathine, cloxacillin sodium, cloxyquin, colistimethate sodium, colistin sulfate, coumermycin, coumermycin sodium, cyclacillin, cycloserine, dalfopristin, dapsone, daptomycin, demeclocycline, demeclocycline hydrochloride, demecycline, denofungin, diaveridine, dicloxacillin, dicloxacillin sodium, dihydrostreptomycin sulfate, dipyrithione, dirithromycin, doxycycline, doxycycline calcium, doxycycline fosfatex, doxycycline hyclate, droxacin sodium, enoxacin, epicillin, epitetracycline hydrochloride, erythromycin, erythromycin acistrate, erythromycin estolate, erythromycin ethylsuccinate, erythromycin gluceptate, erythromycin lactobionate, erythromycin propionate, erythromycin stearate, ethambutol hydrochloride, ethionamide, fleroxacin, floxacillin, fludalanine, flumequine, fosfomycin, fosfomycin tromethamine, fumoxicillin, furazolium chloride, furazolium tartrate, fusidate sodium, fusidic acid, gentamicin sulfate, gloximonam, gramicidin, haloprogin, hetacillin, hetacillin potassium, hexedine, ibafloxacin, imipenem, isoconazole, isepamicin, isoniazid, josamycin, kanamycin sulfate, kitasamycin, levofuraltadone, levopropylcillin potassium, lexithromycin, lincomycin, lincomycin hydrochloride, lomefloxacin, lomefloxacin hydrochloride, lomefloxacin mesylate, loracarbef, mafenide, meclocycline, meclocycline sulfosalicylate, megalomicin potassium phosphate, mequidox, meropenem, methacycline, methacycline hydrochloride, methenamine, methenamine hippurate, methenamine mandelate, methicillin sodium, metioprim, metronidazole hydrochloride, metronidazole phosphate, mezlocillin, mezlocillin sodium, minocycline, minocycline hydrochloride, mirincamycin hydrochloride, monensin, monensin sodiumr, nafcillin sodium, nalidixate sodium, nalidixic acid, natainycin, nebramycin, neomycin palmitate, neomycin sulfate, neomycin undecylenate, netilmicin sulfate, neutramycin, nifuiradene, nifuraldezone, nifuratel, nifuratrone, nifurdazil, nifurimide, nifiupirinol, nifurquinazol, nifurthiazole, nitrocycline, nitrofurantoin, nitromide, norfloxacin, novobiocin sodium, ofloxacin, onnetoprim, oxacillin sodium, oximonam, oximonam sodium, oxolinic acid, oxytetracycline, oxytetracycline calcium, oxytetracycline hydrochloride, paldimycin, parachlorophenol, paulomycin, pefloxacin, pefloxacin mesylate, penamecillin, penicillin G benzathine, penicillin G potassium, penicillin g procaine, penicillin g sodium, penicillin V, penicillin V benzathine, penicillin V hydrabamine, penicillin V potassium, pentizidone sodium, phenyl aminosalicylate, piperacillin sodium, pirbenicillin sodium, piridicillin sodium, pirlimycin hydrochloride, pivampicillin hydrochloride, pivampicillin pamoate, pivampicillin probenate, polymyxin B sulfate, porfiromycin, propikacin, pyrazinamide, pyrithione zinc, quindecamine acetate, quinupristin, racephenicol, ramoplanin, ranimycin, relomycin, repromicin, rifabutin, rifametane, rifamexil, rifamide, rifampin, rifapentine, rifaximin, rolitetracycline, rolitetracycline nitrate, rosaramicin, rosaramicin butyrate, rosaramicin propionate, rosaramicin sodium phosphate, rosaramicin stearate, rosoxacin, roxarsone, roxithromycin, sancycline, sanfetrinem sodium, sarmoxicillin, sarpicillin, scopafungin, sisomicin, sisomicin sulfate, sparfloxacin, spectinomycin hydrochloride, spiramycin, stallimycin hydrochloride, steffimycin, streptomycin sulfate, streptonicozid, sulfabenz, sulfabenzamide, sulfacetamide, sulfacetamide sodium, sulfacytine, sulfadiazine, sulfadiazine sodium, sulfadoxine, sulfalene, sulfamerazine, sulfameter, sulfamethazine, sulfamethizole, sulfamethoxazole, sulfamonomethoxine, sulfamoxole, sulfanilate zinc, sulfanitran, sulfasalazine, sulfasomizole, sulfathiazole, sulfazamet, sulfisoxazole, sulfisoxazole acetyl, sulfisboxazole diolamine, sulfomyxin, sulopenem, sultamricillin, suncillin sodium, talampicillin hydrochloride, teicoplanin, temafloxacin hydrochloride, temocillin, tetracycline, tetracycline hydrochloride, tetracycline phosphate complex, tetroxoprim, thiamphenicol, thiphencillin potassium, ticarcillin cresyl sodium, ticarcillin disodium, ticarcillin monosodium, ticlatone, tiodonium chloride, tobramycin, tobramycin sulfate, tosufloxacin, trimethoprim, trimethoprim sulfate, trisulfapyrimidines, troleandomycin, trospectomycin sulfate, tyrothricin, vancomycin, vancomycin hydrochloride, virginiamycin, and zorbamycin.

Penicillin G, which is used as an antibacterial agent for infections including pneumonia, meningitis, and skin, bone, joint, stomach, blood, and heart valve infections, is a particular example suitable for use herein. tazobactum, sold under the trade names ZOSYN™ and TAZOCIN™, ceftrioxone, sold under the trade name ROCEPHIN™, and metronidazol, sold under the trade name FLAGYL™, are also used to treat bacterial infections and are further examples of suitable compounds that can be used to prepare the disclosed ionic liquids.

These and other suitable antibacterials can be identified based on the desired properties of the antibacterial and whether the antibacterial active is or can be converted into an ion. As noted, identification of whether an antibacterial active is an ion or can be converted into an ion can be done by a skilled artisan inspecting the chemical structure of the antibacterial.

Specific Examples of Antiviral

When antiviral activity is a desired property of the disclosed ionic liquids, one or more of the ions in the disclosed ionic liquids can be an antiviral. Examples of suitable antiviral actives include, but are not limited to, acemannan, acyclovir, acyclovir sodium, adefovir, alovudine, alvircept sudotox, amantadine hydrochloride, aranotin, arildone, atevirdine mesylate, pyridine, cidofovir, cipamfylline, cytarabine hydrochloride, delavirdine mesylate, desciclovir, didanosine, disoxaril, edoxudine, enviradene, enviroxime, famciclovir, famotine hydrochloride, fiacitabine, fialuridine, fosarilate, foscarnet sodium, fosfonet sodium, ganciclovir, ganciclovir sodium, idoxuridine, kethoxal, lamivudine, lobucavir, memotine hydrochloride, methisazone, nevirapine, penciclovir, pirodavir, ribavirin, rimantadine hydrochloride, saquinavir mesylate, somantadine hydrochloride, sorivudine, statolon, stavudine, tilorone hydrochloride, trifluridine, valacyclovir hydrochloride, vidarabine, vidarabine phosphate, vidarabine sodium phosphate, viroxime, zalcitabine, zidovudine, zinviroxime, and Tamiflu.

These and other suitable antivirals can be identified based on the desired properties of the antiviral and whether the antiviral is or can be converted into an ion. As noted, identification of whether an antiviral is an ion or can be converted into an ion can be done by a skilled artisan inspecting the chemical structure of the antiviral.

Specific Examples of Pesticidal Actives

When pesticidal activity is a desired property of the disclosed ionic liquids, one or more of the ions in the disclosed ionic liquids can be a pesticide. Included within the meaning of "pesticide" are insecticides and fungicides. Examples of suitable pesticides include, but are not limited to, carfentrazone-ethyl, sulfentrazone, clomazone, diclofop-methyl, oxamyl propargite, prosulfuron, pyridate, pyriftalid, S-metolachlor, simazine, terbuthylazine, terbutryn, triasulfuron, trifloxysulfuron, trinexapac-ethyl, ametryn, atrazine, benoxacor, bifenthrin, butafenacil, choline azide, chlortoluron, cinosulfuron, clodinafop, cloquintocet, DEET, desmetryn, dicamba, dimethachlor, dimethametryn, DTPA NaFe, EDDHA NaFe, fenclorim, flumetralin, fluometuron, fluthiacetmethyl, halosulfuron, isoproturon, metobromuron, metolachlor, norflurazon, oxasulfuron, piperophos, pretilachlor, primisulfuron, prometryn, propaquizafop, acibenzolar-s-methyl, chlorothalonil, cyproconazole, cyprodinil, difenoconazole, fenpropidin, fenpropimorph, furalaxyl, metalaxyl, metalaxyl-m, oxadixyl, penconazole, propiconazole, pyrifenox, thiabendazol, abamectin, bromopropylate, cypermethrin, cypermethrin high-cis, cyromazine, diafenthiuron, diazinon, dichlorvos, disulfoton, emamectinbenzoate, fenoxycarb, formothion, furathiocarb, lufenuron, methidathion, permethrine, codlemone, phosphamidon, profenofos, pymetrozine, quinalphos, terrazole, thiamethoxam, thiocyclam, thiometon, triallate, trifloxystrobin, vinclozolin, zetacypermethrin, and the like. Prohexadione is a FDA approved reduced risk fungicide and is also useful for the disclosed ionic liquids. Further examples of suitable pesticides can be found in The Pesticide Manual, 11$^{th}$ Edition, British Crop Protection Council, 1997, which is incorporated by reference herein at least for its teaching of pesticides.

These and other suitable pesticides can be identified based on the desired properties of the pesticide and whether the pesticide is or can be converted into an ion. As noted, identification of whether a pesticide is an ion or can be converted into an ion can be done by a skilled artisan inspecting the chemical structure of the pesticide.

Specific Examples of Herbicidal Actives

When herbicidal activity is a desired property of the disclosed ionic liquids, one or more of the ions in the disclosed ionic liquids can be a herbicide. Examples of suitable herbicides include, but are not limited to, carfentrazone, imazapyr, benefin, acifluorfen, and 2-[2-chloro-3-(2,2,2-trifluoroethoxymethyl)-4-methylsulfonylbenzoyl]cyclohexane-1.

Other suitable herbicides include inhibitors of the biosynthesis of branched amino acids such as ethoxysulfuron, flumetsulam, halosulfuron, imazamox, imazapyr, imazaquin, imazethapyr, metosulam, nicosulfuron, primisulfuron, prosulfuron, rimsulfuron, thifensulfuron-methyl, triflusulfuron, N-[(4,6-dimethoxypyrimidin-2-yl)aminocarbonyl]-2-dimethylaminocarbonyl-5-formylaminobenzenesulfonamide (Foramsulfuron), and the like. Still further, suitable herbicides include inhibitors of the photosynthesis electron transport such as ametryne, atrazine, bromoxynil, cyanazine, diuron, hexazinone, metribuzin, pyridate, terbuthylazine, and the like. In yet further examples, suitable herbicides for the disclosed ionic liquids include synthetic auxins such as copyralid, dicamba, diflufenzopyr, fluoroxypyr, and the like. Inhibitors of fatty acid biosynthesis, such as butylate, EPTC, fenoxaprop-P-ethyl, and the like, can also be used in the disclosed ionic liquid compositions. In other examples, suitable herbicides can include inhibitors of cell division such as acetochlor, alachlor, dimethenamid, flufenacet, mefenacet, metolachlor, S-metolachlor, thenylchlor, and the like. In still other examples, the herbicide can be an inhibitor of protoporphyrinogen oxidase, such as fluthiacet-methyl, carfentrazone-ethyl, and the like. Inhibitors of hydroxyphenylpyruvate dioxygenase, such as isoxaflutole, mesotrione, sulcotrione, 4-(4-trifluoromethyl-2-methylsulfonylbenzoyl)-5-hydroxy-1-methyl-3-methylpyrazole, and the like, can also be used. Further examples of suitable herbicides include, but are not limited to, glyphosate, pendimethalin, trifluralin, asulam, triaziflam, diflufenican, glufosinate-ammonium, and the like. Clofencet, fluoroxypyr, mesosulfuron, diflufenzopyr are further examples of suitable herbicides and they are FDA approved.

Specific Examples of Other Ions

In addition to the pharmaceutical, antibacterial, antiviral, pesticidal, and herbicidal actives disclosed herein, other compounds that are ions or can be converted to ions can be used in the disclosed ionic liquid compositions. Specific examples of these include, but are not limited to, the food additives Allura Red AC (FD&C Red No. 40), Tartrazine (FD&C Yellow No. 5), Indigotine (FD&C Blue No. 2), Erythrosine (FD&C Red No. 3), and Sunset Yellow (FD&C Yellow No. 6), which are FDA-approved color additives for food use. Further, nutraceuticals such as fatty acids, cholesterols, vitamins, minerals, and trace elements can be suitable ions for the disclosed ionic liquid compositions. SEA-NIN-211 is an antifoulant that can be used as an ion id the disclosed compositions.

Specific Examples of Energetics

The disclosed ionic liquid compositions can also include high energy ingredients as well as explosive materials. The ability to prepare a particular composition with high energy content substituents (fuel) on one ion and high oxygen balance (oxidizers) on the other ion opens wide applicability in today's high energy compounds industry. The ability to independently form differentially functionalized groups of ions, then chose two of interest and combining them on demand to form desired strength energetic material (Scheme 1) opens the doors for the quick preparation of customizable energetic materials (e.g., explosives with pre-designed power) and more safe storage technique of those energetic materials since the components are separated before usage. The disclosed compositions can be prepared according to one of the following reaction protocols.

Scheme 1: Protocol 1

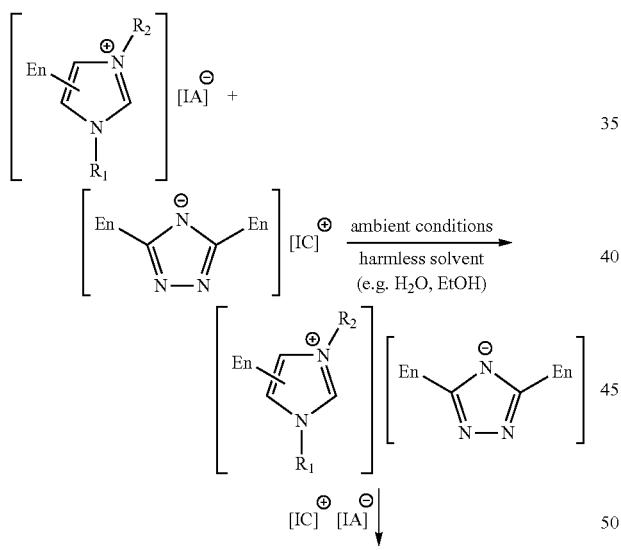

where En is an energetic functional group containing either high oxygen or nitrogen content (including but not limited to: nitro, amino, cyano, azido, alkyl nitro, alkyl amino, alkyl cyano, alkyl azido, alkoxy nitro, alkoxy amino, alkoxy cyano, and alkoxy azido), IA⁻ is an innocuous anion, IC+ is an innocuous cation, and [IC][IA] is an easily removable and harmless byproduct from the metathesis reaction. The reaction proceeds via ion exchange reaction in solvent system media (solvent system is the solvent or the mixture of the solvents in which at least one of the starting materials dissolves). The solvents (or solvent) with substrates dissolved in them separately are being combined, the byproduct is being separated from the product (by solvent extraction or precipitation) (Katritzky et al., "1-Butyl-3-methylimidazolium 3,5-dinitro-1,2,4-triazolate: a Novel IL Containing a Rigid, Planar Energetic Anion," Chem Commun 868, 2005, which is incorporated by reference herein).

Examples of those ionic liquid compositions include, but are not limited to, the mixture of at least two components of functionalized 5- and 6-membered, and bicyclic fused ring heterocyclic cations and anions containing 1, 2, 3, 4, or 5 atoms of nitrogen in the ring structure, where all carbon and nitrogen atoms in the ring structure can be functionalized with additional substituents such as alkyl, allyl, aryl, nitro, nitrile, azido, hydroxyl, carboxylic acid, ester, amide, amine, aldehyde, ketone, epoxy, or functionalized alkyl and aryl groups (with any functional mentioned above). Examples of such components (cations and/or anions) are shown below.

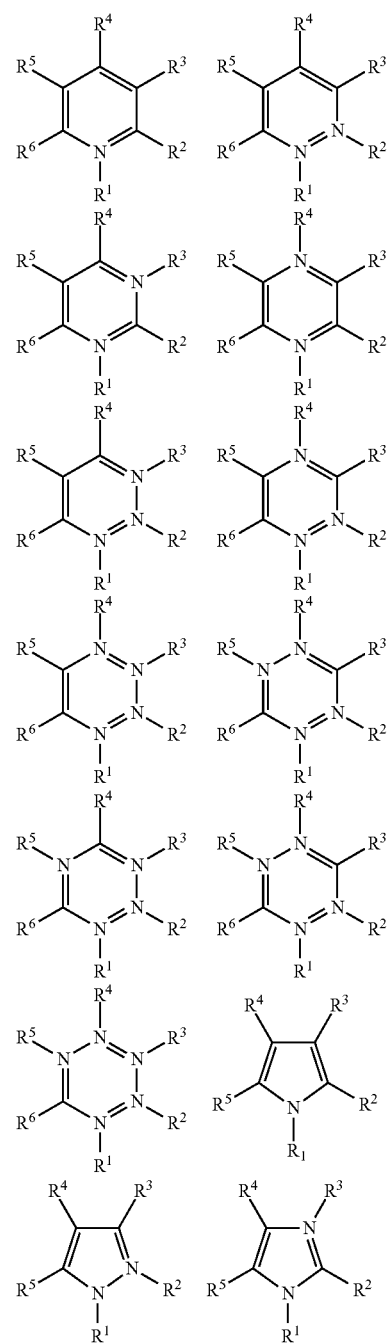

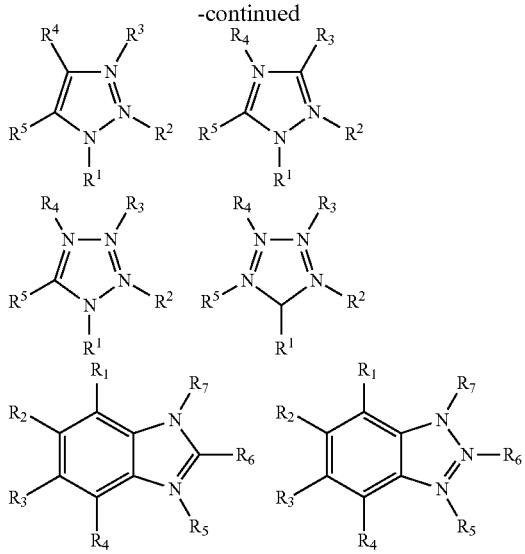

where $R^1$, $R^2$, $R^3$, $R^4$, $R^5$, $R^6$, and $R^7$, are, independent of one another, not present, H, alkyl, alkenyl, alkynyl, allyl, aryl, nitro, amino, cyano, azido, alkyl nitro, alkyl amino, alkyl cyano, alkyl azido, alkoxy nitro, alkoxy amino, alkoxy cyano, and alkoxy azido, nitrile, isonitrile, carboxylic acid, ester, ether, $CO_2NR^8{}_2$, $CO_2NHR^8$, $CO_2NH_2$, amine, $NHR^8$, $NR^8{}_2$, ketone, aldehyde, or epoxy, wherein $R^8$ is H, alkyl, alkenyl, alkynyl, allyl, aryl, carboxylic acid, ester, ether, ketone, or aldehyde.

Scheme 1: Protocol 2

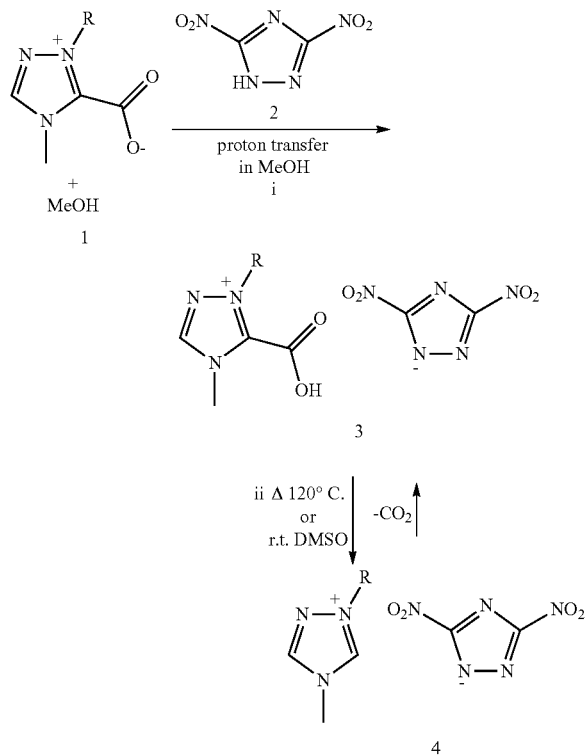

Utilizing this protocol, model compounds (4), which may undergo further modification in terms of introduced functions (on the cation precursor (1), anion precursors (2), and homologous heterocycle core (both 1, and 2) (e.g., but not limited to: imidazole, triazole, tetrazole, benzimidazole, and benztriazole systems) can be formed.

The protocol for the formation of azolium azolate salts via the reaction of two neutral components requires: zwitterionic cation precursor (1) with carboxylate group appended on the heterocycle core, and neutral heterocycle (2) with the pKa value lower then that of carboxylate group in cation precursor (1). The reaction can be carried in any solvent systems (pure solvent or mixture of solvents) that allows for the dissolution of both components, or without solvents at all. The reaction protocol comprises the following steps:

Proton transfer reactions (protonation of carboxylate group in zwitterionic cation precursor (1); (step i) which is thermodynamically favored due to the difference in the pKa values of the zwitterionic salt carboxylate group and azolate anion (formed from deprotonation of anion precursor (2)).

Decarboxylation of the system containing the protonated carboxylic acid group on the cation precursor in the intermediate (cationic part of compound 3) (step ii). The decarboxyaltion may be performed in the presence of either polar solvents (e.g., but not limited to, DMSO, DMF, THF, trialkylamine, $H_2O$) or heat (temp between 25° C.-150° C.). Additionally, the driving force for this conversion is the production of gaseous $CO_2$ which, upon removal from the reaction mixture, shifts the thermodynamic equilibrium in favor of product formation.

Examples of those ionic liquid compositions made utilizing above protocol include, but are not limited to, the mixture of at least two components of functionalized 5-, 6-membered, and bicyclic fused ring heterocyclic cation precursors and anion precursors containing 1, 2, 3, 4, or 5 atoms of nitrogen in the ring structure.

The cation precursors are neutral, zwitterionic species (neutral molecule that within itself contains both: cation and anion species) containing at least one cationic site (e.g., but not limited to, protonated or alkylated nitrogen atom) and one anionic site (carboxylate (COO—) group). In the cation precursors all carbon and nitrogen atoms in the ring structure can be functionalized with additional substituents such as alkyl, allyl, aryl, nitro, nitrile, azido, hydroxyl, carboxylic acid, ester, amide, amine, aldehyde, ketone, epoxy, or functionalized alkyl and aryl groups (with any functional mentioned above).

The anion precursors are neutral, substituted, or not substituted, heterocyclic species containing at least one acidic proton site on any of the nitrogen atoms. This hydrogen atom will be utilized for the proton transfer reaction and consecutive decarboxylation reaction to form final azolium azolate product (4) as described in the protocol above. In the anion precursors all carbon and nitrogen atoms in the ring structure can be functionalized with additional substituents such as alkyl, allyl, aryl, nitro, nitrile, azido, hydroxyl, carboxylic acid, ester, amide, amine, aldehyde, ketone, epoxy, or functionalized alkyl and aryl groups (with any functional mentioned above).

Examples of such components (cation precursors and/or anion precursors) are shown below.

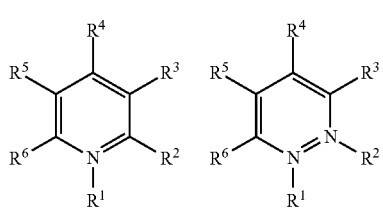

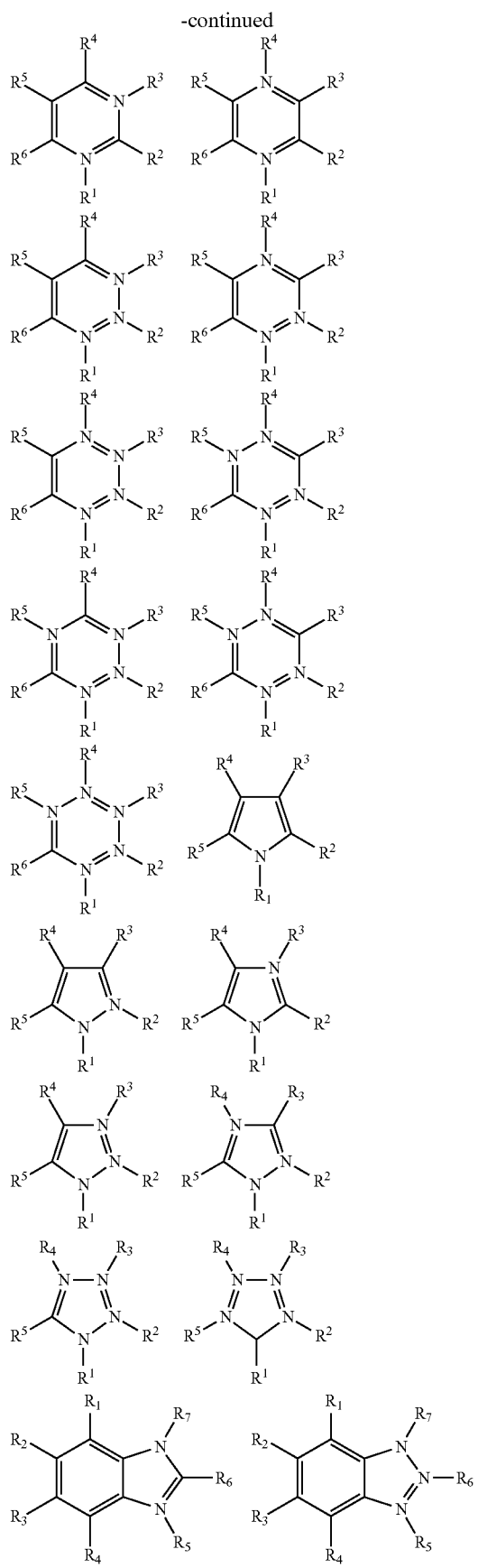
-continued where for the cation precursor: at least one of the $R^1$-$R^9$ substituent groups (only among the ones directly appended to carbon in heterocyclic ring) can be a carboxylate anion group. The remaining groups can be, independent of one another, not present, H, alkyl, alkenyl, alkynyl, allyl, aryl, nitro, amino, cyano, azido, alkyl nitro, alkyl amino, alkyl cyano, alkyl azido, alkoxy nitro, alkoxy amino, alkoxy cyano, and alkoxy azido, isonitrile, carboxylic acid, ester, ether, $CO_2NR^8_2$, $CO_2NHR^8$, $CO_2NH_2$, amine, $NHR^8$, $NR^8_2$, ketone, aldehyde, or epoxy, wherein $R^8$ is H, alkyl, alkenyl, allynyl, allyl, aryl, carboxylic acid, ester, ether, ketone, or aldehyde.

And, where for the anion precursor: at least one of the $R^1$-$R^9$ substituent groups (only among the once directly appended to nitrogen in heterocyclic ring) can be an H atom suitable for deprotonation to form stable heterocyclic azolate anion. The remaining groups can be, independent of one another, not present, H, alkyl, alkenyl, alkynyl, allyl, aryl, nitro, amino, cyano, azido, alkyl nitro, alkyl amino, alkyl cyano, alkyl azido, alkoxy nitro, alkoxy amino, alkoxy cyano, and alkoxy azido, isonitrile, carboxylic acid, ester, ether, $CO2NR^8_2$, $CO_2NHR^8$, $CO_2NH_2$, amine, $NHR^8$, $NR^8_2$, ketone, aldehyde, or epoxy, wherein $R^8$ is H, alkyl, alkenyl, alkynyl, allyl, aryl, carboxylic acid, ester, ether, ketone, or aldehyde.

Specific Ionic Liquids

Because the disclosed ionic liquid compositions can have multiple functionalities or properties, each arising from the various ions that make up the ionic liquid, the disclosed ionic liquid compositions can be custom designed for numerous uses. As disclosed herein, any combination of cations and anions, as disclosed herein, can be made as long as the combination results in an ionic liquid as described herein. That is, any compound or active disclosed herein that has a given charge or can be made to have a given charge (the "first ion(s)") can be combined with any other compound or active disclosed herein having a charge opposite to that of the first ion(s) or any compound that can be made to have a charge opposite to that of the first ion(s). Thus, in many examples, the ionic liquid compositions can have one type of cation and one type of anion, in a 1:1 relationship, so that the net charge of the ionic liquid is zero.

Furthermore, many of the ions disclosed herein can have multiple charges. Thus, when one ion having a multiple charge is used, more counterion(s) is needed, which will affect the ratio of the two ions. For example, if a cation having a plus 2 charge is used, then twice as much anion having a minus 1 charge is needed. If a cation having a plus 3 charge is used, then three times as much anion having a minus 1 charge is needed, and so on. While the particular ratio of ions will depend on the type of ion and their respective charges, the disclosed ionic liquids can have a cation to anion ratio of 1:1, 2:1, 3:1, 4:1, 1:3, 2:1, 3:2, 2:3, and the like.

Many of the ionic liquid compositions disclosed herein can also have more than one different kind of cation and/or more than one different kind of anion. The use of more than one kind of cation and/or anion can be particularly beneficial when one prepares an ionic liquid composition comprising two or more bioactive ions that are not desired to be in a 1:1 relationship. In other words, according to the disclosed methods, ionic liquid compositions that contain varying effective amounts (or doses) of active substances can be prepared by varying the ratios of ions in the composition, as long as the total amount of cations is balanced by the total amount of anions. For example, an ionic liquid composition disclosed herein can contain one type of cation with a given property and two different anions (e.g., a first and second anion), each with another different property. The resulting ionic liquid in this example will be 1 part cation, 0.5 part first anion, and 0.5 part second anion. Another example of this adjustment in ion amounts can arise when one ion is particularly potent and thus dilution is desired. For example, a first cation that is particularly potent can be combined with a second (or third, forth, etc.) cation that is inert or has so other property that is desired. When these cations are combined with one or more kinds of anions to form an ionic liquid, the amount of the first cation is diluted by the other the cation(s). As will be appreciated, many other such variations in the amount of cations and anions can be present in the disclosed methods and compositions. Thus, while specific ionic liquid compositions having particular combinations of cations and anions are disclosed herein, it is understood that the ratio of the particular ions can be varied or adjusted by adding other ions, so long as there is a balance of charge and the final composition is an ionic liquid.

When the disclosed ionic liquid compositions have two or more ions with a bioactive property (e.g., pharmaceutical active ingredients, pesticidal actives, herbicidal actives, and the like), these compositions can be particularly desired because each of the active ingredients in the composition would have the same solubility and would dissolve together when formulated or administered. This can be particularly useful when overcoming formulation, solubility, bioavailability, size, and polymorphism issues. Further, when exact dosages of an active ingredient are needed, the active ingredient as an ion can be combined with a counterion that is innocuous or GRAS (generally recognized as safe). As noted above, for example, if one active ingredient (cation) is needed at half the dosage of another active ingredient (anion), then an innocuous cation could be used as filler to balance the charges. This same concept applies if more cation is needed than anion.

A few specific examples of ionic liquid compositions prepared from combinations of quaternary ammonium compounds and saccharinates or acesulfamates have been demonstrated. Burgard disclosed a process for preparing hexadecylpyridinium acesulfamate and its use in the oral hygiene sector (Eur Pat Appl 2003-1270580 A1; US Pat Appl 2003-023084 A1). Hydrophilic quaternary ammonium sacchrinates and acesulfamates and hydrophobic phosphonium acesulfamates have been recently published (Carter et al., *Chem Comm*, 2004, 630-631; Pernak et al., *Eur J Org Chem*, 2005, 650-652). Saccharin, acting as a weak acid, can form salts with basic active pharmaceutical ingredients including tertiary amines to form quaternary nitrogen atoms (Bhatt et al., *Chem Comm*, 2005, 1073-1075). Also known in the literature is N-hexadecylpyridinium saccharinate (CAS No. 7428-34-4).

Some other specific examples of the disclosed ionic liquids include, but are not limited to, ionic liquids where any of the cations in the ionic liquid are aliphatic benzylalkyl ammonium cations (e.g., benzalkonium), dialiphatic dialkyl ammonium cations (e.g., didecyldimethylammonium), and aliphatic heteroaryl cations (e.g., hexadecylpyridinium) are combined with any of the anions of sulfacetamide, ibuprofen, and saccharinate.

Benzalkonium (BA) is used chiefly as an antiseptic and disinfectant. It is found in many over the counter and prescription eye products, disinfectants, shampoos, and deodorants. It also acts as a preservative in many pharmaceutical preparations. Didecyldimethylammonium (DDA) is used as an antiseptic and surfactant. N-hexadecylpyridinium (HEX) is used as an antiseptic agent alone or in combination with other drugs for oral and throat care. HEX is essentially non-toxic and can be applied to the skin or mucous membranes.

Sulfacetamide is used to control antibacterial activity and is sold under the trade name KLARON™ in the treatment of acne. Ibuprofen is used as an anti-inflammatory and pain reliever. Saccharinate is used as a sweetener.

Some specific examples of suitable ionic liquids include, but are not limited to, benzalkonium sulfacetamide (BA-sulfacetamide), didecyldimethylammonium sulfacetamide (DDA-sulfacetamide), N-hexadecylpyridinium sulfacetamide (HEX-sulfacetamide), benzalkonium ibuprofen (BA-ibuprofen), didecyldimethylammonium ibuprofen (DDA-ibuprofen), N-hexadecylpyridinium ibuprofen (HEX-ibuprofen), and benzalkonium acesulfamate, didecyldimethylammonium acesulfamate, N-hexadecylpyridinium acesulfamate, and benzalkonium saccharinate (BA-SAC).

In other examples, an ion that is antiseptic can be combined with an ion that is antibacterial agent. For example, an ionic liquid can comprise benzalkonium and sulfacetamide, which is shown in formula X.

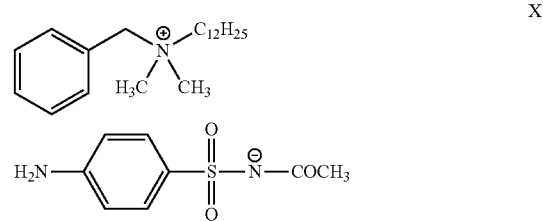

Another example is the combination of didecyldimethylammonium sulfacetamide, which is shown in formula XI.

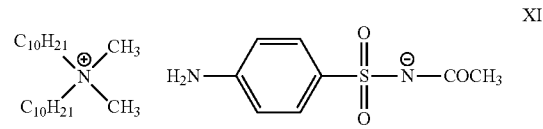

Still another example is the combination of N-hexadecylpyridinium sulfacetamide, which is shown in formula XII.

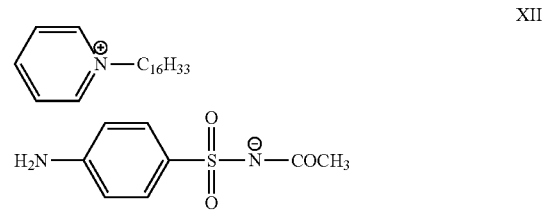

Such antiseptic/antibacterial compositions can be used in the treatment of wounds, for example, wounds near the scalp where a composition with both disinfectant and antibacterial properties is desirable. Such compounds could also be used for skin care, e.g., to treat acne.

In still further examples, an ion that is antibacterial can be combined with an anti-inflammatory and/or pain reliever. Such compositions can be used as a disinfectant and for pain relief. For example, an ionic liquid can comprise benzalkonium and ibuprofen, which is shown in formula XIII.

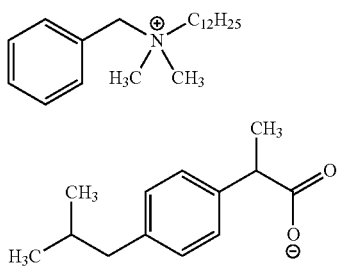

XIII

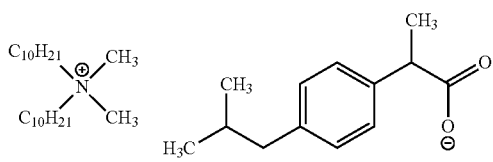

Also, the ionic liquid composition can comprise didecyldimethylammonium and ibuprofen, which is shown in formula XIV.

XIV

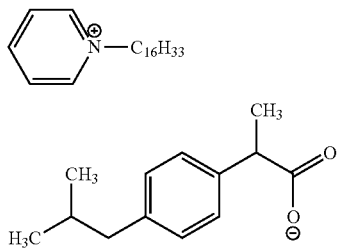

Further, the ionic liquid composition can comprise N-hexadecylpyridinium and ibuprofen, which is shown in formula XV.

XV

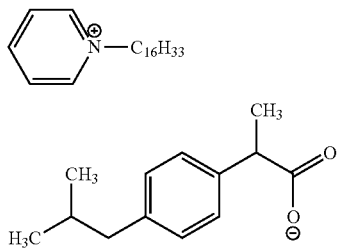

In other examples of ionic liquid compositions disclosed herein, an ion that is an antibacterial can be combined with an ion that is a sweetener. Such compositions can be used to improve the taste of medicines and hygiene products and can be used in, for example, toothpaste, and children's medicine. Some specific examples of such ionic liquids is prepared by combining the antibacterial agents benzalkonium, didecyldimethylammonium, or N-hexadecylpyridinium and the sweetener acesulfamate, as shown in formulas XVI, XVII, and XVIII, respectively.

XVI

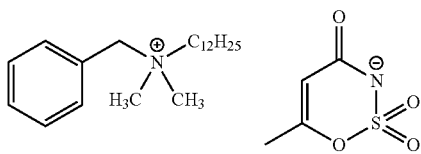

-continued

XVII

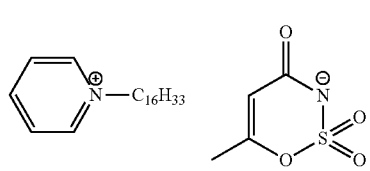

XVIII

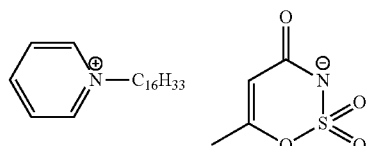

The antibacterial agents benzalkonium, didecyldimethylammonium, and N-hexadecylpyridinium can also be combined with the sweetener saccharinate, as shown in formulas XIV, XX, and XXI, respectively.

XIX

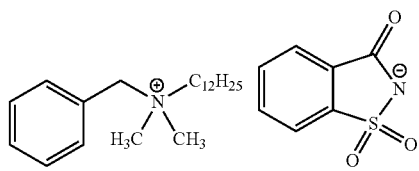

XX

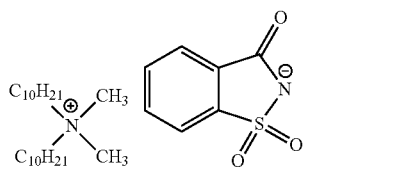

XXI

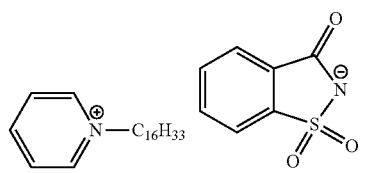

In still other examples, the ionic liquid composition can comprise an ion that is an antibacterial agent with an ion that is a UV-blocker, such as trans-cinnamate. Such compositions can be used as disinfectants and for protection against UV radiation, as would be desirable for treating wounds exposed to the Sun's radiation. Specific examples of such composition include, but are not limited to, compositions where the cation is an antibacterial agent such as benzalkonium, didecyldimethylammonium, or N-hexadecylpyridinium, and the anion is trans-cinnamate, as is shown in formulas XXII, XXIII, and XXIV respectively.

XXII

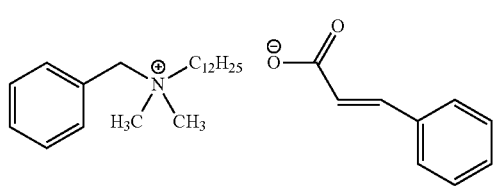

-continued

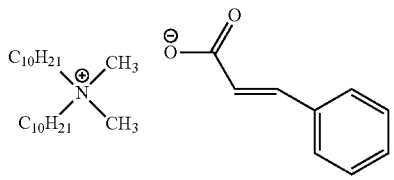
XXIII

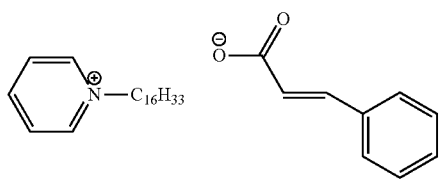
XXIV

In still other examples, the disclosed ionic liquids can comprise an ion that is an antibacterial and an ion that can provide wetting and controls reaction rate, particle size, viscosity, polymer molecular weight, and stability in emulsion polymerization systems, e.g., sodium dihexylsulfosuccinate (e.g., Colawet MA-80 from Colonial Chemicals, South Pittsburg, Tenn.)). Specific examples of such compositions include, but are not limited to, compositions where the cation is an antibacterial agent such as benzalkonium, didecyldimethylammonium, or n-hexadecylpyridinium, and the anion is Colawet MA-80, as shown in formulas XXV, XXVI, and XXVII, respectively.

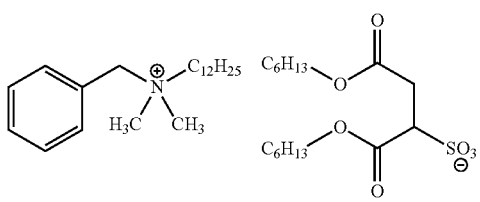
XXV

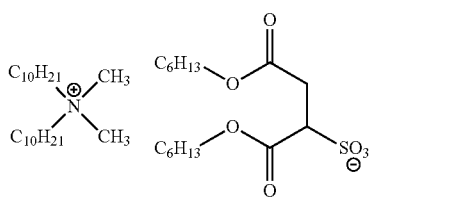
XXVI

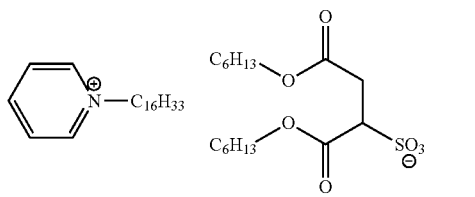
XXVII

In further examples, the disclosed ionic liquid compositions can comprise an ion that is antibacterial and an ion that is a food colorant. Examples of such ionic liquid compositions include, but are not limited to, compositions where the cation is an antibacterial agent such as benzalkonium, didecyldimethylammonium, or N-hexadecylpyridinium, and the anion is Fast Green FCF, an FDA approved color additive that provides a sea green hue and is used in products such as beverages, puddings, ice cream, sherbet, cherries, confections, baked goods, and dairy products. Other food coloring anions, which are well known in the art, can be used as well.

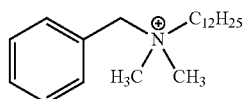
XXVIII

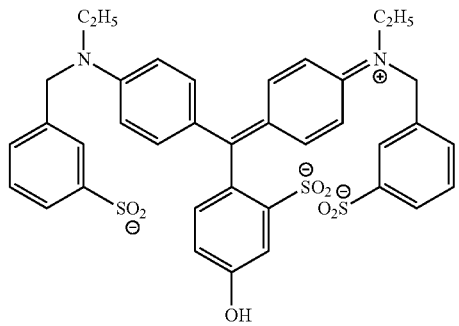

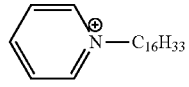
XXIX

XXX

In still further examples, the disclosed ionic liquid compositions can comprise a cation that is an antibacterial and an anion that is an antibacterial. For example, the cationic antibacterial agents disclosed herein can be combined with the anionic piperacillin, which is an extended-spectrum penicillin. Piperacillin is primarily used in the treatment of susceptible infections such as septicemia, acute and chronic respiratory tract infections, skin and soft tissue infections, and urinary tract infections.

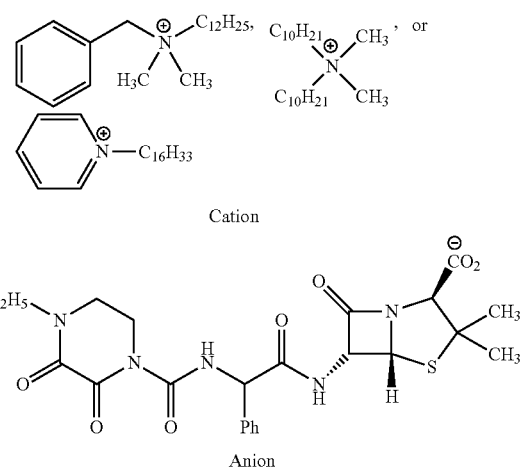

Cation

Anion

Still further specific examples of the disclosed ionic liquid compositions are those where the anion is benzoate and the cation comprises one or more of (2-acetoxyethyl)-dodecyloxymethyldimethylammonium, (2-acetoxyethyl)-heptyloxymethyldimethylammonium, (2-hydroxyethyl)-cyclododecyloxymethyldimethylammonium, or (2-hydroxyethyl)-dimethylundecyloxymethylammonium.

Other examples of the disclosed ionic liquid compositions are those where the cation comprises benzalkonium, didecyldimethylammonium, or N-hexadecylpyridinium and the anion comprises one or more of acesulfamate, benzoate, colawet ma-80, fast green FCF, ibuprofen, penicillin G, piperacillin, saccharinate, salicylate, salicylate, sulfacetamide, trans-cinnamate, sulfathiazole, thimerosal, valproic acid, mepenzolate, docusate. In three specific examples, benzalkonium is combined with mepenzolate and docusate in a 1:1:2 ratio, a 2:1:3 ratio, or a 1:2:3 ration. In another example, benzalkonium is combined with sulfathiazole and saccharinate in a 2:1:1 ratio.

Further specific examples of the disclosed ionic liquid compositions are those where the cation is didecyldimethylammonium and the anion comprises one or more of saccharinate, (S)-6-methoxy-α-methyl-2-naphthaleneacetate, 2-[(2,6-dichlorophenyl)amino]-benzeneacetate, 2-[(2,6-dichlorophenyl)amino]-benzeneacetate, 2-acetoxybenzoate, acesulfamate, benzoate, colawet ma-80, fast green FCF, ibuprofen, mandelate, N-[4-[[(2-amino-1,4-dihydro-4-oxo-6-pteridinyl)methyl]amino]benzoyl]-L-glutamate, nicotinate, penicillin G, piperacillin, p-toluenesulfonate, salicylate, sulfacetamide, or trans-cinnamate.

Other specific examples of the disclosed ionic liquid compositions are those where the cation is hexadecylpyridinium and the anion comprises one or more of colawet ma-80, fast green FCF, penicillin G, piperacillin, or sulfacetamide.

Still further specific examples of the disclosed ionic liquid compositions are those where the cation is hexadecylpyridinium and the anion comprises one or more of clofencet, fluoroxypyr, diflufenzopyr, mesosulfuron, prohexadione, pantoprazole, risedronate, losartan, rabeprazole, fosinopril, ceftioxone, atorvastatin, pravastatin, alendronate, montelukast, tazobactam, Allura Red AC, tartrazine, indigotine, erythrosine, or Sunset Yellow.

Further specific examples of the disclosed ionic liquid compositions are those where the cation is didecyldimethylammonium and the anion comprises one or more of clofencet, fluoroxypyr, diflufenzopyr, mesosulfuron, prohexadione, pantoprazole, risedronate, losartan, rabeprazole, fosinopril, ceftioxone, atorvastatin, pravastatin, alendronate, montelukast, tazobactam, Allura Red AC, tartrazine, indigotine, erythrosine, or Sunset Yellow.

Other specific examples of the disclosed ionic liquid compositions are those where the cation is benzalkonium and the anion comprises one or more of clofencet, fluoroxypyr, diflufenzopyr, mesosulfuron, prohexadione, pantoprazole, risedronate, losartan, rabeprazole, fosinopril, ceftioxone, atorvastatin, pravastatin, alendronate, montelukast, tazobactam, Allura Red AC, tartrazine, indigotine, erythrosine, or Sunset Yellow.

Still further examples include the compositions docusate lidocaine, miconazole/econazole docusate, streptomycin docusate, and isoniazide docusate. Docusate combined with any of the cationic 5 and 6 membered quaternary ammonium ring compounds disclosed herein are also contemplated herein.

Still further examples include a cation that is an anticholinergic like mepenzolate and the anion is docusate.

Another example comprises itraconazole, which inhibits cytochrome p540 oxidase mediated synthesis of ergosterol. Itraconazole is a 1:1:1 racemic mixture of four diastereomers comprising 2 enantiomeric pairs. Generally, it has poor adsorption especially when given in capsule form. This is though to occur because 99.8% of the drug becomes bound to proteins in the body. It has been shown that absorption is improved with acid as the pKa is 3.70; therefore, it is recommended that this drug be taken with orange juice. The compound is insoluble in water, slightly soluble in alcohol, and freely soluble in dichloromethane. This compound can be combined with any of the anions disclosed herein, for example, sulfacetamide, colawet MA-80, and docusate.

Also contemplated are ionic liquids that are prodrugs. A prodrug is a pharmacologically inactive compound that is converted to an active drug by a metabolic biotransformation. Prodrugs are used when there are concerns regarding a drugs solubility, absorption and distribution, site specificity, stability, prolonged release, toxicity, patient acceptability, and formulation concerns. Carrier linked prodrugs are also contemplated. A carrier linked prodrug is a compound that contains an active drug linked to a carrier group that can be removed enzymatically, such as an ester, which is hydrolyzed to an active carboxylicacid containing drug. Other types of carrier linkages include alcohols and carboxylic acids, amines, and carbonyl compounds. Also contemplated are mutual prodrugs, which comprise two drugs attached to each other where one is the carrier for the other and vice versa.

Still further examples include compositions comprising lidocaine and silver. This composition has a component that is functional for topical anesthesia (lidocaine) with one Ag+ that has antimicrobial properties. This can be used in conjunction with lidocaine docusate, as described herein, to create ointments or bandage materials that are capable of providing a palliative effect as well as suppression of microorganism growth. Similarly, silver docusate can be prepared, which can provide a lipophilic salt of silver that would be soluble in lidocaine docusate, other ILs, or even non-IL crème bases, for end-use as a topical antimicrobial agent.

Still further examples include compositions comprising ranitidine and docusate. This compound can generate a rather lipophilic, hydrophobic version of ranitidine, which would be both non-crystalline and sufficiently sluggish in its rate of dissolution against biofluids that it could serve as a slow-release form of the drug. Lidocain docusate is another example contemplated herein.

Methods

The disclosed ionic liquid compositions can be prepared by combining one or more kinds of cations or cation precursors with one or more kinds of anions or anion precursor.

Providing of the particular ions is largely based on the identifying desired properties of the ion (e.g., its charge and whether it has a particular bioactivity that is desired to be present in the resulting ionic liquid). Methods of identifying suitable ions are disclosed herein, for example, by considering the chemical structure and charge of the compounds and whether the ion combination will produce an ionic liquid.

Typically, when preparing an ionic liquid composition as disclosed herein, an ion that minimizes coulombic interactions by diffusing its charge over several atoms in the ion is identified. An example of this is the alkylheteroaryl cations disclosed herein where the positive charge is spread over the atoms of the heteroaryl ring. Then a weakly coordinating counterion, which also delocalizes charge over several atoms, is chosen. In general, more-complex and higher molecular weight cations and anions have a greater number of intermolecular contacts, which serves to raise melting point and increase the viscosity of the ionic liquid composition.

Further, when preparing an ionic liquid composition as disclosed herein, molecular asymmetry can be particularly desired. Low-symmetry cations and anions typically reduce packing efficiency in the crystalline state and lower melting points.

It is also desirable that the cation should not be more nucleophilic than the neutral form of the cation. If this is the case, then suitable anions can be selected by considering their pKa. For example, by utilizing the pKa of acid functionalized compounds and the pKb of base functionalized compounds, one can combine the neutral species of acids and bases into one neutral compound possessing the functions of both compounds. To successfully produce an ionic liquid by this method, the pKa or pKb of compound A should be different by approximately 5 orders of magnitude from the pKa or pKb of compound B. This insures that the acidity or basicity at that hydrogen is sufficient to remove or add a hydrogen at that position. This will then produce an anion on the acidic compound and a cation on the basic compound.

One method for identifying a suitable ion combination for preparing an ionic liquid as disclosed herein is by computer program. It is also possible to use a computer to select various cation and anion combinations. For example, the program called ERWIN™, sold by Computer Associates (Islandia, N.Y.), can be used. This computer program is comprised of two models: a forward model which predicts the melting points and drug delivery rates of a formulation of ionic liquids, and a backwards model will allow the user to select which type of pharmaceutical agents that are desired along with liquid range and delivery rates and the program will give all the formulations which meet these criterion.

Figure 3:
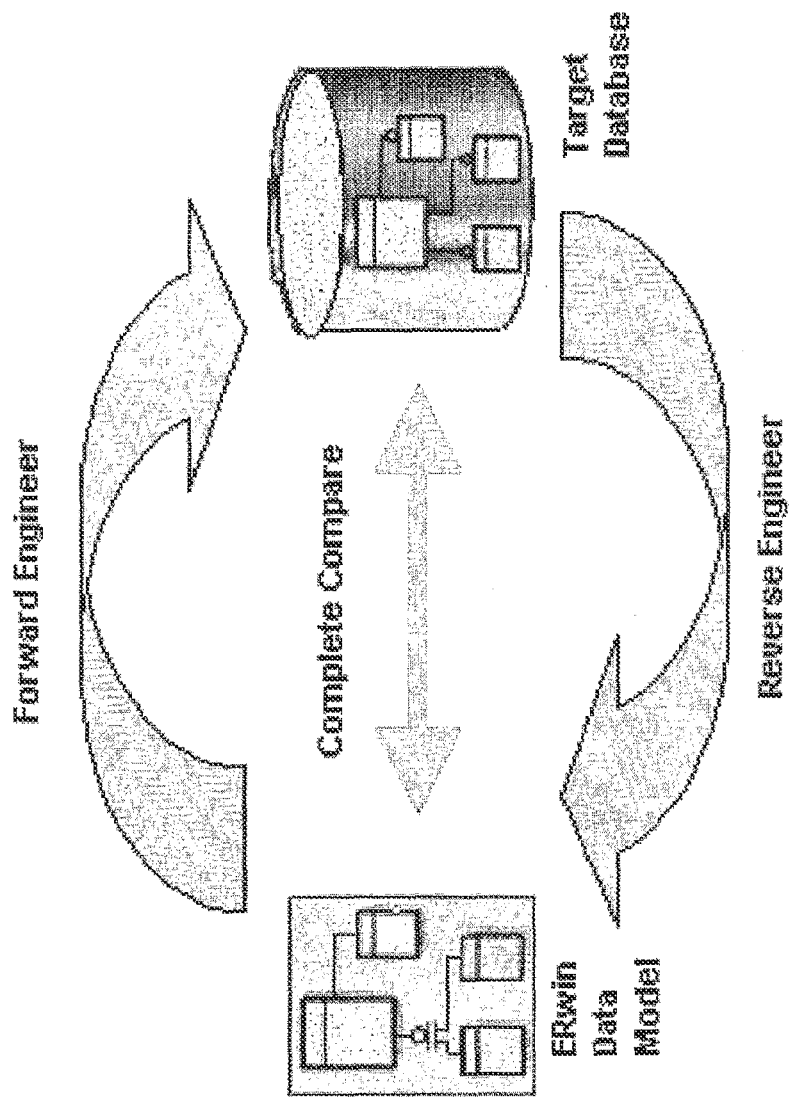
FIG. 3 is a schematic of a computer model used to identify ion combinations suitable for the disclosed ionic liquid combinations.

FIG. 3 illustrates how the two models interact. CODESSA™ (Semichem, Inc. Shawnee Mission, Kans.) can be used to calculate the descriptors that can be used to construct the forward model. For example, if a researcher desires a formulation to have antibacterial and painkilling therapeutic agents as well as the formulation to exist as a liquid at room temperature and have a delivery rate of 1 gram absorbed per minute, the researcher would feed this request into the program and all of the formulations meeting these requirements and being composed entirely of a balanced ionic liquid formula would be suggested to the researcher.

Once the desired ions are provided, the ions can be combined to form the disclosed ionic liquids. There are generally two methods for preparing an ionic liquid: (1) metathesis of a salt of the desired cation (e.g., a halide salt) with a salt of the desired anion (e.g., transition metal, like Ag, salt, Group I or II metal salt, or ammonium salt). Such reactions can be performed with many different types of salts; and (2) an acid-base neutralization reaction. Another method for forming the disclosed ionic liquid compostions involves a reaction between a salt of a desired cation, say CationX where X is an appropriate balancing anion (including but not necessarily a halide), and an acid to yield the ionic liquid and HX byproduct. Conversely, the disclosed ionic liquid compositions can be formed by reacting a salt of a desired anion, say YAnion where Y is an appropriate balancing cation, with a base to yield the ionic liquid and Ybase byproduct.

Many of the bioactive compounds (e.g., pharmaceutical actives, pesticidal actives, herbicidal actives, etc.) and energetic compounds disclosed herein are cationic or can be made cationic, the identification of which can be made by simple inspection of the chemical structure as disclosed herein. Further, many of these compounds are commercially available as their halide salts or can be converted to their halide salts by reactions with acids (e.g., HF, HCl, HBr, or HI) or by treating a halogenated compound with a nucleophile such as an amine. Further many of the anions disclosed herein are commercially available as metal salts, Group I or II metal salts, or ammonium salts. Combining such cations and anions in a solvent with optional heating can thus produce the ionic liquid compositions. For a review of the synthesis of ionic liquids see, for example, Welton, Chem Rev 1999, 99:2071-2083, which is incorporated by reference herein for at least its teachings of ionic liquid synthesis.

Ionic liquids which are immiscible with water are often conveniently prepared by the combination of aqueous solutions of two precursor salts, each of which contains one of the two requisite ions of the targeted ionic liquids. On combination, the desired salt forms a separate phase from the aqueous admixture. Such phases are readily washed free of byproduct salts with additional water, and may subsequently subjected to other procedures (e.g., as disclosed in the Examples) to separate them from non-water soluble impurities. In certain cases, it is also possible to prepare water immiscible ionic liquids by the addition to a neutral amine-containing compound (e.g., an active pharmaceutical ingredient) of an acid such as aqueous $HTf_2N$. Certain $Tf_2N^-$ salts of N—H containing cations are known to be water-immiscible.

The purification of ionic liquids can be accomplished by techniques familiar to those skilled in the art of organic and inorganic synthesis, with the notable exception of purification by distillation of the ionic liquid. One particularly useful approach is the use of conventional or reverse-phase chromatography to separate the salt of interest from other ionic or non-ionic materials, followed by the separation of the ionic liquid from the eluting solvent, commonly by evaporation of the latter. In some cases, ionic liquids can be purified by crystallization or thermal zone crystallization at appropriate conditions of temperature and pressure. Such techniques can include the use of a solvent from which the ionic liquid can be crystallized at an appropriate temperature. Other purification techniques include exchange column chromatography and supercritical $CO_2$ fluid extraction.

Uses

The disclosed ionic liquid compositions have many uses. For example, the disclosed ionic liquid compositions can be used to allow fine tuning and control of the rate of dissolution, solubility, and bioavailability, to allow control over physical properties and mechanical strength, to improve homogenous dosing, and to allow easier formulations. The disclosed ionic liquid compositions also make having compositions with additional functionality possible.

One notable advantage of the disclosed ionic liquid compositions is that they can be used to alleviate the problems associated with polymorphism. For example, a compound subject to polymorphism can be used as an ion in the disclosed ionic liquid compositions. In this way, the compound will become part of the ionic liquid composition and thus not a crystalline solid that is subject to polymorphism. Alternatively, polymorphism can be prevented by dissolving the compound in the ionic liquid. An advantage of having ionic liquid compositions is that the solubility and bioavailability can be known and predicted. This allows homogeneous and predictable dosing and tableting.

Another notable advantage is that the disclosed ionic liquid compositions can be used to alleviate side effects associated with various compounds. For example, the disclosed ionic liquid compositions can contain an ion from a drug known to have an undesirable side effect along with a counterion that is a drug known to alleviate or counteract that side effect. An example of this is an ionic liquid composition that comprises the ions of morphine and docusate. Such a composition can be used to treat pain due to the presence of morphine and relieve constipation due to the presence of docusate. Along the same lines, many pharmaceuticals are known to cause constipation, and ionic liquids of these compounds with docusate or other laxatives are contemplated herein.

Generally, any use that exists for one or more of the ionic components in the ionic liquid is also a use for the ionic liquid composition itself. For example, if one of the ions in an ionic liquid composition disclosed herein is a pharmaceutical active, then the ionic liquid composition can also be used for the same indication as the pharmaceutical active. In fact, many of the compounds disclosed herein as being suitable ions for the disclosed ionic liquids have already been proven to be effective alone or in some other preparation. Many of the disclosed compounds are even FDA approved. When such compounds are prepared as part of an ionic liquid, as disclosed herein, they can still maintain their efficacy, and can even have their efficacy enhanced by being part of the ionic liquid composition. For example, when an ionic liquid having a pharmaceutical active as one or more of its cations or anions is administered to a subject, the pharmaceutical active will dissociate from the ionic liquid and be available to the subject in the same way as had a solid form (e.g., tablet) or solution of the pharmaceutical active been administered. This effect is also observed for the antibacterial, antiviral, pesticidal, herbicidal, nutritional, food additives and other compounds and actives disclosed herein.

Other uses of the disclosed ionic liquid compositions include the dissolution of the ionic liquid into liquid bandages. Liquid bandages are available from commercial suppliers such as Johnson and Johnson. By dissolving the disclosed ionic liquid compositions into a liquid bandage, the various ions in the ionic liquid (e.g., antiinfective, steroidal, anesthetic, etc. ions) can be released into a wound and provide beneficial effects.

Further, the disclosed ionic liquids can be coated onto a cellulosic bandage (e.g., a gauze or dressing). Thus, by soaking, spraying, or otherwise contacting a bandage with the disclosed ionic liquid compositions, the bandage will contain the various active ions of the ionic liquid along with their associated functionality. In this regard, it may be desirable to use an ionic liquid composition that melts at or around body temperature. In this way, the ionic liquid composition can "leach" out of the bandage and onto the site contacted by the bandage.

Additionally, the disclosed ionic liquids can be melted by a consumer or physician (e.g., with hot water) and then "painted" onto an area of interest. It would then cool as a thin, solid coating of the ionic liquid. This use can provide a slow release form of the API in the ionic liquid or impart a desirable barrier on the area of interest.

Depending on the particular ions, the disclosed ionic liquid compositions can be used to treat a subject diagnosed with, for example, endocrine disorders, diabetes, infertility, hormone deficiencies, osteoporosis, ophthalmological disorders, neurodegenerative disorders, Alzheimer's disease, dementia, Parkinson's disease, multiple sclerosis, Huntington's disease, cardiovascular disorders, atherosclerosis, hyper-coagulable states, hypo-coagulable states, coronary disease, cerebrovascular events, metabolic disorders, obesity, vitamin deficiencies, renal disorders, renal failure, haematological disorders, anemia of different entities, immunologic and rheumatologic disorders, autoimmune diseases, immune deficiencies, infectious diseases, viral infections, bacterial infections, fungal infections, parasitic infections, neoplastic diseases, multi-factorial disorders, impotence, chronic pain, depression, and different fibrosis states.

Similarly, with herbicidal and pesticidal actives, the ionic liquid compositions disclosed herein that contain ionic pesticidal and herbicidal actives can be used in the same way as the actives themselves. Thus, any use contemplated for a pesticidal and herbicidal active is contemplated herein for an ionic liquid composition containing that active.

Furthermore, because the disclosed ionic liquid compositions are liquid at a given temperature, they avoid problems associated with polymorphism. For example, one can vary the individual ions and the combination of ions to fine tune the characteristics of the compositions, thus obtaining a composition with desired properties (e.g., better dissolution, solubility, or bioavailability). This can lead to easier dosing and formulating of the actives in the compositions. By preparing and using the disclosed ionic liquid compositions, one need not need to prepare, screen, and characterize numerous crystalline forms of the actives.

In one aspect, disclosed herein are methods for using ionic liquid compositions that comprise administering an effective amount of at least one ionic liquid composition as disclosed herein. By the term "effective amount" of a compound as provided herein is meant a nontoxic but sufficient amount to provide the desired result. As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation. The dose, schedule of doses, and route of administration can be varied.

The efficacy of administration of a particular dose of the ionic liquid compositions according to the methods described herein can be determined by evaluating the particular aspects of the medical history, signs, symptoms, and objective laboratory tests that are known to be useful in evaluating the status of a subject in need of attention for the treatment of a disease and/or condition. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular individual: (1) a subject's physical condition is shown to be improved, (2) the progression of the disease or condition is shown to be stabilized, or slowed, or reversed, or (3) the need for other medications for treating the disease or condition is lessened or obviated, then a particular treatment regimen will be considered efficacious.

Many of the disclosed ionic liquid compositions can be used therapeutically as neat ionic liquids. Also, the disclosed ionic liquids can be used in combination with a pharmaceutically acceptable carrier. By "pharmaceutically acceptable" is meant a material that is not biologically or otherwise undesirable, i.e., the material may be administered to a subject without causing any undesirable biological effects or interacting in a deleterious manner with any of the other components of the pharmaceutical formulation in which it is contained. The carrier would naturally be selected to minimize any degradation of the active ingredient and to minimize any adverse side effects in the subject, as would be well known to one of skill in the art. In another aspect, many of the disclosed ionic liquids can be used prophylactically, i.e., as a preventative agent, either neat or with a pharmaceutically acceptable carrier. The ionic liquid compositions disclosed herein can be conveniently formulated into pharmaceutical compositions composed of neat ionic liquid or in association with a pharmaceutically acceptable carrier. See e.g., *Remington's Pharmaceutical Sciences*, latest edition, by E.W. Martin Mack Pub. Co., Easton, Pa., which discloses typical carriers and conventional methods of preparing pharmaceutical compositions that can be used in conjunction with the preparation of formulations of the compounds described herein and which is incorporated by reference herein. Such pharmaceutical carriers, most typically, would be standard carriers for administration of compositions to humans and non-humans, including solutions such as sterile water, saline, and buffered solutions at physiological pH. Other compounds can be administered according to standard procedures used by those skilled in the art. For example, pharmaceutical compositions can also include one or more additional active ingredients such as antimicrobial agents, anti-inflammatory agents, anesthetics, and the like.

Examples of pharmaceutically-acceptable carriers include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the disclosed compounds, which matrices are in the form of shaped articles, e.g., films, liposomes, microparticles, or microcapsules. It will be apparent to those persons skilled in the art that certain carriers can be more preferable depending upon, for instance, the route of administration and concentration of composition being administered. Other compounds can be administered according to standard procedures used by those skilled in the art.

Pharmaceutical formulations can include additional carriers, as well as thickeners, diluents, buffers, preservatives, surface active agents and the like in addition to the compounds disclosed herein. Pharmaceutical formulations can also include one or more additional active ingredients such as antimicrobial agents, anti-inflammatory agents, anesthetics, and the like.

The pharmaceutical formulation can be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed compounds can be administered intravenously, intraperitoneally, intramuscularly, subcutaneously, intracavity, or transdermally as is described more fully elsewhere herein.

Administration and Delivery

In one aspect, disclosed herein are uses of a delivery device to deliver an ionic liquid composition as disclosed herein to a subject. Further, disclosed are methods for delivering an ionic liquid composition to a subject by administering to the subject any of the nutritional supplements, pharmaceutical formulations, controlled release vehicles, delivery and/or devices.

The compositions described herein can be administered to the subject in a number of ways depending on whether local or systemic treatment is desired, and on the area to be treated. Thus, for example, a composition described herein can be administered as an ophthalmic solution and/or ointment to the surface of the eye. Moreover, a compound or pharmaceutical composition can be administered to a subject vaginally, rectally, intranasally, orally, by inhalation, or parenterally, for example, by intradermal, subcutaneous, intramuscular, intraperitoneal, intrarectal, intraarterial, intralymphatic, intravenous, intrathecal and intratracheal routes. Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system such that a constant dosage is maintained. In one example an ionic liquid composition such as lidocaine docusate is contacted to the skin of a subject to provide an anesthetic effect.

Preparations for parenteral administration include sterile aqueous or non-aqueous solutions, suspensions, and emulsions which can also contain buffers, diluents and other suitable additives. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives, such as antimicrobials, anti-oxidants, chelating agents, and inert gases and the like, can also be present.

Formulations for topical administration can include ointments, lotions, creams, gels, drops, suppositories, sprays, liquids and powders. The disclosed ionic liquid compositions having hydrophobic ions can be particularly useful in such applications because they can adhere to the surface longer when exposed to water or other fluids than would a similar hydrophilic salt. Likewise, ionic liquids comprising disinfectant, herbicide, or pesticide ions and hydrophobic counterions can be expected to resist erosion from rainfall. Conventional pharmaceutical carriers, aqueous, powder or oily bases, thickeners and the like can be necessary or desirable. When applied to skin or mucous tissues (e.g., oral applications) ionic liquid compositions containing pharmaceutical actives formulated with highly hydrophobic anions or cations (as appropriate) can have longer durations of adhesion when exposed to water or other fluids than would similar hydrophilic salts applied in these environments. This would be particularly beneficial for sun screens. It should also be noted that disinfectants, pesticides, or herbicides applied to plant leaves can be less prone to be lost by rain even if it follows application.

When one or more ions in the disclosed ionic liquid compositions are an antibacterial, an effective amount of the composition can be contacted (i.e., administered) to any surface that has bacteria. Similarly, when one or more ions in the disclosed ionic liquid composition are a pesticidal active, an effective amount of the composition can be administered to an area to control pests. When one or more ions in the disclosed ionic liquid composition are a herbicidal active, an effective amount of the composition can be administered to an area to control plants. Techniques for contacting such surfaces and areas with the disclosed ionic liquid compositions can include, spraying, coating, dipping, immersing, or pouring the composition into or onto the surface or area. The precise technique will depend on such factors as the type and amount of infestation or contamination, the size of the area, the amount of composition needed, preference, cost and the like.

Delivery Devices

Any of the compounds described herein can be incorporated into a delivery device. Examples of delivery devices include, but are not limited to, microcapsules, microspheres, nanospheres or nanoparticles, liposomes, noisome, nanoerythrosome, solid-liquid nanoparticles, gels, gel capsules, tablets, lotions, creams, sprays, emulsions, or powders. Other examples of delivery devices that are suitable for non-oral administration include pulmospheres. Examples of particular delivery devices useful herein are described below.

The disclosed compounds can be incorporated into liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The disclosed compositions in liposome form can contain, in addition to a compound disclosed herein, stabilizers, preservatives, excipients, and the like. Examples of suitable lipids are the phospholipids and the phosphatidyl cholines (lecithins), both natural and synthetic. Methods of forming liposomes are known in the art. See, e.g., Prescott, Ed., Methods in Cell Biology, Volume XIV, Academic Press, New York, p. 33 et seq., 1976, which is hereby incorporated by reference herein for its teachings of liposomes and their preparation.

In other examples, the liposomes can be cationic liposomes (e.g., DOTMA, DOPE, DC cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham, et al., *Am J Resp Cell Mol Biol* 1:95-100, 1989; Feigner, et al., *Proc Natl Acad Sci USA* 84:7413-7, 1987; and U.S. Pat. No. 4,897,355, which are incorporated by reference herein for their teachings of liposomes. As one example, delivery can be via a liposome using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. Liposomes where the diffusion of the compound or delivery of the compound from the liposome is designed for a specific rate or dosage can also be used.

As described herein, niosomes are delivery devices that can be used to deliver the compositions disclosed herein. Noisomes are multilamellar or unilamellar vesicles involving non-ionic surfactants. An aqueous solution of solute is enclosed by a bilayer resulting from the organization of surfactant macromolecules. Similar to liposomes, noisomes are used in targeted delivery of, for example, anticancer drugs, including methotrexate, doxorubicin, and immunoadjuvants. They are generally understood to be different from transferosomes, vesicles prepared from amphiphilic carbohydrate and amino group containing polymers, e.g., chitosan.

As described herein, nanoerythrosomes are delivery devices that can be used to deliver the compositions disclosed herein. Nanoerythrosomes are nano-vesicles made of red blood cells via dialysis through filters of defined pore size. These vesicles can be loaded with a diverse array of biologically active molecules, including proteins and the compositions disclosed herein. They generally serve as ideal carriers for antineoplastic agents like bleomycin, actinomycin D, but can be used for steroids, other lipids, etc.

Artificial red blood cells, as described herein, are further delivery devices that can be used to deliver the compositions disclosed herein. Artificial red blood cells can be generated by interfacial polymerization and complex emulsion methods. Generally, the "cell" wall is made of polyphtaloyl L-lysine polymer/polystyrene and the core is made of a hemoglobin solution from sheep hemolysate. Hemoglobin loaded microspheres typically have particle sizes of from about 1 to about 10 mm. Their size, flexibility, and oxygen carrying capacity is similar to red blood cells.

Solid-lipid nanoparticles, as described herein, are other delivery devices that can be used to deliver the compositions disclosed herein. Solid-lipid nanoparticles are nanoparticles, which are dispersed in an aqueous surfactant solution. They are comprised of a solid hydrophobic core having a monolayer of a phospholipid coating and are usually prepared by high-pressure homogenization techniques. Immunomodulating complexes (ISCOMS) are examples of solid-lipid nanoparticles. They are cage-like 40 nm supramolecular assemblies comprising of phospholipid, cholesterol, and hydrophobic antigens and are used mostly as immunoadjuvants. For instance, ISCOMs are used to prolong blood-plasma levels of subcutaneously injected cyclosporine.

Microspheres and micro-capsules, as described herein, are yet other delivery devices that can be used to deliver the compositions disclosed herein. In contrast to liposomal delivery systems, microspheres and micro-capsules typically do not have an aqueous core but a solid polymer matrix or membrane. These delivery devices are obtained by controlled precipitation of polymers, chemical cross-linking of soluble polymers, and interfacial polymerization of two monomers or high-pressure homogenization techniques. The encapsulated compound is gradually released from the depot by erosion or diffusion from the particles. Successful formulations of short acting peptides, such as LHRH agonists like leuprorelin and triptoreline, have been developed. Poly(lactide co-glycolide (PLGA) microspheres are currently used as monthly and three monthly dosage forms in the treatment of advanced prostrate cancer, endometriosis, and other hormone responsive conditions. Leuprolide, an LHRH superagonist, was incorporated into a variety of PLGA matrices using a solvent extraction/evaporation method. As noted, all of these delivery devices can be used in the methods disclosed herein.

Pulmospheres are still other examples of delivery devices that can be used herein. Pulmospheres are hollow porous particles with a low density (less than about 0.1 gm/mL). Pulmospheres typically have excellent re-dispersibility and are usually prepared by supercritical fluid condensation technology. Co-spray-drying with certain matrices, such as carbohydrates, human serum albumin, etc., can improve the stability of proteins and peptides (e.g., insulin) and other biomolecules for pulmonary delivery. This type of delivery could be also accomplished with micro-emulsions and lipid emulsions, which are ultra fine, thin, transparent oil-in-water (o/w) emulsions formed spontaneously with no significant input of mechanical energy. In this technique, an emulsion can be prepared at a temperature, which should be higher than the phase inversion temperature of the system. At elevated temperature the emulsion is of water-in-oil (w/o) type and as it cools at the phase inversion temperature, this emulsion is inverted to become o/w. Due to their very small inner phase, they are extremely stable and used for sustained release of steroids and vaccines. Lipid emulsions comprise a neutral lipid core (i.e., triglycerides) stabilized by a monolayer of amphiphilic lipid (i.e., phospholipid) using surfactants like egg lecithin triglycerides and miglyol. They are suitable for passive and active targeting.

There are other oral delivery systems under investigation that are based on osmotic pressure modulation, pH modulation, swelling modulation, altered density and floating systems, mucoadhesiveness etc. These formulations and time-delayed formulations to deliver drugs in accordance with circadian rhythm of disease that are currently in use or investigation can be applied for delivery of the compositions disclosed herein.

It is also contemplated that the disclosed ionic liquid compositions can be formulated as part of a controlled release vehicle. For example, microspheres and microcapsules, implants, and the like containing liquid bioactive agents are well known, as are methods for their preparation. As such, these methods can be used with the disclosed ionic liquid compositions to produce controlled release vehicles that can release the disclosed ionic liquid composition with a desired release profile.

Also contemplated are pills prepared from the disclosed ionic liquid compositions that are glasses. For example, a glass ionic liquid composition can be cooled to form a pill. That is, glasses are "cast-able" above their glass transition temperature ($T_g$) into shapes with specific surface areas, allowing predictable release/pharmacokinetic properties. Below $T_g$, these disclosed glass ionic liquid composition can be milled into specific shapes and sizes. Alternatively, the disclosed ionic liquid compositions can be tableted as liquids that upon cooling form glasses. Such a method can allow the homogeneous distribution of a pharmaceutical active into the tablet.

A particular example includes ionic liquid compositions that are in the glass form but melt at or slightly above body temperature. Such compositions can allow formulation as a solid, but have known solubility, bioavailability, etc. as a liquid. These compositions can have uses in, for example, bandages, patches, or wound dressings. Further, glass compositions that "melt" slightly above room temperature can be "melted" by a consumer or physician with, e.g., hot water or body heat, and "painted" onto an area of interest (infected area). Cooling of the composition can then provide a thin, solid coating of material which is both a slow release form of an active ingredient ion (e.g., anti-infective, steroid, anesthetic, or combination thereof), plus serve as a physical barrier.

Further, the disclosed ionic liquids can be used as carriers for other active compounds, many of which are disclosed herein. For example, prodrugs, ionic and neutral active molecules can be dissolved in the disclosed ionic liquid compositions.

Further methods of administration can include incorporating the disclosed ionic liquid composition in to a food stuff or beverage, which can be ingested by a subject.

The disclosed ionic liquids can also be encapsulated in a polymer matrix by methods known in the art.

Also, the disclosed ionic liquid compositions can be dissolved in a suitable solvent or carrier as are disclosed herein. This method can enhance the delivery of one or more active ions in the ionic liquid. Further, as is disclosed herein, this method can create a synergistic effect among the various ions present. While not wishing to be bound by theory, the dissociate coefficient of various ions in an ionic liquid can be different in different solvents. Thus, ions in an ionic liquid can dissociate freely in one solvent and cluster in another. This phenomenon can be utilized to provide formulations of compound that are difficult to deliver (e.g., increase the water solubility of steroids). That is, compounds can be formed into an ionic liquid, as described herein, and then dissolved in a suitable solvent to provide an easily deliverable solution. A synertistic effect can be observed upon administration to a subject, when ions cluster and act together, rather than independently.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process. Only reasonable and routine experimentation will be required to optimize such process conditions. All chemicals used were of analytical grade, purchased from Sigma-Aldrich (Milwaukee, Wis.), and used without further purification unless otherwise noted.

Example I

Didecyldimethylammonium Saccharinate
[DDA][Sac]

To the reaction flask, equipped with stirring bar and thermometer, 0.03 mol of didecyldimethylammonium bromide and 0.03 mol of saccharin sodium salt, and 50 mL of water were put in. The mixture was intensively stirred for one hour at room temperature. Afterwards 50 mL of chloroform was added. After phases separated, chloroform phase was isolated (separated), and washed with fresh distilled water (so many times) until all chloride ions were washed out (removed). Chloroform was distilled off (evaporated) and the residue (remains) was dried at 60° C. in vacuum. Saccharinate in form of liquid, with high viscosity was obtained in 95% yield. It is hydrophobic liquid (fluid), lighter than water, poorly dissolvable in cold and warm water. Thermal stability of this salt is presented in Table 2. Synthesized salt appear to be sweet and active against microorganisms. The activity is high in comparison with starting material, didecyldimethylammonium chloride, which is confirmed by MIC and MBC values (Table 3 and Table 4).

Elemental analysis: CHN: $C_{29}H_{52}N_2O_3S$ (508.80) calculated values: C=68.46%, H=10.30% i N=5.51%; experimental values C=68.78%, H=10.69%, N=5.31%. $^1$H NMR (DMSO-$d_6$) cation: 3.22 (m, 4H); 3.00 (s, 6H); 1.63 (m, 4H); 1.24 (m, 28H); 0.85 (t, J=7 Hz, 6H); anion: 7.58 (m, 4H); $^{13}$C NMR cation: 62.7; 49.9; 31.2; 28.8; 28.7; 28.6; 28.4; 25.6; 22.0; 21.6; 13.8; anion: 167.7; 145.2; 134.8; 131.3; 130.8; 122.3; 118.9.

TABLE 2

Thermal stability data of synthesized salts

| Temperature | [BA][Sac] | [DDA][Sac] | [BA][Ace] | [DDA][Ace] |
|---|---|---|---|---|
| $T_g$ | | −52.5 | | −58 |
| $T_c$ | 21.5 | 18.0 | 26.4 | −45.5 |
| $T_{s-s}$ | | 65.5 | | |
| $T_m$ | 82.5 | 22.5 | 89 | −29 |
| $T_{onset(5\%)}$ | 176 | 184 | 186 | 182 |
| $T_{onset}$ | 206 | 211 | (203)258 | 201 |
| $T_d$ | 227 | 221 | (225)273 | 245 |

$T_g$—glass transition.
$T_c$—crystallization temperature recorded by the DSC.
$T_{s-s}$—solid-solid transitions recorded by the DSC.
$T_m$—melting point recorded by the DSC.
$T_{onset(5\%)}$—onset temperature for 5% of the decomposition,
$T_{onset}$—onset temperature of the decomposition,
$T_d$—temperature of total decomposition.

TABLE 3

MIC* values for investigated salts

| culture | [BA][Sac] | [DDA][Sac] | [BA][Ace] | [DDA][Ace] | BAC** | DDAC*** |
|---|---|---|---|---|---|---|
| S. aureus | 4 | 4 | 4 | 8 | 2 | 2 |
| E. faecium | 8 | 8 | 8 | 8 | 4 | 4 |
| E. coli | 16 | 16 | 31.2 | 16 | 8 | 8 |
| C. albicans | 16 | 16 | 16 | 16 | 8 | 8 |
| Average value | 11 | 11 | 14.8 | 12 | 5.5 | 5.5 |

*in ppm.
**benzalkonium chloride.
***didecyldimethylammonium chloride

TABLE 4

MBC* values for investigated salts.

| Culture | [BA][Sac] | [DDA][Sac] | [BA][Ace] | [DDA][Ace] | BAC** | DDAC*** |
|---|---|---|---|---|---|---|
| S. aureus | 31.2 | 62.5 | 31.2 | 16 | 62.5 | 31.2 |
| E. faecium | 16 | 16 | 31.2 | 31.2 | 31.2 | 31.2 |
| E. coli | 62.5 | 16 | 125 | 62.5 | 62.5 | 31.2 |
| C. albicans | 31.2 | 16 | 31.2 | 16 | 16 | 16 |
| Average value | 35.2 | 27.6 | 54.7 | 31.4 | 43.1 | 27.4 |

*in ppm.
**benzalkonium chloride.
***didecyldimethylammonium chloride

Example II

Benzalkonium Saccharinate [BA][Sac]

To the saturated water solution of saccharin sodium, the water solution of benzalkonium chloride (alkyl substituent—dodecyl and tetradecyl) was added in the molar ratio of 1:1.5. The mixture was stirred for 1 h at the temperature of 60° C. After the mixture was cooled down to the room temperature, white wax was formed. The wax was dissolved in chloroform. Chloroform phase was washed with fresh distilled water (so many times) until all chloride ions were washed out (removed). The progress was monitored by using water solution of $AgNO_3$. Afterwards chloroform was distilled off (evaporated) and the residue (remains) wax was dried at 50° C. in vacuum. Synthesized benzalkonium saccharinate was obtained with 98% yield. It is very sweet in taste. Obtained wax is poorly dissolvable in cold and warm water. Crystalline benzalkonium saccharinate, with the melting point of 80-82° C., was obtained form the mixture of dry (no water) acetone and diethylether in the volume ratio of 10:1.

$^1$H NMR (DMSO-$d_6$) 7.59 (m, 9H), 4.53 (s, 2H), 3.24 (m, 2H), 2.95 (s, 6H), 1.77 (m, 2H), 1.24 (m, 20H), 0.85 (t, J=7 Hz, 3H); $^{13}$C NMR cation: 132.8, 130.1, 128.8, 128.0, 66.1, 63.4, 49.0, 31.2, 28.9, 28.85, 28.7, 28.6, 28.4, 25.7, 22.0, 21.7, 13.8, anion: 167.7, 145.2, 134.8, 131.4, 130.8, 122.3, 118.9.

Example III

Benzalkonium Acesulfamate [BA][Ace]

To the reactor the water solution of 1 mol of benzalkonium chloride (alkyl substituent is the mixture of the following groups: octyl, decyl, dodecyl, tetradecyl, hexadecyl and octydecyl) and water solution of 1.5 mol of acesulfamate sodium were put in (placed). The mixture was stirred for 1 h at the temperature of 60° C. After the mixture was cooled down to the room temperature. Formed wax was dissolved in chloroform and separated water phase was removed. Chloroform phase was washed with fresh distilled water (so many times) until all chloride ions were washed out (removed). The progress was monitored by using water solution of $AgNO_3$. Chloroform was distilled off (evaporated) and the product dried at 60° C. in vacuum. Obtained wax, with the 95% yield, was crystallized out (re-crystallized) from the mixture of THF, acetone and diethylether in the volume ratio of 10:10:1. Crystalline benzalkonium acesulfamate, which has sweet taste, melts between 90 and 91° C. The melting point recorded on the by the DSC (diffraction scanning calorimeter) was 89° C. This salt is poorly dissolvable in cold and warm water.

Measured thermal decomposition temperature of obtained salt are placed in Table 2, while biological activity data in Table 3 and Table 4. Calculated average values for MIC and MBC indicate high activity of the salt, slightly lower than that of the starting benzalkonium chloride $^1$H NMR (DMSO-$d_6$) cation: 7.52 (m, 5H), 4.53 (s, 2H), 3.24 (m, 2H), 2.95 (s, 6H), 1.78 (m, 2H), 1.25 (m, 20H), 0.85 (t, J=7 Hz, 3H), anion: 5.28 (s, 1H), 1.90 (s, 3H); $^{13}$C NMR cation: 132.8, 130.1, 128.8, 128.0, 66.1, 63.4, 49.0, 31.2, 28.9, 28.87, 28.7, 28.6, 28.4, 25.7, 22.0, 21.7, 13.8, anion: 167.6, 159.5, 102.0, 19.3.

Example IV

Didecyldimethylammonium Acesulfamate [DDA][Ace]

0.03 mol of didecyldimethylammonium bromide, in form of gel (75%) in water, and water solution of 0.03 mol (6.04 g)

of acesulfamate potassium salt were put in (placed) into the reactor. The mixture was stirred for 1 h at the room temperature. Afterwards 50 mL of chloroform was added. Water phase was separated and chloroform phase was washed with fresh distilled water (so many times) util all chloride ions were washed out (removed). The progress was monitored by using water solution of $AgNO_3$. After the chloroform was evaporated, the liquid (fluid) was obtained with 94% yield, and dried at 65° C. in vacuum.

The hydrophobic, sweet liquid, with high viscosity, lighter than water and thermally stable was obtained (Table 2). Calculated MIC and MBC values are shown in the Table 3 and Table 4. Comparing average values of MIC and MBC for the synthesized salt with the values for didecyldimethylammonium chloride the only slight difference in the biological activity is seen (recorded).

Elemental analysis: CHN: $C_{26}H_{52}N_2O_4S$ (488.77) calculated values C=63.89%, H=10.72% i N=5.73%; experimental values C=64.09%, H=10.99%, N=5.41%. $^1$H NMR (DMSO-$d_6$) cation: 3.22 (m, 4H), 2.99 (s, 6H), 1.63 (m, 4H), 1.26 (m, 28H), 0.86 (t, J=7 Hz, 6H), anion: 5.26 (q, J=1 Hz, 1H), 1.89 (d, J=2 Hz, 3H); $^{13}$C NMR cation: 62.7, 49.8, 31.2, 28.8, 28.7, 28.6, 28.4, 25.7, 22.0, 21.6, 13.8, anion: 167.6, 159.4, 102.0, 19.3.

In the biological activity measurements (tests) following bacteria were used: *Staphylococcus aureus* ATCC 6538, *Enterococcus faecium* ATCC 49474, *Escherichia coli* ATCC 25922 and fungi *Candida albicans* ATCC 10231.

Microbiological activity tests were performed using dissolution method. Determinations were performed on liquid base (background): Mueller-Hinton for bacteria and Sabouraud for fungi. Starting solution had the concentration of 1 g/cm$^3$. From this solution, all other solutions (lower concentrations) were prepared. To those solutions, 0.1 cm$^3$ of the suspensions of standard microorganisms at a concentration of $10^6$ cfu cm$^3$ were added. The samples with bacteria were incubated for 24 h at the temperature of 37° C., and with fungi there were incubated for 48 h at the temperature of 22° C. After incubation time the MIC, Minimal Inhibitory Concentration, minimal concentration of the investigated compound at which the growth of the microorganisms is stopped (visually), was specified (recorded) for every sample. To define the MBC, Minimal Bactericidal Concentration, additionally to each solution the $10^{-6}$ cm$^3$ of the inactivator was added on the base (background) (0.3% lecithin, 3% polysorbate 80 and 0.1% L-cysteine). The samples with bacteria were incubated for 48 h in the temperature of 37° C. The fungi samples were incubated for 5 days at the temperature of 22° C. MBC values were defined (specified) as the concentration at which the level of the reduction of the microorganisms was not lower than 99.99%.

Example V

Benzalkonium Sulfacetamide

Benzalkonium chloride (0.001 mol) was dissolved in 60 mL of distilled water by gentle heating and stirring. Sodium sulfacetamide (0.001 mol) was dissolved in 60 mL of distilled water by gentle heating and stirring. The two solutions were combined and the reaction mixture was heated and stirred for 30 minutes. The reaction mixture cooled to room temperature and then 60 mL of chloroform was added. The reaction mixture was stirred for an additional 30 minutes. The two phases were separated and the chloroform phase was washed several times with cool distilled water to remove any inorganic salt. The presence of chloride anions was monitored by silver nitrate test. A rotary evaporator removed the chloroform and a yellowish gel was obtained in 76.99% yield. $^1$H and $^{13}$C NMR (DMSO) were obtained. Melting point (hot plate apparatus)=35-40° C. Thermal data determined by thermalgravimetric analysis (TGA): $T_{onset5\%}$=164° C. and $T_{onset}$=181° C.

Example VI

Didecyldimethylammonium Sulfacetamide

Didceyldimethylammonium bromide (0.001 mol) was dissolved in 60 mL of distilled water by gentle heating and stirring. Sodium sulfacetamide (0.001 mol) was dissolved in 60 mL of distilled water by gentle heating and stirring. The two solutions were combined and the reaction mixture was heated and stirred for 30 minutes. The reaction mixture cooled to room temperature and then 60 mL of chloroform was added. The reaction mixture was stirred for an additional 30 minutes. The two phases were separated and the chloroform phase was washed several times with cool distilled water to remove any inorganic salt. The presence of chloride anions was monitored by silver nitrate test. A rotary evaporator removed the chloroform and a yellowish gel was obtained in 87.74% yield. $^1$H and $^{13}$C NMR (DMSO) were obtained. Melting point (hot plate apparatus)=25-30° C. Thermal data determined by thermalgravimetric analysis (TGA): $T_{onset5\%}$=183.3° C. and $T_{onset}$=200.2° C.

Example VII

Hexadecylpyridinium Sulfacetamide

Hexadecylpyridinium chloride (0.001 mol) was dissolved in 60 mL of distilled water by gentle heating and stirring. Sodium sulfacetamide (0.001 mol) was dissolved in 60 mL of distilled water by gentle heating and stirring. The two solutions were combined and the reaction mixture was heated and stirred for 30 minutes. The reaction mixture cooled to room temperature and then 60 mL of chloroform was added. The reaction mixture was stirred for an additional 30 minutes. The two phases were separated and the chloroform phase was washed several times with cool distilled water to remove any inorganic salt. The presence of chloride anions was monitored by silver nitrate test. A rotary evaporator removed the chloroform and an orange wax was obtained in 99.22% yield. $^1$H and $^{13}$C NMR (DMSO) were obtained. Melting point (hot plate apparatus)=30-40° C. Thermal data determined by thermalgravimetric analysis (TGA): $T_{onset5\%}$=211° C. and $T_{onset}$=219° C.

Example VIII

Benzalkonium Ibuprofen

Benzalkonium chloride (0.001 mol) was dissolved in 60 mL of distilled water by gentle heating and stirring. Ibuprofen (0.001 mol) was dissolved in 60 mL of distilled water by gentle heating and stirring. The two solutions were combined and the reaction mixture was heated and stirred for 30 minutes. The reaction mixture cooled to room temperature and then 60 mL of chloroform was added. The reaction mixture was stirred for an additional 30 minutes. The two phases were separated and the chloroform phase was washed several times with cool distilled water to remove any inorganic salt. The presence of chloride anions was monitored by silver nitrate test. A rotary evaporator removed the chloroform and a % yield. $^1$H and $^{13}$C NMR (DMSO) were obtained. Melting point (hot plate apparatus)=° C. Thermogravimetric analysis: $T_g$=−41.1° C., $T_{onset5\%}$=133° C. and $T_{onset}$=153° C.

Example IX

Didecyldimethylammonium Ibuprofen

Didecyldimethylammonium bromide (0.001 mol) was dissolved in 60 mL of distilled water by gentle heating and stirring. Ibuprofen (0.001 mol) was dissolved in 60 mL of distilled water by gentle heating and stirring. The two solutions were combined and the reaction mixture was heated and stirred for 30 minutes. The reaction mixture cooled to room temperature and then 60 mL of chloroform was added. The reaction mixture was stirred for an additional 30 minutes. The two phases were separated and the chloroform phase was washed several times with cool distilled water to remove any inorganic salt. The presence of chloride anions was monitored by silver nitrate test. A rotary evaporator removed the chloroform and a % yield. $^1$H and $^{13}$C NMR (DMSO) were obtained. Melting point (hot plate apparatus)=° C. Thermogravimetric analysis: $T_g$=57.1° C., $T_{onset5\%}$=153° C. and $T_{onset}$=172° C.

Example X

Didecyldimethylammonium Trans-Cinnamate

Didecyldimethylammonium bromide (0.001 mol) was dissolved in 50 mL of hot distilled water. trans-Cinnamic acid (0.001 mol) was added to the didecyldimethylammonium solution. The reaction solution was stirred at 90° C. for 4 h. The reaction solution was cooled to room temperature and then 60 mL of chloroform was added. The two phases were separated and the chloroform phase was washed several times with cool distilled water to remove any inorganic salt. The presence of chloride anions was monitored by silver nitrate test. A rotary evaporator removed the chloroform and a wax was obtained in 93% yield. $^1$H and $^{13}$C NMR (DMSO) were obtained. Melting point (hot plate apparatus)=54-55° C.

Example XI

Benzalkonium Trans-Cinnamate

Benzalkonium chloride (0.001 mol) was dissolved in warm distilled water. trans-Cinnamic acid (0.001 mol) was added to the benzalkonium solution. The reaction solution was stirred at 90° C. for 4 hours. The reaction solution was cooled to room temperature then 60 mL of chloroform was added. The two phases were separated and the chloroform phase was washed several times with cool distilled water to remove any inorganic salt. The presence of chloride anions was monitored by silver nitrate test. A rotary evaporator removed the chloroform and an orange viscous liquid was obtained in 90% yield. $^1$H and $^{13}$C NMR (DMSO) were obtained. Melting point (hot plate apparatus)=liquid at room temperature.

Example XII

Hexadecylpyridinium Colawet MA-80

Hexadecylpyridinium chloride (0.001 mol) was dissolved in 60 mL of distilled water by gentle heating and stirring. Sodium dihexylsulfosuccinate (Colawet MA-80 from Colonial Chemicals, South Pittsburg, Tenn.; 0.001 mol) was dissolved in 60 mL of distilled water by gentle heating and stirring. The two solutions were combined and the reaction mixture was heated and stirred for 30 minutes. The reaction mixture cooled to room temperature and then 60 mL of chloroform was added. The reaction mixture was stirred for an additional 30 minutes. The two phases were separated and the chloroform phase was washed several times with cool distilled water to remove any inorganic salt. The presence of chloride anions was monitored by silver nitrate test. A rotary evaporator removed the chloroform and a yellowish viscous liquid was obtained in 96.93% yield. $^1$H and $^{13}$C NMR (DMSO) were obtained. Melting point (hot plate apparatus)= liquid at room temperature. Thermal data determined by thermalgravimetric analysis (TGA): $T_{onset5\%}$=248° C. and $T_{onset}$=262° C.

Example XIII

Didecyldimethylammonium Colawet MA-80

Decyldimethylammonium bromide (0.001 mol) was dissolved in 60 mL of distilled water by gentle heating and stirring. Sodium dihexylsulfosuccinate (Colawet MA-80 from Colonial Chemicals, South Pittsburg, Tenn.; 0.001 mol) was dissolved in 60 mL of distilled water by gentle heating and stirring. The two solutions were combined and the reaction mixture was heated and stirred for 30 minutes. The reaction mixture cooled to room temperature and then 60 mL of chloroform was added. The reaction mixture was stirred for an additional 30 minutes. The two phases were separated and the chloroform phase was washed several times with cool distilled water to remove any inorganic salt. The presence of chloride anions was monitored by silver nitrate test. A rotary evaporator removed the chloroform and a yellowish viscous liquid was obtained in 96.93% yield. $^1$H and $^{13}$C NMR (DMSO) were obtained. Melting point (hot plate apparatus)= liquid at room temperature. Thermal data determined by thermalgravimetric analysis (TGA): $T_{onset5\%}$=218° C. and $T_{onset}$=226° C.

Example XIV

Benzalkonium Colawet MA-80

Benzalkonium chloride (0.001 mol) was dissolved in 60 mL of distilled water by gentle heating and stirring. Sodium dihexylsulfosuccinate (Colawet MA-80 from Colonial Chemicals, South Pittsburg, Tenn.; 0.001 mol) was dissolved in 60 mL of distilled water by gentle heating and stirring. The two solutions were combined and the reaction mixture was heated and stirred for 30 minutes. The reaction mixture cooled to room temperature and then 60 mL of chloroform was added. The reaction mixture was stirred for an additional 30 minutes. The two phases were separated and the chloroform phase was washed several times with cool distilled water to remove any inorganic salt. The presence of chloride anions was monitored by silver nitrate test. A rotary evaporator removed the chloroform and a clear viscous liquid was obtained in 75.56% yield. $^1$H and $^{13}$C NMR (DMSO) were obtained. Melting point (hot plate apparatus)=liquid at room temperature. Thermal data determined by thermalgravimetric analysis (TGA): $T_{onset5\%}$=223° C. and $T_{onset}$=262° C.

Example XV

Didecyldimethylammonium Fast Green FCF

Didecyldimethylammonium bromide (0.003 mol) was dissolved in 100 mL of distilled water by gentle heating and stirring. Fast Green FCF (0.001 mol) was dissolved in 60 mL of distilled water by gentle heating and stirring. The two solutions were combined and the reaction mixture was heated and stirred for 30 minutes. The reaction mixture cooled to room temperature and then 60 mL of chloroform was added. The reaction mixture was stirred for an additional 30 minutes. The two phases were separated and the chloroform phase was washed several times with cool distilled water to remove any inorganic salt. The presence of chloride anions was monitored by silver nitrate test. A rotary evaporator removed the chloroform and a dark blue liquid was obtained in 65.54% yield. Melting point (hot plate apparatus)=liquid at room temperature. Thermal data determined by thermalgravimetric analysis (TGA): $T_{onset5\%}$=194° C. and $T_{onset}$=200° C.

Example XVII

Hexadecylpyridinium Fast Green FCF

Hexadecylpyridinium chloride (0.003 mol) was dissolved in 100 mL of distilled water by gentle heating and stirring. Fast Green FCF (0.001 mol) was dissolved in 60 mL of distilled water by gentle heating and stirring. The two solutions were combined and the reaction mixture was heated and stirred for 30 minutes. The reaction mixture cooled to room temperature and then 60 mL of chloroform was added. The reaction mixture was stirred for an additional 30 minutes. The two phases were separated and the chloroform phase was washed several times with cool distilled water to remove any inorganic salt. The presence of chloride anions was monitored by silver nitrate test. A rotary evaporator removed the chloroform and a dark blue solid was obtained in 28.14% yield. Melting point (hot plate apparatus)=40-50° C. Thermal data determined by thermalgravimetric analysis (TGA): $T_{onset5\%}$=216° C. and $T_{onset}$=218° C./307° C./504° C.

Example XVIII

Benzalkonium Fast Green FCF

Benzalkonium chloride (0.003 mol) was dissolved in 100 mL of distilled water by gentle heating and stirring. Fast Green FCF (0.001 mol) was dissolved in 60 mL of distilled water by gentle heating and stirring. The two solutions were combined and the reaction mixture was heated and stirred for 30 minutes. The reaction mixture cooled to room temperature and then 60 mL of chloroform was added. The reaction mixture was stirred for an additional 30 minutes. The two phases were separated and the chloroform phase was washed several times with cool distilled water to remove any inorganic salt. The presence of chloride anions was monitored by silver nitrate test. A rotary evaporator removed the chloroform and a dark blue gel was obtained in 91.52% yield. Melting point (hot plate apparatus)=35-45° C. Thermal data determined by thermalgravimetric analysis (TGA): $T_{onset5\%}$=136° C. and $T_{onset}$=195° C.

Example XIX

Hexadecylpyridinium Piperacillin

Hexadecylpyridinium chloride (0.001 mol) was dissolved in 60 mL of distilled water by gentle heating and stirring. Sodium piperacillin (0.001 mol) was dissolved in 60 mL of distilled water by gentle heating and stirring. The two solutions were combined and the reaction mixture was heated and stirred for 30 minutes. The reaction mixture cooled to room temperature, and then 60 mL of chloroform was added. The reaction mixture was stirred for an additional 30 minutes. The two phases were separated and the chloroform phase was washed several times with cool distilled water to remove any inorganic salt. The presence of chloride anions was monitored by silver nitrate test. A rotary evaporator removed the chloroform and a soft orange solid was obtained in 58.66% yield. Melting point (hot plate apparatus)=30-40° C.

Example XX

Didecyldimethylammonium Piperacillin

Didceyldimethylammonium bromide (0.001 mol) was dissolved in 60 mL of distilled water by gentle heating and stirring. Sodium piperacillin (0.001 mol) was dissolved in 60 mL of distilled water by gentle heating and stirring. The two solutions were combined and the reaction mixture was heated and stirred for 30 minutes. The reaction mixture cooled to room temperature and then 60 mL of chloroform was added. The reaction mixture was stirred for an additional 30 minutes. The two phases were separated and the chloroform phase was washed several times with cool distilled water to remove any inorganic salt. The presence of chloride anions was monitored by silver nitrate test. A rotary evaporator removed the chloroform and a clear gel was obtained in 50.65% yield. $^1$H and $^{13}$C NMR (DMSO) were obtained. Melting point (hot plate apparatus)=25-30° C. Thermal data determined by thermalgravimetric analysis (TGA): $T_{onset5\%}$=181° C. and $T_{onset}$=205° C.

Example XXI

Benzalkonium Piperacillin

Benzalkonium chloride (0.001 mol) was dissolved in 60 mL of distilled water by gentle heating and stirring. Sodium piperacillin (0.001 mol) was dissolved in 60 mL of distilled water by gentle heating and stirring. The two solutions were combined and the reaction mixture was heated and stirred for 30 minutes. The reaction mixture cooled to room temperature and then 60 mL of chloroform was added. The reaction mixture was stirred for an additional 30 minutes. The two phases were separated and the chloroform phase was washed several times with cool distilled water to remove any inorganic salt. The presence of chloride anions was monitored by silver nitrate test. A rotary evaporator removed the chloroform and a cloudy solid was obtained in 26.12% yield. $^1$H and $^{13}$C NMR (DMSO) were obtained. Melting point (hot plate apparatus)=30-40° C. Thermal data determined by thermalgravimetric analysis (TGA): $T_{onset5\%}$=165° C. and $T_{onset}$=177° C.

Example XXII

Benzalkonium Penicillin G

Benzalkonium chloride (0.001 mol) was dissolved in 60 mL of distilled water by gentle heating and stirring. Potassium penicillin G (0.001 mol) was dissolved in 60 mL of distilled water by gentle heating and stirring. The two solutions were combined and the reaction mixture was heated and stirred for 30 minutes. The reaction mixture cooled to room temperature and then 60 mL of chloroform was added. The reaction mixture was stirred for an additional 30 minutes. The two phases were separated and the chloroform phase was washed several times with cool distilled water to remove any inorganic salt. The presence of chloride anions was monitored by silver nitrate test. A rotary evaporator removed the chloroform and a yellowish soft solid was obtained in 93.60% yield. $^1$H and $^{13}$C NMR (DMSO) were obtained. Melting point (hot plate apparatus)=30-40° C.

Example XXIII

Didecyldimethylammonium Penicillin G

Didecyldimethylammonium bromide (0.001 mol) was dissolved in 60 mL of distilled water by gentle heating and stirring. Potassium penicillin G (0.001 mol) was dissolved in 60 mL of distilled water by gentle heating and stirring. The two solutions were combined and the reaction mixture was heated and stirred for 30 minutes. The reaction mixture cooled to room temperature and then 60 mL of chloroform was added. The reaction mixture was stirred for an additional 30 minutes. The two phases were separated and the chloroform phase was washed several times with cool distilled water to remove any inorganic salt. The presence of chloride anions was monitored by silver nitrate test. A rotary evaporator removed the chloroform and an orange gel was obtained in 76% yield. $^1$H and $^{13}$C NMR (DMSO) were obtained. Melting point (hot plate apparatus)=25-30° C.

Example XXIV

Hexadecylpyridinium Penicillin G

Hexadecylpyridinium chloride (0.001 mol) was dissolved in 60 mL of distilled water by gentle heating and stirring. Potassium penicillin G (0.001 mol) was dissolved in 60 mL of distilled water by gentle heating and stirring. The two solutions were combined and the reaction mixture was heated and stirred for 30 minutes. The reaction mixture cooled to room temperature and then 60 mL of chloroform was added. The reaction mixture was stirred for an additional 30 minutes. The two phases were separated and the chloroform phase was washed several times with cool distilled water to remove any inorganic salt. The presence of chloride anions was monitored by silver nitrate test. A rotary evaporator removed the chloroform and an orange gel was obtained in about 99% yield. Melting point (hot plate apparatus)=35-40° C.

Example XXV

Didecyldimethylammonium Salicylate

Didecyldimethylammonium bromide (0.03 mol) (tech., 75% gel in water) was dissolved in 50 mL hot, distilled water. Salicylic acid (0.03 mol) was added to the solution. The mixture was stirred vigorously at 90° C. for 4 h. After cooling to room temperature, 60 mL of chloroform was added. Chloroform phase was washed with distilled water until bromide ions were no longer detected using AgNO$_3$. The obtained wax (93% yield) was dried in vacuum. Thermogravimetric analysis: $T_c$=−1.0° C., $T_m$=30.4° C., $T_{onset5\%}$=169° C. and $T_{onset}$=200° C. $^1$H and $^{13}$C NMR (DMSO) were obtained.

Example XXVI

Benzalkonium Salicylate

Benzalkonium chloride (0.03 mol) was dissolved in warm distilled water and stechiometric amount of salicylic acid was added. The reaction mixture was stirred at 90° C. for 4 h. After cooling, chloroform was added. The organic phase was washed with distilled water until chloride ions were no longer detected using AgNO$_3$. Organic solvent was removed and the residue was dried in vacuum. Benzalkonium salicylate was obtained with 90% yield as wax at room temperature; it is soluble in hot water. Thermogravimetric analysis: $T_g$=−43.5° C., $T_{onset5\%}$=150° C., and $T_{onset}$=180° C. $^1$H and $^{13}$C NMR (DMSO) were obtained.

Example XXVII (2-hydroxyethyl)dimethylundecyloxymethylammonium Benzoate 2-(dimethylamino)ethanol (0.05 mol) was dissolved in anhydrous hexane (20 mL) and a solution of chloromethyl undecyl ether (0.05 mol) was added dropwise at room temperature. The reaction mixture was stirred for 15 minutes. The obtained precipitate was washed with dry hexane (40 mL). The material was used in the next step, without further purification. The prepared ammonium chloride was dissolved in water and an aqueous solution of sodium benzoate (0.07 mol) was added. The solution was stirring for 15 min. After 10 h, the reaction mixture was concentrated using a rotary evaporator. To a dry crude product, anhydrous acetone (30 mL) was added. The solid product was filtered and acetone was removed. The product was dried for 10 h at 50° C. in vacuum to obtain (2-hydroxyethyl)dimethylundecyloxymethylammonium benzoate as a grease in 80% yield. Thermogravimetric analysis: $T_{onset}$=127° C. $^1$H and $^{13}$C NMR (DMSO) were obtained.

Example XXVIII (2-acetoxyethyl)heptyloxymethyldimethylammonium Benzoate

In a two-necked, round bottomed flask, equipped with a condenser and addition funnel, 2-(dimethylamino)ethyl acetate (0.1 mol) was mixed with 150 mL of anhydrous hexane. Chloromethyl hexyl ether (0.1 mol) was slowly added over 15 minutes. After 30 minutes, the reaction mixture was cooled to the temperature of minus 18° C. and the crude product was separated. The crude product was washed with 100 mL of hexane and used in the next step without further purification. The material was dissolved in 100 mL of water and aqueous solution of sodium benzoate was added in stoichiometric amount. After 30 minutes, two phases were separated. The water phase was removed and 100 mL of anhydrous acetone was added to the residue. Precipitated NaCl was filtered off and the obtained liquid product, (2-acetoxyethyl)heptyloxymethyldimethylammonium benzoate, was dried for 12 h at 60° C. in vacuum. The product was obtained as viscous liquid in 65% yield. Thermogravimetric analysis: $T_{onset}$=120° C. $^1$H and $^{13}$C NMR (DMSO) were obtained.

Example XXIX (2-acetoxyethyl)dodecyloxymethyldimethylammonium Benzoate

In a two-necked, round bottomed flask, equipped with a condenser and addition funnel, the 2-(dimethylamino)ethyl acetate (0.05 mol) was mixed with 30 mL of anhydrous hexane. Chloromethyl dodecyl ether (0.055 mol) was slowly added over 5 minutes. After 15 minutes, the reaction mixture was cooled to the temperature of minus 18° C. and the crude product was separated. The precipitate was washed with 30 mL of hexane and used in the next step without further purification. The crude (2-acetooxyethyl)-dodecyloxymethyldimethylammonium chloride was dissolved in 30 mL of water and aqueous solution of potassium benzoate (0.065 mol) was added. After 30 min, 30 mL of chloroform was added. The chloroform phase was separated and washed with distilled water until chloride ions were no longer detected using $AgNO_3$. The obtained grease was dried under vacuum. The product was obtained as grease in 67% yield. Thermogravimetric analysis: $T_{onset}$=122° C. $^1H$ and $^{13}C$ NMR (DMSO) were obtained.

Example XXX

Didecyldimethylammonium Salicylate

Didecyldimethylammonium chloride (0.03 mol) was dissolved in 50 mL distilled water and sodium salicylate (0.04 mol) was added to solution. The mixture was stirred at 40° C. ifor 1 h. After cooling to room temperature, 60 mL of chloroform was added. The chloroform phase was separated and washed with distilled water until chloride ions were no longer detected using $AgNO_3$. The didecyldimethylammonium salicylate was obtained in 95% yield. The product is insoluble in water and was dried under vacuum.

Example XXXI

Didecyldimethylammonium Salicylate (Alternative Synthesis)

The stechiometric amounts of didecyldimethylammonium saccharinate and sodium salicylate were mixed in distilled water and stirred at 60° C. for 2 h. After that time the solution was cooled to room temperature. The product was extracted from the aqueous solution with chloroform. The chloroform phase was removed and solvent was evaporated. Synthesized didecyldimethylammonium salicylate (90% yield) was dried under vacuum.

Example XXXII

Benzalkonium Salicylate

Benzalkonium saccharinate (0.01 mol) and benzoic acid (0.01 mol) were dissolved in 25 mL of hot acetone. The mixture was stirred at room temperature for 5 h. Distilled water was added. The organic phase was separated and washed with distilled water. Organic phase was evaporated and the product, benzalkonium salicylate, was dried under vacuum. $^1H$ and $^{13}C$ NMR (DMSO) were obtained.

Example XXXII

Didecyldimethylammonium 2-[(2,6-dichlorophenyl)amino]-benzeneacetate

Didecyldimethylammonium chloride (0.03 mol) was dissolved in 40 mL distilled water and diclofenac sodium salt (0.04 mol) was added to the solution. The solution was stirred at room temperature for 30 min. Chloroform (40 mL) was added to the reaction mixture and the mixture was stirred. After separation of the phases, the organic phase was washed with 40 mL distilled, cold water until chloride ions were no longer detected using $AgNO_3$. Chloroform was removed and the residue was dried at 50° C. in vacuum. The product, didecyldimethylammonium 2-[(2,6-dichlorophenyl)amino] benzeneacetate (100% yield), was obtained as a grease that is soluble in chloroform, acetone, and DMSO. The product lacks miscibility with water and hexane. Thermogravimetric analysis: $T_{onset5\%}$=162° C., and $T_{onset}$=183° C. $^1H$ and $^{13}C$ NMR (DMSO) were obtained.

Example XXXIV

Didecyldimethylammonium 2-[(2,6-dichlorophenyl)amino]-benzeneacetate (Alternative Synthesis)

A solution of didecyldimethylammonium acesulfamate (0.01 mol) in acetone was prepared. The aqueous solution of sodium diclofenac (0.02 mol) was added and the reaction mixture was stirred at 60° C. for 2 h. The solution was extracted with ethyl acetate. Organic phase was separated and evaporated. The product, didecyldimethylammonium 2-[(2,6-dichlorophenyl)amino]benzeneacetate (88% yield), was dried under vacuum. $^1H$ and $^{13}C$ NMR (DMSO) were obtained.

Example XXXV

Didecyldimethylammonium N-[4-[[(2-amino-1,4-dihydro-4-oxo-6-pteridinyl)methyl]amino]benzoyl]-L-glutamate Didecyldimethylammonium chloride (0.025 mol) was dissolved in 40 mL distilled water and the folic acid sodium salt (0.01 mol) was added. The solution was stirred at room temperature for 30 min. After separation of the phases, the organic phase was washed with distilled, cold water until chloride ions were no longer detected using $AgNO_3$. The organic phase was separated and solvent was evaporated. The product (90% yield), didecyldimethylammonium N-[4-[[(2-amino-1,4-dihydro-4-oxo-6-pteridinyl)methyl]amino]benzoyl]-L-glutamate, was dried at 50° C. under vacuum. Product is soluble in chloroform, acetone, DMSO. It lacks miscibility with water and hexane. $^1H$ and $^{13}C$ NMR (DMSO) were obtained. Thermogravimetric analysis: $T_{onset5\%}$=153° C., and $T_{onset}$=201° C. $^1H$ and $^{13}C$ NMR (DMSO) were obtained.

Example XXXVI

Didecyldimethylammonium (S)-6-methoxy-α-methyl-2-naphthaleneacetate

The stoichiometric mixture (0.025 mol) of didecyldimethylammonium chloride and naproxen sodium salt were dissolved in distilled water and stirred at room temperature for 1 h. The product was extracted by ethyl acetate and organic phase was separated and then washed with distilled water. Ethyl acetate phase was removed and solvent evaporated. The product, didecyldimethylammonium (S)-6-methoxy-α-methyl-2-naphthaleneacetate (95% yield), was dried under vacuum. The product is soluble in chloroform, acetone, and DMSO. It lacks miscibility with water and hexane. Thermogravimetric analysis: $T_{onset5\%}$=156° C., and $T_{onset}$=190° C. $^1H$ and $^{13}C$ NMR (DMSO) were obtained.

Example XXXVII

Lidocaine Docusate

Lidocaine hydrochloride (0.0188 mol) was dissolved in 50 mL methanol and sodium docusate [bis(2-ethylhexyl)sulfosuccinate sodium salt] (0.0188 mol) was dissolved in 50 mL. The two solutions were combined and stirred for two hours, during this time a white precipitate (NaCl) formed. The methanol was removed by rotary evaporation which leaves a white sticky solid. To this solid, 150 mL of chloroform was added. A portion of the product dissolved the chloroform while the byproduct (NaCl) remained as a suspended solid. The NaCl was removed by filtration, and the solvent was removed by rotary evaporation. The product, lidocaine docusate, is a colorless syrup and is dried under high vacuum. $^1$H and $^{13}$C NMR (CDCl$_3$) were obtained.

Example XXXVIII

Didecyldimethylammonium Benzoate

Didecyldimethylammonium chloride (0.02 mol) was dissolved in distilled water and 0.015 mol of benzoic acid sodium salt was added. The solution was stirred at 80° C. for 7 h. The reaction mixture was extracted by chloroform. Chloroform phase was removed and washed with distilled, cold water until chloride ions were no longer detected using AgNO$_3$. Then chloroform was removed. Obtained benzoate in 85% yield was dried in vacuum. $^1$H NMR and $^{13}$C NMR (CDCl$_3$) were obtained.

Example XXXIX

Benzalkonium Benzoate 10 g of benzalkonium chloride (in which alkyl represents a mixture of the alkyls from C$_8$H$_{17}$ to C$_{18}$H$_{37}$) was soluble in distilled water and 7.2 g of sodium benzoate was added. The reaction mixture was stirred at 90° C. for 6 h. After cooling, 50 mL of chloroform was added. The organic phase was washed with distilled water until chloride ions were detected using AgNO$_3$. Chloroform was removed and the residue was dried in vacuum. Benzoate was obtained with 84% yield.

Example XL (2-hydroxyethyl)cyclododecyloxymethyldimethylammonium Benzoate 0.1 mol of (2-hydroxyethyl)cyclododecyloxymethyldimethylammonium chloride was dissolved in 100 mL of anhydrous acetone and sodium benzoate was added. After 5 h of stirring, NaCl was filtered and the reaction mixture was concentrated using a rotary evaporator. The obtained was dried for 10 h at 50° C. in vacuum.

Example XLI

Didecyldimethylammonium Mandelate

To 0.03 mol of didecyldimethylammonium chloride dissolved in 50 mL distilled water was added 0.03 mol of mandelic acid and 0.03 mol of NaOH. The mixture was stirred at 50° C. for 2 h. After cooling to room temperature, 60 mL of chloroform was added. Chloroform phase was washed with distilled water until chloride ions were no longer detected using AgNO$_3$. The obtained mandelate with 96% yield is insoluble in water and was dried in vacuum.

Example XLII

Didecyldimethylammonium 2-acetoxybenzoate

A stoichiometric mixture of didecyldimethylammonium chloride, acetylsalicyclic acid, and NaOH in distilled water was stirred at 60° C. for 2 h and then cooled to room temperature. The aqueous solution was extracted by chloroform. Chloroform was removed and prepared didecyldimethylammonium 2-acetoxybenzoate with 90% yield was dried in vacuum.

Example XLIII

Didecyldimethylammonium p-toluenesulfonate 0.015 mol of didecyldimethylammonium chloride, 0.01 mol of p-toluenesulfonic acid, 0.01 mol of NaOH and 100 mL of distilled water were charged to a round bottomed flask and heated. The mixture was stirred for 2 h at 40° C., whence the phases were allowed to separate. The organic layer was then washed three times with distilled water. The aqueous phases were tested for the presence of chloride ion using silver nitrate solution. Finally, the organic layer was vacuum stripped to remove water. The obtained didecyldimethylammonium p-toluenesulfonate with 95% yield is soluble in chloroform, acetone, DMSO, and insoluble in water and hexane.

Example XLIV

Didecyldimethylammonium nicotinate

To 0.002 mol of didecyldimethylammonium bromide (tech., 75% gel in water) dissolved in 60 mL hot, distilled water was added 0.002 mol of nicotinic acid. The mixture was stirred vigorously at 90° C. for 4 h. After cooling to room temperature 60 mL of chloroform was added. Chloroform phase was washed with distilled water until bromide ions were no longer detected using AgNO$_3$. The obtained waxy, white solid was dried in vacuum.

Example XLV

MultiComponent Ionic Liquids

Multicomponent ionic liquids containing 3 or more different ions were prepared to show the tenability of the disclosed compositions and methods. Three ionic liquids were prepared
1. benzalkonium, acesulfamate, and saccharinate
2. benzalkonium, mepenzolate, and docusate
3. hexadecylpyridinium, acesulfamate, and saccharinate The ionic liquids were prepared by dissolving each compound in a common solvent such as water, methanol, or ethanol. The solutions were combined and stirred. The solvent was then evaporated to reveal the ionic liquid and the inorganic salt. The ionic liquid was purified by dissolving it in a solvent, such as hexane, methanol, or ethanol. The inorganic salt was filtered off. The solvent was evaporated to produce the pure ionic liquid.

| Ionic Liquid | Ratio of ions | Form | Melting Point (° C.) | % Yield |
|---|---|---|---|---|
| 1 | 2:1:1 | Brownish solid | 40-45 | 75.4% |
| 1 | 3:1:2 | White solid | 30-40 | 82.7% |
| 1 | 3:2:1 | Orange solid | 35-45 | 72.2% |
| 3 | 2:1:1 | Yellow solid | 30-35 | 95.8% |
| 3 | 3:1:2 | Yellow solid | 30-40 | 76.8% |
| 3 | 3:2:1 | Orange solid | 30-35 | 87.3% |
| 2 | 2:1:3 | Colorless gel | | |
| 2 | 1:2:3 | Clear wax | | |
| 2 | 1:1:2 | Whitish gel | | |

Example XLVI

Lidocaine Complex of Ag+

In a reaction vessel charged with a magnetic stirbar and shielded from light, 1.0 g (5.9 mmol) AgNO$_3$ was dissolved in approximately 25 mL of deionized water. In a separate reaction vessel, similarly chared with a stirbar and shielded from light, 5.51 g (0.024 mol) of lidocaine (free-base form) was dissolved/suspended in 25 mL of deionized water. To the latter solution was added in one portion the aqueous solution of silver nitrate. A copious white precipitate forms quickly, which (all the while protected from light) was quickly isolated by suction filtration. The recovered solid was dried in vacuum, and subsequently recrystallized by slow evaporation of a methanol/acetonitrile solution to give well-formed colorless crystals that are moderately light-stable.

Example XLVII

Ranitidine Docusate

In a reaction vessel charged with a magnetic stirbar, 2.50 g (7.12 mmol) of Ranitidine hydrochloride was dissolved in approximately 25 mL of deionized water. In a separate reaction vessel, similarly charged with a stirbar, 3.17 g (7.12 mmol) of sodium docusate was dissolved/suspended in 25 mL of warm, deionized water. To the latter solution was added in one portion the aqueous solution of sodium docusate. The deep orange-brown milieu was stirred overnight, after which time the aqueous system was repeatedly extracted with 100 mL portions of chloroform. Emulsification of the two phases was quite pronounced, so each time the system was heated to about 60° C., then allowed to cool and settle for 5-7 days, after which point the dark chloroform phase was separated, dried over anhydrous MgSO$_4$, filtered, and rotary evaporated to yield a viscous, deep brown-orange oil (Ranitidine docusate). The two ions have known histamine H2-receptor antagonist and an emollient properties, respectively.

Example XLVIII

Silver Docusate

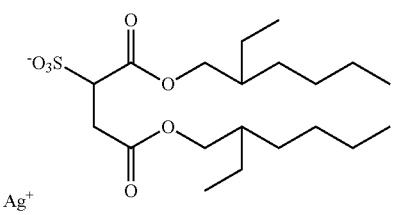

In a reaction vessel charged with a magnetic stirbar and protected from light, 5.0 g (29 mmol) of silver nitrate was dissolved in approximately 100 mL of deionized water. To the stirred solution was added, is small portions, 13.1 g (29 mmol) of sodium docusate. As the docusate was added, the solution became gradually gelatinous with attendant difficulties in stirring that were remedied by gently heating the solution. After addition of the final portion of sodium docusate, the warmed solution/suspension was stirred overnight, after which point it was rotary evaporated to yield a slightly tan mass. The mass was extracted with a chloroform-acetonitrile mixture, into which much of the material dissolved but some white solid (presumed to be NaNO$_3$) did not. The mixture was filtered and evaporated under reduced pressure to give a soft mass of slightly off-white final product (which should be stored away from light because it is photosensitive). This material was soluble in lidocaine docusate, some organic solvents, and was relatively slow to dissolve in water, doing so to only a limited degree. The two ions have known antimicrobial and emollient properties, respectively.

Example XLIX

Benzalkonium Sulfathiazole

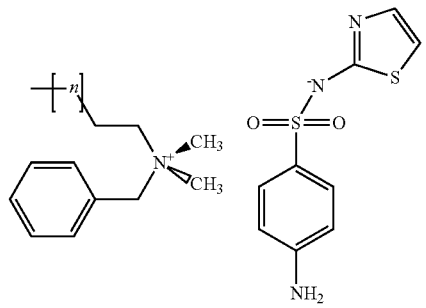

n = 5 to 15

Benzalkonium chloride (0.003 mol) was dissolved in 100 mL of distilled water by gentle stirring and heating. Sulfathiazole sodium (0.003 mol) was dissolved in 60 mL of distilled water by gentle stirring and heating. The two solutions were combined and the reaction mixture was stirred and heated for 1 h. The reaction mixture was cooled to room temperature and 60 mL of chloroform was added to the reaction mixture. The two phases were separated and the chloroform phase was washed several times with cool distilled water to remove any inorganic salt. The presence of chloride ions was monitored by silver nitrate test. A rotary evaporator removed the chloroform and an orange wax was obtained in a 50.04% yield. $^1$H and $^{13}$C NMR (DMSO) were obtained. Melting point (hot plate apparatus)=40-50° C. Thermal data was determined by thermalgravimetric analysis: $T_{onset5\%}$=156° C. and $T_{onset}$=173° C. The benzalkonium ion is a known antibacterial and the other ion is used to treat, for example, gonorrhea and other bacterial infections.

Example L

Benzalkonium Docusate

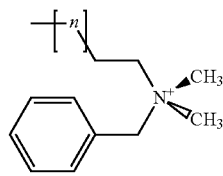

-continued

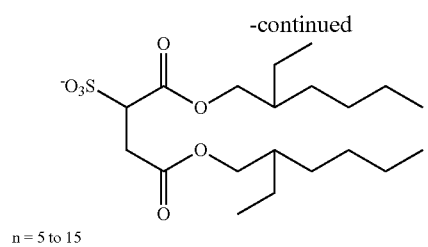

n = 5 to 15

Benzalkonium chloride (0.003 mol) was dissolved in 100 mL of 95% ethanol by gentle stirring and heating. Docusate sodium (0.003 mol) was dissolved in 100 mL of 95% ethanol by gentle stirring and heating. The two solutions were combined and the reaction mixture was stirred at room temperature for 1 h. A rotary evaporator was used to remove the 95% ethanol and produced the ionic liquid and NaCl salt. Hexane was used to dissolve the ionic liquid while the NaCl salt precipitated. The NaCl salt was filtered from the reaction solution. A rotary evaporator was used to remove the hexane and a white solid was obtained in a 78.32% yield. $^1$H (DMSO) was obtained. Melting point (hot plate apparatus)=25-30° C. The two ions have known antibacterial and emollient properties, respectively.

Example LI

Benzalkonium Thimerosal

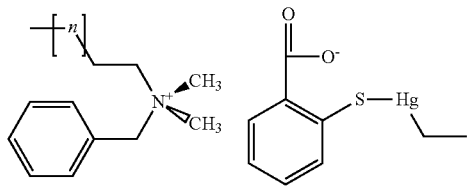

n = 5 to 15

Benzalkonium chloride (0.003 mol) was dissolved in 100 mL of 95% ethanol by gentle stirring and heating. Thimerosal sodium (0.003 mol) was dissolved in 100 mL of 95% ethanol by gentle stirring and heating. The two solutions were combined and the reaction mixture was stirred at room temperature for 1 h. A rotary evaporator was used to remove the 95% ethanol and produced the ionic liquid and NaCl salt. Chloroform was used to dissolve the ionic liquid while the NaCl salt precipitated. The NaCl salt was filtered from the reaction solution. A rotary evaporator was used to remove the chloroform and a clear gel was obtained in a 72.92% yield. Melting point (hot plate apparatus)=liquid at room temperature. The benzalkonium ion has known antibacterial properties and the thimerosal ion is a known preservative in vaccines, ophthalmic and nasal products, and tattoo inks.

Example LII

Hexadecylpyridinium Valproic Acid

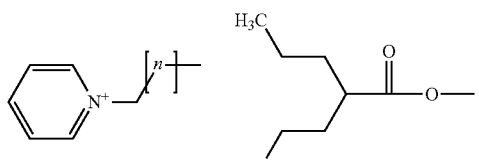

n = 14

Hexadecylpyridinium chloride (0.003 mol) was dissolved in 100 mL of distilled water by gentle stirring and heating. Valproic acid sodium salt (0.003 mol) was dissolved in 60 mL of distilled water by gentle stirring and heating. The two solutions were combined and the reaction mixture was stirred at room temperature for 1 h. A rotary evaporator was used to remove the 95% ethanol and produced the ionic liquid and NaCl salt. Tetrahydrofuran (THF) was used to dissolve the ionic liquid while the NaCl salt precipitated. The NaCl salt was filtered from the reaction solution. A rotary evaporator was used to remove the THF and a dark yellow liquid was obtained in a 77.14% yield. Melting point (hot plate apparatus)=liquid at room temperature. The two ions are used as an antibacterial and an anti-convulsant and mood stabilizer in bipolar disorder, respectively.

Example LIII

Hexadecylpyridinium Sulfathiazole

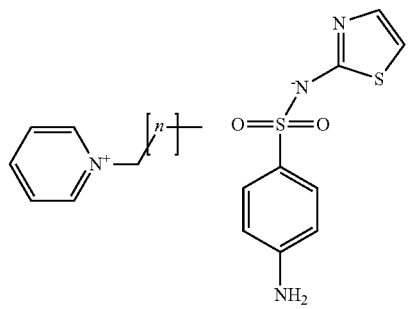

n = 14

Hexadecylpyridinium chloride (0.003 mol) was dissolved in 100 mL of distilled water by gentle stirring and heating. Sulfathiazole sodium (0.003 mol) was dissolved in 60 mL of distilled water by gentle stirring and heating. The two solutions were combined and the reaction mixture was stirred at room temperature for 1 h. A rotary evaporator was used to remove the distilled water and produced the ionic liquid and NaCl salt. Benzene was used to dissolve the ionic liquid while the NaCl salt precipitated. The NaCl salt was filtered from the reaction solution. A rotary evaporator was used to remove the benzene and a yellow solid was obtained in a 77.22% yield. NMR (DMSO) was obtained. Melting point (hot plate apparatus)=40-50° C. The hexadecylpyridinium ion is known to have antibacterial properties and the sulfathiazole is known for the treatment of gonorrhea and other bacterial infections.

Example LIV

Mepenzolate Docusate

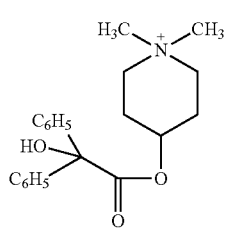

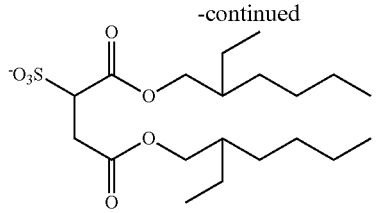

Mepenzolate bromide (0.003 mol) was dissolved in 100 mL 99% methanol by gentle stirring and heating. Docusate sodium (0.003 mol) was dissolved in 60 mL 99% methanol by gentle stirring and heating. The two solutions were combined and the reaction mixture was stirred at room temperature for 1 h. A rotary evaporator was used to remove the 99% methanol and produced the ionic liquid and NaBr salt. Hexane was used to dissolve the ionic liquid while the NaBr salt precipitated. The NaBr salt was filtered from the reaction solution. A rotary evaporator was used to remove the hexane and a white wax was obtained in a 62.75% yield. Melting point (hot plate apparatus)=50-55° C. The two ions are know to have anticholinergic and emollient properties, respectively.

Example LV

Benzalkonium Mepenzolate Docusate Ratio (1:1:2)

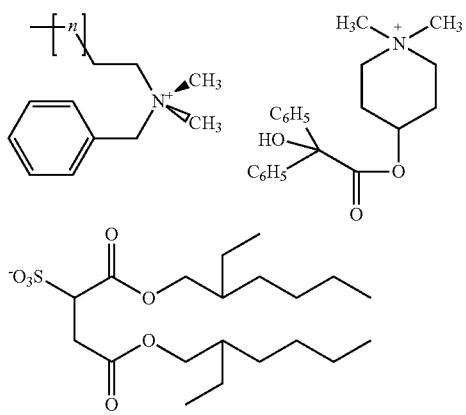

n = 5 to 15

Benzalkonium chloride (0.0015 mol) was dissolved in 100 mL 95% ethanol by gentle stirring and heating. Mepenzolate bromide (0.003 mol) was dissolved in 100 mL 99% methanol by gentle stirring and heating. Docusate sodium (0.003 mol) was dissolved in 60 mL 95% ethanol by gentle stirring and heating. The three solutions were combined and the reaction mixture was stirred at room temperature for 2 h. A rotary evaporator was used to remove the 95% ethanol and the 99% methanol. It produced the ionic liquid and NaBr and NaCl salt. Hexane was used to dissolve the ionic liquid while the NaBr and NaCl salt precipitated. The NaBr and NaCl salt was filtered from the reaction solution. A rotary evaporator was used to remove the hexane and a clear viscous liquid was obtained in a 44.09% yield. Melting point (hot plate apparatus)=liquid at room temperature. The three ions have known antibacterial, anticholinergic, and emollient properties.

Example LVI

Benzalkonium Mepenzolate Docusate Ratio (2:1:3)

Benzalkonium chloride (0.002 mol) was dissolved in 100 mL 95% ethanol by gentle stirring and heating. Mepenzolate bromide (0.001 mol) was dissolved in 100 mL 99% methanol by gentle stirring and heating. Docusate sodium (0.003 mol) was dissolved in 60 mL 95% ethanol by gentle stirring and heating. The three solutions were combined and the reaction mixture was stirred at room temperature for 2 h. A rotary evaporator was used to remove the 95% ethanol and the 99% methanol. It produced the ionic liquid and NaBr and NaCl salt. Hexane was used to dissolve the ionic liquid while the NaBr and NaCl salt precipitated. The NaBr and NaCl salt was filtered from the reaction solution. A rotary evaporator was used to remove the hexane and a whitish gel was obtained in a 68.84% yield. Melting point (hot plate apparatus)=liquid at room temperature.

Example LVII

Benzalkonium Mepenzolate Docusate Ratio (1:2:3)

Benzalkonium chloride (0.001 mol) was dissolved in 100 mL 95% ethanol by gentle stirring and heating. Mepenzolate bromide (0.002 mol) was dissolved in 100 mL 99% methanol by gentle stirring and heating. Docusate sodium (0.003 mol) was dissolved in 60 mL 95% ethanol by gentle stirring and heating. The three solutions were combined and the reaction mixture was stirred at room temperature for 2 h. A rotary evaporator was used to remove the 95% ethanol and the 99% methanol. It produced the ionic liquid and NaBr and NaCl salt. Hexane was used to dissolve the ionic liquid while the NaBr and NaCl salt precipitated. The NaBr and NaCl salt was filtered from the reaction solution. A rotary evaporator was used to remove the hexane and a clear gel was obtained in a 53.68% yield. Melting point (hot plate apparatus)=liquid at room temperature.

Example LVIII

Benzalkonium Sulfathiazole Saccharinate Ratio (2:1:1)

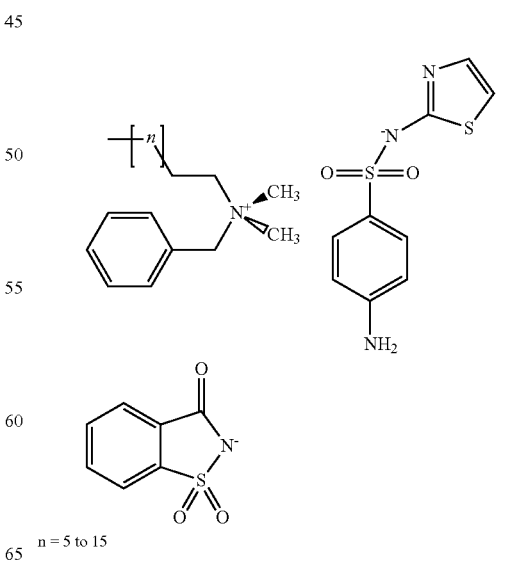

n = 5 to 15

Benzalkonium chloride (0.003 mol) was dissolved in 100 mL of distilled water by gentle stirring and heating. Sulfathiazole sodium (0.0015 mol) was dissolved in 50 mL of distilled water by gentle stirring and heating. Acesulfamate potassium (0.0015 mol) was dissolved in 50 mL of distilled water by gentle stirring and heating. The three solutions were combined and the reaction mixture was stirred and heated for 1 h. A rotary evaporator was used to remove the distilled water. It produced the ionic liquid and NaCl salt. 99% methanol was used to dissolve the ionic liquid while the NaCl salt precipitated. The NaCl salt was filtered from the reaction solution. A rotary evaporator was used to remove the 99% methanol and an orange gel was obtained in a 97.02% yield. Melting point (hot plate apparatus)=liquid at room temperature. The first two ions have known antibacterial properties and the third ion is a known artificial sweetener.

Example LIX

Benzalkonium Saccharinate Acesulfamate Ratio (2:1:1)

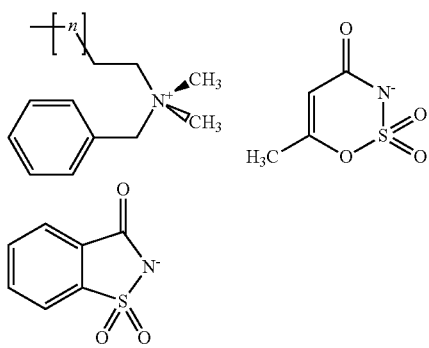

n = 5 to 15

Benzalkonium chloride (0.003 mol) was dissolved in 100 mL of distilled water by gentle stirring and heating. Saccharinate sodium (0.0015 mol) was dissolved in 50 mL of distilled water by gentle stirring and heating. Acesulfamate potassium (0.0015 mol) was dissolved in 50 mL of distilled water by gentle stirring and heating. The three solutions were combined and the reaction mixture was stirred and heated for 1 h. A rotary evaporator was used to remove the distilled water. It produced the ionic liquid and NaCl and KCl salt. 95% ethanol was used to dissolve the ionic liquid while the NaCl and KCl salt precipitated. The NaCl and KCl salt was filtered from the reaction solution. A rotary evaporator was used to remove the 95% ethanol and a brown solid was obtained in a 75.41% yield. Melting point (hot plate apparatus)=40-45° C. The first ion has known antibacterial properties and the next two ions are known artificial sweeteners.

Example LX

Benzalkonium Saccharinate Acesulfamate Ratio (3:1:2)

Benzalkonium chloride (0.003 mol) was dissolved in 100 mL of distilled water by gentle stirring and heating. Saccharinate sodium (0.001 mol) was dissolved in 50 mL of distilled water by gentle stirring and heating. Acesulfamate potassium (0.002 mol) was dissolved in 50 mL of distilled water by gentle stirring and heating. The three solutions were combined and the reaction mixture was stirred and heated for 1 h. A rotary evaporator was used to remove the distilled water. It produced the ionic liquid and KCl and NaCl salt. 95% ethanol was used to dissolve the ionic liquid while the KCl and NaCl salt precipitated. The KCl and NaCl salt was filtered from the reaction solution. A rotary evaporator was used to remove the 95% ethanol and a white solid was obtained in an 82.70% yield. Melting point (hot plate apparatus)=30-40° C.

Example LXI

Benzalkonium Saccharinate Acesulfamate Ratio (3:2:1)

Benzalkonium chloride (0.003 mol) was dissolved in 100 mL of distilled water by gentle stirring and heating. Saccharinate sodium (0.002 mol) was dissolved in 50 mL of distilled water by gentle stirring and heating. Acesulfamate potassium (0.001 mol) was dissolved in 50 mL of distilled water by gentle stirring and heating. The three solutions were combined and the reaction mixture was stirred and heated for 1 h. A rotary evaporator was used to remove the distilled water. It produced the ionic liquid and KCl and NaCl salt. 95% ethanol was used to dissolve the ionic liquid while the KCl and NaCl salt precipitated. The KCl and NaCl salt was filtered from the reaction solution. A rotary evaporator was used to remove the 95% ethanol and a white solid was obtained in a 72.16% yield. Melting point (hot plate apparatus)=35-45° C.

Example LXII

Hexadecylpyridinium Saccharinate Acesulfamate Ratio (2:1:1)

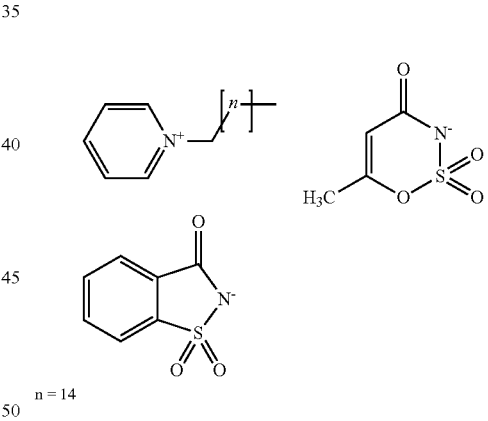

n = 14

Hexadecylpyridinium chloride (0.003 mol) was dissolved in 100 mL of distilled water by gentle stirring and heating. Saccharinate sodium (0.0015 mol) was dissolved in 50 mL of distilled water by gentle stirring and heating. Acesulfamate potassium (0.0015 mol) was dissolved in 50 mL of distilled water by gentle stirring and heating. The three solutions were combined and the reaction mixture was stirred and heated for 1 h. A rotary evaporator was used to remove the distilled water. It produced the ionic liquid and KCl and NaCl salt. 99% methanol was used to dissolve the ionic liquid while the KCl and NaCl salt precipitated. The KCl and NaCl salt was filtered from the reaction solution. A rotary evaporator was used to remove the 99% methanol and a yellow solid was obtained in a 95.78% yield. Melting point (hot plate apparatus)=30-35° C. The first ion has known antibacterial properties and the next two ions are known artificial sweeteners.

Example LXIII

Hexadecylpyridinium Saccharinate Acesulfamate Ratio (3:1:2)

Hexadecylpyridinium chloride (0.003 mol) was dissolved in 100 mL of distilled water by gentle stirring and heating. Saccharinate sodium (0.001 mol) was dissolved in 50 mL of distilled water by gentle stirring and heating. Acesulfamate potassium (0.002 mol) was dissolved in 50 mL of distilled water by gentle stirring and heating. The three solutions were combined and the reaction mixture was stirred and heated for 1 h. A rotary evaporator was used to remove the distilled water. It produced the ionic liquid and KCl and NaCl salt. 99% methanol was used to dissolve the ionic liquid while the KCl and NaCl salt precipitated. The KCl and NaCl salt was filtered from the reaction solution. A rotary evaporator was used to remove the 99% methanol and a yellowish solid was obtained in a 76.76% yield. Melting point (hot plate apparatus)=30-40° C.

Example LXIV

Diundecyldimethlammonium Saccharinate

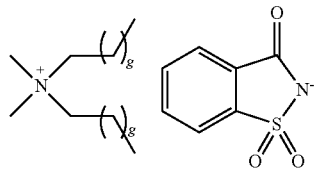

Diundecyldimethlammonium bromide (0.0023 mol) was dissolved in 7 mL of distilled water by gentle heating and stirring. Sodium saccharinate (0.001 mol) was dissolved in 7 mL of distilled water by gentle heating and stirring. The two solutions were combined and the reaction mixture was heated and stirred for 90 minutes. The reaction mixture was cooled to room temperature and then 7 mL of chloroform was added. The reaction mixture was stirred for an additional 30 minutes. The two phases were separated and the chloroform phase was washed several times with cool distilled water to remove any inorganic salt. The presence of bromide anions was monitored by silver nitrate test. Chloroform was removed on a rotary evaporator and remaining product was dried removed at 60° C. under vacuum. Product, as viscous liquid, was obtained in 81.00% yield. $^1$H and $^{13}$C NMR (DMSO) were obtained. The two ions have known antimicrobial and sweetener properties, respectively.

Example LXV

Diundecyldimethylammonium Acesulfamate

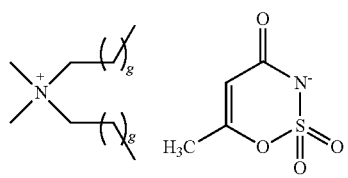

Diundecyldimethlammonium bromide (0.0023 mol) was dissolved in 7 mL of distilled water by gentle heating and stirring. Potassium acesulfamate (0.001 mol) was dissolved in 7 mL of distilled water by gentle heating and stirring. The two solutions were combined and the reaction mixture was heated and stirred for 90 minutes. The reaction mixture was cooled to room temperature and then 7 mL of chloroform was added. The reaction mixture was stirred for an additional 20 minutes. The two phases were separated and the chloroform phase was washed several times with cool distilled water to remove any inorganic salt. The presence of bromide anions was monitored by silver nitrate test. Chloroform was removed on a rotary evaporator and remaining product was dried removed at 60° C. under vacuum. Product, as viscous liquid, was obtained in 92% yield. $^1$H and $^{13}$C NMR (DMSO) were obtained. The two ions have known antimicrobial and sweetener properties, respectively.

Example LXVI

Didecyldimethylammonium Docusate

Didecyldimethylammonium bromide (0.005 mol) was dissolved 100 mL of 95% ethanol by gentle stirring. Docusate sodium was dissolved in 50 mL of 95% ethanol by gentle stirring. The two solutions were combined and the reaction mixture was stirred for 1 hour at room temperature. A rotary evaporator removed the ethanol to give the ionic liquid and NaBr. The ionic liquid was dissolved in hexane and the NaBr was filtered off. A rotary evaporator removed the hexane to give a white solid obtained in a 78.00% yield. $^1$H and $^{13}$C NMR (DMSO) were obtained. Melting point (hot plate apparatus)=25-30° C.

Example LXVII

Lidocaine Docusate Rat Tail Flick Test

The rat tail flick test is used to determine the local anesthetic ability of lidocaine docusate compared with lidocaine hydrochloride. The rat is immobilized in a restraining sock, so that the tail is only exposed. The tail is dipped into hot water and the number of times the rat flicks its tail is recorded. When the anesthetic is applied, the rat's tail should be numb therefore it will not feel the hot water and the number of tail flicks should decrease.

Figure 4A:
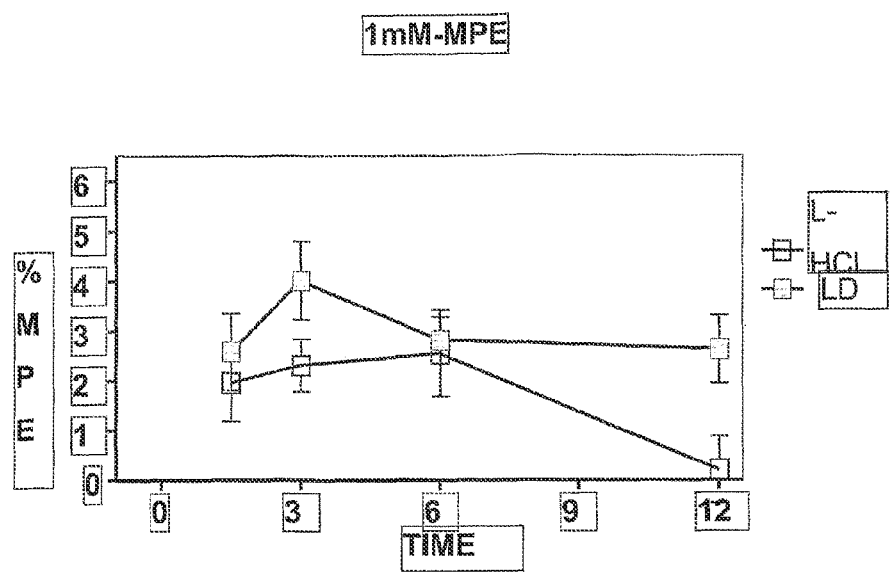
FIG. 4A is a graph showing a comparison of lidocaine hydrochloride and lidocaine docusate at 1 millmolar concentration.
Figure 4B:
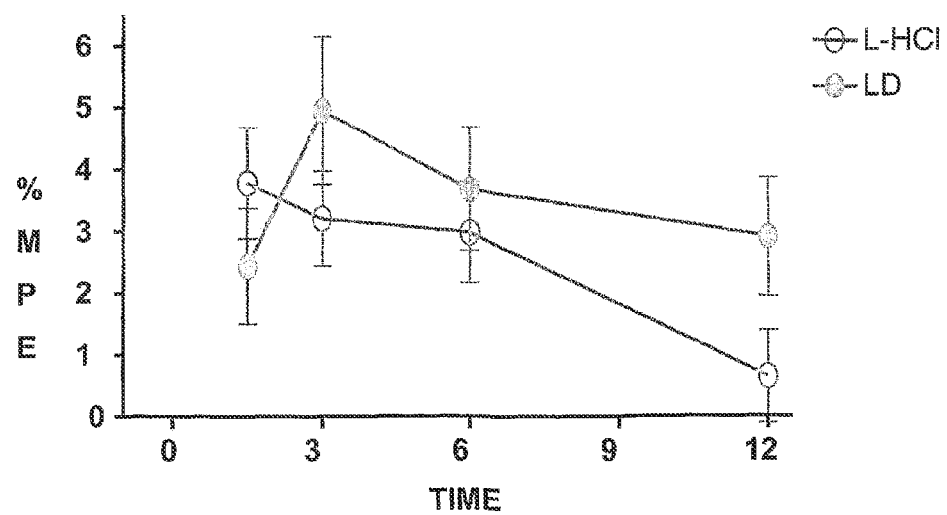
FIG. 4B is a graph showing a comparison of lidocaine hydrochloride and lidocaine docusate at 100 millimolar concentration.
Figure 5:
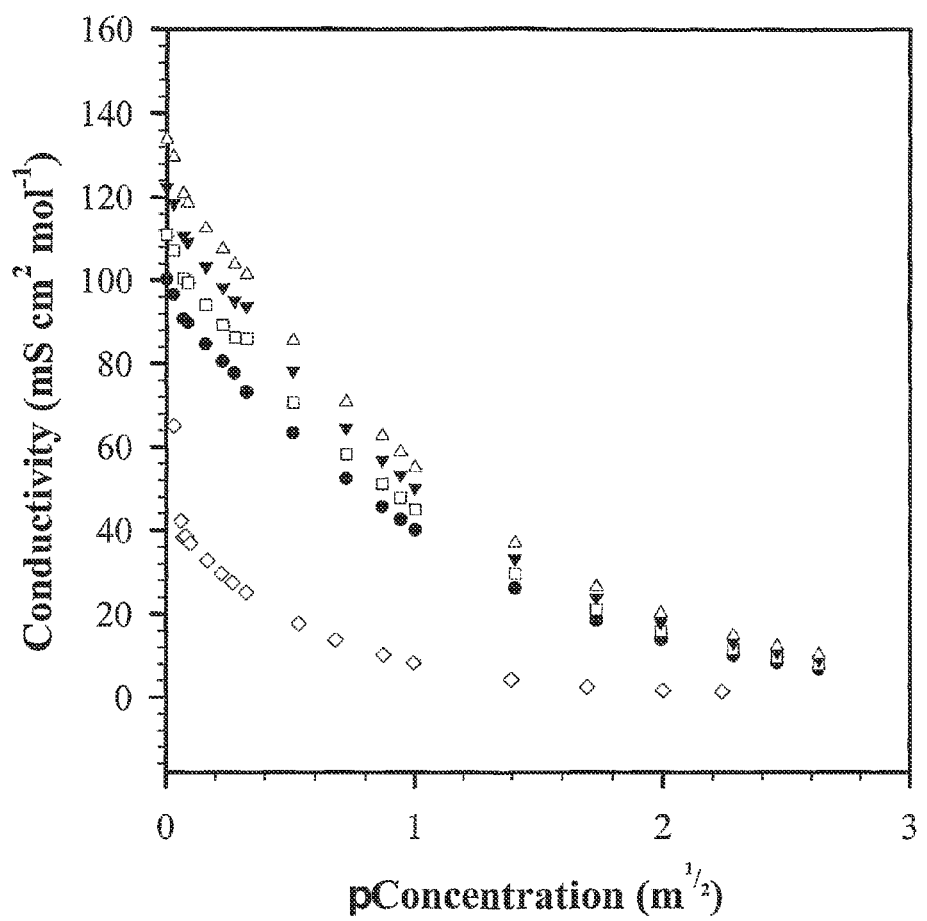
FIG. 5 is a graph showing molar conductivity for [$C_4$mim]Cl solutions at variable temperature; (●) 291.0 K; (□) 295.3 K; (▼) 300.2 K; (Δ) 305.0 K in water and (◊) in DMSO at 295.3 K.
Figure 6:
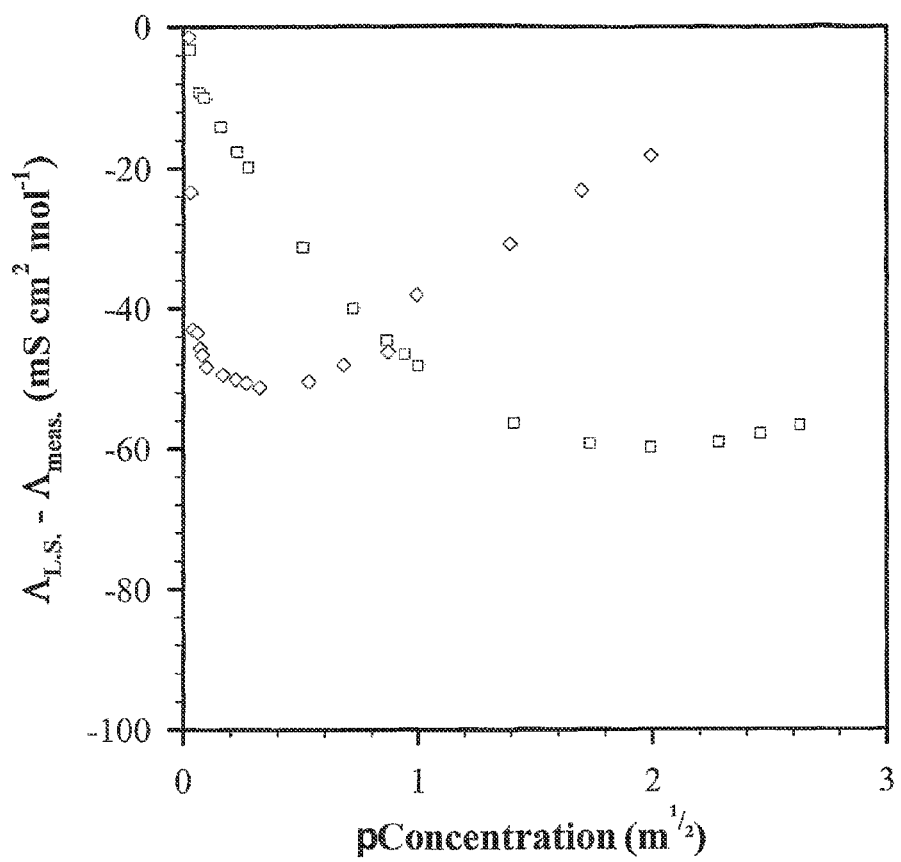
FIG. 6 is a graph showing the difference in calculated limiting slope and actually measured (□) [$C_4$mim]Cl in $H_2O$ at 295.3 K ; (◊) [$C_4$mim]Cl in DMSO at 295.3 K.

For this test Swiss-Webster male mice were used. They were habituated in a restraining sock 3 times during a 10 day period. A baseline tail flick was determined for each rat in 47.5° C. water bath. The rat's tail was then dipped into a solution of dimethyl sulfoxide (DMSO) and lidocaine hydrochloride or lidocaine docusate for 60 seconds. The number of tail flicks was determined at 15, 30, 60, and 120 minutes in the 47.5° C. water bath. FIGS. 4A and B are two graphs with the results at concentrations of DMSO lidocaine hydrochloride solution and lidocaine docusate of 1 mM and 100 mM. Using the following equation, one can determine the % MPE at each time for the two compounds in question.

$$\% MPE = (TF_i - BL)/(10 - BL) * 100$$

$TF_i$=latency to withdraw tail from hot water

BL=baseline withdrawal time without the drug

One can see from the graphs that lidocaine docusate has a higher and longer anesthetic ability than lidocaine hydrochloride in DMSO. This is likely due to the synergistic effects.

Prophetic Example LXVIII

Hexadecylpyridinium Clofencet, Fluoroxypyr, Diflufenzopyr, Mesosulfuron, Prohexadione, Pantoprazole, Risedronate, Losartan, Rabeprazole, Fosinopril, Ceftioxone, Atorvastatin, Pravastatin, Alendronate, Montelukast, Tazobactam, Allura Red AC, Tartrazine, Indigotine, Erythrosine, and Sunset Yellow (Depending on each compound's solubility, the following procedure can be alternated to compensate). Hexadecylpyridinium chloride (0.001 mol) is dissolved in 60 mL of distilled water by gentle heating and stirring. The anion (0.001 mol) is dissolved in 60 mL of distilled water by gentle heating and stirring. The two solutions are combined and the reaction mixture is heated and stirred for 30 minutes. The reaction mixture is cooled to room temperature and then 60 mL of chloroform is added. The reaction mixture is stirred for an additional 30 minutes. The two phases are separated and the chloroform phase is washed several times with cool distilled water to remove any inorganic salt. The presence of chloride anions is monitored by silver nitrate test. A rotary evaporator is used to remove the chloroform and a product will be obtained. Hot plate apparatus can be used to determine melting point and percent yield of the compound can be calculated. Also $^1$H and $^{13}$C NMR and thermalgravimetric analysis can be performed.

Prophetic Example LXIX

Didecyldimethylammonium Clofencet, Fluoroxypyr, Diflufenzopyr, Mesosulfuron, Prohexadione, Pantoprazole Risedronate, Losartan, Rabeprazole, Fosinopril, Ceftioxone, Atorvastatin, Pravastatin, Alendronate, Montelukast, Tazobactam, Allura Red AC, Tartrazine, Indigotine, Erythrosine, and Sunset Yellow (Depending on each compound's solubility, the following procedure can be alternated to compensate). Didecyldimethylammonium bromide (0.001 mol) is dissolved in 60 mL of distilled water by gentle heating and stirring. The anion (0.001 mol) is dissolved in 60 mL of distilled water by gentle heating and stirring. The two solutions are combined and the reaction mixture is heated and stirred for 30 minutes. The reaction mixture is cooled to room temperature, and then 60 mL of chloroform is added. The reaction mixture is stirred for an additional 30 minutes. The two phases are separated and the chloroform phase is washed several times with cool distilled water to remove any inorganic salt. The presence of chloride anions is monitored by silver nitrate test. A rotary evaporator is used to remove the chloroform and a product will be obtained. Hot plate apparatus can be used to determine melting point and percent yield of the compound can be calculated. Also $^1$H and $^{13}$C NMR and thermalgravimetric analysis can be performed.

Prophetic Example LXX

Benzalkonium Clofencet, Fluoroxypyr; Diflufenzopyr, Mesosulfuron, Prohexadione, Pantoprazole, Risedronate, Losartan, Rabeprazole, Fosinopril, Ceftioxone, Atorvastatin, Pravastatin, Alendronate, Montelukast, Tazobactam, Allura Red AC, Tartrazine, Indigotine, Erythrosine, and Sunset Yellow (Depending on each compound's solubility, the following procedure can be alternated to compensate). Benzalkonium chloride (0.001 mol) is dissolved in 60 mL of distilled water by gentle heating and stirring. The anion (0.001 mol) is dissolved in 60 mL of distilled water by gentle heating and stirring. The two solutions are combined and the reaction mixture is heated and stirred for 30 minutes. The reaction mixture is cooled to room temperature and then 60 mL of chloroform is added. The reaction mixture is stirred for an additional 30 minutes. The two phases are separated and the chloroform phase is washed several times with cool distilled water to remove any inorganic salt. The presence of chloride anions is monitored by silver nitrate test. A rotary evaporator is used to remove the chloroform and a product will be obtained. Hot plate apparatus can be used to determine melting point and percent yield of the compound can be calculated. Also $^1$H and $^{13}$C NMR and thermalgravimetric analysis can be performed.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

The invention claimed is:

1. An ionic liquid comprising a cation and an anion, wherein the ionic liquid is liquid at a temperature of from about −30° C. to about 125° C., and wherein the cation is a herbicidal active selected from the group consisting of carfentrazone, imazapyr, benefin, flumetsulam, metosulam, ametryne, atrazine, cyanazine, diuron, hexazinone, metribuzin, pyridate, terbuthylazine, fluoroxypyr, fenoxaprop-P-ethyl, dimethenamid, flufenacet, mefenacet, metolachlor, S-metolachlor, thenylchlor, fluthiacet-methyl, carfentrazone-ethyl, isoxaflutole, (4-trifluoromethyl-2-methylsulfonylbenzoyl)-5-hydroxy-1-methyl-3-methylpyrazole, glyphosate, pendimethalin, trifluralin, and triaziflam, or an ionic derivative thereof; and the anion is selected from the group consisting of halide, sulfate, carbonate, bicarbonate, phosphate, nitrate, nitrate, acetate, $PF_6^-$, $BF_4^-$, triflate, nonaflate, bis(triflyl)amide, trifluoroacetate, heptaflurorobutanoate, and haloaluminate.

2. The ionic liquid of claim 1, wherein the ionic liquid is liquid at a temperature at below or about 75° C.

3. The ionic liquid of claim 1, wherein the ionic liquid is liquid at a temperature at below or about 50° C.

4. The ionic liquid of claim 1, wherein the ionic liquid is liquid at a temperature at below or about 25° C.

5. The ionic liquid of claim 1, wherein the ionic liquid further comprises a solvent, preservative, dye, colorant, thickener, surfactant, a viscosity modifier, or mixture thereof at less than or about 10 wt. % of the total ionic liquid.

6. A method of controlling plant growth in an area, comprising administering an effective amount of the ionic liquid of claim 1 to the area thereby controlling plant growth.

7. A method for preparing an ionic liquid, comprising:
   a. providing cations and anions, or providing cation precursors and anion precursors, the cation or cation precursor is an herbicidal active selected from the group consisting of carfentrazone, imazapyr, benefin, flumetsulam, metosulam, ametryne, atrazine, cyanazine, diuron, hexazinone, metribuzin, pyridate, terbuthylazine, fluoroxypyr, fenoxaprop-P-ethyl, dimethenamid, flufenacet, mefenacet, metolachlor, S-metolachlor, thenylchlor, fluthiacet-methyl, carfentrazone-ethyl, isoxaflutole, 4-(4-trifluoromethyl-2-methylsulfonylbenzoyl)-5-hydroxy-1-methyl-3-methylpyrazole, glyphosate, pendimethalin, trifluralin, and triaziflam, or an ionic derivative thereof; and the anion or anion precursor is selected from the group consisting of halide, sulfate, carbonate, bicarbonate, phosphate, nitrate, nitrite, acetate, $PF_6^-$, $BF_4^-$, triflate, nonaflate, bis(triflyl) amide, trifluoroacetate, heptafluororobutanoate, and haloaluminate b. combining the cations and anions or the cation precursors and anion precursors, thereby producing an ionic liquid that is liquid at a temperature of from about −30° C. to about 125° C.

8. The method of claim 7, wherein the ionic liquid is liquid at a temperature at below or about 125° C.

9. The method of claim 7, wherein the ionic liquid is liquid at a temperature at below or about 75° C.

10. The method of claim 7, wherein the ionic liquid is liquid at a temperature at below or about 50° C.

11. The method of claim 7, wherein the ionic liquid is liquid at a temperature at below or about 25° C.

12. The method of claim 7, wherein combining the cations and anions is accomplished by a metathesis reaction.

13. The method of claim 7, wherein combining the cation precursor and anion precursor is accomplished by an acid-base neutralization reaction.

* * * * *